United States Patent
Xu

(10) Patent No.: US 12,390,484 B2
(45) Date of Patent: *Aug. 19, 2025

(54) ADENOSINE DERIVATIVE AND PHARMACEUTICAL COMPOSITION COMPRISING THE SAME

(71) Applicant: Brii Biosciences, Inc., Durham, NC (US)

(72) Inventor: Lianhong Xu, Palo Alto, CA (US)

(73) Assignee: Brii Biosciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,985

(22) Filed: Sep. 15, 2023

(65) Prior Publication Data
US 2024/0245716 A1    Jul. 25, 2024

Related U.S. Application Data

(63) Continuation of application No. 17/583,805, filed on Jan. 25, 2022, now Pat. No. 11,793,827.

(60) Provisional application No. 63/141,450, filed on Jan. 25, 2021.

(51) Int. Cl.
| | |
|---|---|
| *C07H 19/16* | (2006.01) |
| *A61K 31/4439* | (2006.01) |
| *A61K 31/4985* | (2006.01) |
| *A61K 31/7076* | (2006.01) |
| *A61K 47/10* | (2017.01) |

(52) U.S. Cl.
CPC ...... *A61K 31/7076* (2013.01); *A61K 31/4439* (2013.01); *A61K 31/4985* (2013.01); *A61K 47/10* (2013.01); *C07H 19/16* (2013.01)

(58) Field of Classification Search
None
See application file for complete search history.

(56) References Cited

U.S. PATENT DOCUMENTS

| | | |
|---|---|---|
| 3,407,191 A | 10/1968 | Koert et al. |
| 5,880,154 A | 3/1999 | Boukrinskaia et al. |
| 7,339,053 B2 | 3/2008 | Kohgo et al. |
| 7,625,877 B2 | 12/2009 | Kohgo et al. |
| 8,039,614 B2 | 10/2011 | Kohgo et al. |
| 11,793,827 B2 * | 10/2023 | Xu .................. A61K 47/10 |
| 11,890,297 B2 | 2/2024 | Xu et al. |
| 2005/0215512 A1 | 9/2005 | Kohgo et al. |
| 2018/0002366 A1 | 1/2018 | Girijavallabhan et al. |
| 2018/0099989 A1 | 4/2018 | Ivachtchenko et al. |
| 2019/0185508 A1 | 6/2019 | Alexandre et al. |
| 2020/0079814 A1 | 3/2020 | Ivachtchenko et al. |
| 2022/0233567 A1 | 7/2022 | Xu |
| 2022/0249532 A1 | 8/2022 | Xu et al. |
| 2022/0288098 A1 | 9/2022 | Xu |
| 2023/0226093 A1 | 7/2023 | Xu |

FOREIGN PATENT DOCUMENTS

| | | |
|---|---|---|
| CN | 109053803 A | 12/2018 |
| RU | 2728829 C1 | 7/2020 |
| WO | WO-2005025583 A2 | 3/2005 |
| WO | WO-2007022073 A2 | 2/2007 |
| WO | WO-2008011406 A2 | 1/2008 |
| WO | WO-2011058582 A1 | 5/2011 |
| WO | WO-2015187596 A2 | 12/2015 |
| WO | WO-2017053216 A2 | 3/2017 |
| WO | WO-2018022221 A1 | 2/2018 |
| WO | WO-2020031131 A1 | 2/2020 |
| WO | WO-2020044257 A1 | 3/2020 |
| WO | WO-2020178767 A1 | 9/2020 |
| WO | WO-2021021717 A1 | 2/2021 |
| WO | WO-2021038509 A1 | 3/2021 |
| WO | WO-2021050961 A1 | 3/2021 |
| WO | WO-2022159872 A1 | 7/2022 |

OTHER PUBLICATIONS

Belikov, V.G, "Pharmaceutical Chemistry. Chapter 2.6 Relationship between the chemical structure, properties of substances and their effect on the body", MEDpress-inform (2007); pp. 27-29; 14 pages with English translation.

Dyson, G., et al., "Chemistry of Synthetic Drugs", Moscow, MIR, 1964, pp. 12-19; 25 pages with English machine translation.

Extended European Search Report for European Application No. EP20848596.1 dated Sep. 15, 2023, 9 pages.

Final Office Action for U.S. Appl. No. 18/176,204 dated Aug. 30, 2023, 21 pages.

Ghosh et al., "Organic Carbamates in Drug Design and Medical Chemistry," Journal of Medicinal Chemistry, American Chemical Society, Jan. 7, 2015, vol. 58, Issue 7, pp. 2895-2940.

Hayakawa et al., "Potential of 4'-C-substituted nucleosides for the treatment of HIV-1," Antiviral Chemistry & Chemotherapy, 15: 169-187, Aug. 2004.

International Preliminary Report on Patentability for Application No. PCT/US2022/013660, mailed Aug. 3, 2023, 7 pages.

International Preliminary Report on Patentability for International Application No. PCT/US2020/043713, mailed Feb. 10, 2022, 8 Pages.

International Search Report and Written Opinion for Application No. PCT/US2020/043713, mailed Dec. 15, 2020, 10 pages.

International Search Report and Written Opinion for Application No. PCT/US2022/013660, mailed Jun. 14, 2022, 10 pages.

Invitation to Pay Additional Fees for Application No. PCT/US2022/013660, mailed Apr. 6, 2022, 2 pages.

Iyidogan et al., "Current Perspectives on HIV-1 Antiretroviral Drug Resistance," Viruses, Oct. 2014, 6, pp. 4095-4139.

Kageyama, M., et al., "Enantioselective Total Synthesis of the Potent Anti-HIV Nucleoside EFdA", Organic Letters, vol. 13, No. 19, Oct. 7, 2011, pp. 5264-5266.

(Continued)

*Primary Examiner* — Traviss C McIntosh, III
(74) *Attorney, Agent, or Firm* — Cooley LLP

(57) ABSTRACT

Disclosed herein are adenosine derivative prodrugs and compositions thereof that can be used for the treatment of HIV infection or RNA virus infection.

19 Claims, 4 Drawing Sheets

(56) References Cited

OTHER PUBLICATIONS

Kümmerer, K., "Pharmaceuticals in the Environment", Annual Review of Environment and Resources (2010); 35: 57-75.

Mashkovskiy, M.D., "Drugs", Moscow: "Medicine" (1993) Part 1, pp. 8; 3 pages with English Summary.

Michailidis et al., "4'-Ethynyl-2-fluoro—2'-deoxyadenosine (EFdA) Inhibits HIV-1 Reverse Transcriptase with Multiple Mechanisms," The Journal of Biological Chemistry, Aug. 2014, vol. 289, No. 35, pp. 24533-24548.

Non-Final Office Action for U.S. Appl. No. 17/583,805 dated Mar. 16, 2023, 11 pages.

Non-Final Office Action for U.S. Appl. No. 17/630,403 mailed Aug. 27, 2024, 15 pages.

Non-Final Office Action for U.S. Appl. No. 18/176,204 dated May 9, 2023, 19 pages.

Non-Final Office Action for U.S. Appl. No. 18/176,204 dated May 22, 2024, 23 pages.

Notice of Reasons for Refusal for Japanese Application No. 2022-505447 mailed Sep. 5, 2024, with English translation, 10 pages.

Office Action and Search report for Chinese Application No. CN20208066036 dated Jul. 6, 2023, 13 pages.

Office Action and Search Report for Chinese Patent Application No. CN202080066036.3 dated Jan. 26, 2024, with English Translation, 16 pages.

Office Action and Search report for Russian Application No. RU2022104985 dated Dec. 29, 2023, 29 pages.

Office Action and Search Report for Singapore Application No. SG11202200159S dated Apr. 2, 2024, 7 pages.

Office Action for Chinese Application No. CN20208066036 dated May 21, 2024, 6 pages.

Office Action for Eurasian Application No. 202392087 mailed Jul. 29, 2024, 12 pages.

Office Action for Indian Application No. IN202217003901 mailed May 13, 2024, 7 pages.

Office Action for Taiwan Patent Application No. TW20200125342 dated Mar. 7, 2024, 9 pages.

Ohrui et al., "Syntheses of 4'-C-Ethynyl-β-D-arabino-and 4'-C-Ethynyl-2'-deoxy-β-D-ribo-pentofuranosylpyrimidines and -purines and Evaluation of Their Anti-HIV Activity," Journal of Medicinal Chemistry, Nov. 2000, 43, pp. 4516-4525.

Patel et al., "Synthesis of Islatravir Enabled by a Catalytic, Enantioselective Alkynylation of a Ketone," Organic Letters, vol. 22, No. 12, Jun. 9, 2020, pp. 4659-4664, https://doi.org/10.1021/acs.orglett.0c01431.

Pauwels, Rudi, "Aspects of successful drug discovery and development", Antiviral Research 71(2-3), Sep. 2006, pp. 77-89.

PubChem [Internet]. Bethesda (MD): National Library of Medicine (US), National Center for Biotechnology Information; 2004-. PubChem Compound Summary for CID 6483431, 4'-Ethynyl-2-Fluoro-2'-Deoxyadenosine; [cited Jul. 31, 2024], 34 pages. Available from: https://pubchem.ncbi.nlm.nih.gov/compound/4_-Ethynyl-2-Fluoro-2_-Deoxyadenosine.

Rautio et al., "Prodrugs: design and clinical applications". Nature reviews Drug discovery. Mar. 2008; 7(3): 255-70.

Simplicio et al., "Prodrugs for amines". Molecules. Mar. 3, 2008; 13(3): 519-47.

Singh et al., "Long-Acting Anti-HIV Drugs Targeting HIV-1 Reverse Transcriptase and Integrase," Pharmaceuticals, 12, 62, Jun. 2019, 14 pages.

Solyev et al., "Synthesis and Anti-HIV Properties of New Carbamate Prodrugs of AZT," Chemical Biology & Drug Design, Dec. 2012, vol. 80, pp. 947-952.

Stella et al, eds, "Prodrugs: Challenges and Rewards," Part 2, Chapter "Prodrugs of Carboxylic Acids", Springer, 2007, 35 pages.

Subbaiah et al., "Coupling of an Acyl Migration Prodrug Strategy with Bio-activation to Improve Oral Delivery of the HIV-1 Protease Inhibitor Atazanavir," Journal of Medicinal Chemistry, Apr. 2018, vol. 61, pp. 4176-4188.

Tatani et al., "Identification of 8-aminoadenosine derivatives as a new class of human concentrative nucleoside transporter 2 inhibitors". ACS Medicinal Chemistry Letters. Mar. 12, 2015; 6(3): 244-8.

Third Party Observation for European Application No. 20848596.1, mailed Mar. 4, 2022, 10 pages.

Tichy et al., "New prodrugs of Adefovir and Cidofovir," Bioorganic & Medicinal Chemistry, vol. 19, Issue 11, Elsevier Science, Apr. 22, 2011, pp. 3527-3539.

Wanka et al., "The lipophilic bullet hits the targets: medicinal chemistry of adamantane derivatives". Chemical reviews. May 8, 2013; 113(5): 3516-604.

Extended European Search Report for European Application No. 22743369.5 mailed Jan. 21, 2025, 15 pages.

Liu et al., "The many faces of the adamantyl group in drug design". European journal of medicinal chemistry. Jun. 1, 2011;46(6):1949-63.

Stimac et al., "Adamantane in drug delivery systems and surface recognition". Molecules. Feb. 1, 20176;22(2): 14 pages.

Office Action and Search Report for Chinese Application No. 202280009277.3 mailed Apr. 14, 2025, with English translation, 20 pages.

\* cited by examiner

ADENOSINE DERIVATIVE AND PHARMACEUTICAL COMPOSITION COMPRISING THE SAME

CROSS REFERENCE TO RELATED APPLICATION

This application is a continuation of U.S. Non-provisional application Ser. No. 17/583,805, filed Jan. 25, 2022, which claims the benefit of and priority to U.S. Provisional Application No. 63/141,450, filed Jan. 25, 2021, each of which is incorporated herein by reference in its entirety.

FIELD

The present disclosure is directed to adenosine derivative prodrugs that can inhibit reverse transcriptase. This disclosure is also directed to pharmaceutical compositions comprising an adenosine derivative prodrug that can be used for the treatment of acquired immunodeficiency syndrome (AIDS), HIV-1, HIV-2, multidrug resistant HIV or a combination thereof.

BACKGROUND

Retroviruses such as human immunodeficiency virus (HIV) have been linked to the immunosuppressive disease known as acquired immunodeficiency syndrome (AIDS). Multiple strains of retrovirus, such as HIV type-1 (HIV-1) and type-2 (HIV-2) are known to be related to the diseases. The HIV retrovirus infected individuals can be initially asymptomatic, but then develop AIDS related complex (ARC) followed by AIDS. Replication of HIV by a host cell requires integration of the viral genome into the DNA of host cells. A key step in the process involves transcription of the viral RNA genome into DNA via an enzyme known as reverse transcriptase (RT).

A reverse transcriptase typically can have multiple enzymatic functions that can act (1) as an RNA-dependent DNA polymerase transcribing a single-stranded DNA copy of the viral RNA (first DNA), (2) as a ribonuclease destroying the original viral RNA and frees the DNA just produced from the original RNA, and (3) as a DNA-dependent DNA polymerase producing a second, complementary DNA strand using the first DNA strand as a template. The two DNA strands then form double-stranded DNA, which is integrated into the genome of the host cells by an integrase enzyme.

A number of compounds can inhibit reverse transcriptase (RT) activity. These compounds can be useful for the treatment of HIV infection in humans by inhibiting HIV replication in infected cells or individuals. Examples of the compounds approved for use in treating HIV infection and AIDS include nucleoside RT inhibitors (NRTI) such as 3'-azido-3'-deoxythymidine (AZT, also known as Zidovudine (ZDV), azidothymidine (AZT)), 2',3'-dideoxyinosine (ddI), 2',3'-dideoxycytidine (ddC), d4T, 3TC, abacavir, emtricitabine, and tenofovir disoproxil fumarate, as well as non-nucleoside RT inhibitors (NNRTI) such as nevirapine, delavirdine, efavirenz, rilpivirine and doravirine (DHHS guidelines: https://aidsinfo.nih.gov/understanding-hiv-aids, Iyidogan & Anderson, Viruses, 6, 4095-4139, 2014, doi: 10.3390/v6104095; Hayakawa et al., Antiviral Chem & Chemotherapy, 15:169-187, 2004; Ohrul et al., J. Med. Chem. 43, 4516-4525, 2000; Pauwels, Antiviral Research, 71, 77-89, 2006.).

An adenosine derivative EFdA (4'-ethynyl-2-fluoro-2'-deoxyadenosine, also known as MK-8591, islatravir) is a NRTI that has been demonstrated to have anti-HIV activity via inhibiting reverse transcriptase by preventing translocation (U.S. Pat. Nos. 7,339,053, 7,625,877, 8,039,614. Singh et al., Pharmaceuticals, 12, 62, 2019, DOI: 10.3390/ph12020062, each of which is incorporated by reference herein in its entirety). This compound has broad inhibitory activity and potency for different subtypes and mutations including HIV-1, HIV-2, and multidrug resistant (MDR) and wildtype (WT) strains, and reverse transcriptase inhibitor (RTI) resistant viruses. Some modified EFdAs and prodrugs have been described in U.S. Patent Publication No.: 2018/0002366, incorporated by reference herein in its entirety.

A common issue that arises from the treatment of HIV infection with anti-retroviral inhibitory compounds is resistance of the viruses to the inhibitors. Such resistance is typically the result of mutations that occur in the reverse transcriptase segment of the pol gene. The continued use of antiviral compounds, such as the inhibitory compounds, to prevent HIV infection will inevitably result in the emergence of new resistant strains of HIV. Therefore, there is a continuing need for new RT inhibitors that are effective against HIV strains including mutant HIV and multidrug-resistant HIV strains.

Another common issue is the medication adherence. Medication adherence is essential for individuals with HIV to have successful therapy over a lifetime. Adherence to a daily regimen can be challenging, which also has negative impact on the patient's quality of life with daily reminders of their HIV status. Accordingly, there is a need to identify long-acting compounds or regimens (for example, once a week, once a month or once every two-month therapy) for patients to overcome these challenges tied to taking daily, oral medication.

SUMMARY

The present disclosure is related to adenosine derivatives and compositions thereof that can be used to treat retroviral diseases such as HIV and AIDS.

In some embodiments, the present disclosure provides an adenosine derivative having a structure of formula (I) or a pharmaceutically acceptable salt, tautomer, or solvate thereof:

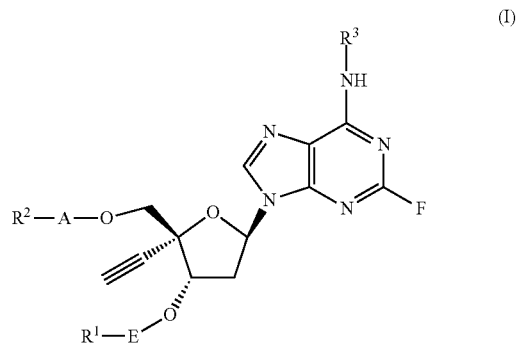

(I)

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H;

$R^1$ and $R^2$ can join together with the atoms to which they are attached to form a 3- to 25-membered heterocyclic ring; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Ia), (Ib), or a pharmaceutically acceptable salt, tautomer, or solvate thereof:

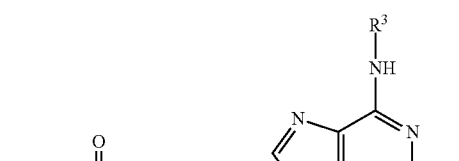

(Ia)

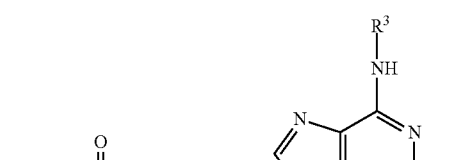

(Ib)

wherein:
$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Ic), (Id), or a pharmaceutically acceptable salt, tautomer, or solvate thereof:

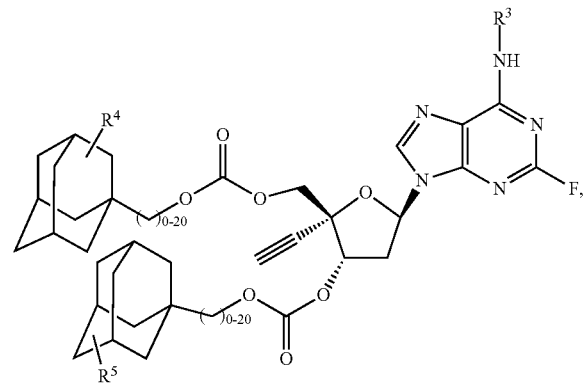

(Ic)

(Id)

wherein:
$R^3$ is selected from the group consisting of H, —(CO)-G-$C_{1-10}$alkyl, and $C_{1-10}$alkyl;

$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Ie), (If), or a pharmaceutically acceptable salt, tautomer, or solvate thereof:

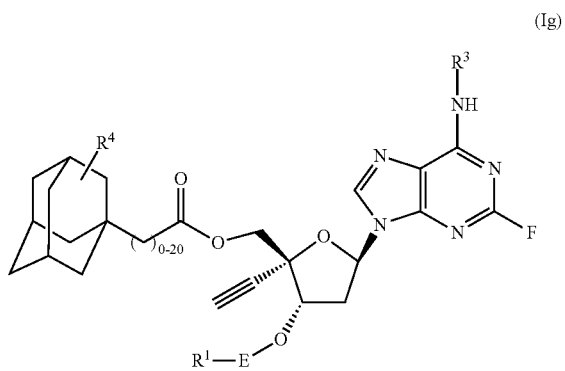

(Ie)

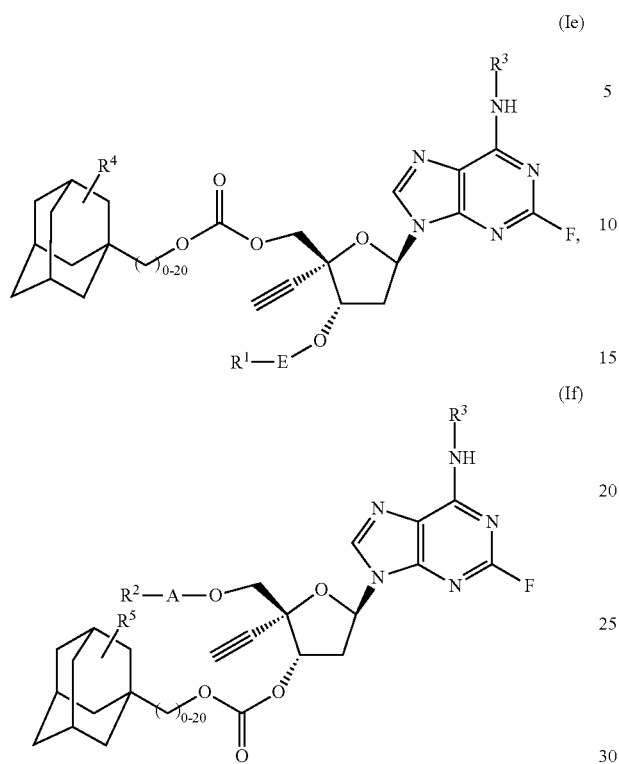

(If)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;

$R^2$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;

$R^3$ is selected from the group consisting of H, —(CO)—O—$C_{1-10}$alkyl, and $C_{1-10}$alkyl;

$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Ig) or a pharmaceutically acceptable salt, tautomer, or solvate thereof:

(Ig)

wherein:

E is selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;

$R^3$ is selected from the group consisting of H, —(CO)—O—$C_{1-10}$alkyl, and $C_{1-10}$alkyl; and $R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Ih) or a pharmaceutically acceptable salt, tautomer, or solvate thereof:

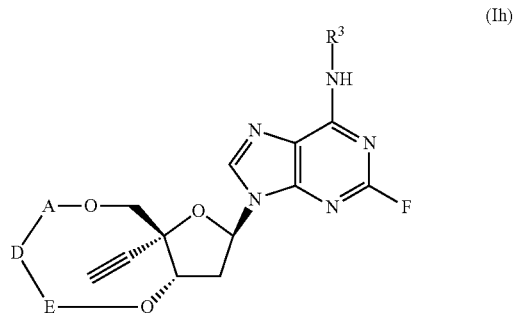

(Ih)

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

D is selected from the group consisting of —$C_{1-20}$alkylene-, —$C_{2-20}$alkenylene-, —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and R³ is selected from the group consisting of H, —(CO)—O—C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, the present disclosure provides an adenosine derivative having a structure of formula (Ii), (Ij), or a pharmaceutically acceptable salt, tautomer, or solvate thereof:

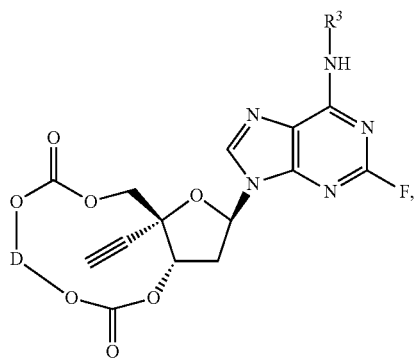
(Ii)

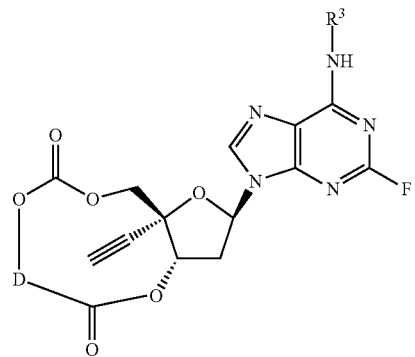
(Ij)

wherein:
D is selected from the group consisting of —C$_{1-20}$alkylene-, —C$_{2-20}$alkenylene-, and —C$_{2-20}$alkynylene-, —C$_{1-20}$haloalkylene-, —C$_{1-20}$alkoxyalkylene-, C$_{3-20}$cycloalkyl, 3- to 20-membered heterocycloalkyl, aryl, and heteroaryl; and R³ is selected from the group consisting of H, —(CO)—O—C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, the present disclosure provides an adenosine derivative having a structure of formula (Ik), (Il), or a pharmaceutically acceptable salt, tautomer, or solvate thereof:

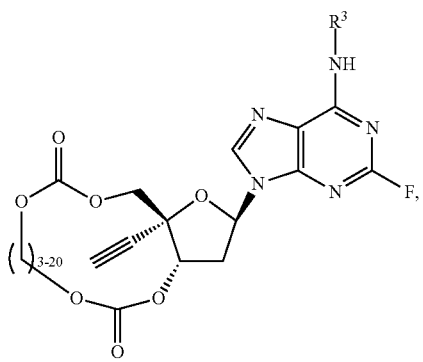
(Ik)

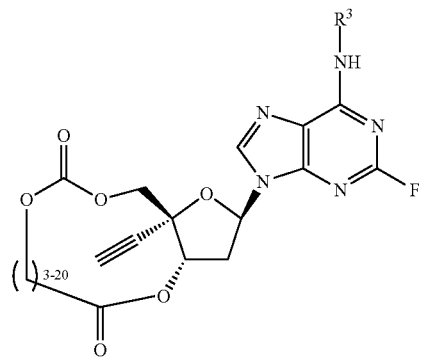
(Il)

wherein:
R³ is selected from the group consisting of H, —(CO)—O—C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, the present disclosure provides an adenosine derivative having a structure of formula (Im) or a pharmaceutically acceptable salt, tautomer, or solvate thereof:

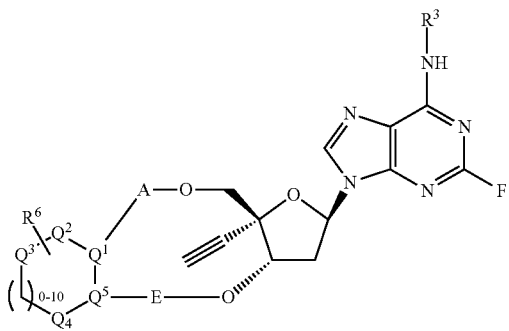
(Im)

A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;
R³ is selected from the group consisting of H, —(CO)-G-C$_{1-10}$alkyl, C$_{1-10}$alkyl, C$_{1-10}$haloalkyl, C$_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (In), (Io), or a pharmaceutically acceptable salt, tautomer, or solvate thereof:

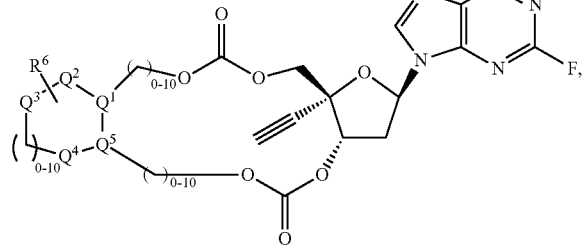

(In)

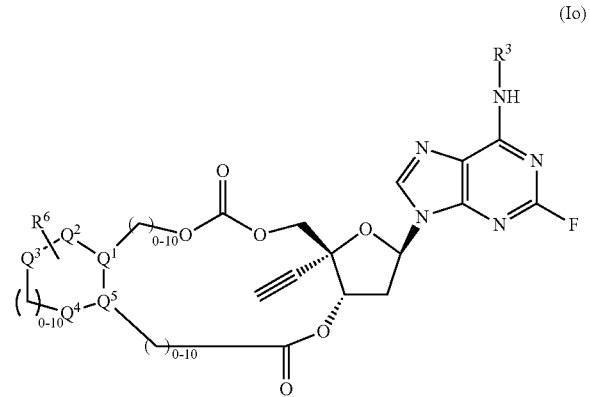

(Io)

wherein:
R³ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Ip) or a pharmaceutically acceptable salt, tautomer, or solvate thereof:

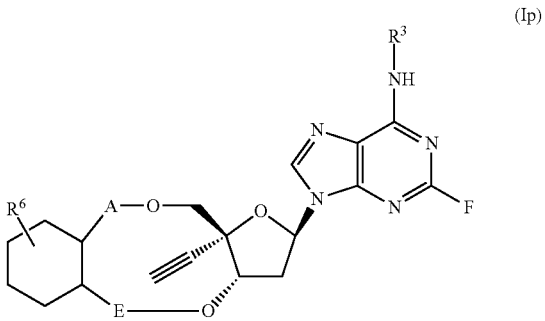

(Ip)

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the present disclosure provides an adenosine derivative having a structure of formula (Iq), (Ir), or a pharmaceutically acceptable salt, tautomer, or solvate thereof:

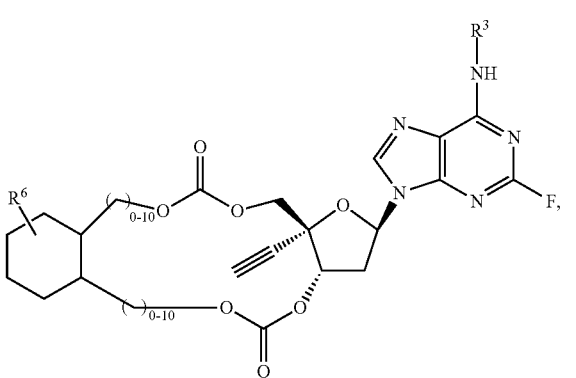

(Iq)

-continued (Ir)

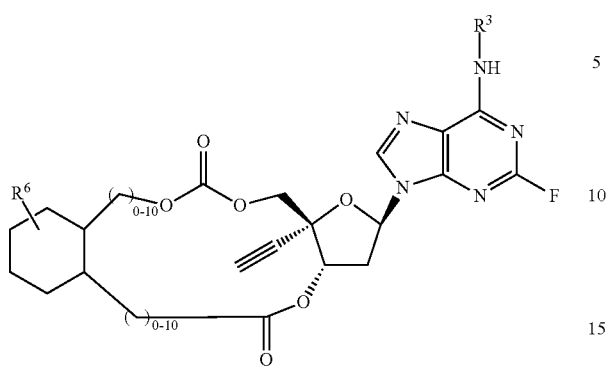

wherein:

R³ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl; and R⁶ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments, the adenosine derivative is selected from the group consisting of:

| Compound No | Structure | Chemical Name |
|---|---|---|
| 1 | 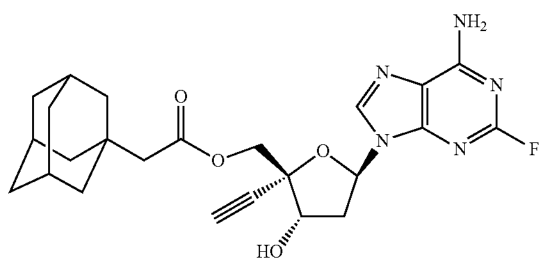 [SMILES: C#C[C@]1(COC(=O)CC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 2-(1-adamantyl) acetate |
| 2 | 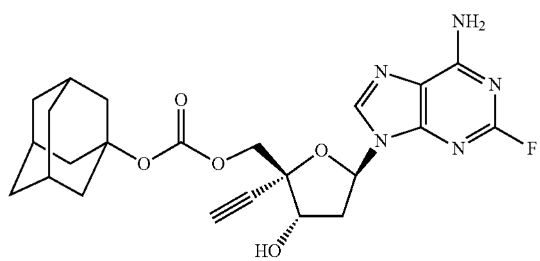 [SMILES: C#C[C@]1(COC(=O)OC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 1-adamantylmethyl carbonate |
| 3 | 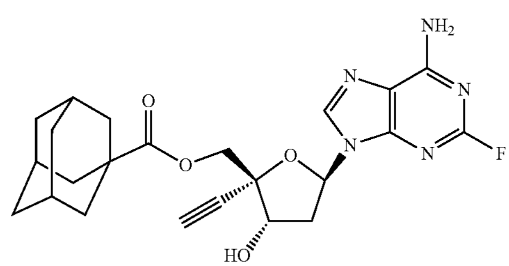 [SMILES: C#C[C@]1(COC(=O)C23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl adamantane-1-carboxylate |
| 4 | 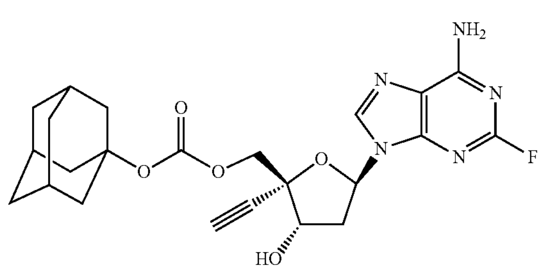 [SMILES: C#C[C@]1(COC(=O)OC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 1-adamantyl carbonate |

-continued

| Compound No | Structure | Chemical Name |
|---|---|---|
| 5 | 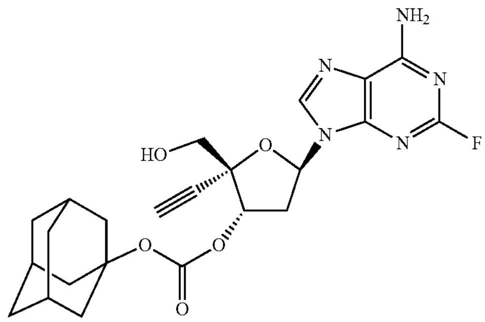 [SMILES: C#C[C@]1(CO)O[C@@H](n2cnc3c(N)nc(F)nc32)C[C@@H]1OC(=O)OC12CC3CC(CC(C3)C1)C2] | ((2R,3S,5R)-5-(6-amino-2-fluoro-9H-purin-9-yl)-2-ethynyl-2-(hydroxymethyl)tetrahydrofuran-3-yl) 1-adamantyl carbonate |
| 6 | 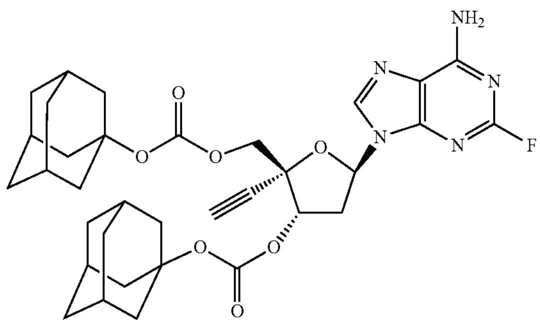 [SMILES: C#C[C@]1(COC(=O)OC23CC4CC(CC(C4)C2)C3)O[C@@H](n2cnc3c(N)nc(F)nc32)C[C@@H]1OC(=O)OC12CC3CC(CC(C3)C1)C2] | (((2R,3S,5R)-3-((((1-adamantyl)oxy)carbonyl)-oxy)-5-(6-amino-2-fluoro-9H-purin-9-yl)-2-ethynyl-tetrahydrofuran-2-yl)-methyl) 1-adamantyl carbonate |
| 7 | 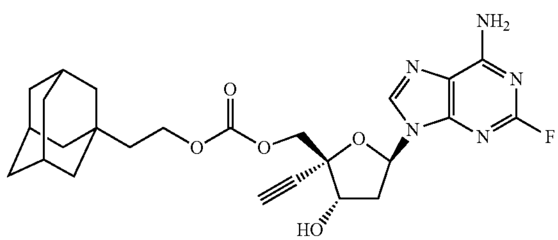 [SMILES: C#C[C@]1(COC(=O)OCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 2-(1-adamantyl)ethyl carbonate |
| 8 | 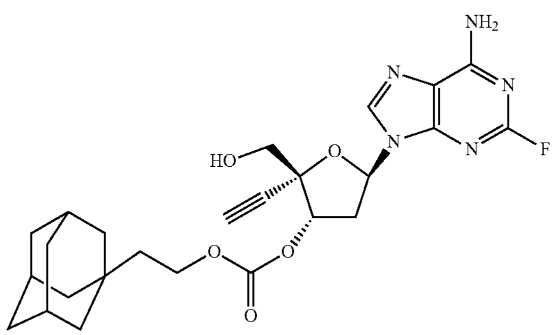 [SMILES: C#C[C@]1(CO)O[C@@H](n2cnc3c(N)nc(F)nc32)C[C@@H]1OC(=O)OCCC12CC3CC(CC(C3)C1)C2] | ((2R,3S,5R)-5-(6-amino-2-fluoro-9H-purin-9-yl)-2-ethynyl-2-(hydroxymethyl)tetrahydrofuran-3-yl) 2-(1-adamantyl)ethyl carbonate |
| 9 | 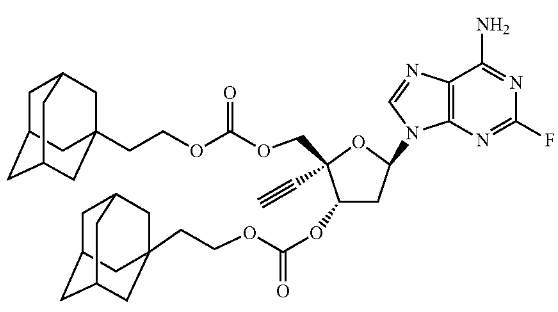 [SMILES: C#C[C@]1(COC(=O)OCCC23CC4CC(CC(C4)C2)C3)O[C@@H](n2cnc3c(N)nc(F)nc32)C[C@@H]1OC(=O)OCCC12CC3CC(CC(C3)C1)C2] | ((2R,3S,5R)-2-((((2-(1-adamantyl)ethoxy)-carbonyl)oxy)methyl)-5-(6-amino-2-fluoro-9H-purin-9-yl)-2-ethynyltetrahydrofuran-3-yl) 2-(1-adamantyl)ethyl carbonate |

-continued

| Compound No | Structure | Chemical Name |
|---|---|---|
| 10 | 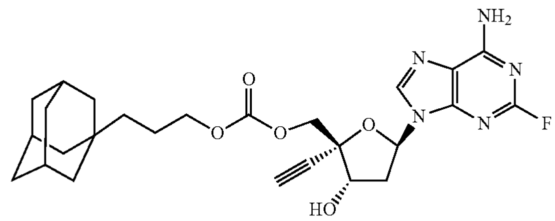 [SMILES: C#C[C@]1(COC(=O)OCCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 3-(1-adamantyl)propyl carbonate |
| 11 | 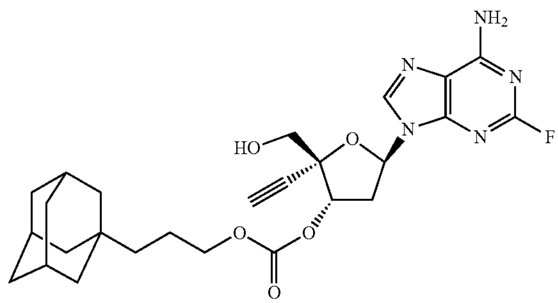 [SMILES: C#C[C@]1(CO)O[C@@H](n2cnc3c(N)nc(F)nc32)C[C@@H]1OC(=O)OCCCC12CC3CC(CC(C3)C1)C2] | ((2R,3S,5R)-5-(6-amino-2-fluoro-9H-purin-9-yl)-2-ethynyl-2-(hydroxymethyl)tetrahydrofuran-3-yl) 3-(1-adamantyl)propyl carbonate |
| 12 | 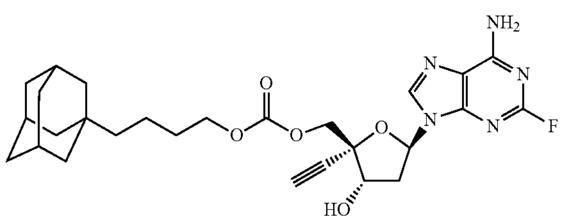 [SMILES: C#C[C@]1(COC(=O)OCCCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 4-(1-adamantyl)-butyl carbonate |
| 13 | 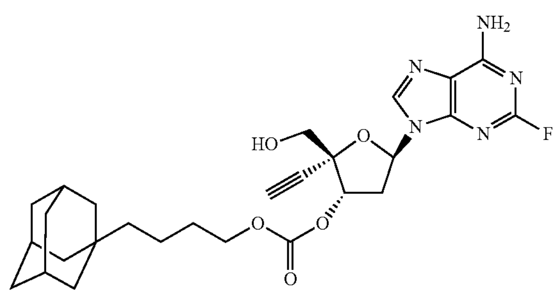 [SMILES: C#C[C@]1(CO)O[C@@H](n2cnc3c(N)nc(F)nc32)C[C@@H]1OC(=O)OCCCCC12CC3CC(CC(C3)C1)C2] | ((2R,3S,5R)-5-(6-amino-2-fluoro-9H-purin-9-yl)-2-ethynyl-2-(hydroxymethyl)tetrahydrofuran-3-yl) 4-(1-adamantyl)butyl carbonate |
| 14 | 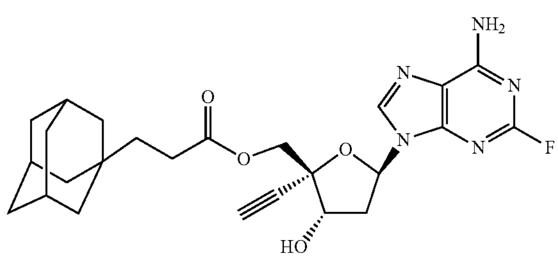 [SMILES: C#C[C@]1(COC(=O)CCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 3-(1-adamantyl)propanoate |
| 15 | 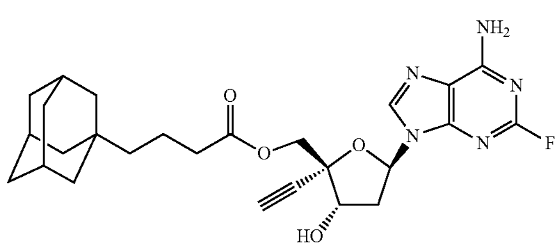 [SMILES: C#C[C@]1(COC(=O)CCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 4-(1-adamantyl)butanoate |

-continued

| Compound No | Structure | Chemical Name |
|---|---|---|
| 16 | 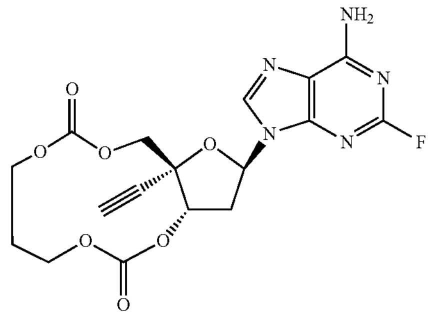 [SMILES: C#C[C@@]12COC(=O)OCCCOC(=O)O[C@H]1C[C@H](n1cnc3c(N)nc(F)nc31)O2] | (10aR,12R,13aS)-12-(6-amino-2-fluoro-9H-purin-9-yl)-10a-ethynylhexahydro-4H,10H-furo[3,2-d][1,3,7,9]tetraoxacyclododecine-2,8-dione |
| 17 | 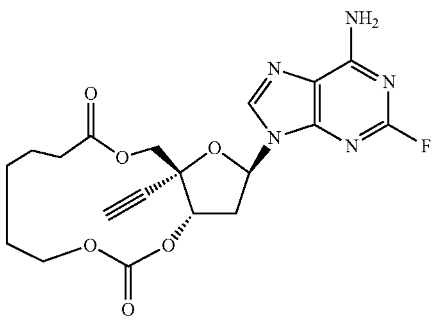 [SMILES: C#C[C@@]12COC(=O)CCCCCOC(=O)O[C@H]1C[C@H](n1cnc3c(N)nc(F)nc31)O2] | (11aR,13R,14aS)-13-(6-amino-2-fluoro-9H-purin-9-yl)-11a-ethynyloctahydro-11H-furo[3,2-d][1,3,7]trioxacyclotridecine-2,9(4H)-dione |
| 18 | 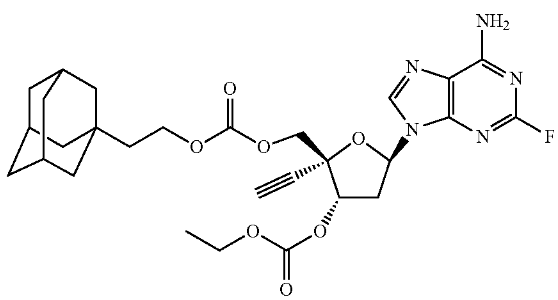 [SMILES: C#C[C@]1(COC(=O)OCCC23CC4CC(CC(C4)C2)C3)O[C@@H](n2cnc3c(N)nc(F)nc32)C[C@@H]1OC(=O)OCC] | ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) ethyl carbonate |
| 19 | 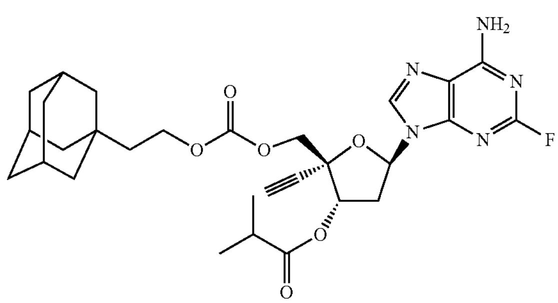 [SMILES: C#C[C@]1(COC(=O)OCCC23CC4CC(CC(C4)C2)C3)O[C@@H](n2cnc3c(N)nc(F)nc32)C[C@@H]1OC(=O)C(C)C] | ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) isobutyrate |
| 20 | 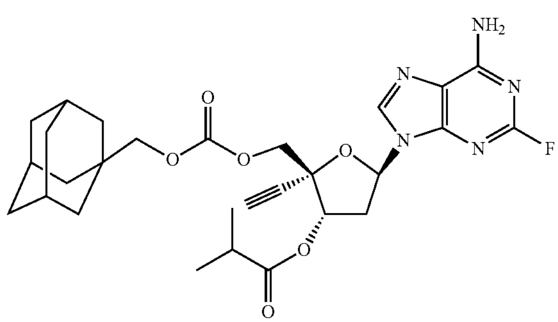 [SMILES: C#C[C@]1(COC(=O)OCC23CC4CC(CC(C4)C2)C3)O[C@@H](n2cnc3c(N)nc(F)nc32)C[C@@H]1OC(=O)C(C)C] | ((2R,3S,5R)-2-(((((1-adamantyl)methoxy)carbonyl)oxy)methyl)-5-(6-amino-2-fluoro-9H-purin-9-yl)-2-ethynyltetrahydrofuran-3-yl) isobutyrate |

-continued

| Compound No | Structure | Chemical Name |
|---|---|---|
| 21 | 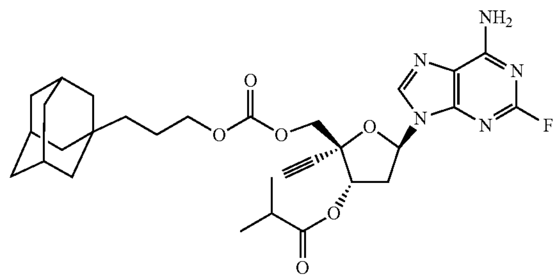 [SMILES: C#C[C@]1(COC(=O)OCCCC23CC4CC(CC(C4)C2)C3)O[C@@H](n2cnc3c(N)nc(F)nc32)C[C@@H]1OC(=O)C(C)C] | ((2R,3S,5R)-2-((((3-(1-adamantyl)propoxy)carbonyl)oxy)methyl)-5-(6-amino-2-fluoro-9H-purin-9-yl)-2-ethynyltetrahydrofuran-3-yl) isobutyrate |
| 22 | 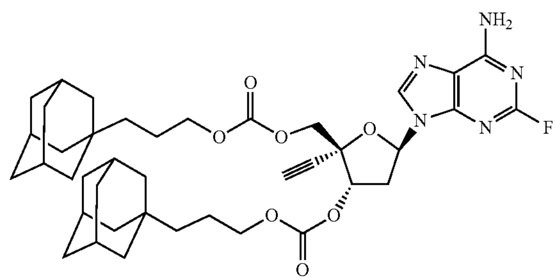 [SMILES: C#C[C@]1(COC(=O)OCCCC23CC4CC(CC(C4)C2)C3)O[C@@H](n2cnc3c(N)nc(F)nc32)C[C@@H]1OC(=O)OCCCC12CC3CC(CC(C3)C1)C2] | ((2R,3S,5R)-3-[3-(1-adamantyl)propoxycarbonyloxy]-5-(6-amino-2-fluoro-9H-purin-9-yl)-2-ethynyl-tetrahydrofuran-2-yl)methyl 3-(1-adamantyl)propyl carbonate |
| 23 | 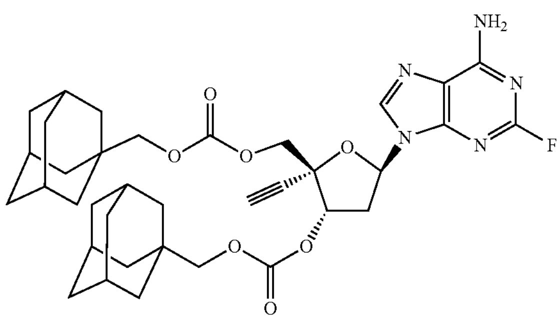 [SMILES: C#C[C@]1(COC(=O)OCC23CC4CC(CC(C4)C2)C3)O[C@@H](n2cnc3c(N)nc(F)nc32)C[C@@H]1OC(=O)OCC12CC3CC(CC(C3)C1)C2] | ((2R,3S,5R)-3-(1-adamantylmethoxycarbonyloxy)-5-(6-amino-2-fluoro-9H-purin-9-yl)-2-ethynyl-tetrahydrofuran-2-yl)methyl 1-adamantylmethyl carbonate |
| 24 | 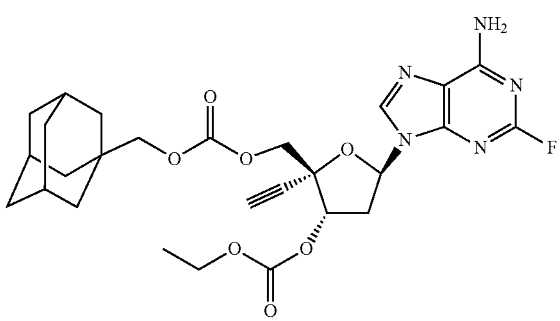 [SMILES: C#C[C@]1(COC(=O)OCC23CC4CC(CC(C4)C2)C3)O[C@@H](n2cnc3c(N)nc(F)nc32)C[C@@H]1OC(=O)OCC] | ((2R,3S,5R)-2-(1-adamantylmethoxycarbonyloxymethyl)-5-(6-amino-2-fluoro-9H-purin-9-yl)-2-ethynyl-tetrahydrofuran-3-yl) ethyl carbonate |
| 25 | 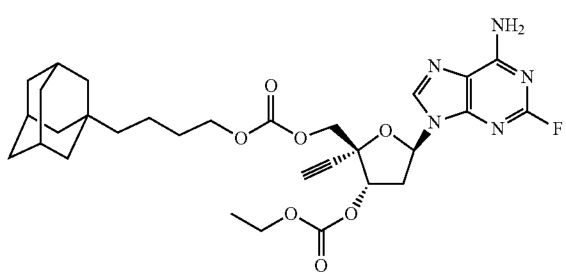 [SMILES: C#C[C@]1(COC(=O)OCCCCC23CC4CC(CC(C4)C2)C3)O[C@@H](n2cnc3c(N)nc(F)nc32)C[C@@H]1OC(=O)OCC] | ((2R,3S,5R)-2-[4-(1-adamantyl)butoxycarbonyloxymethyl]-5-(6-amino-2-fluoro-9H-purin-9-yl)-2-ethynyl-tetrahydrofuran-3-yl) ethyl carbonate |

-continued

| Compound No | Structure | Chemical Name |
|---|---|---|
| 26 | 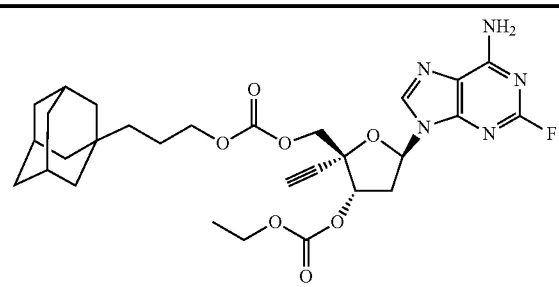 | ((2R,3S,5R)-2-[3-(1-adamantyl)propoxycarbonyloxymethyl]-5-(6-amino-2-fluoro-9H-purin-9-yl)-2-ethynyl-tetrahydrofuran-3-yl) ethyl carbonate |
| 27 | 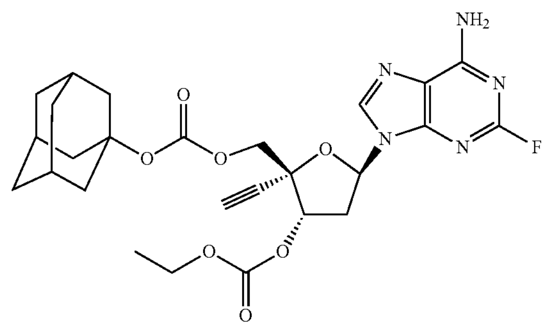 [SMILES: C#C[C@]1(COC(=O)OC23CC4CC(CC(C4)C2)C3)O[C@@H](n2cnc3c(N)nc(F)nc32)C[C@@H]1OC(=O)OCC] | 1-adamantyl ((2R,3S,5R)-5-(6-amino-2-fluoro-purin-9-yl)-3-ethoxycarbonyloxy-2-ethynyl-tetrahydrofuran-2-yl)methyl carbonate |
| 28 | 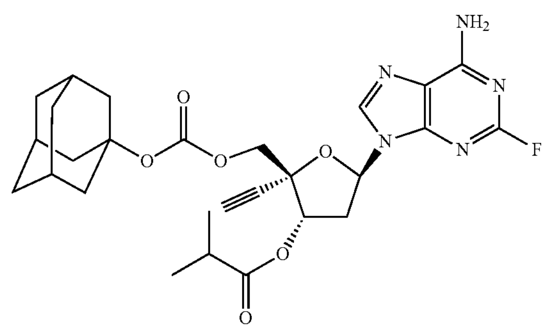 [SMILES: C#C[C@]1(COC(=O)OC23CC4CC(CC(C4)C2)C3)O[C@@H](n2cnc3c(N)nc(F)nc32)C[C@@H]1OC(=O)C(C)C] | ((2R,3S,5R)-2-(1-adamantyloxycarbonyloxymethyl)-5-(6-amino-2-fluoro-9H-purin-9-yl)-2-ethynyl-tetrahydrofuran-3-yl) 2-methylpropanoate |
| 29 | 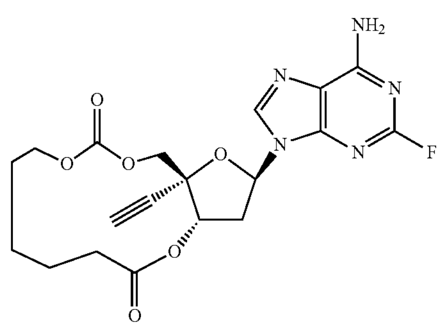 [SMILES: C#C[C@@]12COC(=O)OCCCCCC(=O)O[C@H]1C[C@H](n1cnc3c(N)nc(F)nc31)O2] | (1R,13R,15R)-15-(6-amino-2-fluoro-9H-purin-9-yl)-13-ethynyl-2,9,11,14-tetraoxabicyclo[11.3.0]hexadecane-3,10-dione |
| 30 | | (6R,8R,10R)-8-(6-amino-2-fluoro-9H-purin-9-yl)-10-ethynyl-3,5,9,12,14-pentaoxatricyclo[14.4.0.06,10]icosane-4,13-dione | and a pharmaceutically acceptable salt, tautomer, or solvate thereof.

The present disclosure is further directed to a pharmaceutical composition comprising one or more adenosine derivatives, pharmaceutically acceptable salts, stereoisomers, tautomer, or solvate or a combination thereof disclosed herein, and one or more pharmaceutically acceptable carriers.

The present disclosure is also directed to a process for making compound having formula (I). In one embodiment, the process for making compound having formula (I) is as described in the Examples provided herein.

The present disclosure is also directed to a method for the treatment of a disease (e.g., Acquired Immune Deficiency Syndrome (AIDS) or human immunodeficiency virus (HIV)), the method comprising administering to a subject in need thereof an effective dosage of a pharmaceutical composition comprising one or more of the adenosine derivatives disclosed herein.

The present disclosure is also directed to a method for the prevention of an infection, the method comprising administering to a subject in need thereof an effective dosage of a pharmaceutical composition comprising one or more of the adenosine derivatives disclosed herein.

INCORPORATION BY REFERENCE

Figure 1:
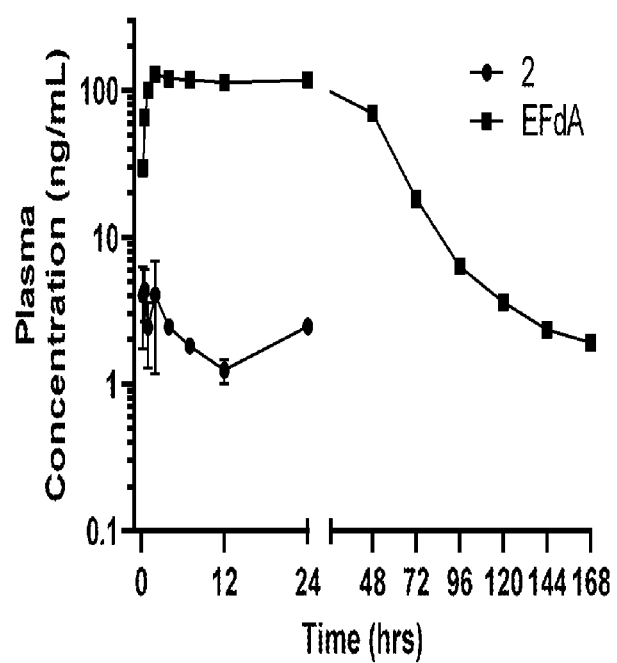
FIG. 1 shows a Plasma Concentration—Time profile of Compound 2 and EFdA after single IM injection of Compound 2 (10 mg/kg) in cynomolgus monkeys.

All publications, patents, and patent applications mentioned in this specification are herein incorporated by reference to the same extent as if each individual publication, patent, or patent application was specifically and individually indicated to be incorporated by reference.

DETAILED DESCRIPTION

Following are more detailed descriptions of various concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

As used herein, the term "alkyl" or "alkyl group" refers to a fully saturated, straight or branched hydrocarbon chain radical having from one to twenty carbon atoms, and which is attached to the rest of the molecule by a single bond. Alkyls comprising any number of carbon atoms from 1 to 20 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{20}$ alkyl includes all the foregoing moieties, but also includes $C_{11}$ and $C_{20}$ alkyls. Non-limiting examples of $C_1$-$C_{20}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

As used herein, the term "alkylene" or "alkylene chain" refers to a fully saturated, straight or branched divalent hydrocarbon chain radical, and having from one to twenty carbon atoms. Non-limiting examples of $C_1$-$C_{20}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

As used herein, the term "alkenyl" or "alkenyl group" refers to a straight or branched hydrocarbon chain radical containing at least one carbon-carbon double bond and having a number of carbon atoms in the specified range, and which is attached to the rest of the molecule by a single bond. For example, "$C_2$-$C_{20}$ alkenyl" (or "$C_2$-$C_{20}$ alkenyl") refers to any of alkenyl having 2 to twenty carbon atoms that is linear or branched, or isomers. In another example $C_2$-$C_6$ alkenyl can have 1-butenyl, 2-butenyl, 3-butenyl, isobutenyl, 1-propenyl, 2-propenyl, and ethenyl (or vinyl). Unless stated otherwise specifically in the specification, an alkenyl group can be optionally substituted.

As used herein, the term "alkenylene" or "alkenylene chain" refers to an unsaturated, straight or branched divalent hydrocarbon chain radical having one or more carbon-carbon double bond and from two to twenty carbon atoms. Non-limiting examples of $C_2$-$C_{20}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

As used herein, the term "alkynyl" or "alkynyl group" refers to a straight or branched hydrocarbon chain radical containing at least one carbon-carbon triple bond and having a number of carbon atoms in the specified range, and which is attached to the rest of the molecule by a single bond. For example, "$C_2$-$C_{20}$ alkynyl" (or "$C_2$-$C_{20}$ alkynyl") refers to any of alkynyl having 2 to 20 carbon atoms that is linear or branched, or isomers. In another example $C_2$-$C_6$ alkynyl can have 1-butynyl, 2-butynyl, 3-butynyl, isobutynyl, 1-propynyl, 2-propynyl, and ethynyl. Unless stated otherwise specifically in the specification, an alkynyl group chain can be optionally substituted.

As used herein, the term "alkynylene" or "alkynylene chain" refers to an unsaturated, straight or branched divalent hydrocarbon chain radical having one or more carbon-carbon triple bond and from two to twenty carbon atoms. Non-limiting examples of $C_2$-$C_{20}$ alkynylene include ethynylene, propynylene, n-butynylene, and the like. The alkynylene chain is attached to the rest of the molecule through a single bond and to a radical group (e.g., those described herein) through a single bond. The points of attachment of the alkynylene chain to the rest of the molecule and to the radical group can be through one carbon or any two carbons within the chain. Unless stated otherwise specifically in the specification, an alkynylene chain can be optionally substituted.

As used herein, the term "cycloalkyl" refers to a stable non-aromatic monocyclic or polycyclic fully saturated hydrocarbon consisting solely of carbon and hydrogen atoms, which can include fused or bridged ring systems, having from three to twenty-five carbon atoms and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. In some embodiments, "cycloalkyl" refers to any monocyclic ring of an alkane having a number of carbon atoms in the specified range. For example, "$C_3$-$C_{25}$ cycloalkyl" (or "$C_3$-$C_{25}$ cycloalkyl") refers to monocyclic ring of an alkane having 3 to 25 carbon atoms, such as cyclopropyl, cyclobutyl, cyclopentyl, cyclohexyl, and cycloheptyl. Unless otherwise stated specifically in the specification, a cycloalkyl group can be optionally substituted.

As used herein, the term "heterocycloalkyl", "heterocyclic ring" or "heterocycle" refers to a saturated, or partially saturated 3- to 25-membered ring which consists of two to twenty-four carbon atoms and from one to six heteroatoms selected from the group consisting of nitrogen, oxygen and sulfur, and which is attached to the rest of the molecule by a single bond. Unless stated otherwise specifically in the specification, the heterocycloalkyl can be a monocyclic, bicyclic, tricyclic or tetracyclic ring system, which can include fused or bridged ring systems; and the nitrogen, carbon or sulfur atoms in the heterocycloalkyl can be optionally oxidized, e.g., to form an N-oxide, sulfoxide, or sulfone and/or the nitrogen atom can be optionally quaternized, e.g., to form a quaternary ammonium cation. Examples of such heterocycloalkyls include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, 1-oxo-thiomorpholinyl, and 1,1-dioxo-thiomorpholinyl. In some embodiments, "3- to 10-membered heterocycloalkyl" refers to a cycloalkyl comprising one or more heteroatoms, selected from the group consisting of N, O, and S. In some embodiments, heterocycloalkyl," "heterocyclic ring" or "heterocycle" refers to a 3-10 member ring structure having carbon atoms and one or more heteroatoms selected from N, O, S or a combination thereof as members of the ring structure. Unless stated otherwise specifically in the specification, a heterocycloalkyl group can be optionally substituted and include saturated and/or unsaturated rings.

As used herein, the term "aryl" refers to a hydrocarbon ring system comprising hydrogen, 6 to 18 carbon atoms and at least one aromatic ring, and which is attached to the rest of the molecule by a single bond. For purposes of the present disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, "aryl" refers to phenyl or one or more fused cyclic hydrocarbon ring systems in which at least one ring is aromatic. Unless stated otherwise specifically in the specification, the "aryl" can be optionally substituted.

As used herein, the term "heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of the present disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized, e.g., to form an N-oxide, sulfoxide, or sulfone and/or the nitrogen atom can be optionally quaternized, e.g., to form a quaternary ammonium cation. Non-limiting examples of heteroaryls can include pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydro uinolinyl, tetrahydroisoquinolinyl, isoindolyl, benzodioxolyl, benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl. Unless stated otherwise specifically in the specification, a heteroaryl group can be optionally substituted.

It is understood that, unless expressly stated to the contrary in a particular context, any of the various cyclic rings and ring systems described herein may be attached to the rest of the compound at any ring atom (i.e., any carbon atom or any heteroatom) or may be attached to the rest of the compound at any two ring atoms provided that the attachment is chemically allowed.

As used herein, the term "halogen" (or "halo") refers to fluorine, chlorine, bromine and iodine (alternatively referred to as fluoro (—F), chloro (—Cl), bromo (—Br), and iodo (—I)).

As used herein, the term "substituted" means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the term "isomer" refers to a structural isomer, such as a group or an atom positioned at different locations of a molecule; stereoisomer, such as a chiral isomer, enantiomer, diastereomer and cis/trans isomer; a tautomer, such as amino isomer, imino isomer, or a combination thereof. In non-limiting examples, an adenosine derivative of the present disclosure can have an amino isomer, an imino isomer or a combination thereof. In another non-limiting example, in instances where an —OH substituent is permitted on a heteroaromatic ring and keto-enol tautomerism is possible, it is understood that the substituent might in fact be present, in whole or in part, in the oxo (=O) form. A mixture of isomers can also be suitable. A mixture of isomers can comprise the respective isomers in all ratios. A salt of an isomer can also be suitable. An adenosine derivative of the present disclosure can comprise isomers thereof, one or more salts thereof, one or more solvates including hydrates thereof, solvated salts thereof or a mixture thereof. Absolute stereochemistry or isomer configuration may be determined by X-ray crystallography, by Vibrational Circular Dichroism (VCD) spectroscopy analysis or a combination thereof.

The adenosine derivatives can be identified by names based on the nomenclature recommended by International Union of Pure and Applied Chemistry (IUPAC) or based on nucleosides (Nucleoside-based nomenclature). The adenosine derivatives can also be identified by chemical structure drawings. Unless expressly stated to the contrary in a particular context, the names and the structures may be used interchangeably.

Any of the atoms in a compound disclosed herein may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds disclosed herein.

The compounds can be administered in the form of pharmaceutically acceptable salts or solvates. The term "pharmaceutically acceptable salt" refers to a salt or a solvate which is not biologically or otherwise undesirable (e.g., is neither toxic nor otherwise deleterious to the recipient or subject thereof). A mixture of a compound disclosed herein and one or more salts or solvates thereof is also contemplated herein. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

Furthermore, compounds disclosed herein can exist in amorphous form and/or one or more crystalline forms, or a combination thereof.

The term "RNA virus infection" refers to a disease caused by an RNA virus, such as the common cold, influenza, SARS, COVID-19, hepatitis C, hepatitis E, West Nile fever, Ebola virus disease, rabies, polio, and measles.

The term "HIV infection" refers to a disease caused by the human immunodeficiency virus (HIV), such as HIV-1 and HIV-2. In some cases, the HIV infection can be caused by wild-type HIV-1, NRTI-resistant HIV-1, HIV-2, HIV having M184V mutations, HIV having K65R, or multidrug resistant HIV. The term "AIDS" refers to acquired immunodeficiency syndrome, which is caused by HIV infection and an advanced form of the disease.

The term "prodrug" refers to a compound that may be converted under physiological conditions or by solvolysis to a biologically active compound described herein. Thus, the term "prodrug" refers to a precursor of a biologically active compound that is pharmaceutically acceptable. A prodrug may be a biologically inactive or substantially inactive compound which can be metabolized in the body, i.e., in vivo, to produce a drug having a desired activity. The term "substantially inactive" means that a prodrug can have about 1% to about 10% of the activity of the corresponding drug or after being metabolized in vivo, percentage based on weight of the prodrug. In some embodiments, the term "substantially inactive" means that a prodrug has less than about 5% of the activity of the corresponding drug or after being metabolized in vivo, percentage based on weight of the prodrug. The doses for a prodrug and its biologically active compound are considered to be does-equivalent when they are the same molar amount.

The term "anti-HIV agent", "anti-viral agent" or a grammatical variant refers to a compound, a mixture of one or more compounds, a formulation, a chemical agent or a biological agent such as antibody, protein, peptides, nucleotide, other biological compound, or a combination thereof, that can be directly or indirectly effective in the inhibition of HIV, the treatment or prophylaxis of HIV infection, and/or the treatment, prophylaxis or delay in the onset or progression of AIDS and/or diseases or conditions arising therefrom or associated therewith, an RNA virus infection, or a combination thereof. The anti-HIV agents can comprise HIV antiviral agents, immunomodulators, anti-infectives, vaccines or a combination thereof useful for treating HIV infection or AIDS. Examples of antiviral agents for Treating HIV infection or AIDS include, but are not limited to, under respective trademarks or registered trademarks with respective owners, atazanavir (Reyataz®), darunavir (Prezista®), dolutegravir (Tivicay®), doravirine (MK-1439), efavirenz (EFV, Sustiva®, Stocrin®), cabotegravir, bictegravir, emtricitabine (FTC, Emtriva®), rilpivirine, etravirine (TMC-125), maraviroc (Selzentry®), rilpivirine (Edurant®), tenofovir DF (DF=disoproxil fumarate, TDF, Viread®), tenofovir hexadecyloxypropyl (CMX-157), tenofovir alafenamide fumarate (GS-7340), lenacapavir (GS-6207), MK-8507. Some of the anti-HIV agents shown above can be used in a salt form; for example, atazanavir sulfate, tenofovir alafenamide fumarate or other salts. An anti-HIV agent can have one or more activities such as entry inhibitor (EI), fusion inhibitor (FI); integrase inhibitor (InI); protease inhibitor (PI); nucleoside reverse transcriptase inhibitor (nRTI or NRTI) or non-nucleoside reverse transcriptase inhibitor (nnRTI or NNRTI), capsid inhibitor. An anti-HIV agent can comprise two or more agents disclosed herein. The adenosine derivative of the present disclosure can be an anti-HIV agent along or in combination with other anti-HIV agent or agents.

Unless expressly stated to the contrary, all ranges cited herein are inclusive. For example, a heteroaryl ring described as comprising in a range of from "1 to 4 heteroatoms" means the ring can comprise 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. In other examples, C1-C10 alkyl means an alkyl comprises 1, 2, 3, 4, 5, 6, 7, 8, 9 and 10 carbon atoms including all sub-ranges. Thus, a C1-C10 alkyl can be a methyl, ethyl, C4 alkyl, C5 alkyl, C6 alkyl, C7 alkyl, C8 alkyl, C9 alkyl and C10 alkyl, linear or branched. A divalent C1-C10 alkyl can be a —CH$_2$—, —C$_2$H$_4$—, —C$_3$H$_6$—, —C$_4$H$_8$—, —C$_5$H$_{10}$—, —C$_6$H$_{12}$—, —C$_7$H$_{17}$—, —C$_8$H$_{18}$—, —C$_9$H$_{18}$— or —C$_{10}$H$_{20}$—, linear or a branched. Similarly, C2-C10 alkenyl means an alkenyl comprises 2, 3, 4, 5, 6, 7, 8, 9 and 10 carbon atoms, linear or branched, including all sub-ranges. A linear or a branched alkenyl can be suitable. A C3-C10 cycloalkyl means a cycloalkyl comprises 3, 4, 5, 6, 7, 8, 9 and 10 carbon atoms, linear or branched.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present disclosure.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The pharmaceutical composition can be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, the pharmaceutical compositions of the present disclosure are formulated for intramuscular injection and/or subcutaneous injection. Alternatively, the pharmaceutical composition can be administered via a non-parenteral route, such as a topical, epidermal or mucosal route of administration, e.g., intranasally, orally, vaginally, rectally, sublingually or topically. The pharmaceutical composition can be in the form of sterile aqueous solutions or dispersions. The pharmaceutical composition can also be formulated in a microemulsion, liposome, or other ordered structure suitable to high drug concentration.

In some embodiments, the present disclosure provides an adenosine derivative having a structure of formula (I) or pharmaceutically acceptable salt, tautomer, or solvate thereof:

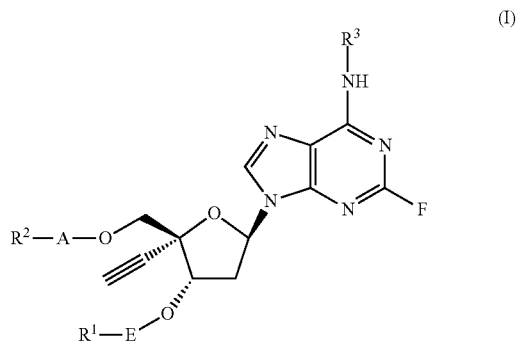

wherein:
  A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
    G is selected form the group consisting of a bond, O, NH, and S;
  J is selected form the group consisting of a bond, O, NH, S, —(CO)-G-; R$^1$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl;
  R$^2$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl, wherein at least one of R$^1$ and R$^2$ is not H;

R$^1$ and R$^2$ can join together with the atoms to which they are attached to form a 3- to 25-membered heterocyclic ring; and R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, A is selected from the group consisting of a bond, —(CO)—, —(CO)-G-, and —(CO)-G-(C$_{1-5}$alkylene)-J-. In some embodiments, A is selected from the group consisting of a bond, —(CO)—, —(CO)-G-, and —(CO)-G-(C$_{1-5}$alkylene)-. In some embodiments, A is —(CO)-G- or —(CO)-G-(C$_{1-5}$alkylene)-. In some embodiments, A is —(CO)-G-(C$_{1-5}$alkylene)-. In some embodiments, A is selected from the group consisting of a bond, —(CO)—, —(CO)—O—, and —(CO)—O—(C$_{1-5}$alkylene)-. In some embodiments, A is selected from the group consisting of a bond, —(CO)—, —(CO)—O—, and —(CO)—O—(C$_{1-5}$alkylene)-. In some embodiments, A is —(CO)—O— or —(CO)—O—(C$_{1-5}$alkylene)-. In some embodiments, A is —(CO)—O—(C$_{1-5}$alkylene)-. In some embodiments, G is a bond or O. In some embodiments, G is O. In some embodiments, J is a bond or O. In some embodiments, J is a bond.

In some embodiments, E is selected from the group consisting of a bond, —(CO)—, —(CO)-G-, and —(CO)-G-(C$_{1-5}$alkylene)-J-. In some embodiments, E is selected from the group consisting of a bond, —(CO)—, —(CO)-G-, and —(CO)-G-(C$_{1-5}$alkylene)-. In some embodiments, E is selected from the group consisting of a bond, —(CO)—, —(CO)—O—, and —(CO)—O—(C$_{1-5}$alkylene)-. In some embodiments, E is a bond. In some embodiments, G is a bond or O. In some embodiments, G is O. In some embodiments, J is a bond or O. In some embodiments, J is a bond.

In some embodiments, R$^1$ is H, C$_{1-20}$alkyl, or C$_{3-20}$cycloalkyl. In some embodiments, R$^1$ is H, C$_{1-5}$alkyl, or C$_{3-15}$cycloalkyl. In some embodiments, R$^1$ is H or C$_{3-20}$cycloalkyl. In some embodiments, R$^1$ is H, C$_{1-5}$alkyl, or adamantyl. In some embodiments, R$^1$ is H or adamantyl. In some embodiments, the C$_{1-5}$alkyl is methyl, ethyl, or isopropyl. In some embodiments, the C$_{3-20}$cycloalkyl is adamantyl.

In some embodiments, R$^2$ is H, C$_{1-20}$alkyl, or C$_{3-20}$cycloalkyl. In some embodiments, R$^2$ is H, C$_{1-10}$alkyl, or C$_{3-20}$cycloalkyl. In some embodiments, R$^2$ is H, C$_{1-10}$alkyl, or C$_{5-15}$cycloalkyl. In some embodiments, R$^2$ is H, C$_{1-5}$alkyl, or C$_{5-15}$cycloalkyl. In some embodiments, R$^2$ is C$_{5-15}$cycloalkyl. In some embodiments, R$^2$ is H, C$_{1-5}$alkyl, or adamantyl. In some embodiments, the C$_{1-5}$alkyl is methyl, ethyl, or isopropyl. In some embodiments, the C$_{3-20}$cycloalkyl is adamantyl.

In some embodiments, R$^1$ and R$^2$ can join together with the atoms to which they are attached to form a 6- to 25-membered heterocyclic ring. In some embodiments, R$^1$ and R$^2$ can join together with the atoms to which they are attached to form a 6- to 15-membered heterocyclic ring. In some embodiments, R$^1$ and R$^2$ can join together with the atoms to which they are attached to form a 10- to 15-membered heterocyclic ring. In some embodiments, at least one of R$^1$ and R$^2$ is not H. In some embodiments, R$^1$ is H, C$_{1-5}$alkyl, or C$_{3-20}$cycloalkyl and R$^2$ is H, C$_{1-5}$alkyl, or C$_{3-20}$cycloalkyl. In some embodiments, R$^1$ is H, C$_{1-5}$alkyl, or adamantyl and R$^2$ is H, C$_{1-5}$alkyl, or adamantyl. In some embodiments, R$^1$ is H, C$_{1-5}$alkyl, or adamantyl and R$^2$ is H. In some embodiments, the C$_{1-5}$alkyl is methyl, ethyl, or isopropyl. In some embodiments, the C$_{3-20}$cycloalkyl is adamantyl.

In some embodiments, R$^3$ is H, —(CO)-G-C$_{1-10}$alkyl, or C$_{1-10}$alkyl. In some embodiments, R$^3$ is H, —(CO)—C$_{1-5}$alkyl, —(CO)—O—C$_{1-5}$alkyl, or C$_{1-5}$alkyl. In some embodiments, the C$_{1-5}$alkyl is methyl, ethyl, or isopropyl. In some embodiments, R$^3$ is H, —(CO)—CH$_3$, —(CO)—O—CH$_3$, or CH$_3$. In some embodiments, R$^3$ is H.

In some embodiments, R$^1$ and R$^2$ are each as defined herein and R$^3$ is H.

In some embodiments, the present disclosure provides an adenosine derivative having a structure of formula (Ia), (Ib), or a pharmaceutically acceptable salt, tautomer, or solvate thereof:

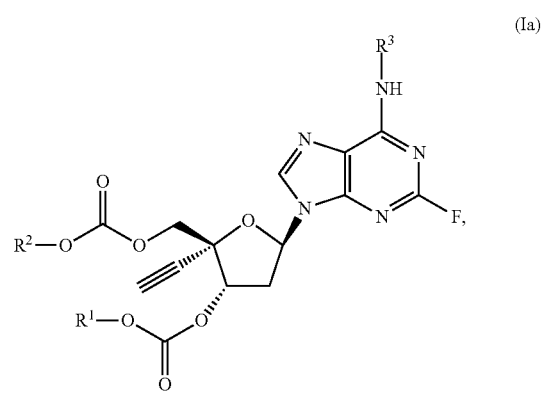

(Ia)

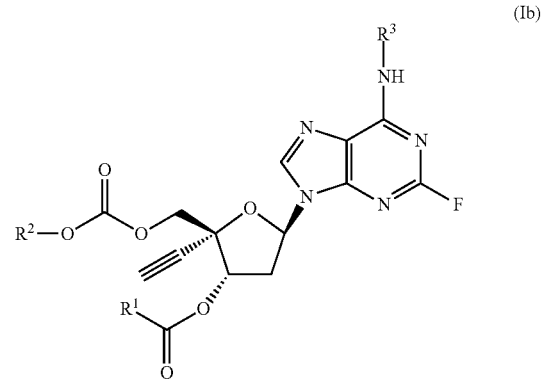

(Ib)

wherein:
R$^1$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl;

R$^2$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl, wherein at least one of R$^1$ and R$^2$ is not H; and R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, R$^1$ is H, C$_{1-20}$alkyl, or C$_{3-20}$cycloalkyl. In some embodiments, R$^1$ is H, C$_{1-5}$alkyl, or C$_{3-15}$cycloalkyl. In some embodiments, R$^1$ is H or C$_{3-20}$cycloalkyl. In some embodiments, R$^1$ is H, C$_{1-5}$alkyl, or adamantyl. In some embodiments, R$^1$ is H or adamantyl. In some embodiments, the C$_{1-5}$alkyl is methyl, ethyl, or isopropyl. In some embodiments, the C$_{3-20}$cycloalkyl is adamantyl.

In some embodiments, $R^2$ is H, $C_{1-20}$alkyl, or $C_{3-20}$cycloalkyl. In some embodiments, $R^2$ is H, $C_{1-10}$alkyl, or $C_{3-20}$cycloalkyl. In some embodiments, $R^2$ is H, $C_{1-10}$alkyl, or $C_{5-15}$cycloalkyl. In some embodiments, $R^2$ is H, $C_{1-5}$alkyl, or $C_{5-15}$cycloalkyl. In some embodiments, $R^2$ is $C_{5-15}$cycloalkyl. In some embodiments, $R^2$ is H, $C_{1-5}$alkyl, or adamantyl. In some embodiments, the $C_{1-5}$alkyl is methyl, ethyl, or isopropyl. In some embodiments, the $C_{3-20}$cycloalkyl is adamantyl.

In some embodiments, $R^1$ and $R^2$ can join together with the atoms to which they are attached to form a 6- to 25-membered heterocyclic ring. In some embodiments, $R^1$ and $R^2$ can join together with the atoms to which they are attached to form a 6- to 15-membered heterocyclic ring. In some embodiments, $R^1$ and $R^2$ can join together with the atoms to which they are attached to form a 10- to 15-membered heterocyclic ring. In some embodiments, at least one of $R^1$ and $R^2$ is not H. In some embodiments, $R^1$ is H, $C_{1-5}$alkyl, or $C_{3-20}$cycloalkyl and $R^2$ is H, $C_{1-5}$alkyl, or $C_{3-20}$cycloalkyl. In some embodiments, $R^1$ is H, $C_{1-5}$alkyl, or adamantyl and $R^2$ is H, $C_{-5}$alkyl, or adamantyl. In some embodiments, $R^1$ is H, $C_{1-5}$alkyl, or adamantyl and $R^2$ is H. In some embodiments, the $C_{1-5}$alkyl is methyl, ethyl, or isopropyl. In some embodiments, the $C_{3-20}$cycloalkyl is adamantyl.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^1$ and $R^2$ are each as defined herein and $R^3$ is H.

In some embodiments, the present disclosure provides an adenosine derivative having a structure of formula (Ic), (Id), or pharmaceutically acceptable salt, tautomer, or solvate thereof:

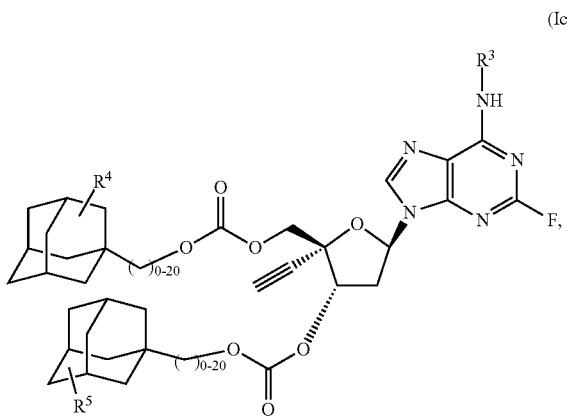

(Ic)

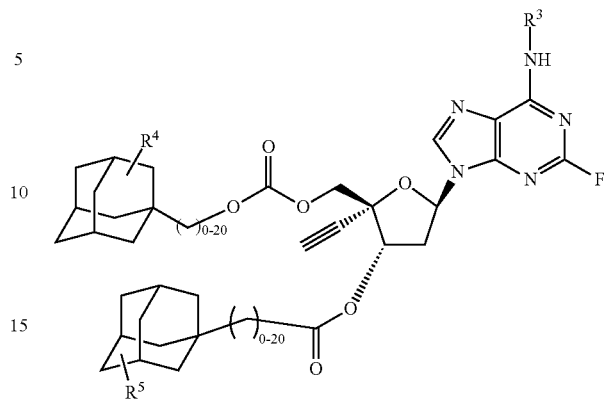

(Id)

wherein:

$R^3$ is selected from the group consisting of H, —(CO)-G-$C_{1-10}$alkyl, and $C_{1-10}$alkyl;

$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^4$ is selected from the group consisting of H, $C_{1-5}$alkyl, $C_{1-5}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^4$ is selected from the group consisting of H, $C_{1-5}$alkyl, $C_{1-5}$haloalkyl, and $C_{1-5}$alkoxy. In some embodiments, $R^4$ is selected from the group consisting of H, $C_{1-3}$alkyl, $C_{1-2}$haloalkyl, and $C_{1-3}$alkoxy. In some embodiments, $R^4$ is H.

In some embodiments, $R^5$ is selected from the group consisting of H, $C_{1-5}$alkyl, $C_{1-5}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^5$ is selected from the group consisting of H, $C_{1-5}$alkyl, $C_{1-5}$haloalkyl, and $C_{1-5}$alkoxy. In some embodiments, $R^5$ is selected from the group consisting of H, $C_{1-3}$alkyl, $C_{1-2}$haloalkyl, and $C_{1-3}$alkoxy. In some embodiments, $R^5$ is H.

In some embodiments, the present disclosure provides an adenosine derivative having a structure of formula (Ie), (If), or a pharmaceutically acceptable salt, tautomer, or solvate thereof:

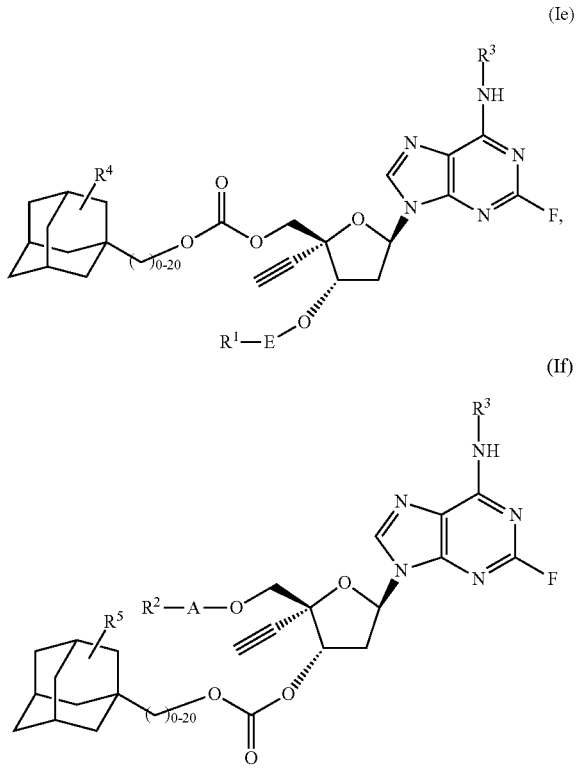

wherein:
  A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
    G is selected form the group consisting of a bond, O, NH, and S;
    J is selected form the group consisting of a bond, O, NH, S, —(CO)-G-;
  $R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
  $R^2$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
  $R^3$ is selected from the group consisting of H, —(CO)—O—$C_{1-10}$alkyl, and $C_{1-10}$alkyl;
  $R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and
  $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, A is selected from the group consisting of a bond, —(CO)—, —(CO)-G-, and —(CO)-G-($C_{1-5}$alkylene)-J-. In some embodiments, A is selected from the group consisting of a bond, —(CO)—, —(CO)-G-, and —(CO)-G-($C_{1-5}$alkylene)-. In some embodiments, A is —(CO)-G- or —(CO)-G-($C_{1-5}$alkylene)-. In some embodiments, A is —(CO)-G-($C_{1-5}$alkylene)-. In some embodiments, A is selected from the group consisting of a bond, —(CO)—, —(CO)—O—, and —(CO)—O—($C_{1-5}$alkylene)-. In some embodiments, A is selected from the group consisting of a bond, —(CO)—, —(CO)—O—, and —(CO)—O—($C_{1-5}$alkylene)-. In some embodiments, A is —(CO)—O— or —(CO)—O—($C_{1-5}$alkylene)-. In some embodiments, A is —(CO)—O—($C_{1-5}$alkylene)-. In some embodiments, G is a bond or O. In some embodiments, G is O. In some embodiments, J is a bond or O. In some embodiments, J is a bond.

In some embodiments, E is selected from the group consisting of a bond, —(CO)—, —(CO)-G-, and —(CO)-G-($C_{1-5}$alkylene)-J-. In some embodiments, E is selected from the group consisting of a bond, —(CO)—, —(CO)-G-, and —(CO)-G-($C_{1-5}$alkylene)-. In some embodiments, E is selected from the group consisting of a bond, —(CO)—, —(CO)—O—, and —(CO)—O—($C_{1-5}$alkylene)-. In some embodiments, E is a bond. In some embodiments, G is a bond or O. In some embodiments, G is O. In some embodiments, J is a bond or O. In some embodiments, J is a bond.

In some embodiments, $R^1$ is H, $C_{1-20}$alkyl, or $C_{3-20}$cycloalkyl. In some embodiments, $R^1$ is H, $C_{1-5}$alkyl, or $C_{3-15}$cycloalkyl. In some embodiments, $R^1$ is H or $C_{3-20}$cycloalkyl. In some embodiments, $R^1$ is H, $C_{1-5}$alkyl, or adamantyl. In some embodiments, $R^1$ is H or adamantyl. In some embodiments, the $C_{1-5}$alkyl is methyl, ethyl, or isopropyl. In some embodiments, the $C_{3-20}$cycloalkyl is adamantyl.

In some embodiments, $R^2$ is H, $C_{1-20}$alkyl, or $C_{3-20}$cycloalkyl. In some embodiments, $R^2$ is H, $C_{1-10}$alkyl, or $C_{3-20}$cycloalkyl. In some embodiments, $R^2$ is H, $C_{1-10}$alkyl, or $C_{5-15}$cycloalkyl. In some embodiments, $R^2$ is H, $C_{1-5}$alkyl, or $C_{5-15}$cycloalkyl. In some embodiments, $R^2$ is $C_{5-15}$cycloalkyl. In some embodiments, $R^2$ is H, $C_{1-5}$alkyl, or adamantyl. In some embodiments, the $C_{1-5}$alkyl is methyl, ethyl, or isopropyl. In some embodiments, the $C_{3-20}$cycloalkyl is adamantyl.

In some embodiments, E is a bond and $R^1$ is H.
In some embodiments, A is a bond and $R^2$ is H.
In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^4$ is selected from the group consisting of H, $C_{1-5}$alkyl, $C_{1-5}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^4$ is selected from the group consisting of H, $C_{1-5}$alkyl, $C_{1-5}$haloalkyl, and $C_{1-5}$alkoxy. In some embodiments, $R^4$ is selected from the group consisting of H, $C_{1-3}$alkyl, $C_{1-2}$haloalkyl, and $C_{1-3}$alkoxy. In some embodiments, $R^4$ is H.

In some embodiments, $R^5$ is selected from the group consisting of H, $C_{1-5}$alkyl, $C_{1-5}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^5$ is selected from the group consisting of H, $C_{1-5}$alkyl, $C_{1-5}$haloalkyl, and $C_{1-5}$alkoxy. In some embodiments, $R^5$ is selected from the group consisting of H, $C_{1-3}$alkyl, $C_{1-2}$haloalkyl, and $C_{1-3}$alkoxy. In some embodiments, $R^5$ is H.

In some embodiments, the adenosine derivative of formula (Ie) has the structure:

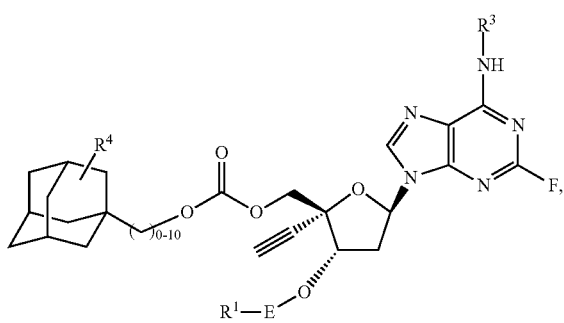

or a pharmaceutically acceptable salt, tautomer, or solvate thereof, wherein E, $R^1$, $R^3$, and $R^4$ are as defined above.

In some embodiments, the adenosine derivative of formula (Ie) has the structure:

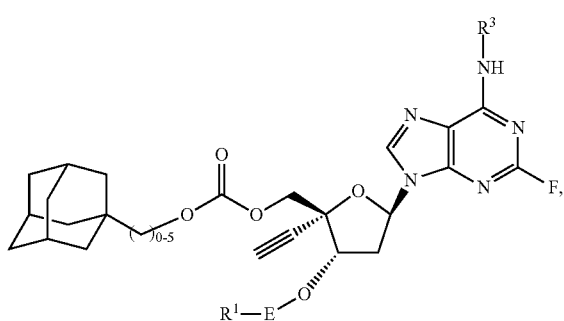

or a pharmaceutically acceptable salt, tautomer, or solvate thereof, wherein E, $R^1$, and $R^3$ are as defined above.

In some embodiments, the adenosine derivative of formula (Ie) has the structure:

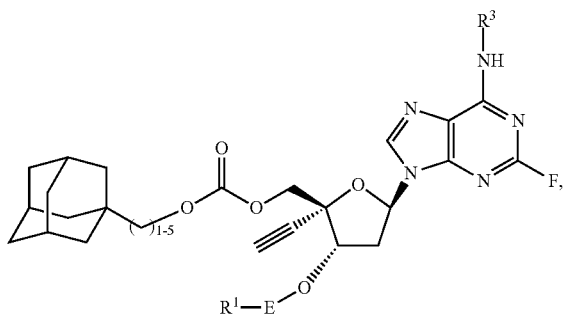

or a pharmaceutically acceptable salt, tautomer, or solvate thereof, wherein E, $R^1$, and $R^3$ are as defined above.

In some embodiments, the adenosine derivative of formula (Ie) has the structure:

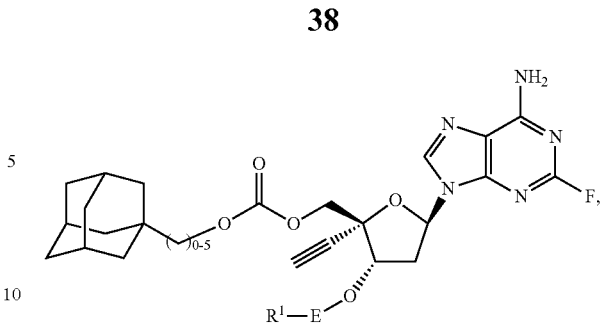

or a pharmaceutically acceptable salt, tautomer, or solvate thereof, wherein E and $R^1$ are as defined above.

In some embodiments, the adenosine derivative of formula (Ie) has the structure:

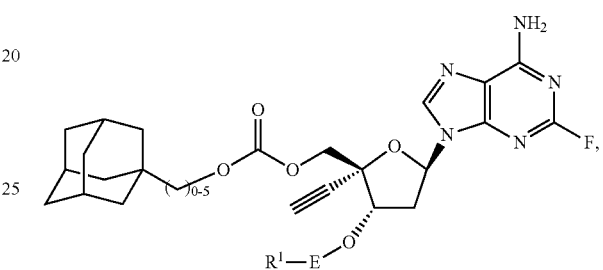

or a pharmaceutically acceptable salt, tautomer, or solvate thereof, wherein E and $R^1$ are as defined above.

In some embodiments, the present disclosure provides an adenosine derivative having a structure of formula (Ig) or a pharmaceutically acceptable salt, tautomer, or solvate thereof:

(Ig)

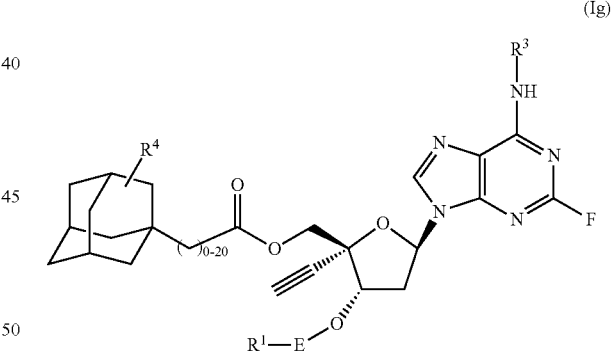

wherein:
E is selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
$R^3$ is selected from the group consisting of H, —(CO)—O—$C_{1-10}$alkyl, and $C_{1-10}$alkyl; and $R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, E is selected from the group consisting of a bond, —(CO)—, —(CO)-G-, and —(CO)-G-($C_{1-5}$alkylene)-J-. In some embodiments, E is selected from the group consisting of a bond, —(CO)—, —(CO)-G-, and —(CO)-G-($C_{1-5}$alkylene)-. In some embodiments, E is selected from the group consisting of a bond, —(CO)—, —(CO)—O—, and —(CO)—O—($C_{1-5}$alkylene)-. In some embodiments, E is a bond. In some embodiments, G is a bond or O. In some embodiments, G is O. In some embodiments, J is a bond or O. In some embodiments, J is a bond.

In some embodiments, $R^1$ is H, $C_{1-20}$alkyl, or $C_{3-20}$cycloalkyl. In some embodiments, $R^1$ is H, $C_{1-5}$alkyl, or $C_{3-15}$cycloalkyl. In some embodiments, $R^1$ is H or $C_{3-20}$cycloalkyl. In some embodiments, $R^1$ is H, $C_{1-5}$alkyl, or adamantyl. In some embodiments, $R^1$ is H or adamantyl. In some embodiments, the $C_{1-5}$alkyl is methyl, ethyl, or isopropyl. In some embodiments, the $C_{3-20}$cycloalkyl is adamantyl.

In some embodiments, E is a bond and $R^1$ is H.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^4$ is selected from the group consisting of H, $C_{1-5}$alkyl, $C_{1-5}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^4$ is selected from the group consisting of H, $C_{1-5}$alkyl, $C_{1-5}$haloalkyl, and $C_{1-5}$alkoxy. In some embodiments, $R^4$ is selected from the group consisting of H, $C_{1-3}$alkyl, $C_{1-2}$haloalkyl, and $C_{1-3}$alkoxy. In some embodiments, $R^4$ is H.

In some embodiments, the present disclosure provides an adenosine derivative having a structure of formula (Ih) or a pharmaceutically acceptable salt, tautomer, or solvate thereof:

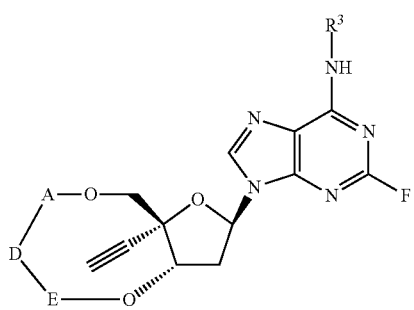

(Ih)

wherein:
A and E are independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;

D is selected from the group consisting of —$C_{1-20}$alkylene-, —$C_{2-20}$alkenylene-, and —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and
$R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, A is selected from the group consisting of a bond, —(CO)—, —(CO)-G-, and —(CO)-G-($C_{1-5}$alkylene)-J-. In some embodiments, A is selected from the group consisting of a bond, —(CO)—, —(CO)-G-, and —(CO)-G-($C_{1-5}$alkylene)-. In some embodiments, A is —(CO)-G- or —(CO)-G-($C_{1-5}$alkylene)-. In some embodiments, A is —(CO)-G-($C_{1-5}$alkylene)-. In some embodiments, A is selected from the group consisting of a bond, —(CO)—, —(CO)—O—, and —(CO)—O—($C_{1-5}$alkylene)-. In some embodiments, A is selected from the group consisting of a bond, —(CO)—, —(CO)—O—, and —(CO)—O—($C_{1-5}$alkylene)-. In some embodiments, A is —(CO)—O— or —(CO)—O—($C_{1-5}$alkylene)-. In some embodiments, A is —(CO)—O—($C_{1-5}$alkylene)-. In some embodiments, G is a bond or O. In some embodiments, G is O. In some embodiments, J is a bond or O. In some embodiments, J is a bond.

In some embodiments, D is a $C_{1-20}$alkylene. In some embodiments, D is a $C_{1-10}$alkylene. In some embodiments, D is a $C_{3-10}$alkylene. In some embodiments, D is a $C_{3-6}$alkylene.

In some embodiments, E is selected from the group consisting of a bond, —(CO)—, —(CO)-G-, and —(CO)-G-($C_{1-5}$alkylene)-J-. In some embodiments, E is selected from the group consisting of a bond, —(CO)—, —(CO)-G-, and —(CO)-G-($C_{1-5}$alkylene)-. In some embodiments, E is selected from the group consisting of a bond, —(CO)—, —(CO)—O—, and —(CO)—O—($C_{1-5}$alkylene)-. In some embodiments, E is a bond. In some embodiments, G is a bond or O. In some embodiments, G is O. In some embodiments, J is a bond or O. In some embodiments, J is a bond.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, the present disclosure provides an adenosine derivative having a structure of formula (Ii), (Ij), or a pharmaceutically acceptable salt, tautomer, or solvate thereof:

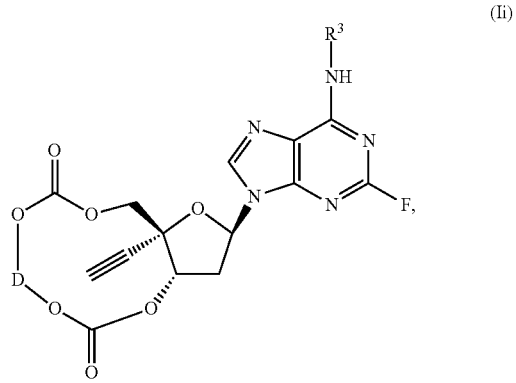

(Ii)

-continued

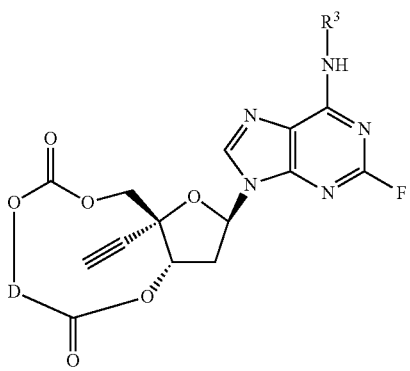

(Ij)

wherein:
D is selected from the group consisting of —C$_{1-20}$alkylene-, —C$_{2-20}$alkenylene-, and —C$_{2-20}$alkynylene-, —C$_{1-20}$haloalkylene-, —C$_{1-20}$alkoxyalkylene-, C$_{3-20}$cycloalkyl, 3- to 20-membered heterocycloalkyl, aryl, and heteroaryl; and R$^3$ is selected from the group consisting of H, —(CO)—O—C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, D is a C$_{1-20}$alkylene. In some embodiments, D is a C$_{1-10}$alkylene. In some embodiments, D is a C$_{3-10}$alkylene. In some embodiments, D is a C$_{3-6}$alkylene.

In some embodiments, R$^3$ is H, —(CO)-G-C$_{1-10}$alkyl, or C$_{1-10}$alkyl. In some embodiments, R$^3$ is H, —(CO)—C$_{1-5}$alkyl, —(CO)—O—C$_{1-5}$alkyl, or C$_{1-5}$alkyl. In some embodiments, the C$_{1-5}$alkyl is methyl, ethyl, or isopropyl. In some embodiments, R$^3$ is H, —(CO)—CH$_3$, —(CO)—O—CH$_3$, or CH$_3$. In some embodiments, R$^3$ is H.

In some embodiments, the present disclosure provides an adenosine derivative having a structure of formula (Ik), (Il), or a pharmaceutically acceptable salt, tautomer, or solvate thereof:

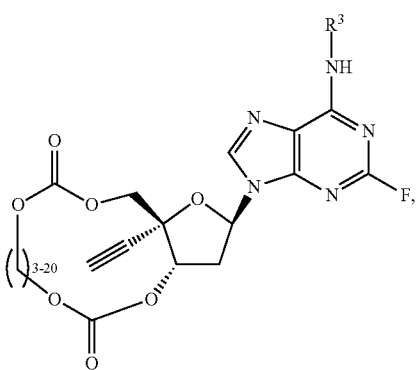

(Ik)

-continued

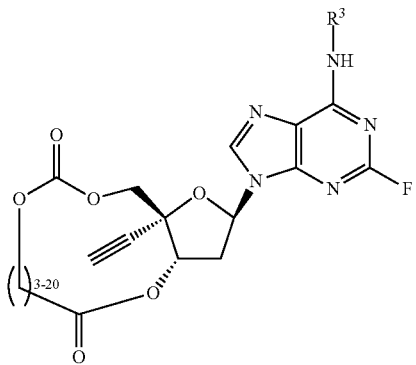

(Il)

wherein:
R$^3$ is selected from the group consisting of H, —(CO)—O—C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, R$^3$ is H, —(CO)-G-C$_{1-10}$alkyl, or C$_{1-10}$alkyl. In some embodiments, R$^3$ is H, —(CO)—C$_{1-5}$alkyl, —(CO)—O—C$_{1-5}$alkyl, or C$_{1-5}$alkyl. In some embodiments, the C$_{1-5}$alkyl is methyl, ethyl, or isopropyl. In some embodiments, R$^3$ is H, —(CO)—CH$_3$, —(CO)—O—CH$_3$, or CH$_3$. In some embodiments, R$^3$ is H.

In some embodiments, the present disclosure provides an adenosine derivative having a structure of formula (Im) or a pharmaceutically acceptable salt, tautomer, or solvate thereof:

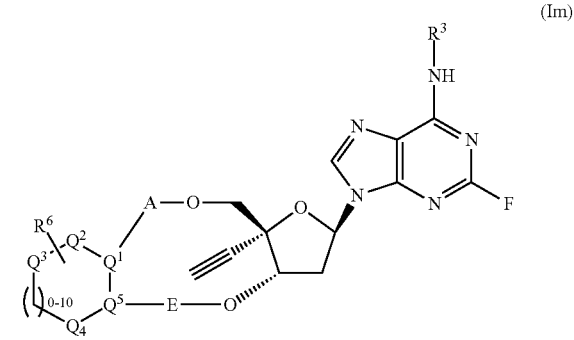

(Im)

wherein:
A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;
R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl;
Q$^1$, Q$^2$, Q$^3$, Q$^4$, and Q$^5$ form a cyclic ring, wherein said ring is selected from the group consisting of cycloalkyl, heterocycloalkyl, aryl, and heteroaryl; and
R$^6$ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments, A is selected from the group consisting of a bond, —(CO)—, —(CO)-G-, and —(CO)-G-($C_{1-5}$alkylene)-J-. In some embodiments, A is selected from the group consisting of a bond, —(CO)—, —(CO)-G-, and —(CO)-G-($C_{1-5}$alkylene)-. In some embodiments, A is —(CO)-G- or —(CO)-G-($C_{1-5}$alkylene)-. In some embodiments, A is —(CO)-G-($C_{1-5}$alkylene)-. In some embodiments, A is selected from the group consisting of a bond, —(CO)—, —(CO)—O—, and —(CO)—O—($C_{1-5}$alkylene)-. In some embodiments, A is selected from the group consisting of a bond, —(CO)—, —(CO)—O—, and —(CO)—O—($C_{1-5}$alkylene)-. In some embodiments, A is —(CO)—O— or —(CO)—O—($C_{1-5}$alkylene)-. In some embodiments, A is —(CO)—O—($C_{1-5}$alkylene)-. In some embodiments, G is a bond or O. In some embodiments, G is O. In some embodiments, J is a bond or O. In some embodiments, J is a bond.

In some embodiments, E is selected from the group consisting of a bond, —(CO)—, —(CO)-G-, and —(CO)-G-($C_{1-5}$alkylene)-J-. In some embodiments, E is selected from the group consisting of a bond, —(CO)—, —(CO)-G-, and —(CO)-G-($C_{1-5}$alkylene)-. In some embodiments, E is selected from the group consisting of a bond, —(CO)—, —(CO)—O—, and —(CO)—O—($C_{1-5}$alkylene)-. In some embodiments, E is a bond. In some embodiments, G is a bond or O. In some embodiments, G is O. In some embodiments, J is a bond or O. In some embodiments, J is a bond.

In some embodiments, $Q^1$, $Q^2$, $Q^3$, $Q^4$, and $Q^5$ form a cyclic ring, wherein said ring is selected from the group consisting of cyclopentyl, cyclohexyl, pyrrolidinyl, piperidinyl, morpholinyl, thiomorpholinyl, phenyl, pyridinyl, pyrimidinyl, pyrazinyl, or pyridazinyl. In some embodiments, $Q^1$, $Q^2$, $Q^3$, $Q^4$, and $Q^5$ form a cyclic ring, wherein said ring is selected from the group consisting of cyclopentyl, cyclohexyl, pyrrolidinyl, piperidinyl, morpholinyl, phenyl, or pyridinyl. In some embodiments, $Q^1$, $Q^2$, $Q^3$, $Q^4$, and $Q^5$ form a cyclic ring, wherein said ring is selected from the group consisting of cyclohexyl, piperidinyl, morpholinyl, phenyl, or pyridinyl. In some embodiments, $Q^1$, $Q^2$, $Q^3$, $Q^4$, and $Q^5$ form a cyclic ring, wherein said ring is selected from the group consisting of cyclohexyl, piperidinyl, or morpholinyl. In some embodiments, $Q^1$, $Q^2$, $Q^3$, $Q^4$, and $Q^5$ form a cyclic ring, wherein said ring is cyclohexyl.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, the present disclosure provides an adenosine derivative having a structure of formula (In), (Io), or a pharmaceutically acceptable salt, tautomer, or solvate thereof:

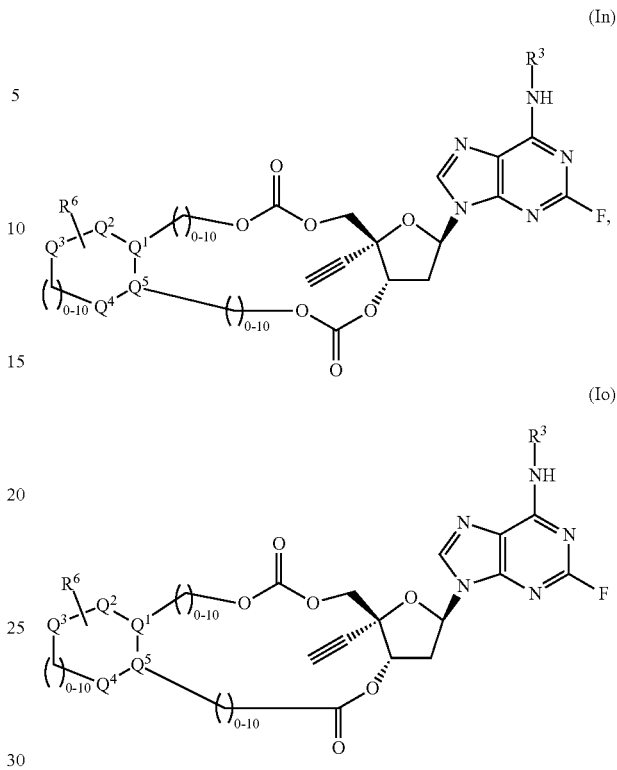

wherein:
  $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;
  $Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and
  $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, $Q^1$, $Q^2$, $Q^3$, $Q^4$, and $Q^5$ form a cyclic ring, wherein said ring is selected from the group consisting of cyclopentyl, cyclohexyl, pyrrolidinyl, piperidinyl, morpholinyl, thiomorpholinyl, phenyl, pyridinyl, pyrimidinyl, pyrazinyl, or pyridazinyl. In some embodiments, $Q^1$, $Q^2$, $Q^3$, $Q^4$, and $Q^5$ form a cyclic ring, wherein said ring is selected from the group consisting of cyclopentyl, cyclohexyl, pyrrolidinyl, piperidinyl, morpholinyl, phenyl, or pyridinyl. In some embodiments, $Q^1$, $Q^2$, $Q^3$, $Q^4$, and $Q^5$ form a cyclic ring, wherein said ring is selected from the group consisting of cyclohexyl, piperidinyl, morpholinyl, phenyl, or pyridinyl. In some embodiments, $Q^1$, $Q^2$, $Q^3$, $Q^4$, and $Q^5$ form a cyclic ring, wherein said ring is selected from the group consisting of cyclohexyl, piperidinyl, or morpholinyl. In some embodiments, $Q^1$, $Q^2$, $Q^3$, $Q^4$, and $Q^5$ form a cyclic ring, wherein said ring is cyclohexyl.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^6$ is selected from the group consisting of $C_{1-5}$alkyl, $C_{1-3}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^6$ is selected from the group consisting of $C_{1-5}$alkyl, $C_{1-3}$haloalkyl, and $C_{1-5}$alkoxy. In some embodiments, $R^6$ is selected from the group consisting of $C_{1-3}$alkyl, $C_{1-2}$haloalkyl, and $C_{1-3}$alkoxy. In some embodiments, $R^6$ is methyl, ethyl, isopropyl, methoxy, isopropyl, $CF_3$, $CH_2CF_3$, methoxy, ethoxy, or isopropoxy.

In some embodiments, the present disclosure provides an adenosine derivative having a structure of formula (Ip) or a pharmaceutically acceptable salt, tautomer, or solvate thereof:

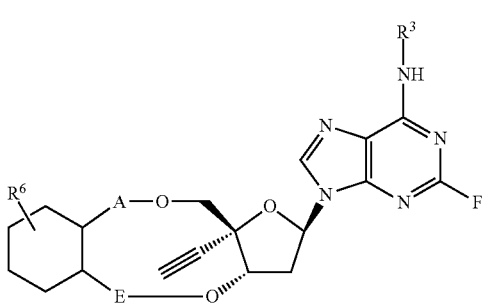

(Ip)

wherein:
  A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
    G is selected form the group consisting of a bond, O, NH, and S;
    J is selected form the group consisting of a bond, O, NH, S, —(CO)-G-;
  $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and
  $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, A is selected from the group consisting of a bond, —(CO)—, —(CO)-G-, and —(CO)-G-($C_{1-5}$alkylene)-J-. In some embodiments, A is selected from the group consisting of a bond, —(CO)—, —(CO)-G-, and —(CO)-G-($C_{1-5}$alkylene)-. In some embodiments, A is —(CO)-G- or —(CO)-G-($C_{1-5}$alkylene)-. In some embodiments, A is —(CO)-G-($C_{1-5}$alkylene)-. In some embodiments, A is selected from the group consisting of a bond, —(CO)—, —(CO)—O—, and —(CO)—O—($C_{1-5}$alkylene)-. In some embodiments, A is selected from the group consisting of a bond, —(CO)—, —(CO)—O—, and —(CO)—O—($C_{1-5}$alkylene)-. In some embodiments, A is —(CO)—O— or —(CO)—O—($C_{1-5}$alkylene)-. In some embodiments, A is —(CO)—O—($C_{1-5}$alkylene)-. In some embodiments, G is a bond or O. In some embodiments, G is O. In some embodiments, J is a bond or O. In some embodiments, J is a bond.

In some embodiments, E is selected from the group consisting of a bond, —(CO)—, —(CO)-G-, and —(CO)-G-($C_{1-5}$alkylene)-J-. In some embodiments, E is selected from the group consisting of a bond, —(CO)—, —(CO)-G-, and —(CO)-G-($C_{1-5}$alkylene)-. In some embodiments, E is selected from the group consisting of a bond, —(CO)—, —(CO)—O—, and —(CO)—O—($C_{1-5}$alkylene)-. In some embodiments, E is a bond. In some embodiments, G is a bond or O. In some embodiments, G is O. In some embodiments, J is a bond or O. In some embodiments, J is a bond.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^6$ is selected from the group consisting of $C_{1-5}$alkyl, $C_{1-3}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^6$ is selected from the group consisting of $C_{1-5}$alkyl, $C_{1-3}$haloalkyl, and $C_{1-5}$alkoxy. In some embodiments, $R^6$ is selected from the group consisting of $C_{1-3}$alkyl, $C_{1-2}$haloalkyl, and $C_{1-3}$alkoxy. In some embodiments, $R^6$ is methyl, ethyl, isopropyl, methoxy, isopropyl, $CF_3$, $CH_2CF_3$, methoxy, ethoxy, or isopropoxy.

In some embodiments, the present disclosure provides an adenosine derivative having a structure of formula (Iq), (Ir), or a pharmaceutically acceptable salt, tautomer, or solvate thereof:

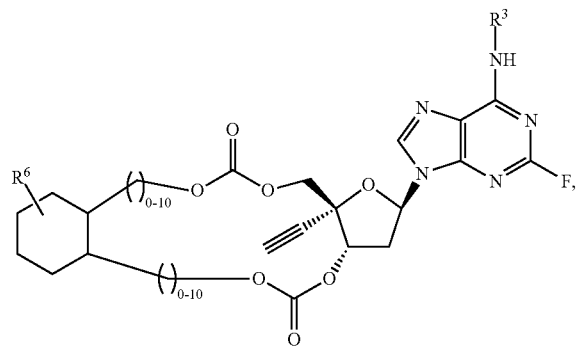

(Iq)

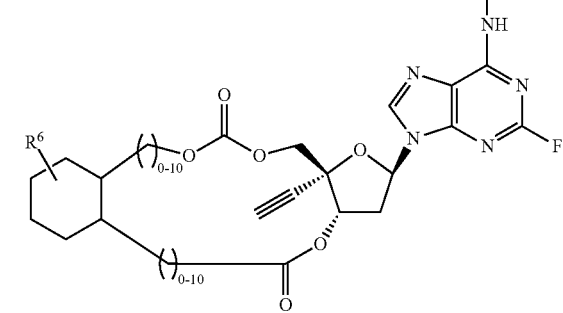

(Ir)

wherein:
  $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and
  $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, $R^3$ is H, —(CO)-G-$C_{1-10}$alkyl, or $C_{1-10}$alkyl. In some embodiments, $R^3$ is H, —(CO)—$C_{1-5}$alkyl, —(CO)—O—$C_{1-5}$alkyl, or $C_{1-5}$alkyl. In some embodiments, the $C_{1-5}$alkyl is methyl, ethyl, or isopropyl. In some embodiments, $R^3$ is H, —(CO)—$CH_3$, —(CO)—O—$CH_3$, or $CH_3$. In some embodiments, $R^3$ is H.

In some embodiments, $R^6$ is selected from the group consisting of $C_{1-5}$alkyl, $C_{1-3}$haloalkyl, $C_{1-5}$alkoxy, $C_{2-5}$alkenyl, $C_{2-5}$alkynyl, $C_{3-6}$cycloalkyl, 3- to 6-membered heterocycloalkyl, phenyl, and 5- to 6-membered heteroaryl. In some embodiments, $R^6$ is selected from the group consisting of $C_{1-5}$alkyl, $C_{1-3}$haloalkyl, and $C_{1-5}$alkoxy. In some embodiments, $R^6$ is selected from the group consisting of $C_{1-3}$alkyl, $C_{1-2}$haloalkyl, and $C_{1-3}$alkoxy. In some embodiments, $R^6$ is methyl, ethyl, isopropyl, methoxy, isopropyl, $CF_3$, $CH_2CF_3$, methoxy, ethoxy, or isopropoxy.

In some embodiments, the adenosine derivative is a compound of Table 1 or a pharmaceutically acceptable salt, tautomer, or solvate thereof.

TABLE 1

Adenosine compounds of the disclosure.

| Compound No | Structure | Chemical Name |
|---|---|---|
| 1 | 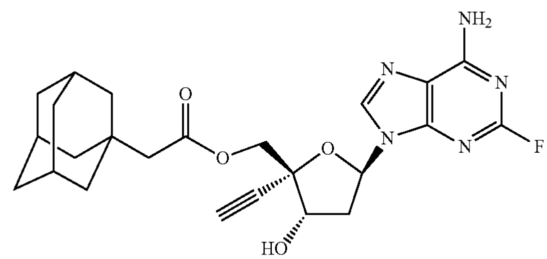 [SMILES: C#C[C@]1(COC(=O)CC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 2-(1-adamantyl) acetate |
| 2 | 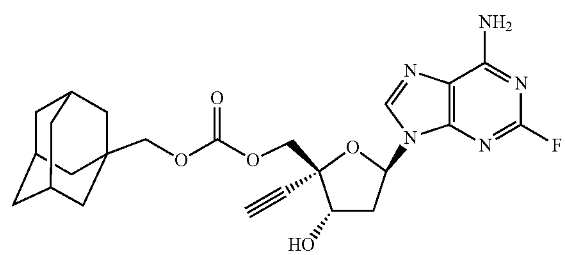 [SMILES: C#C[C@]1(COC(=O)OCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 1-adamantylmethyl carbonate |
| 3 | 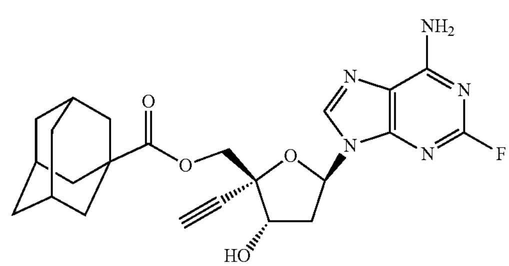 [SMILES: C#C[C@]1(COC(=O)C23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl adamantane-1-carboxylate |
| 4 | 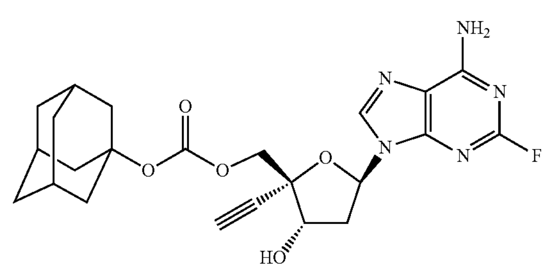 [SMILES: C#C[C@]1(COC(=O)OC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 1-adamantyl carbonate |

TABLE 1-continued

Adenosine compounds of the disclosure.

| Compound No | Structure | Chemical Name |
|---|---|---|
| 5 | 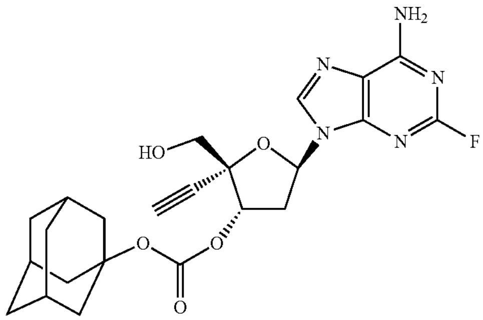 [SMILES: C#C[C@]1(CO)O[C@@H](n2cnc3c(N)nc(F)nc32)C[C@@H]1OC(=O)OC12CC3CC(CC(C3)C1)C2] | ((2R,3S,5R)-5-(6-amino-2-fluoro-9H-purin-9-yl)-2-ethynyl-2-(hydroxymethyl)tetrahydrofuran-3-yl) 1-adamantyl carbonate |
| 6 | 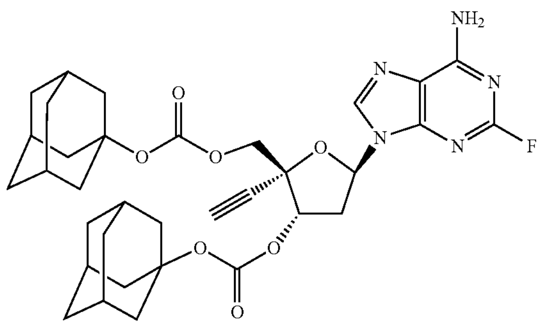 [SMILES: C#C[C@]1(COC(=O)OC23CC4CC(CC(C4)C2)C3)O[C@@H](n2cnc3c(N)nc(F)nc32)C[C@@H]1OC(=O)OC12CC3CC(CC(C3)C1)C2] | (((2R,3S,5R)-3-((((1-adamantyl)oxy)carbonyl)-oxy)-5-(6-amino-2-fluoro-9H-purin-9-yl)-2-ethynyl-tetrahydrofuran-2-yl)-methyl) 1-adamantyl carbonate |
| 7 | 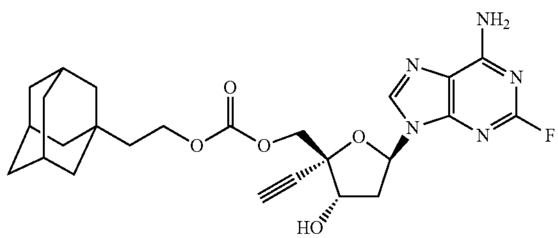 [SMILES: C#C[C@]1(COC(=O)OCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)-methyl 2-(1-adamantyl)-ethyl carbonate |
| 8 | 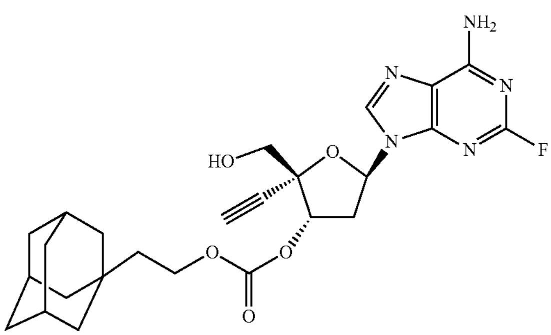 [SMILES: C#C[C@]1(CO)O[C@@H](n2cnc3c(N)nc(F)nc32)C[C@@H]1OC(=O)OCCC12CC3CC(CC(C3)C1)C2] | ((2R,3S,5R)-5-(6-amino-2-fluoro-9H-purin-9-yl)-2-ethynyl-2-(hydroxymethyl)tetrahydrofuran-3-yl) 2-(1-adamantyl)ethyl carbonate |
| 9 | 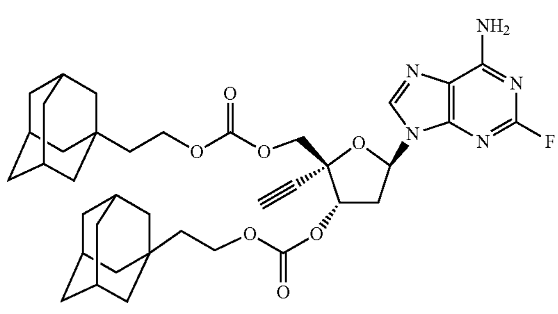 [SMILES: C#C[C@]1(COC(=O)OCCC23CC4CC(CC(C4)C2)C3)O[C@@H](n2cnc3c(N)nc(F)nc32)C[C@@H]1OC(=O)OCCC12CC3CC(CC(C3)C1)C2] | ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) 2-(1-adamantyl)ethyl carbonate |

TABLE 1-continued

Adenosine compounds of the disclosure.

| Compound No | Structure | Chemical Name |
|---|---|---|
| 10 | 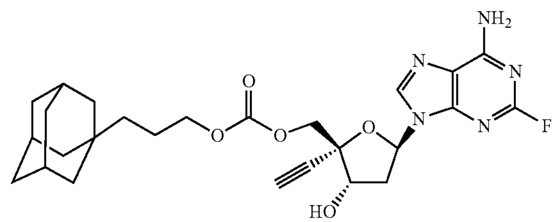 [SMILES: C#C[C@]1(COC(=O)OCCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)-methyl 3-(1-adamantyl)-propyl carbonate |
| 11 | 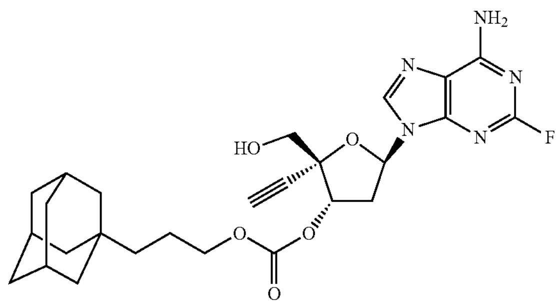 [SMILES: C#C[C@]1(CO)O[C@@H](n2cnc3c(N)nc(F)nc32)C[C@@H]1OC(=O)OCCCC12CC3CC(CC(C3)C1)C2] | ((2R,3S,5R)-5-(6-amino-2-fluoro-9H-purin-9-yl)-2-ethynyl-2-(hydroxy-methyl)tetrahydrofuran-3-yl) 3-(1-adamantyl)-propyl carbonate |
| 12 | 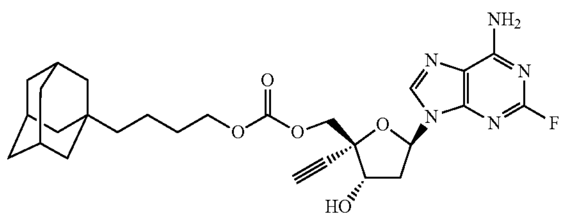 [SMILES: C#C[C@]1(COC(=O)OCCCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)-methyl 4-(1-adamantyl)-butyl carbonate |
| 13 | 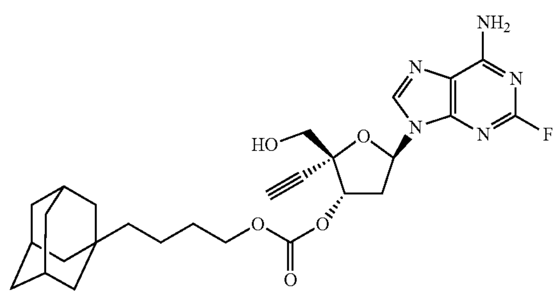 [SMILES: C#C[C@]1(CO)O[C@@H](n2cnc3c(N)nc(F)nc32)C[C@@H]1OC(=O)OCCCCC12CC3CC(CC(C3)C1)C2] | ((2R,3S,5R)-5-(6-amino-2-fluoro-9H-purin-9-yl)-2-ethynyl-2-(hydroxy-methyl)tetrahydrofuran-3-yl) 4-(1-adamantyl)butyl carbonate |
| 14 | 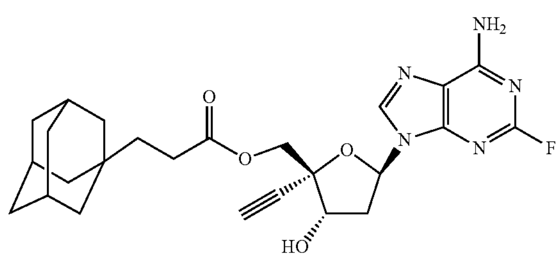 [SMILES: C#C[C@]1(COC(=O)CCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)methyl 3-(1-adamantyl)propanoate |
| 15 | 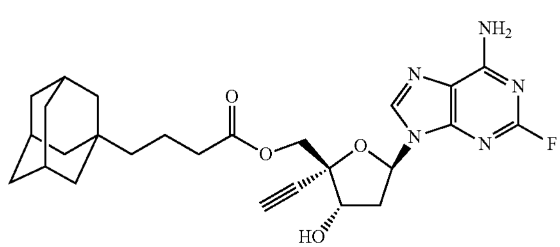 [SMILES: C#C[C@]1(COC(=O)CCCC23CC4CC(CC(C4)C2)C3)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxy-tetrahydrofuran-2-yl)-methyl 4-(1-adamantyl)-butanoate |

TABLE 1-continued

Adenosine compounds of the disclosure.

| Compound No | Structure | Chemical Name |
|---|---|---|
| 16 | 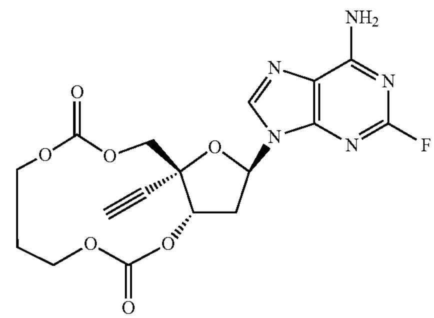 [SMILES: C#C[C@@]12COC(=O)OCCCOC(=O)O[C@H]1C[C@H](n1cnc3c(N)nc(F)nc31)O2] | (10aR,12R,13aS)-12-(6-amino-2-fluoro-9H-purin-9-yl)-10a-ethynylhexahydro-4H,10H-furo[3,2-d][1,3,7,9]tetraoxacyclododecine-2,8-dione |
| 17 | 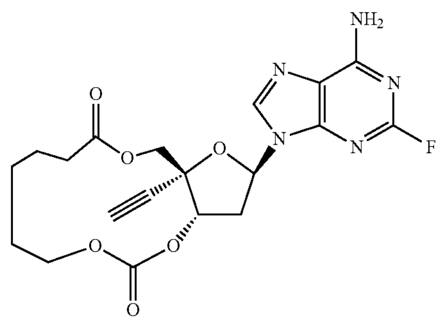 [SMILES: C#C[C@@]12COC(=O)CCCCCOC(=O)O[C@H]1C[C@H](n1cnc3c(N)nc(F)nc31)O2] | (11aR,13R,14aS)-13-(6-amino-2-fluoro-9H-purin-9-yl)-11a-ethynyloctahydro-11H-furo[3,2-d][1,3,7]trioxacyclotridecine-2,9(4H)-dione |
| 18 | 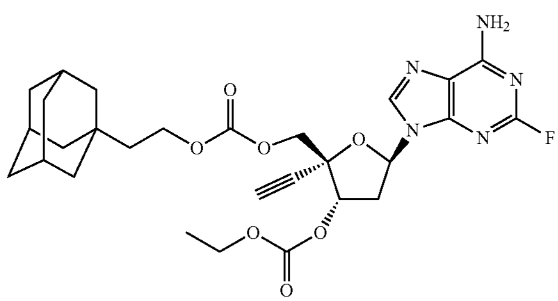 [SMILES: C#C[C@]1(COC(=O)OCCC23CC4CC(CC(C4)C2)C3)O[C@@H](n2cnc3c(N)nc(F)nc32)C[C@@H]1OC(=O)OCC] | ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) ethyl carbonate |
| 19 | 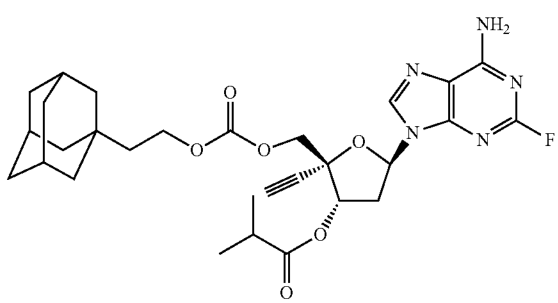 [SMILES: C#C[C@]1(COC(=O)OCCC23CC4CC(CC(C4)C2)C3)O[C@@H](n2cnc3c(N)nc(F)nc32)C[C@@H]1OC(=O)C(C)C] | ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) isobutyrate |
| 20 | 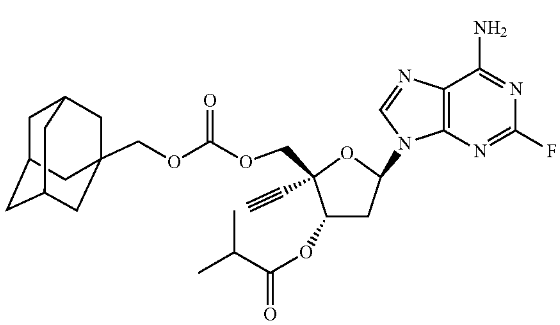 [SMILES: C#C[C@]1(COC(=O)OCC23CC4CC(CC(C4)C2)C3)O[C@@H](n2cnc3c(N)nc(F)nc32)C[C@@H]1OC(=O)C(C)C] | ((2R,3S,5R)-2-(((((1-adamantyl)methoxy)carbonyl)oxy)methyl)-5-(6-amino-2-fluoro-9H-purin-9-yl)-2-ethynyltetrahydrofuran-3-yl) isobutyrate |

TABLE 1-continued

Adenosine compounds of the disclosure.

| Compound No | Structure | Chemical Name |
|---|---|---|
| 21 | 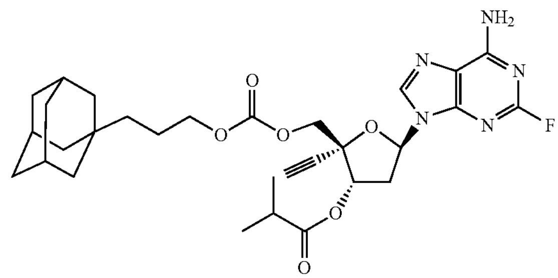 [SMILES: C#C[C@]1(COC(=O)OCCCC23CC4CC(CC(C4)C2)C3)O[C@@H](n2cnc3c(N)nc(F)nc32)C[C@@H]1OC(=O)C(C)C] | ((2R,3S,5R)-2-((((3-(1-adamantyl)propoxy)-carbonyl)oxy)methyl)-5-(6-amino-2-fluoro-9H-purin-9-yl)-2-ethynyl-tetrahydrofuran-3-yl) isobutyrate |
| 22 | 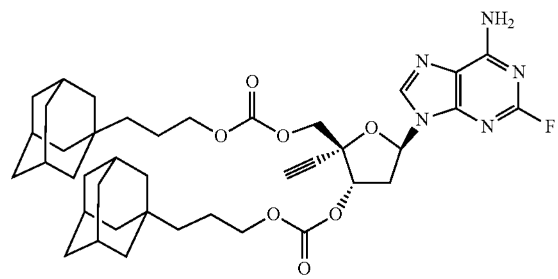 [SMILES: C#C[C@]1(COC(=O)OCCCC23CC4CC(CC(C4)C2)C3)O[C@@H](n2cnc3c(N)nc(F)nc32)C[C@@H]1OC(=O)OCCCC12CC3CC(CC(C3)C1)C2] | ((2R,3S,5R)-3-[3-(1-adamantyl)propoxycarbonyloxy]-5-(6-amino-2-fluoro-9H-purin-9-yl)-2-ethynyl-tetrahydrofuran-2-yl)methyl 3-(1-adamantyl)propyl carbonate |
| 23 | 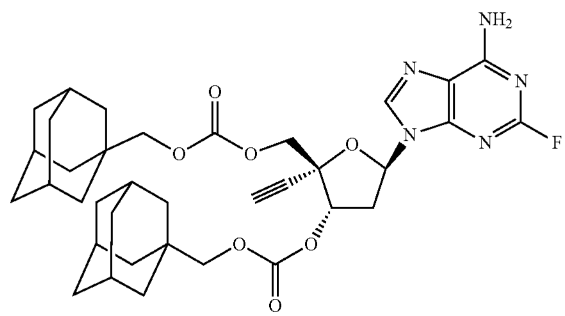 [SMILES: C#C[C@]1(COC(=O)OCC23CC4CC(CC(C4)C2)C3)O[C@@H](n2cnc3c(N)nc(F)nc32)C[C@@H]1OC(=O)OCC12CC3CC(CC(C3)C1)C2] | ((2R,3S,5R)-3-(1-adamantylmethoxycarbonyloxy)-5-(6-amino-2-fluoro-9H-purin-9-yl)-2-ethynyl-tetrahydrofuran-2-yl)methyl 1-adamantyl-methyl carbonate |
| 24 | 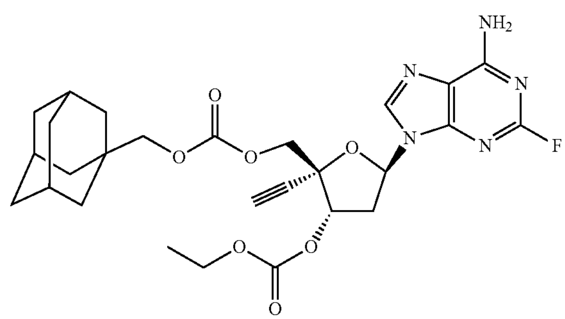 [SMILES: C#C[C@]1(COC(=O)OCC23CC4CC(CC(C4)C2)C3)O[C@@H](n2cnc3c(N)nc(F)nc32)C[C@@H]1OC(=O)OCC] | ((2R,3S,5R)-2-(1-adamantylmethoxycarbonyloxymethyl)-5-(6-amino-2-fluoro-9H-purin-9-yl)-2-ethynyl-tetrahydrofuran-3-yl) ethyl carbonate |
| 25 | 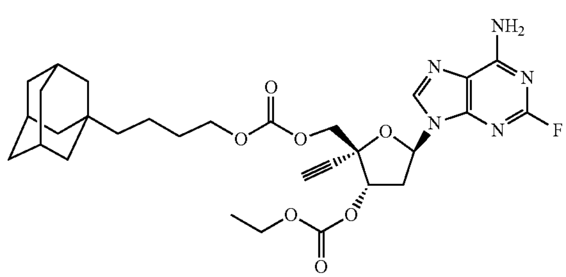 [SMILES: C#C[C@]1(COC(=O)OCCCCC23CC4CC(CC(C4)C2)C3)O[C@@H](n2cnc3c(N)nc(F)nc32)C[C@@H]1OC(=O)OCC] | ((2R,3S,5R)-2-[4-(1-adamantyl)butoxycarbonyloxymethyl]-5-(6-amino-2-fluoro-9H-purin-9-yl)-2-ethynyl-tetrahydrofuran-3-yl) ethyl carbonate |

TABLE 1-continued

Adenosine compounds of the disclosure.

| Compound No | Structure | Chemical Name |
|---|---|---|
| 26 | 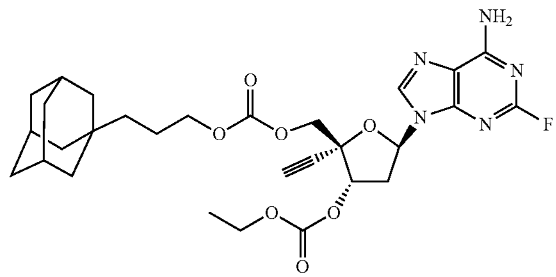 [SMILES: C#C[C@]1(COC(=O)OCCCC23CC4CC(CC(C4)C2)C3)O[C@@H](n2cnc3c(N)nc(F)nc32)C[C@@H]1OC(=O)OCC] | ((2R,3S,5R)-2-[3-(1-adamantyl)propoxycarbonyloxymethyl]-5-(6-amino-2-fluoro-9H-purin-9-yl)-2-ethynyl-tetrahydrofuran-3-yl) ethyl carbonate |
| 27 | 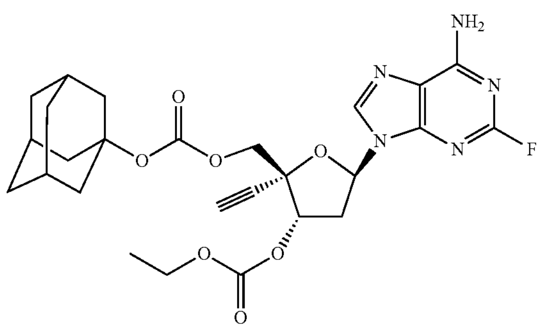 [SMILES: C#C[C@]1(COC(=O)OC23CC4CC(CC(C4)C2)C3)O[C@@H](n2cnc3c(N)nc(F)nc32)C[C@@H]1OC(=O)OCC] | 1-adamantyl ((2R,3S,5R)-5-(6-amino-2-fluoro-purin-9-yl)-3-ethoxycarbonyloxy-2-ethynyl-tetrahydrofuran-2-yl)methyl carbonate |
| 28 | 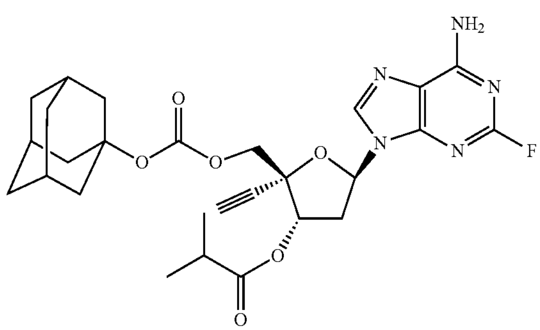 [SMILES: C#C[C@]1(COC(=O)OC23CC4CC(CC(C4)C2)C3)O[C@@H](n2cnc3c(N)nc(F)nc32)C[C@@H]1OC(=O)C(C)C] | ((2R,3S,5R)-2-(1-adamantyloxycarbonyloxymethyl)-5-(6-amino-2-fluoro-9H-purin-9-yl)-2-ethynyl-tetrahydrofuran-3-yl) 2-methylpropanoate |
| 29 | 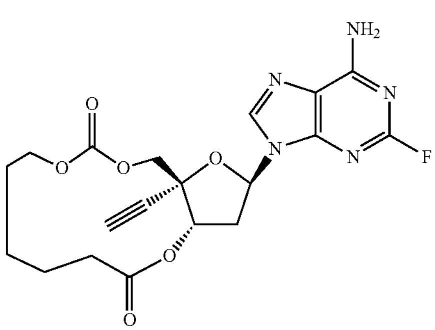 [SMILES: C#C[C@@]12COC(=O)OCCCCCC(=O)O[C@H]1C[C@H](n1cnc3c(N)nc(F)nc31)O2] | (1R,13R,15R)-15-(6-amino-2-fluoro-9H-purin-9-yl)-13-ethynyl-2,9,11,14-tetraoxabicyclo-[11.3.0]hexadecane-3,10-dione |

TABLE 1-continued

Adenosine compounds of the disclosure.

| Compound No | Structure | Chemical Name |
|---|---|---|
| 30 | 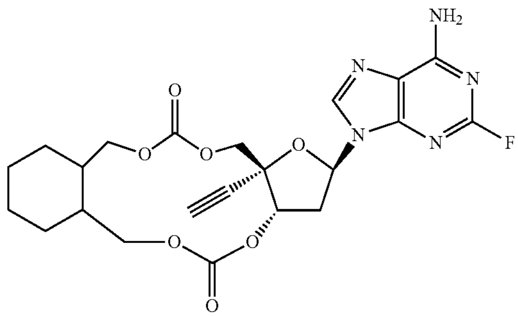 [SMILES: C#C[C@@]12COC(=O)OCC3CCCCC3COC(=O)O[C@H]1C[C@H](n1cnc3c(N)nc(F)nc31)O2] | (6R,8R,10R)-8-(6-amino-2-fluoro-9H-purin-9-yl)-10-ethynyl-3,5,9,12,14-pentaoxatricyclo-[14.4.0.06,10]icosane-4,13-dione |

In some embodiments, the adenosine derivative is selected from the group consisting of:

and a pharmaceutically acceptable salt, tautomer, or solvate thereof.

In some embodiments, the adenosine derivative of formula (I) is selected from the group consisting of:

((2R,3S,5R)-5-(6-amino-2-fluoro-9H-purin-9-yl)-2-ethynyl-3-hydroxy-tetrahydrofuran-2-yl)methyl 2-(1-adamantyl) acetate, ((2R,3S,5R)-5-(6-amino-2-fluoro-9H-purin-9-yl)-2-ethynyl-3-hydroxy-tetrahydrofuran-2-yl)methyl 1-adamantylmethyl carbonate, ((2R,3S,5R)-5-(6-amino-2-fluoro-9H-purin-9-yl)-2-ethynyl-3-hydroxy-tetrahydrofuran-2-yl)methyl adamantane-1-carboxylate, ((2R,3S,5R)-5-(6-amino-2-fluoro-9H-purin-9-yl)-2-ethynyl-3-hydroxy-tetrahydrofuran-2-yl)methyl 1-adamantyl carbonate, ((2R,3S,5R)-5-(6-amino-2-fluoro-9H-purin-9-yl)-2-ethynyl-2-(hydroxymethyl)tetrahydrofuran-3-yl) 1-adamantyl carbonate, (((2R,3S,5R)-3-((((1-adamantyl)oxy)carbonyl)oxy)-5-(6-amino-2-fluoro-9H-purin-9-yl)-2-ethynyltetrahydrofuran-2-yl)methyl) 1-adamantyl carbonate, ((2R,3S,5R)-5-(6-amino-2-fluoro-9H-purin-9-yl)-2-ethynyl-3-hydroxy-tetrahydrofuran-2-yl)methyl 2-(1-adamantyl)ethyl carbonate, ((2R,3S,5R)-5-(6-amino-2-fluoro-9H-purin-9-yl)-2-ethynyl-2-(hydroxymethyl)tetrahydrofuran-3-yl) 2-(1-adamantyl)ethyl carbonate, ((2R,3S,5R)-2-((((2-(1-adamantyl)ethoxy)carbonyl)oxy) methyl)-5-(6-amino-2-fluoro-9H-purin-9-yl)-2-ethynyltetrahydrofuran-3-yl) 2-(1-adamantyl)ethyl carbonate, ((2R,3S,5R)-5-(6-amino-2-fluoro-9H-purin-9-yl)-2-ethynyl-3-hydroxy-tetrahydrofuran-2-yl)methyl 3-(1-adamantyl)propyl carbonate, ((2R,3S,5R)-5-(6-amino-2-fluoro-9H-purin-9-yl)-2-ethynyl-2-(hydroxymethyl)tetrahydrofuran-3-yl) 3-(1-adamantyl)propyl carbonate, ((2R,3S,5R)-5-(6-amino-2-fluoro-9H-purin-9-yl)-2-ethynyl-3-hydroxy-tetrahydrofuran-2-yl)methyl 4-(1-adamantyl)butyl carbonate, ((2R,3S,5R)-5-(6-amino-2-fluoro-9H-purin-9-yl)-2-ethynyl-2-(hydroxymethyl)tetrahydrofuran-3-yl) 4-(1-adamantyl)butyl carbonate, ((2R,3S,5R)-5-(6-amino-2-fluoro-9H-purin-9-yl)-2-ethynyl-3-hydroxy-tetrahydrofuran-2-yl)methyl 3-(1-adamantyl)propanoate, ((2R,3S,5R)-5-(6-amino-2-fluoro-9H-purin-9-yl)-2-ethynyl-3-hydroxy-tetrahydrofuran-2-yl)methyl 4-(1-adamantyl)butanoate, (10aR,12R,13aS)-12-(6-amino-2-fluoro-9H-purin-9-yl)-10a-ethynylhexahydro-4H,10H-furo[3,2-d][1,3,7,9]tetraoxacyclododecine-2,8-dione, (11aR,13R,14aS)-13-(6-amino-2-fluoro-9H-purin-9-yl)-11a-ethynyloctahydro-11H-furo[3,2-d][1,3,7]trioxacyclotridecine-2,9(4H)-dione,
((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) ethyl carbonate,
((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) isobutyrate,
((2R,3S,5R)-2-(((((1-adamantyl)methoxy)carbonyl)oxy)methyl)-5-(6-amino-2-fluoro-9H-purin-9-yl)-2-ethynyltetrahydrofuran-3-yl) isobutyrate,
((2R,3S,5R)-2-((((3-(1-adamantyl)propoxy)carbonyl)oxy)methyl)-5-(6-amino-2-fluoro-9H-purin-9-yl)-2-ethynyltetrahydrofuran-3-yl) isobutyrate,
((2R,3S,5R)-3-[3-(1-adamantyl)propoxycarbonyloxy]-5-(6-amino-2-fluoro-9H-purin-9-yl)-2-ethynyl-tetrahydrofuran-2-yl)methyl 3-(1-adamantyl)propyl carbonate,
((2R,3S,5R)-3-(1-adamantylmethoxycarbonyloxy)-5-(6-amino-2-fluoro-9H-purin-9-yl)-2-ethynyl-tetrahydrofuran-2-yl)methyl 1-adamantylmethyl carbonate,
((2R,3S,5R)-2-(1-adamantylmethoxycarbonyloxymethyl)-5-(6-amino-2-fluoro-9H-purin-9-yl)-2-ethynyl-tetrahydrofuran-3-yl) ethyl carbonate,
((2R,3S,5R)-2-[4-(1-adamantyl)butoxycarbonyloxymethyl]-5-(6-amino-2-fluoro-9H-purin-9-yl)-2-ethynyl-tetrahydrofuran-3-yl) ethyl carbonate,
((2R,3S,5R)-2-[3-(1-adamantyl)propoxycarbonyloxymethyl]-5-(6-amino-2-fluoro-9H-purin-9-yl)-2-ethynyl-tetrahydrofuran-3-yl) ethyl carbonate,
1-adamantyl ((2R,3S,5R)-5-(6-amino-2-fluoro-purin-9-yl)-3-ethoxycarbonyloxy-2-ethynyl-tetrahydrofuran-2-yl) methyl carbonate,
((2R,3S,5R)-2-(1-adamantyloxycarbonyloxymethyl)-5-(6-amino-2-fluoro-9H-purin-9-yl)-2-ethynyl-tetrahydrofuran-3-yl) 2-methylpropanoate,
(1R,13R,15R)-15-(6-amino-2-fluoro-9H-purin-9-yl)-13-ethynyl-2,9,11,14-tetraoxabicyclo[11.3.0]hexadecane-3,10-dione, and
(6R,8R,10R)-8-(6-amino-2-fluoro-9H-purin-9-yl)-10-ethynyl-3,5,9,12,14-pentaoxatricyclo[14.4.0.06,10]icosane-4,13-dione.

An adenosine derivative of the present disclosure can undergo conversion to a target drug that can comprise reverse transcriptase inhibitor activity in vivo, reverse transcriptase chain terminator activity in vivo, DNA translocation inhibitor activity in vivo, or a combination thereof. Accordingly, the adenosine derivatives of the present disclosure can be used to treat HIV, AIDS, a RNA infection, or other disease disclosed herein.

An adenosine derivative of the present disclosure can be a prodrug that has no or limited activity in its original (i.e., parent) form shown herein and can be metabolized in vivo to exhibit the desired activity of a target drug including a reverse transcriptase inhibitor activity, a reverse transcriptase chain terminator activity, DNA translocation inhibitor activity, or a combination thereof.

Not wishing to be bound by a particular mechanism or theory, Applicants discovered that the adenosine derivatives of the present disclosure can be metabolized in vivo to produce a compound or a mixture of compounds similar to or the same as a target drug 4'-ethynyl-2-fluoro-2'-deoxyadenosine (EFdA) that has reverse transcriptase inhibitor and other antiviral activities.

An adenosine derivative of the present disclosure can comprise one or more isomers thereof. In some embodiments, the adenosine derivative of the present disclosure is an isomer of formula (I)—(Ir), or compound (1)-(30). In some embodiments, the isomer is a stereoisomer, e.g., an enantiomer or a diastereomer. In some embodiments, the isomer is an inhibitor of reverse transcriptase having in vivo activity.

The present disclosure is further directed to pharmaceutical compositions comprising an adenosine derivative disclosed herein (e.g., a compound of formula (I)—(Ir) or a compound (1)-(30)) or pharmaceutically acceptable salt, tautomer, or solvate thereof, and a pharmaceutical acceptable carrier.

In some embodiments, the pharmaceutical composition comprises an adenosine derivative having a structure of formula (I) or pharmaceutically acceptable salt, tautomer, or solvate thereof:

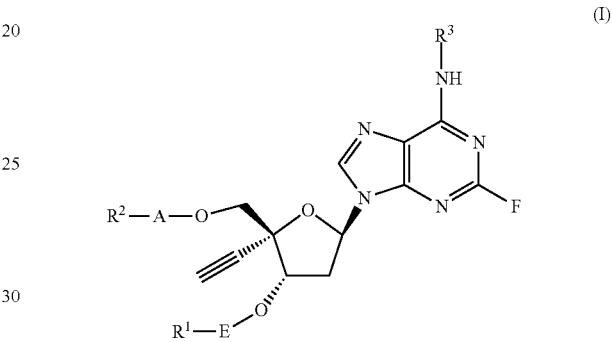

(I)

wherein:
A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;
R$^1$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl;
R$^2$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl, wherein at least one of R$^1$ and R$^2$ is not H;
R$^1$ and R$^2$ can join together with the atoms to which they are attached to form a 3- to 25-membered heterocyclic ring; and
R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ia), (Ib), or a pharmaceutically acceptable salt, tautomer, or solvate thereof:

(Ia)

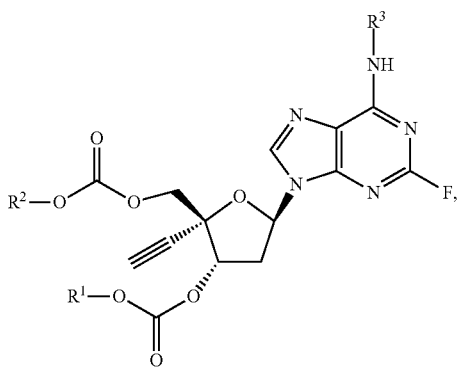

(Ib)

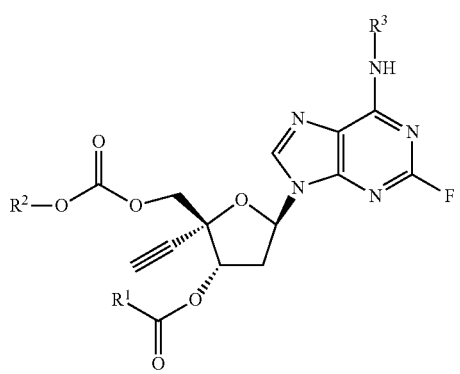

wherein:
  R¹ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;
  R² is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of R¹ and R² is not H; and
  R³ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ic), (Id), or a pharmaceutically acceptable salt, tautomer, or solvate thereof:

(Ic)

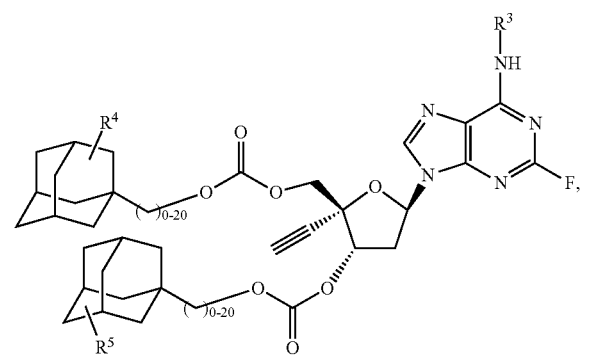

(Id)

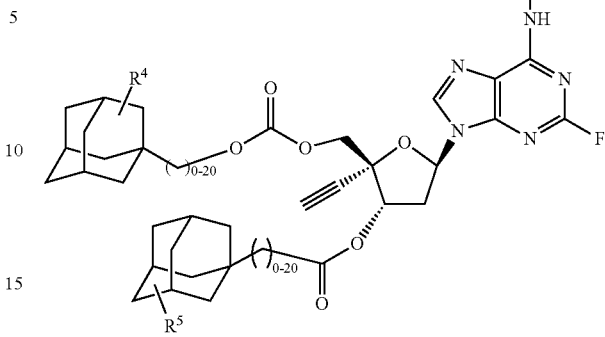

wherein:
  R³ is selected from the group consisting of H, —(CO)-G-$C_{1-10}$alkyl, and $C_{1-10}$alkyl;
  R⁴ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and
  R⁵ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ie), (If), or a pharmaceutically acceptable salt, tautomer, or solvate thereof:

(Ie)

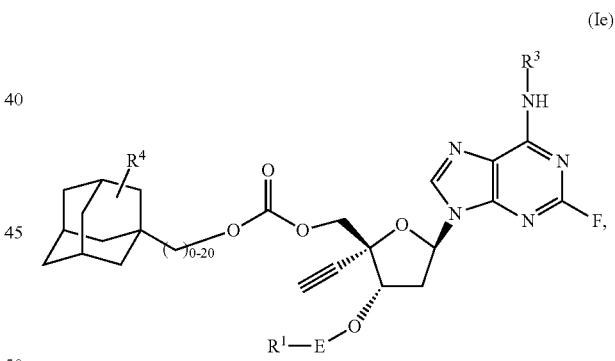

(If)

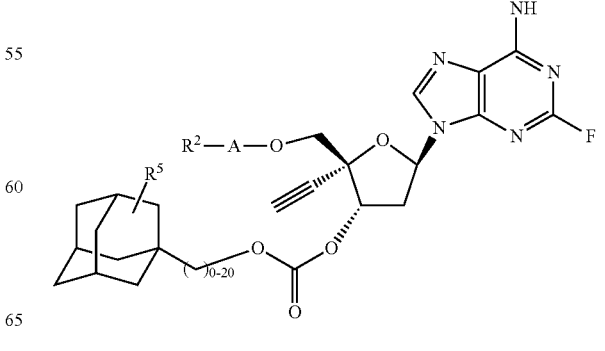

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
$R^2$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
$R^3$ is selected from the group consisting of H, —(CO)—O—$C_{1-10}$alkyl, and $C_{1-10}$alkyl;
$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and
$R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ig) or a pharmaceutically acceptable salt, tautomer, or solvate thereof:

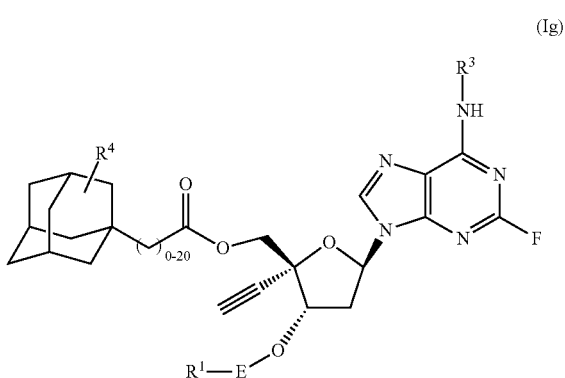

(Ig)

wherein:
E is selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
$R^3$ is selected from the group consisting of H, —(CO)—O—$C_{1-10}$alkyl, and $C_{1-10}$alkyl; and
$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ih) or a pharmaceutically acceptable salt, tautomer, or solvate thereof:

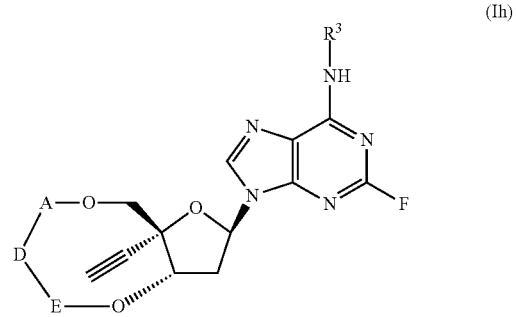

(Ih)

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
D is selected from the group consisting of —$C_{1-20}$alkylene-, —$C_{2-20}$alkenylene-, and —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and
$R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ii), (Ij), or a pharmaceutically acceptable salt, tautomer, or solvate thereof:

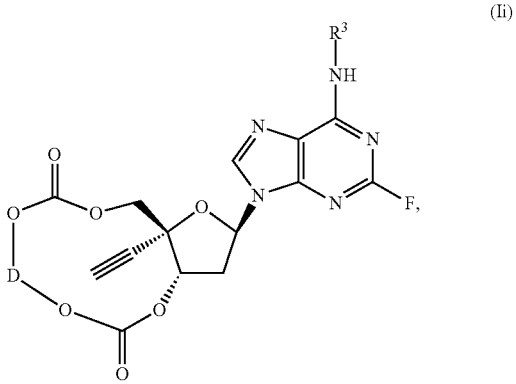

(Ii)

(Ij)

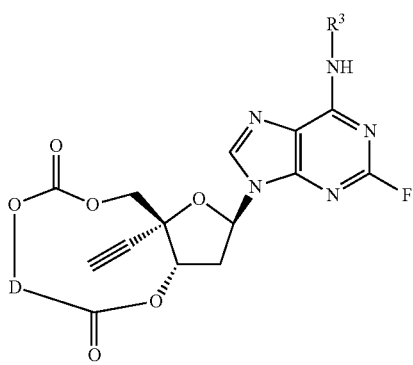

wherein:
D is selected from the group consisting of —$C_{1-20}$alkylene-, —$C_{2-20}$alkenylene-, and —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and $R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ik), (Il), or a pharmaceutically acceptable salt, tautomer, or solvate thereof:

(Ik)

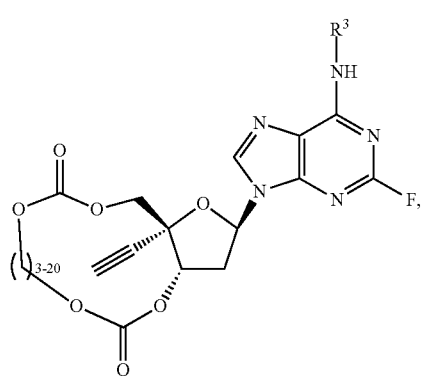

(Il)

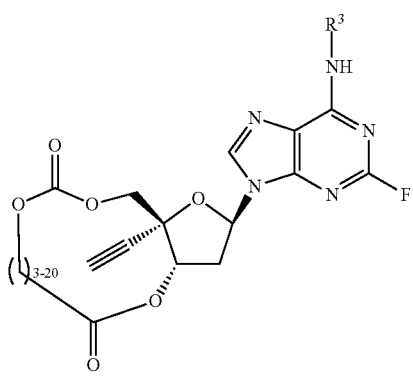

wherein:
$R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Im) or a pharmaceutically acceptable salt, tautomer, or solvate thereof:

(Im)

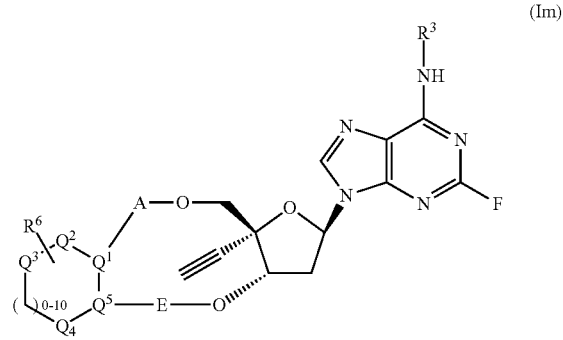

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (In), (Io), or a pharmaceutically acceptable salt, tautomer, or solvate thereof:

(In)

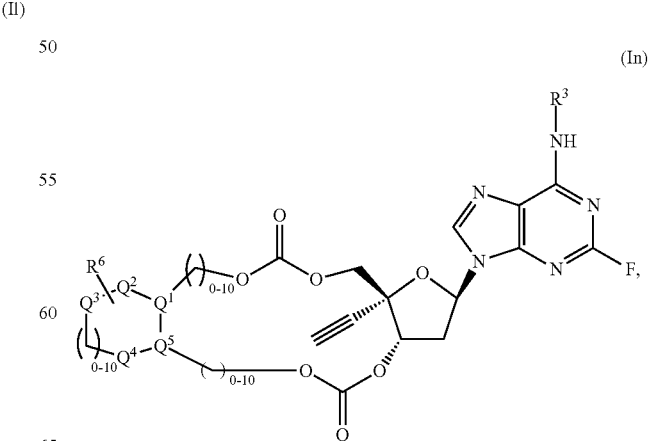

-continued (Io)

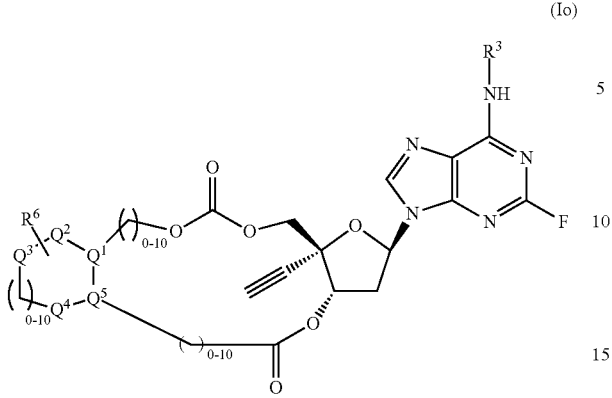

R³ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl;

Q¹, Q², Q³, Q⁴, and Q⁵ form a cyclic ring, wherein said ring is selected from the group consisting of cycloalkyl, heterocycloalkyl, aryl, and heteroaryl; and R⁶ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Ip) or a pharmaceutically acceptable salt, tautomer, or solvate thereof:

(Ip)

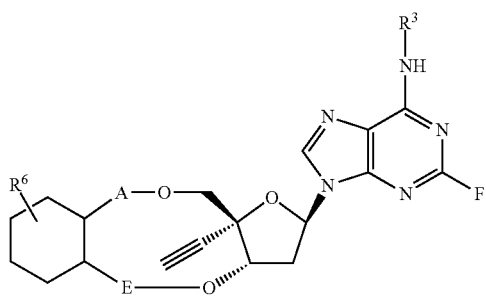

wherein:
A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-; R³ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl; and
R⁶ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments, the pharmaceutical composition of the present disclosure comprises an adenosine derivative having a structure of formula (Iq), (Ir), or a pharmaceutically acceptable salt, tautomer, or solvate thereof:

(Iq)

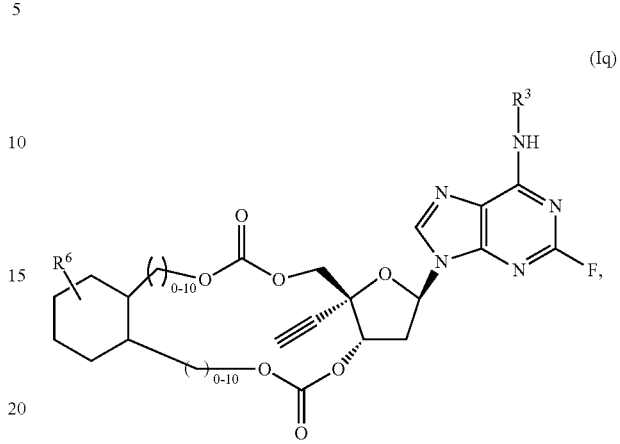

(Ir)

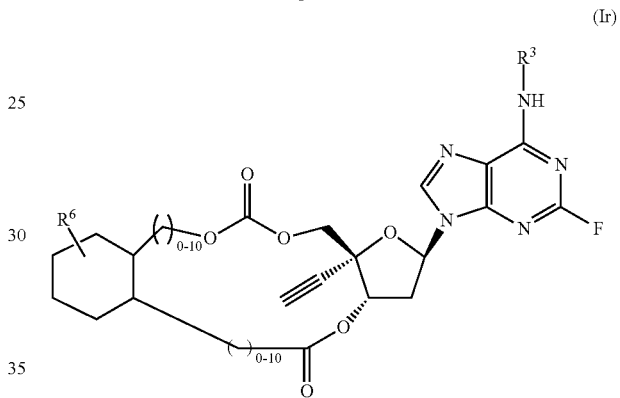

wherein:
R³ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl; and
R⁶ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments, the pharmaceutical composition of the present disclosure comprises an adenosine derivative selected from the group consisting of compound as disclosed in Table 1 and a pharmaceutically acceptable salt, tautomer, or solvate thereof.

An adenosine derivative of the present disclosure can comprise one or more isomers thereof. In some embodiments, the adenosine derivative of the present disclosure is an isomer of formula (I)—(Ir), or compound (1)-(30). In some embodiments, the isomer is a stereoisomer, e.g., an enantiomer or a diastereomer. In some embodiments, the isomer is an inhibitor of reverse transcriptase having in vivo activity.

As disclosed above, a pharmaceutical composition of the present disclosure comprises an adenosine derivative that can be free from monophosphate group, diphosphate group, tri-phosphate group or a combination thereof. In some embodiments, an R¹ and/or R² group of an adenosine derivative of disclosed herein is free from monophosphate group, diphosphate group, tri-phosphate group or a combination thereof.

As described, the pharmaceutical composition of the present disclosure comprises a pharmaceutically acceptable carrier.

Non-limiting examples of a pharmaceutically acceptable carrier include a pharmaceutical excipients surfactant, emulsifier, filler, carrier, isotonicifier, dispersing agent, viscosity modifier, resuspending agent, buffer or a combination thereof. Pharmaceutical excipients typically do not have properties of a medicinal or drug active ingredient, also known as active pharmaceutical ingredient (API) and are typically used to streamline the manufacture process or packaging of the active ingredients, or to deliver an API to a patient or other subject. Pharmaceutical acceptable carrier, excipients or inactive ingredients from the Inactive Ingredients Database available from US FDA (https://www.fda.gov/drugs/drug-approvals-and-databases/inactive-ingredients-database-download) can be suitable. Some of Generally Recognized As Safe (GRAS) food substances available form US FDA's GRAS Substances (SCOGS) Database (https://www.fda.gov/food/generally-recognized-safe-gras/gras-substances-scogs-database) can also be suitable.

In some embodiments of the present disclosure, the pharmaceutical acceptable carrier comprises polyethylene glycol (PEG), sulfobutylether b-cyclodextrin (SRBCD), acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxpropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, or combinations thereof.

In further embodiments, the pharmaceutical acceptable carrier comprises dextrose, glycerin, histidine, hydrochloric acid, hydroxypropyl cellulose, hydroxypropyl-β-cyclodextrin (HPBCD), hypromellose (hydroxypropyl methylcellulose (HPMC)), polyoxyethylene (20) sorbitan monolaurate (Tween 20, Polysorbate 20), polyethylene glycols (PEG 400, PEG 3350, PEG 4000, PEG 6000), polyoxyethylene-polyoxypropylene copolymer (Poloxamer 188, Poloxamer 407), polyoxyethylene (20) sorbitan monooleate (Tween 80, Polysorbate 80), saline, sodium chloride, sodium citrate, sodium citrate dihydrate, sodium lauryl sulfate, sodium phosphate monobasic, sodium phosphate dibasic, or a combination thereof.

The pharmaceutical compositions of the present disclosure can further comprise an effective dosage of one or more additional anti-HIV agents (also referred to as anti-viral agents) selected from the group consisting of lenacapavir, atazanavir, atazanavir sulfate, bictegravir, cabotegravir, darunavir, dolutegravir, doravirine, efavirenz, tenofovir disoproxil fumarate, tenofovir alafenamide, etravirine, a combination of darunavir and cobicistat, rilpivirine, or a combination thereof. In some embodiments, the one or more additional anti-HIV agents are selected from the group consisting of lenacapavir, bictegravir and cabotegravir. In some embodiments, the pharmaceutical compositions of the present disclosure further comprise an effective dosage of one additional anti-HIV agent. In some embodiments, the pharmaceutical compositions of the present disclosure further comprise an effective dosage of two additional anti-HIV agents.

In some embodiments, the pharmaceutical compositions of the present disclosure comprise an adenosine derivative, e.g., a compound of formula (I)—(Ir), or compound (1)-(30), and the one or more additional anti-HIV agents in a single formulation that can be administered to a subject together.

Accordingly, in some embodiments, the pharmaceutical compositions of the present disclosure comprise (1) an effective dosage of: (a) an adenosine derivative or pharmaceutically acceptable salt, tautomer, or solvate thereof (e.g., a compound of formula (I)—(Ir), or compound (1)-(30)); and (b) one or more additional anti-HIV agents disclosed herein; and (2) a pharmaceutically acceptable carrier disclosed herein.

The pharmaceutical composition of the present disclosure can comprise the adenosine derivative and the one or more additional anti-HIV agents in separate formulations that can be administered to a subject simultaneously or sequentially. The pharmaceutical composition of the present disclosure can also be mixed together with one or more additional disclosed anti-HIV agents in separate formulations that can be administered to a subject simultaneously.

The present disclosure is further directed to a method for treating a disease, the method comprising administering a subject in need thereof an effective dosage of a pharmaceutical composition comprising an adenosine derivative (e.g., a compound of formula (I)—(Ir) or compound (1)-(30)) or pharmaceutically acceptable salt, tautomer, or solvate thereof disclosed herein.

In some embodiments of the present methods, the adenosine derivative is a compound of formula (I) or a pharmaceutically acceptable salt, tautomer, or solvate thereof:

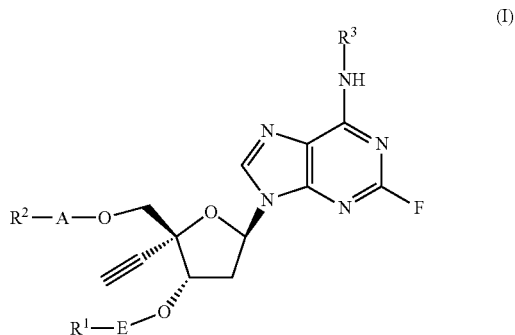

(I)

A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;

$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H;

$R^1$ and $R^2$ can join together with the atoms to which they are attached to form a 3- to 25-membered heterocyclic ring; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Ia), (Ib), or a pharmaceutically acceptable salt, tautomer, or solvate thereof:

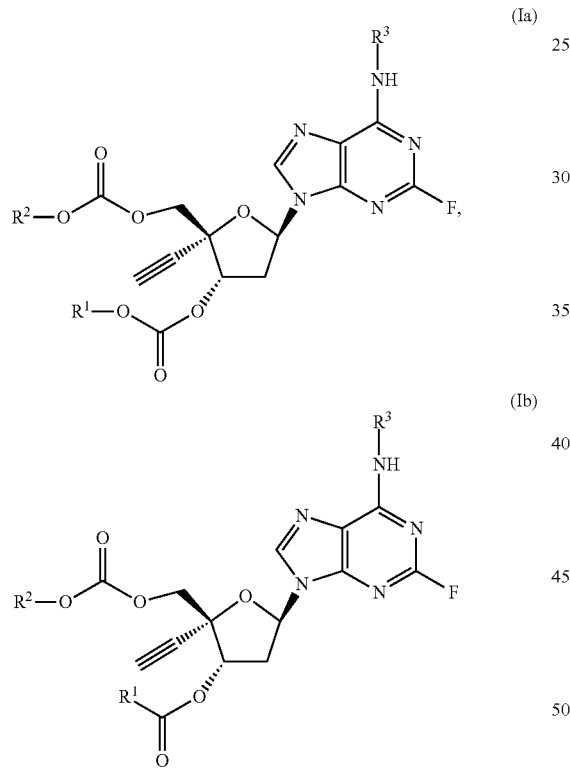

In some embodiments of the present method, the adenosine derivative is a compound of formula (Ic), (Id), or pharmaceutically acceptable salt, tautomer, or solvate thereof:

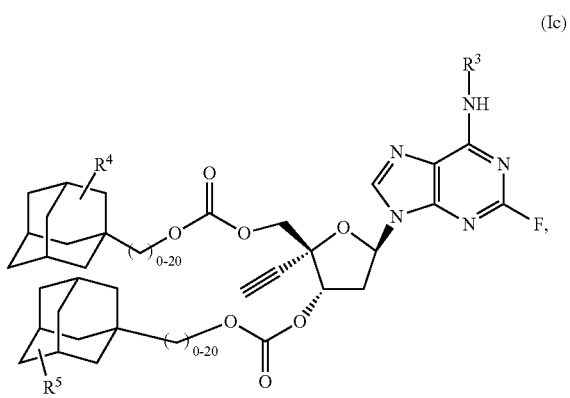

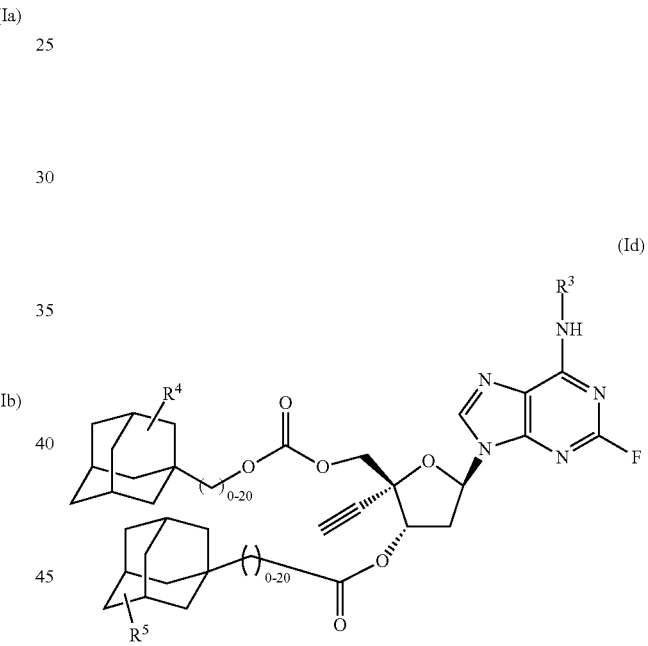

$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

wherein:

$R^3$ is selected from the group consisting of H, —(CO)-G-$C_{1-10}$alkyl, and $C_{1-10}$alkyl;

$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Ie), (If), or a pharmaceutically acceptable salt, tautomer, or solvate thereof:

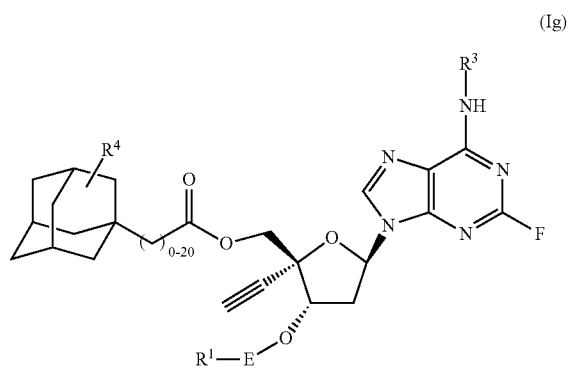

(Ie)

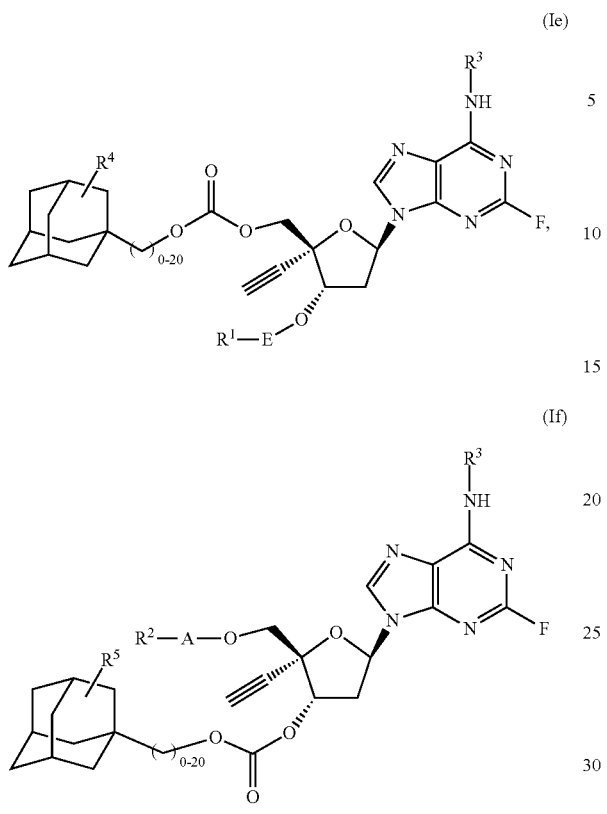

(If)

wherein:
A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;
R$^1$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-20}$cycloalkyl, 3- to 20-membered heterocycloalkyl, aryl, and heteroaryl;
R$^2$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-20}$cycloalkyl, 3- to 20-membered heterocycloalkyl, aryl, and heteroaryl;
R$^3$ is selected from the group consisting of H, —(CO)—O—C$_{1-10}$alkyl, and C$_{1-10}$alkyl;
R$^4$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl; and
R$^5$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments of the present method, the adenosine derivative is a compound of formula (Ig) or a pharmaceutically acceptable salt, tautomer, or solvate thereof:

(Ig)

wherein:
E is selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;
R$^1$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-20}$cycloalkyl, 3- to 20-membered heterocycloalkyl, aryl, and heteroaryl;
R$^3$ is selected from the group consisting of H, —(CO)—O—C$_{1-10}$alkyl, and C$_{1-10}$alkyl; and
R$^4$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments of the present method, the adenosine derivative is a compound of formula (Ih) or a pharmaceutically acceptable salt, tautomer, or solvate thereof:

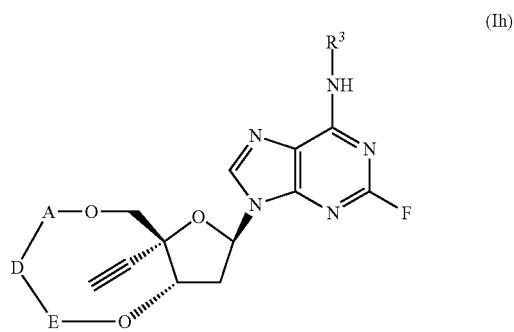

(Ih)

wherein:
A and E are each independently selected from the group consisting of a bond, —(CO)—, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;
D is selected from the group consisting of —C$_{1-20}$alkylene-, —C$_{2-20}$alkenylene-, and —C$_{2-20}$alkynylene-, —C$_{1-20}$haloalkylene-, —C$_{1-20}$alkoxyalkylene-, $C_{3-20}$cycloalkyl, 3- to 20-membered heterocycloalkyl, aryl, and heteroaryl; and $R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Ii), (Ij), or a pharmaceutically acceptable salt, tautomer, or solvate thereof:

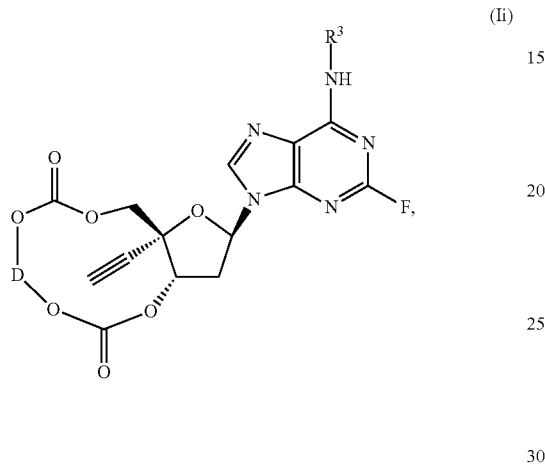

(Ii)

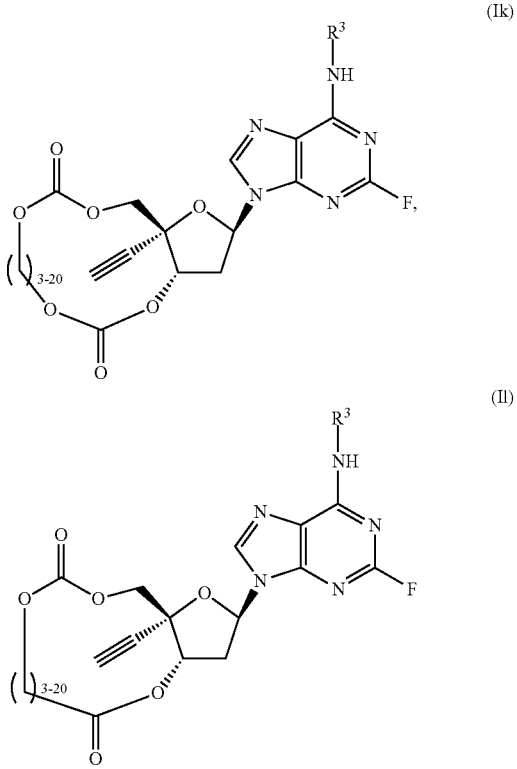

(Ik)

(Il)

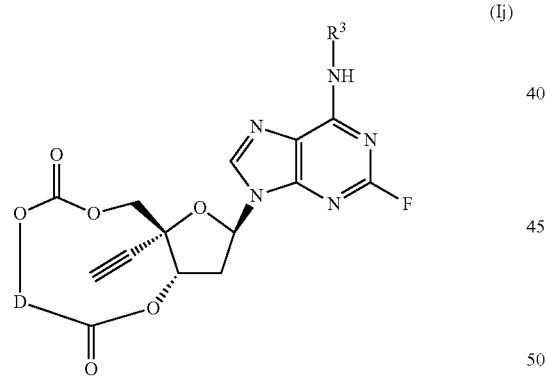

(Ij)

wherein:
D is selected from the group consisting of —$C_{1-20}$alkylene-, —$C_{2-20}$alkenylene-, and —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and $R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Ik), (Il), or a pharmaceutically acceptable salt, tautomer, or solvate thereof:

wherein:
$R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Im) or a pharmaceutically acceptable salt, tautomer, or solvate thereof:

(Im)

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (In), (Io), or a pharmaceutically acceptable salt, tautomer, or solvate thereof:

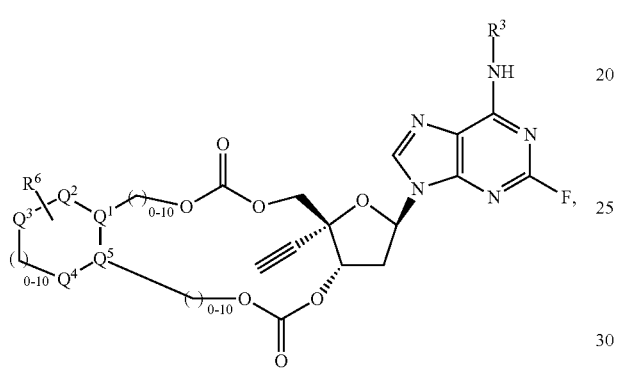
(In)

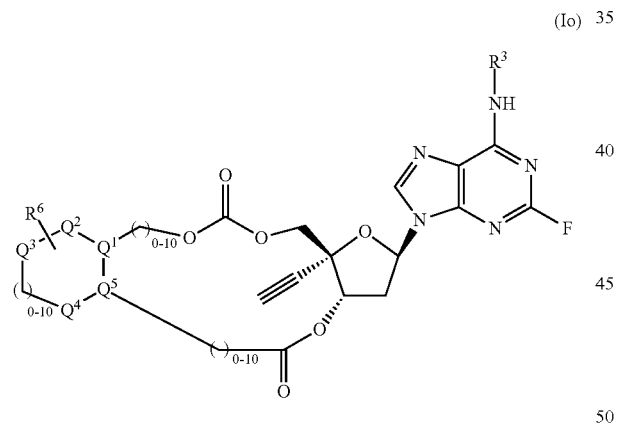
(Io)

wherein:

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Ip) or a pharmaceutically acceptable salt, tautomer, or solvate thereof:

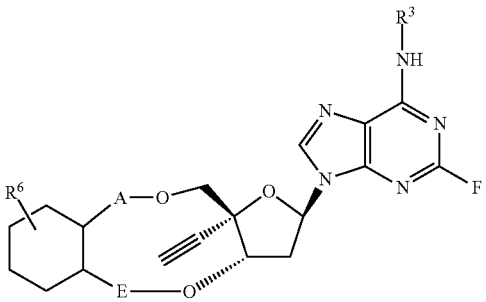
(Ip)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

In some embodiments of the present method, the adenosine derivative is a compound of formula (Iq), (Ir), or a pharmaceutically acceptable salt, tautomer, or solvate thereof:

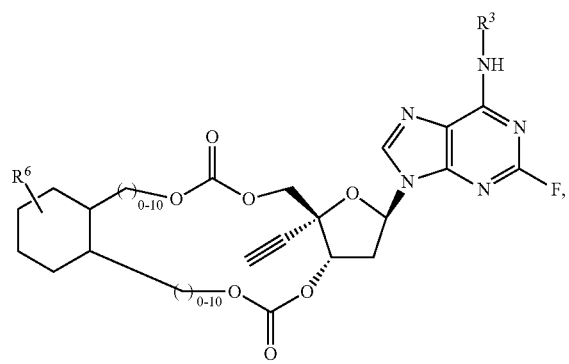
(Iq)

-continued

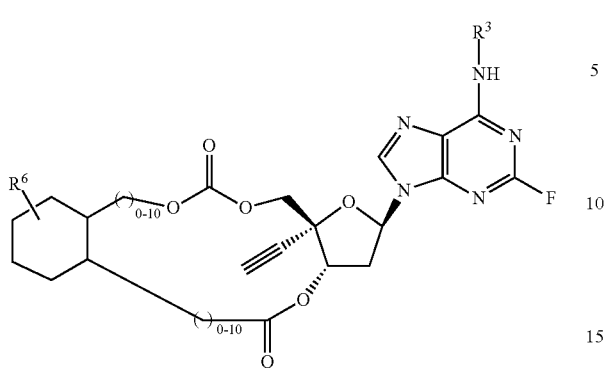

(Ir)

wherein:
R³ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl; and
R⁶ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, 3- to 12-membered heterocycloalkyl, aryl, and heteroaryl.

In some embodiments of the present method, the adenosine derivative is selected from the group consisting of compound as disclosed in Table 1 and a pharmaceutically acceptable salt, tautomer, or solvate thereof.

An adenosine derivative of the present disclosure can comprise one or more isomers thereof. In some embodiments, the adenosine derivative of the present disclosure is an isomer of formula (I)—(Ir), or compound (1)-(30). In some embodiments, the isomer is a stereoisomer, e.g., an enantiomer or a diastereomer. In some embodiments, the isomer is an inhibitor of reverse transcriptase having in vivo activity.

In some embodiments of the present methods, the pharmaceutical composition is administered to a subject via intramuscular (IM) injection, subcutaneous (SC) injection, intravenous (IV) injection, oral administration, topical application, implant application or a combination thereof. In some embodiments, the pharmaceutical compositions of the present disclosure are formulated for intramuscular injection and/or subcutaneous injection. An implant application can include an implantable device or a film that contains the pharmaceutical composition disclosed herein. The implant application can comprise vaginal ring, film, membrane, patch, other devices, or a combination thereof.

The method of the present disclosure can further comprise measuring a specimen of the subject to determine a measured level of a target drug in the specimen, wherein the target drug can have a formula (T-1):

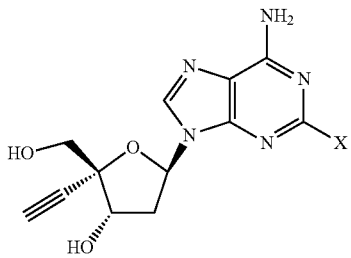

(T-1)

an isomer thereof, or a pharmaceutically acceptable salt thereof. In some embodiments, X is a halogen selected from the group consisting of F, Cl, Br and I. In some embodiments X is I.

In some embodiments, the target drug is a compound having a structure of formula (T-1A):

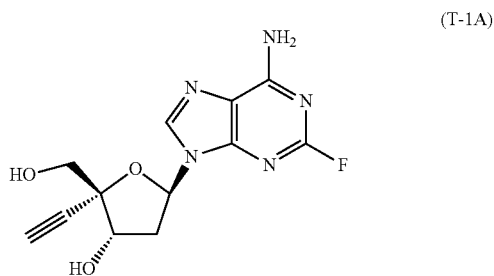 [SMILES: C#C[C@]1(CO)O[C@@H](n2cnc3c(N)nc(F)nc32)C[C@@H]1O]

(T-1A)

or a pharmaceutically acceptable salt, stereoisomer, tautomer thereof. Formula (T-1A) is also referred to herein as EFdA.

In some embodiments, the target drug is (2R,3S,5R)-5-(6-amino-2-fluoro-9H-purin-9-yl)-2-ethynyl-2-(hydroxymethyl)tetrahydrofuran-3-ol (also referred to as 4'-ethynyl-2-fluoro-2'-deoxyadenosine, EFdA), or a pharmaceutically acceptable salt thereof.

In some embodiments, the target drug is a degradation or metabolized product of the compound (T-1), (T-1A) or EFdA.

The specimen can be a blood sample, a urine sample, a body fluid sample, a tissue sample or a combination thereof from the subject, such as a patient.

The measured level of the target drug can be determined with an analytical method known to those skilled in the art, such as, but not limited to, HPLC, GC, MS, GC-MS, or a combination thereof.

The method of the present disclosure can further comprise adjusting the effective dosage to produce a modified effective dosage if the measured level of the target drug is different from a predetermined target level of the target drug and administering the modified effective dosage to the subject.

In some embodiments of the present method, the disease is HIV, Acquired Immune Deficiency Syndrome (AIDS), or an RNA virus infection. In some embodiments, the disease is AIDS, wild-type HIV-1, NRTI-resistant HIV-1, HIV-2, HIV having M184V mutations, HIV having K65R, multidrug resistant HIV, or an RNA virus infection. In some embodiments, the disease is wild-type HIV-1, NRTI-resistant HIV-1, HIV-2, HIV having M184V mutations, HIV having K65R, or multidrug resistant HIV.

In some embodiments, the methods of the present disclosure further comprise administering to a subject an effective dosage of one or more additional anti-HIV agents selected from lenacapavir, atazanavir, atazanavir sulfate, bictegravir, cabotegravir, darunavir, dolutegravir, doravirine, efavirenz, tenofovir disoproxil fumarate, tenofovir alafenamide, etravirine, a combination of darunavir and cobicistat, rilpivirine, MK-8507 or a combination thereof. In some embodiments, the one or more additional anti-HIV agents are selected from the group consisting of lenacapavir, bictegravir and cabotegravir. Other anti-HIV agents identified or developed, or combination thereof, can also be suitable.

Combinations of the adenosine derivative of the present disclosure (e.g., formula (I)—(Ir) or compound (1)-(30) and the one or more additional anti-HIV agents described herein can be useful for the treatment or prophylaxis of AIDS or other HIV related symptoms. The additional anti-HIV agents can be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network.

An adenosine derivative of the present disclosure and the one or more additional anti-HIV agents described herein can be administered to a subject together or separately via oral administration, parenteral administration or a combination thereof. In some embodiments, parenteral administration comprises SC and/or IM injection. The adenosine derivative and the one or more additional anti-HIV agents can be administered to the subject with a daily, weekly, biweekly or monthly administration schedule.

The present disclosure is further directed to a use of the pharmaceutical composition for the treatment of a disease in a subject in need thereof, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. Any of the aforementioned pharmaceutical compositions can be suitable. The pharmaceutical composition can be used together with one or more additional anti-HIV agents for the treatment of the disease mentioned herein. The adenosine derivative and the one or more additional anti-HIV agents can be administered to a subject together or separately via oral administration, parenteral administration or a combination thereof. The adenosine derivative and the one or more additional anti-HIV agents can be administered to the subject with a daily, weekly, biweekly or monthly administration schedule.

The present disclosure is further directed to a use of the adenosine derivative, optionally, one or more pharmaceutically acceptable carriers, disclosed herein for manufacturing a medicament for treating a disease, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. Aforementioned adenosine derivatives can be suitable. Aforementioned pharmaceutically acceptable carriers can be suitable.

The present disclosure is further directed to a method for the prevention of infection in a subject in need thereof, the method comprising administering the subject an effective dosage of a pharmaceutical composition of the present method disclosed herein, wherein the subject is free from detectable symptoms of the infection. In some embodiments, the infection comprises a disease selected from Acquired Immune Deficiency Syndrome (AIDS), an infection of wild-type HIV-1, NRTI-resistant HIV-1, HIV-2, HIV having M184V mutations, HIV having K65R, multidrug resistant HIV, an RNA virus infection, or a combination thereof.

The detectable symptoms include, but are not limited to, symptoms of Acquired Immune Deficiency Syndrome (AIDS), symptoms of infection of HIV viruses comprising wild-type HIV-1, NRTI-resistant HIV-1, HIV-2, HIV having M184V mutations, HIV having K65R, multidrug resistant HIV, or a combination thereof. The detection of the HIV viruses can be done by PCR, reverse PCR, immunodetection of an antigen or an antibody related to AIDS or HIV.

In some embodiments, the pharmaceutical composition of the present method is administered to said subject with a daily, weekly, biweekly or monthly administration schedule.

In some embodiments, the method of the present disclosure further comprises administering the subject an effective dosage of one or more additional anti-HIV agents selected from lenacapavir, atazanavir, atazanavir sulfate, bictegravir, cabotegravir, darunavir, dolutegravir, doravirine, efavirenz, tenofovir disoproxil fumarate, tenofovir alafenamide, etravirine, a combination of darunavir and cobicistat, rilpivirine, MK-8507 or a combination thereof. In some embodiments, the one or more additional anti-HIV agents are selected from the group consisting of lenacapavir, bictegravir and cabotegravir.

The one or more additional anti-HIV agents can be administered to the subject together with the pharmaceutical composition of the present disclosure or separately.

Without being bound by any particular theory, an advantage of the adenosine derivatives disclosed herein (e.g., formula (I)—(Ir), or compound (1)-(30) is the fast conversion to the target drug. In some embodiments, the fast conversion is a time period of less than about 1 h, e.g., a period of from about 30 min to about 45 min. As described below, greater than about 60% of the adenosine derivatives of the present disclosure surprisingly and unexpectedly can be converted to the target drug within about 30 min in contact with human plasma. In some embodiments, greater than about 60%, greater than about 65%, greater than about 70%, greater than about 75%, greater than about 80%, greater than about 85%, greater than about 90%, or greater than about 95% of an adenosine derivative disclosed herein is converted to the target drug without about 30 min in contact with human plasma. In some embodiments, the conversion occurs in vitro. In some embodiments, the conversion occurs in vivo. In some embodiments, the conversion occurs after parenteral (e.g. SC and/or IM) administration. In some embodiments, the conversion occurs after oral administration.

NUMBERED EMBODIMENTS OF THE DISCLOSURE

Other subject matter contemplated by the present disclosure is set out in the following numbered embodiments:

1. An adenosine derivative having a structure of formula (I) or a pharmaceutically acceptable salt, tautomer, or solvate thereof:

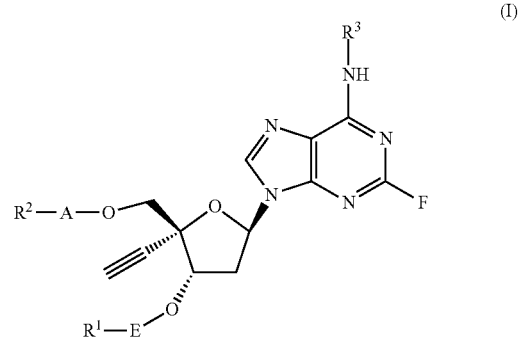

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;
$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H;
$R^1$ and $R^2$ can join together with the atoms to which they are attached to form a 3- to 25-membered heterocyclic ring; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

1a. The adenosine derivative of embodiment 1, wherein A is selected from the group consisting of a bond, —(CO)—, —(CO)-G-, and —(CO)-G-($C_{1-5}$alkylene)-J-.

1b. The adenosine derivative of embodiment 1 or 1a, wherein A is —(CO)-G- or —(CO)-G-($C_{1-5}$alkylene)-J-.

1c. The adenosine derivative of any one of embodiments 1-1b, wherein E is a bond, —(CO)-G-, and —(CO)-G-($C_{1-5}$alkylene)-J-.

1d. The adenosine derivative of any one of embodiments 1-1c, wherein E is a bond.

1e. The adenosine derivative of any one of embodiments 1-1d, wherein G is a bond or O.

1f. The adenosine derivative of any one of embodiments 1-1e, wherein J is a bond or O.

1g. The adenosine derivative of any one of embodiments 1-1f, wherein G is O and J is a bond.

1h. The adenosine derivative of any one of embodiments 1-1g, wherein $R^1$ is H, $C_{1-5}$alkyl, or adamantyl

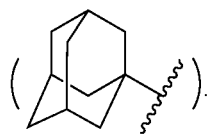

1i. The adenosine derivative of any one of embodiments 1-1h, wherein $R^1$ is H.

1j. The adenosine derivative of any one of embodiments 1-1i, wherein $R^2$ is H, $C_{1-5}$alkyl, or adamantyl.

1k. The adenosine derivative of any one of embodiments 1-1j, wherein $R^2$ is adamantyl

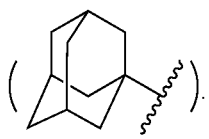

1l. The adenosine derivative of any one of embodiments 1-1g, wherein $R^1$ and $R^2$ taken together with the atoms to which they are attached form a 6- to 15-membered heterocyclic ring.

1m. The adenosine derivative of any one of embodiments 1-1l, wherein $R^3$ is —(CO)—$C_{1-5}$alkyl, —(CO)—O—$C_{1-5}$alkyl, or $C_{1-5}$alkyl.

1n. The adenosine derivative of any one of embodiments 1-1m, wherein $R^3$ is H.

2. The adenosine derivative of embodiment 1, wherein said adenosine derivative is a compound of formula (Ia), (Ib), or a pharmaceutically acceptable salt, tautomer, or solvate thereof:

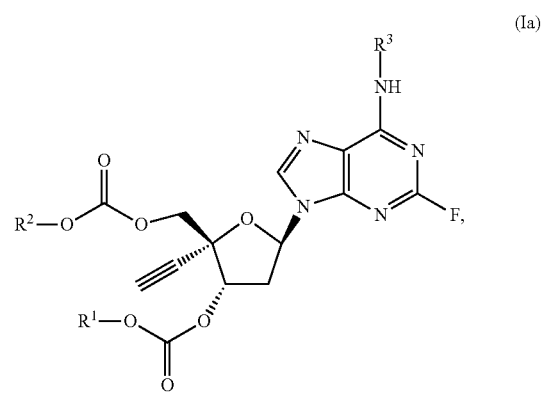

(Ia)

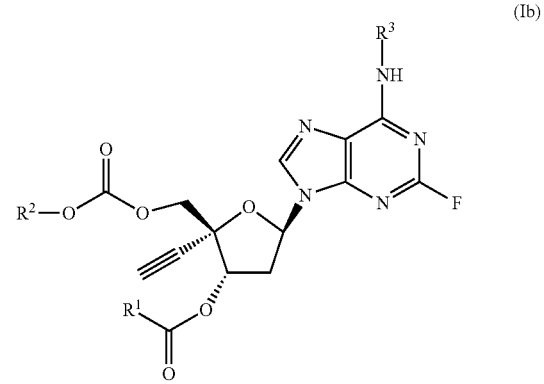

(Ib)

wherein:
$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, $C_{3-20}$heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, $C_{3-20}$heterocycloalkyl, aryl, and heteroaryl, wherein at least one of $R^1$ and $R^2$ is not H; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, $C_{3-12}$heterocycloalkyl, aryl, and heteroaryl.

3. The adenosine derivative of embodiment 1, wherein said adenosine derivative is a compound of formula (Ic), (Id), or a pharmaceutically acceptable salt, tautomer, or solvate thereof:

(Ic)

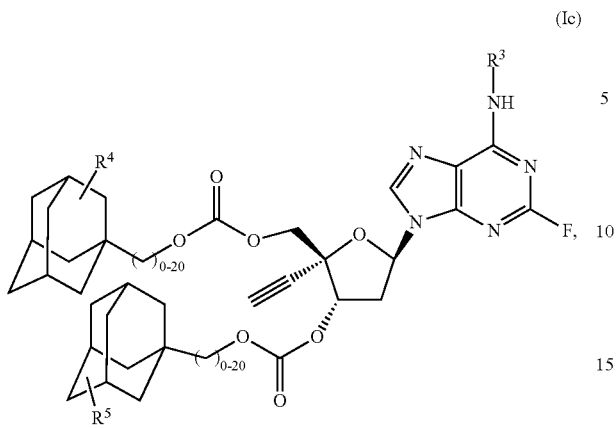

(Id)

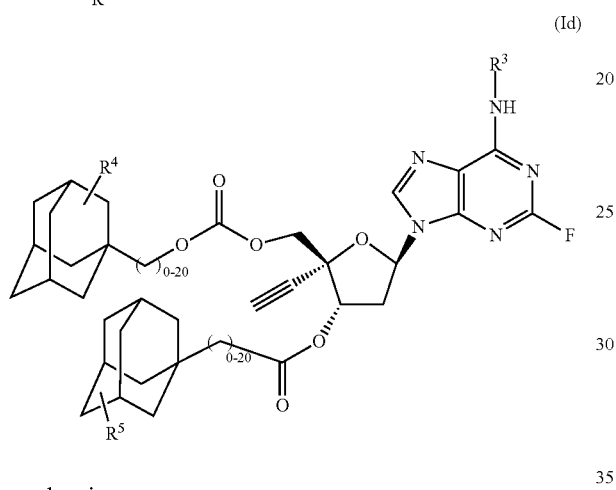

wherein:
R³ is selected from the group consisting of H, —(CO)-G-$C_{1-10}$alkyl, and $C_{1-10}$alkyl;
R⁴ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, $C_{3-12}$heterocycloalkyl, aryl, and heteroaryl; and
R⁵ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, $C_{3-12}$heterocycloalkyl, aryl, and heteroaryl.

4. The adenosine derivative of embodiment 1, wherein said adenosine derivative is a compound of formula (Ie), (If), or a pharmaceutically acceptable salt, tautomer, or solvate thereof:

(Ie)

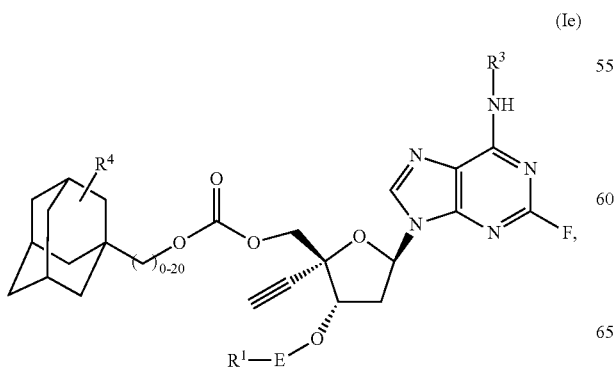

(If)

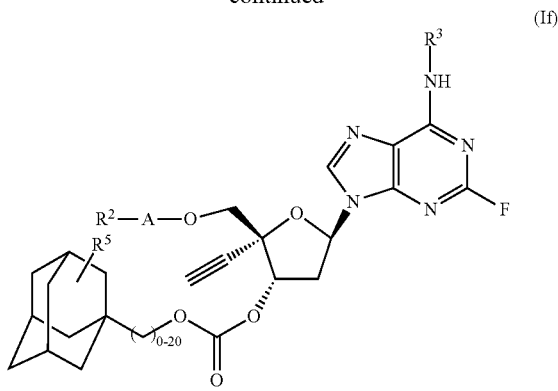

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
R¹ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
R² is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;
R³ is selected from the group consisting of H, —(CO)—O—$C_{1-10}$alkyl, and $C_{1-10}$alkyl; and
R⁴ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and
R⁵ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

5. The adenosine derivative of embodiment 1, wherein said adenosine derivative is a compound of formula (Ig) or a pharmaceutically acceptable salt, tautomer, or solvate thereof:

(Ig)

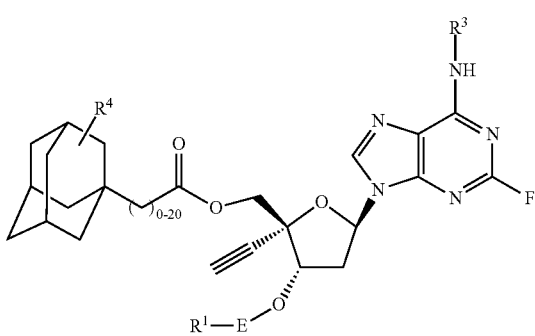

wherein:

E is selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:

G is selected form the group consisting of a bond, O, NH, and S;

J is selected form the group consisting of a bond, O, NH, S, —(CO)-G-;

R$^1$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-20}$cycloalkyl, C$_{3-20}$heterocycloalkyl, aryl, and heteroaryl;

R$^3$ is selected from the group consisting of H, —(CO)—O—C$_{1-10}$alkyl, and C$_{1-10}$alkyl; and R$^4$ is selected from the group consisting of H, C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, C$_{3-12}$heterocycloalkyl, aryl, and heteroaryl.

6. The adenosine derivative of embodiment 1, wherein said adenosine derivative is a compound of formula (Ih) or a pharmaceutically acceptable salt, tautomer, or solvate thereof:

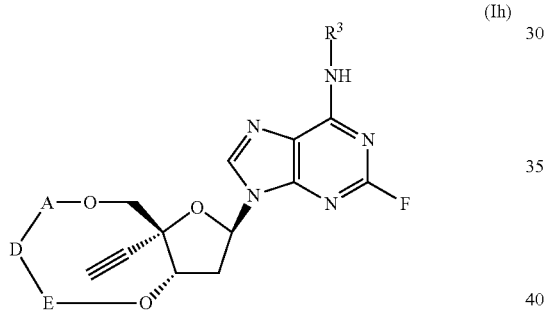

(Ih)

wherein:

A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:

G is selected form the group consisting of a bond, O, NH, and S;

J is selected form the group consisting of a bond, O, NH, S, —(CO)-G-;

D is selected from the group consisting of —C$_{1-20}$alkylene-, —C$_{2-20}$alkenylene-, and —C$_{2-20}$alkynylene-, —C$_{1-20}$haloalkylene-, —C$_{1-20}$alkoxyalkylene-, C$_{3-20}$cycloalkyl, C$_{3-20}$heterocycloalkyl, aryl, and heteroaryl; and R$^3$ is selected from the group consisting of H, —(CO)—O—C$_{1-10}$alkyl, and C$_{1-10}$alkyl.

7. The adenosine derivative of embodiment 1, wherein said adenosine derivative is a compound of formula (Ii), (Ij), or a pharmaceutically acceptable salt, tautomer, or solvate thereof:

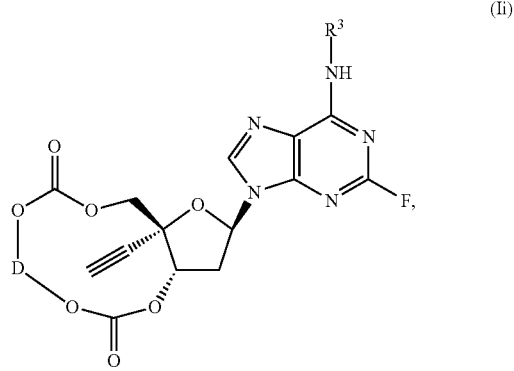

(Ii)

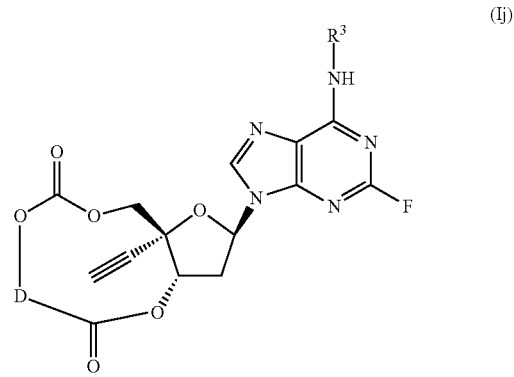

(Ij)

wherein:

D is selected from the group consisting of —C$_{1-20}$alkylene-, —C$_{2-20}$alkenylene-, and —C$_{2-20}$alkynylene-, —C$_{1-20}$haloalkylene-, —C$_{1-20}$alkoxyalkylene-, C$_{3-20}$cycloalkyl, C$_{3-20}$heterocycloalkyl, aryl, and heteroaryl; and R$^3$ is selected from the group consisting of H, —(CO)—O—C$_{1-10}$alkyl, and C$_{1-10}$alkyl.

8. The adenosine derivative of embodiment 1, wherein said adenosine derivative is a compound of formula (Ik), (Il), or a pharmaceutically acceptable salt, tautomer, or solvate thereof:

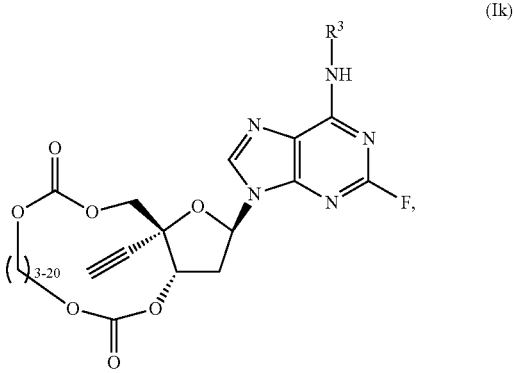

(Ik)

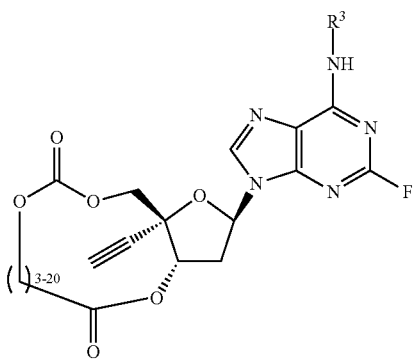

(II)

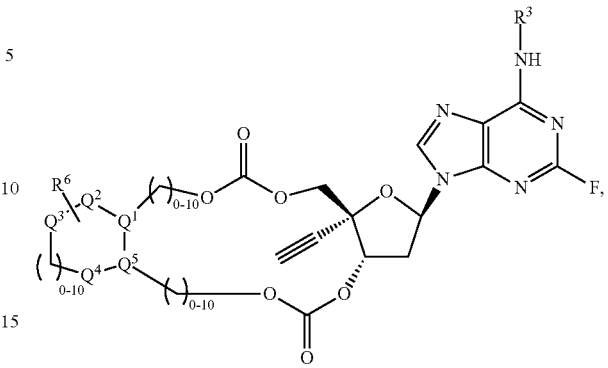

(In)

wherein:
R³ is selected from the group consisting of H, —(CO)—O—C₁₋₁₀alkyl, C₁₋₁₀alkyl, C₁₋₁₀haloalkyl, C₂₋₁₀alkenyl, C₂₋₁₀alkynyl, C₃₋₁₂cycloalkyl, C₃₋₁₂heterocycloalkyl, aryl, and heteroaryl.

9. The adenosine derivative of embodiment 1, wherein said adenosine derivative is a compound of formula (Im) or a pharmaceutically acceptable salt, tautomer, or solvate thereof:

(Io)

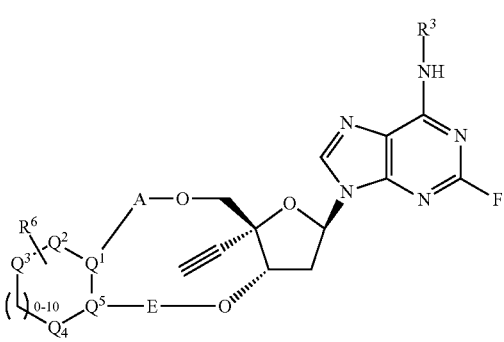

(Im)

wherein:
A and E are each independently selected from the group consisting of a bond, —(CO)—, —(CO)-G-, —(CO)-G-(C₁₋₁₀alkylene)-J-, —(CO)-G-(C₂₋₁₀alkenylene)-J-, and —(CO)-G-(C₂₋₁₀alkynylene)-J-; wherein:
G is selected form the group consisting of a bond, O, NH, and S;
J is selected form the group consisting of a bond, O, NH, S, —(CO)-G-;
R³ is selected from the group consisting of H, —(CO)-G-C₁₋₁₀alkyl, C₁₋₁₀alkyl, C₁₋₁₀haloalkyl, C₂₋₁₀alkenyl, C₂₋₁₀alkynyl, C₃₋₁₂cycloalkyl, C₃₋₁₂heterocycloalkyl, aryl, and heteroaryl;
Q¹, Q², Q³, Q⁴, and Q⁵ form a cyclic ring, wherein said ring is selected from the group consisting of cycloalkyl, heterocycloalkyl, aryl, and heteroaryl; and
R⁶ is selected from the group consisting of C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, C₃₋₁₂heterocycloalkyl, aryl, and heteroaryl.

10. The adenosine derivative of embodiment 1, wherein said adenosine derivative is a compound of formula (In), (Io), or a pharmaceutically acceptable salt, tautomer, or solvate thereof:

wherein:
R³ is selected from the group consisting of H, —(CO)-G-C₁₋₁₀alkyl, C₁₋₁₀alkyl, C₁₋₁₀haloalkyl, C₂₋₁₀alkenyl, C₂₋₁₀alkynyl, C₃₋₁₂cycloalkyl, C₃₋₁₂heterocycloalkyl, aryl, and heteroaryl;
Q¹, Q², Q³, Q⁴, and Q⁵ form a cyclic ring, wherein said ring is selected from the group consisting of cycloalkyl, heterocycloalkyl, aryl, and heteroaryl; and
R⁶ is selected from the group consisting of C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, C₃₋₁₂heterocycloalkyl, aryl, and heteroaryl 11. The adenosine derivative of embodiment 1, wherein said adenosine derivative is a compound of formula (Ip) or a pharmaceutically acceptable salt, tautomer, or solvate thereof:

(Ip)

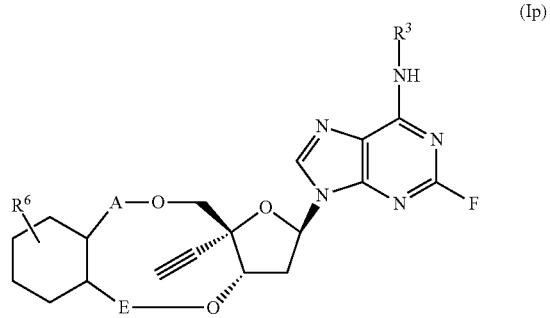

wherein:
A and E are each independently selected from the group consisting of a bond, —(CO)—, —(CO)-G-, —(CO)-

G-(C$_{1-10}$alkylene)-J-, —(CO)-G-(C$_{2-10}$alkenylene)-J-, and —(CO)-G-(C$_{2-10}$alkynylene)-J-; wherein:

G is selected form the group consisting of a bond, O, NH, and S;

J is selected form the group consisting of a bond, O, NH, S, —(CO)-G-;

R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, C$_{3-12}$heterocycloalkyl, aryl, and heteroaryl; and R$^6$ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, C$_{3-12}$heterocycloalkyl, aryl, and heteroaryl.

12. The adenosine derivative of embodiment 1, wherein said adenosine derivative is a compound of formula (Iq), (Ir), or a pharmaceutically acceptable salt, tautomer, or solvate (Iq)

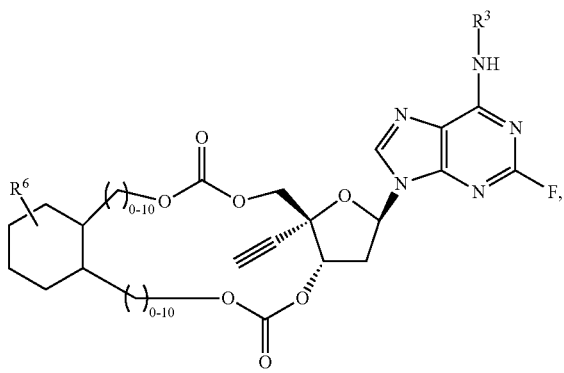

(Ir)

wherein:

R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, C$_{3-12}$heterocycloalkyl, aryl, and heteroaryl; and R$^6$ is selected from the group consisting of C$_{1-10}$alkyl, C$_{1-10}$haloalkyl, C$_{1-10}$alkoxy, C$_{2-10}$alkenyl, C$_{2-10}$alkynyl, C$_{3-12}$cycloalkyl, C$_{3-12}$heterocycloalkyl, aryl, and heteroaryl.

13. The adenosine derivative of embodiment 1, wherein said adenosine derivative is selected from the group consisting of:

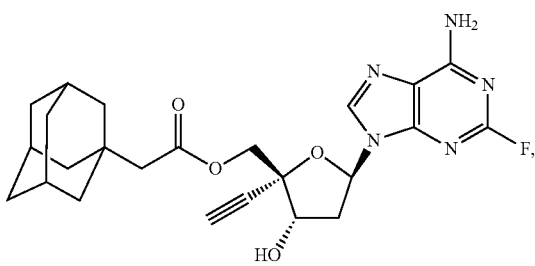

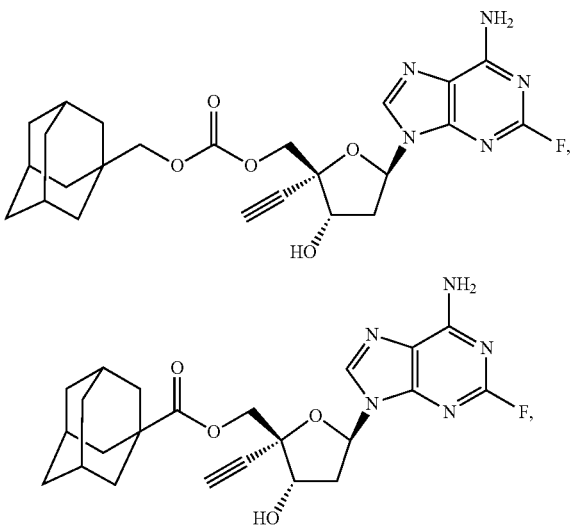

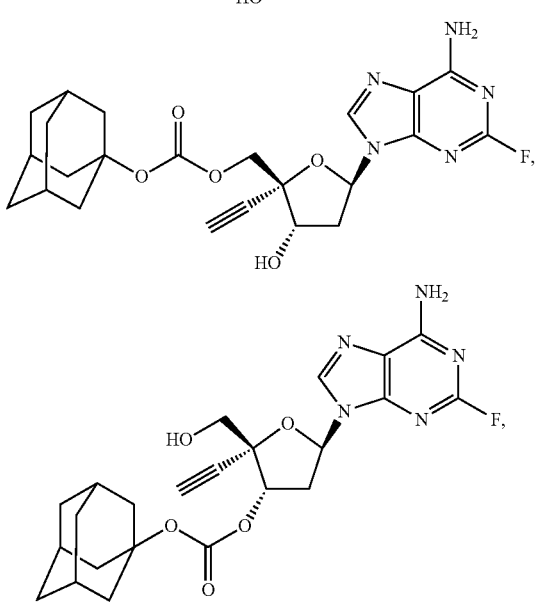

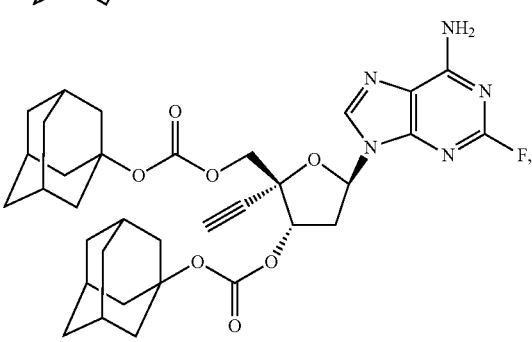

-continued
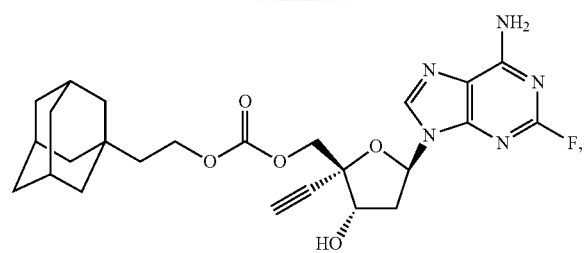
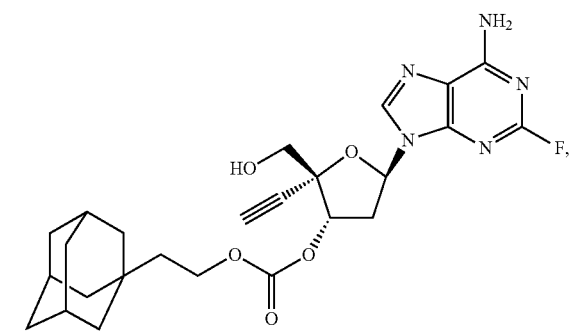
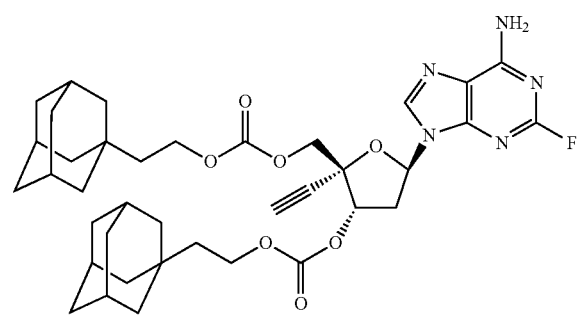
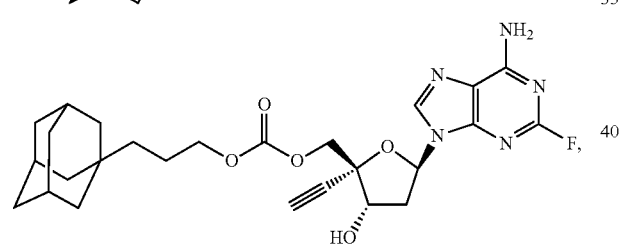
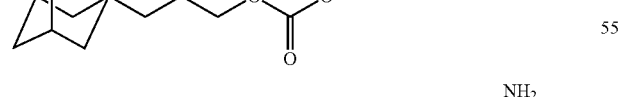
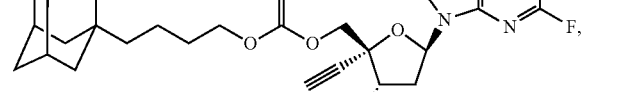
-continued
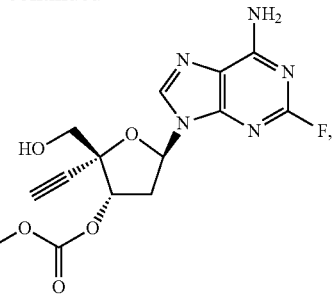
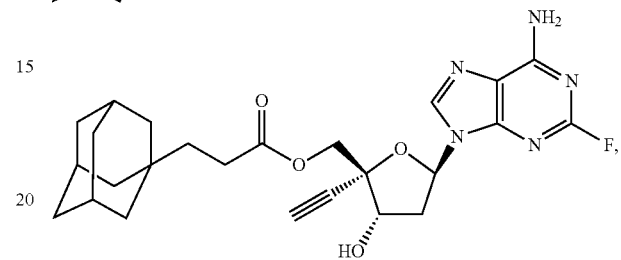
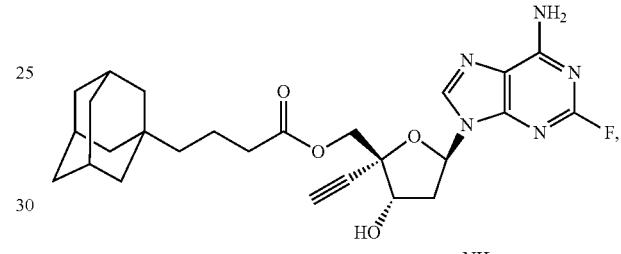
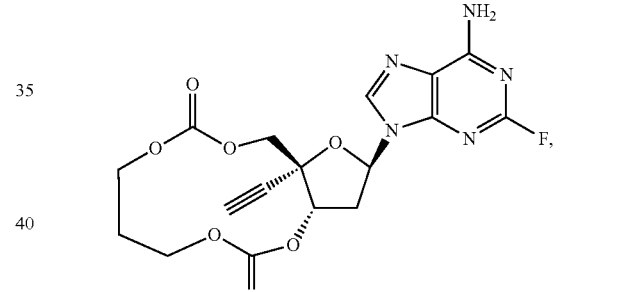
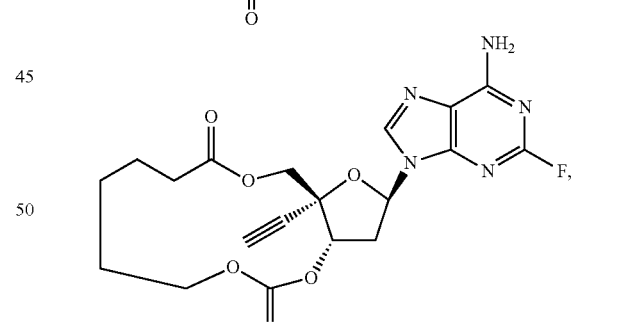
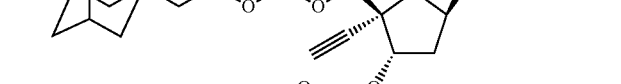

97
-continued
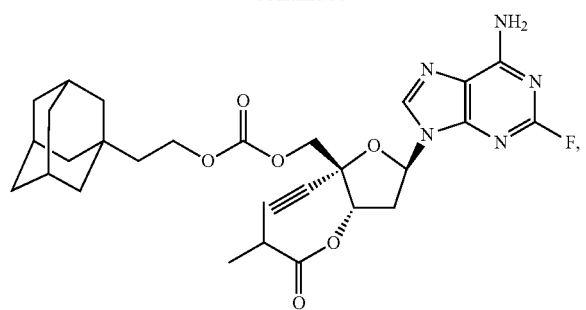
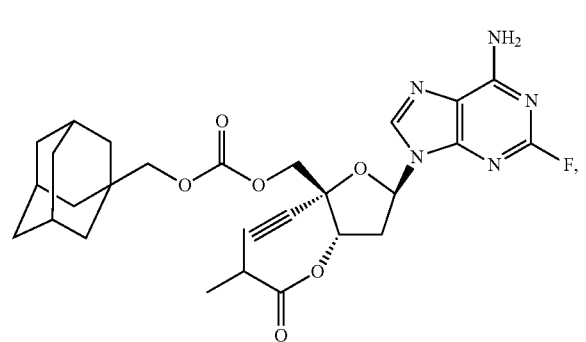
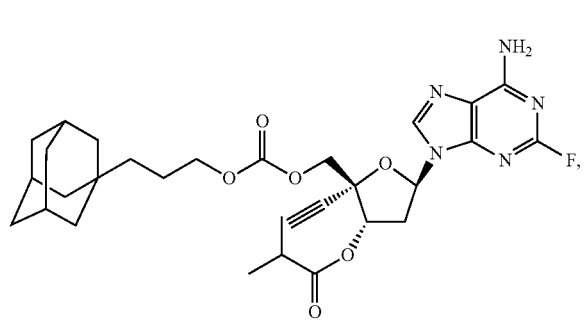
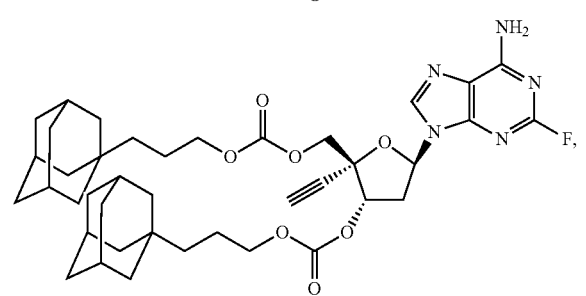
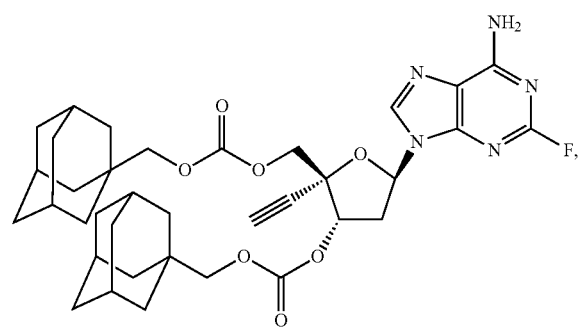
98
-continued
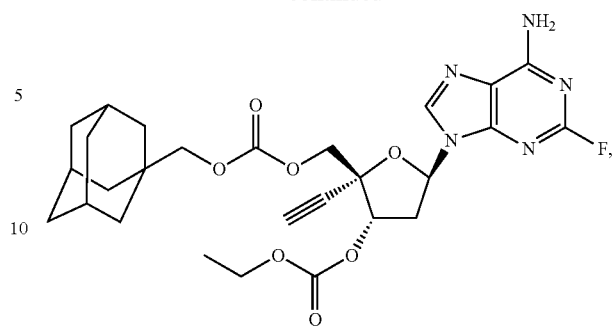
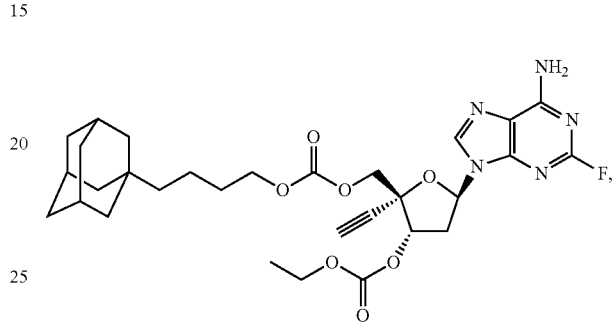
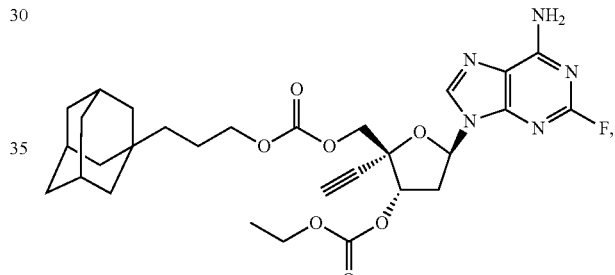
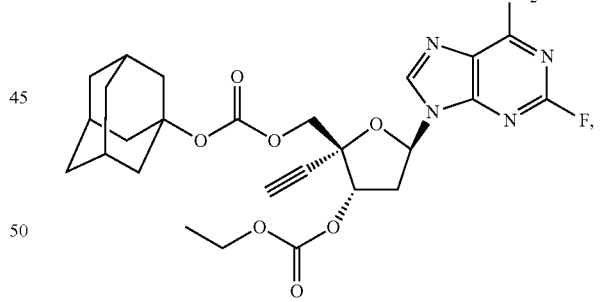
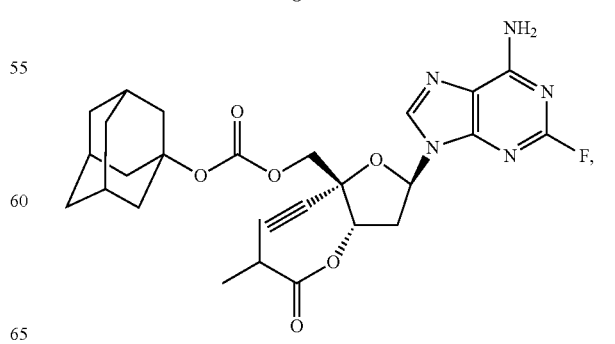

-continued

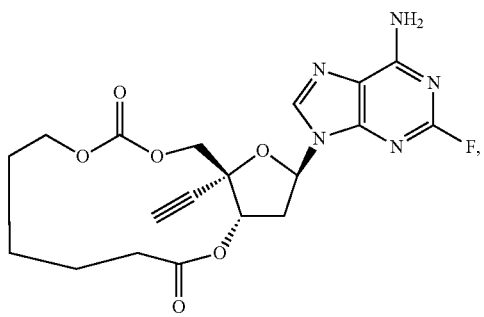

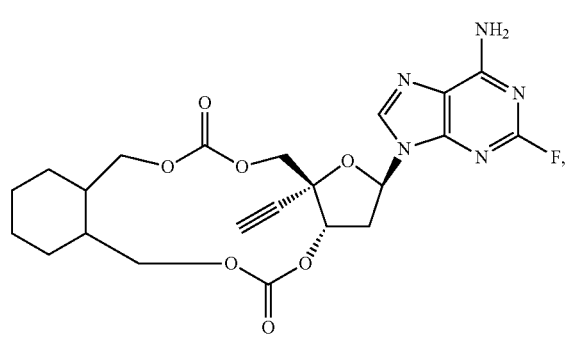

and a pharmaceutically acceptable salt, tautomer, or solvate thereof.

13a. The adenosine derivative of embodiment 1 or 13, wherein said adenosine derivative is selected from the group consisting of:

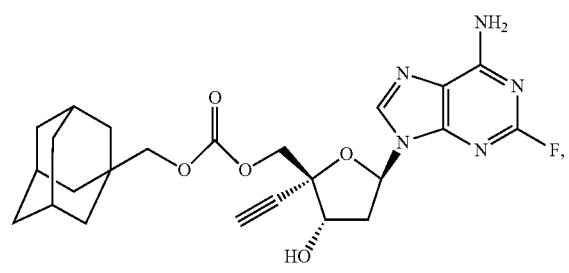

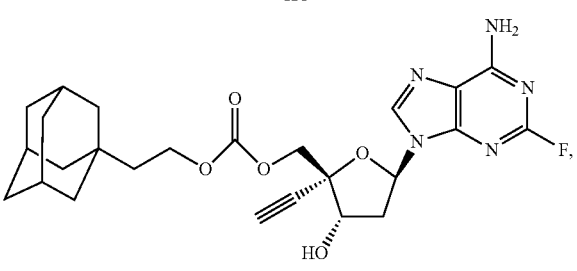

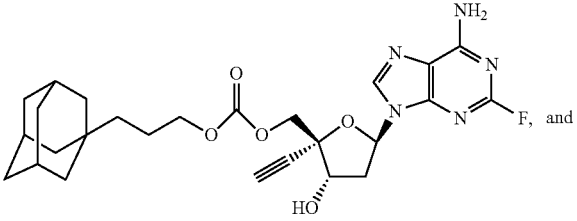

-continued

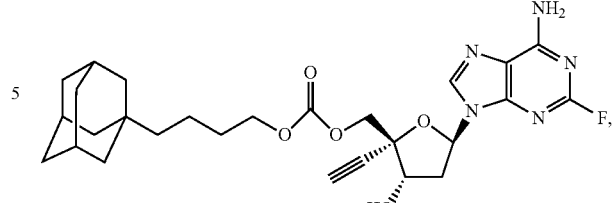

14. The adenosine derivative of any one of embodiments 1-13, wherein said adenosine derivative comprises a reverse transcriptase inhibitor activity in vivo, a reverse transcriptase chain terminator activity in vivo, DNA translocation inhibitor activity in vivo, or a combination thereof.

15. A pharmaceutical composition comprising an adenosine derivative having a structure of formula (I):

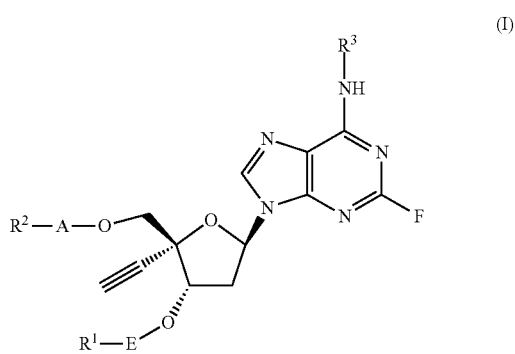

(I)

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;
$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H;
$R^1$ and $R^2$ can join together with the atoms to which they are attached to form a 3- to 25-membered heterocyclic ring; and
$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

15a. The adenosine derivative of embodiment 15, wherein A is selected from the group consisting of a bond, —(CO)—, —(CO)-G-, and —(CO)-G-($C_{1-5}$alkylene)-J-.

15B. The adenosine derivative of embodiment 15 or 15a, wherein A is —(CO)-G- or —(CO)-G-($C_{1-5}$alkylene)-J-.

15c. The adenosine derivative of any one of embodiments 15-15b, wherein E is a bond, —(CO)-G-, and —(CO)-G-($C_{1-5}$alkylene)-J-.

15d. The adenosine derivative of any one of embodiments 15-15c, wherein E is a bond.

15e. The adenosine derivative of any one of embodiments 15-15d, wherein G is a bond or O.

15f. The adenosine derivative of any one of embodiments 15-15e, wherein J is a bond or O.

15g. The adenosine derivative of any one of embodiments 15-15f, wherein G is O and J is a bond.

15h. The adenosine derivative of any one of embodiments 15-15g, wherein $R^1$ is H, $C_{1-5}$alkyl, or adamantyl

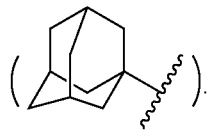

15i. The adenosine derivative of any one of embodiments 15-15h, wherein $R^1$ is H.

15j. The adenosine derivative of any one of embodiments 15-15i, wherein $R^2$ is H, $C_{1-5}$alkyl, or adamantyl.

15k. The adenosine derivative of any one of embodiments 15-15j, wherein $R^2$ is adamantyl

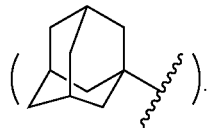

15l. The adenosine derivative of any one of embodiments 15-15g, wherein $R^1$ and $R^2$ taken together with the atoms to which they are attached form a 6- to 15-membered heterocyclic ring.

15m. The adenosine derivative of any one of embodiments 15-15l, wherein $R^3$ is —(CO)—$C_{1-5}$alkyl, —(CO)—O—$C_{1-5}$alkyl, or $C_{1-5}$alkyl.

15n. The adenosine derivative of any one of embodiments 15-15m, wherein $R^3$ is H.

16. The pharmaceutical composition of embodiment 15, wherein said adenosine derivative is a compound of formula (Ia), (Ib), or a pharmaceutically acceptable salt, tautomer, or solvate thereof:

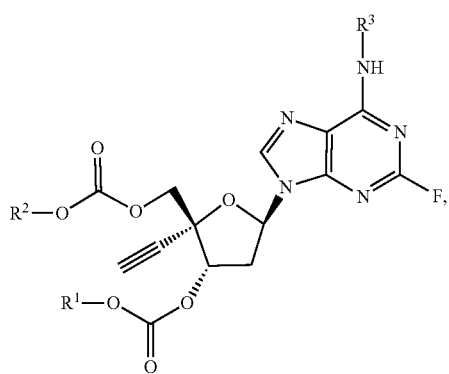

(Ia)

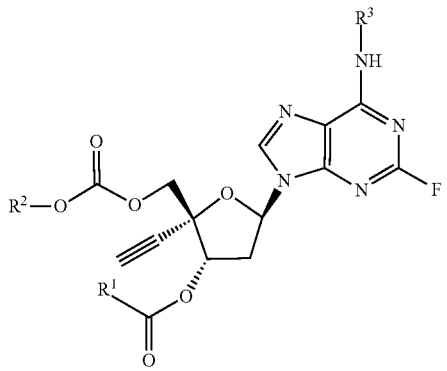

(Ib)

wherein:

$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

17. The pharmaceutical composition of embodiment 15, wherein said adenosine derivative is a compound of formula (Ic), (Id), or a pharmaceutically acceptable salt, tautomer, or solvate thereof:

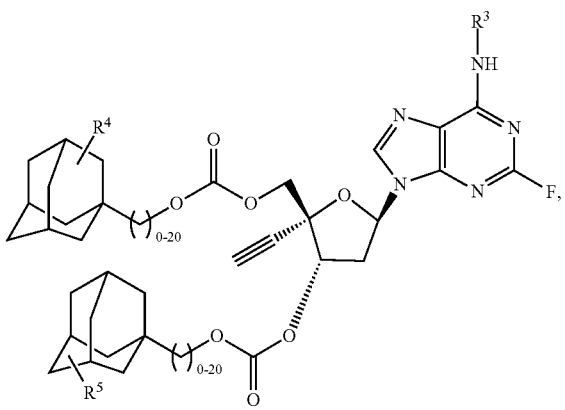

(Ic)

-continued (Id)

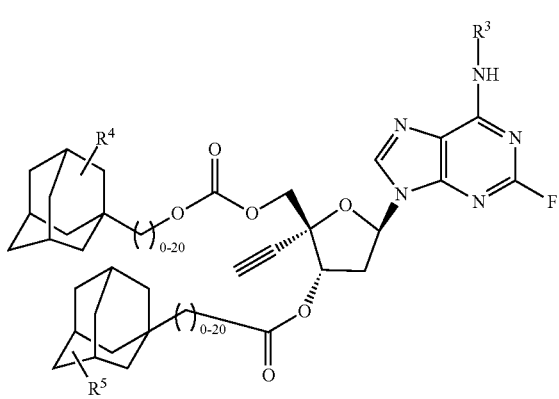

wherein:
R³ is selected from the group consisting of H, —(CO)-G-C₁₋₁₀alkyl, and C₁₋₁₀alkyl;
R⁴ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl; and
R⁵ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl.

18. The pharmaceutical composition of embodiment 15, wherein said adenosine derivative is a compound of formula (Ie), (If), or a pharmaceutically acceptable salt, tautomer, or solvate thereof:

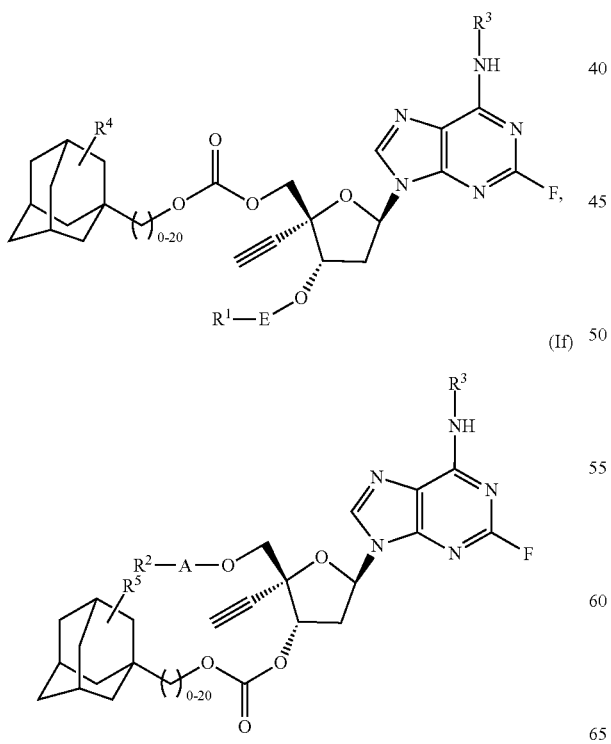

wherein:
A and E are each independently selected from the group consisting of a bond, —(CO)—, —(CO)-G-, —(CO)-G-(C₁₋₁₀alkylene)-J-, —(CO)-G-(C₂₋₁₀alkenylene)-J-, and —(CO)-G-(C₂₋₁₀alkynylene)-J-; wherein:
G is selected form the group consisting of a bond, O, NH, and S;
J is selected form the group consisting of a bond, O, NH, S, —(CO)-G-;
R¹ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₂₀cycloalkyl, 3- to 20-membered heterocycloalkyl, aryl, and heteroaryl;
R² is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₂₀cycloalkyl, 3- to 20-membered heterocycloalkyl, aryl, and heteroaryl;
R³ is selected from the group consisting of H, —(CO)—O—C₁₋₁₀alkyl, and C₁₋₁₀alkyl; and
R⁴ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl; and
R⁵ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl.

19. The pharmaceutical composition of embodiment 15, wherein said adenosine derivative is a compound of formula (Ig) or a pharmaceutically acceptable salt, tautomer, or solvate thereof:

(Ig)

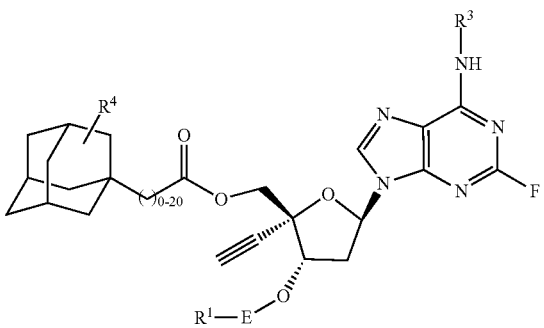

wherein:
E is selected from the group consisting of a bond, —(CO)—, —(CO)-G-, —(CO)-G-(C₁₋₁₀alkylene)-J-, —(CO)-G-(C₂₋₁₀alkenylene)-J-, and —(CO)-G-(C₂₋₁₀alkynylene)-J-; wherein:
G is selected form the group consisting of a bond, O, NH, and S;
J is selected form the group consisting of a bond, O, NH, S, —(CO)-G-;
R¹ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₂₀cycloalkyl, 3- to 20-membered heterocycloalkyl, aryl, and heteroaryl;
R³ is selected from the group consisting of H, —(CO)—O—C₁₋₁₀alkyl, and C₁₋₁₀alkyl; and
R⁴ is selected from the group consisting of H, C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl;

20. The pharmaceutical composition of embodiment 15, wherein said adenosine derivative is a compound of formula (Ih) or a pharmaceutically acceptable salt, tautomer, or solvate thereof:

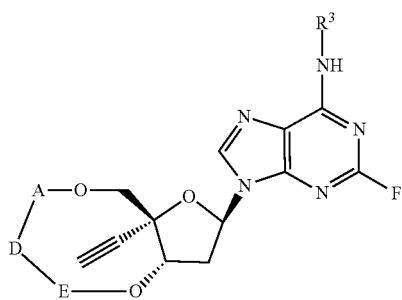

(Ih)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

D is selected from the group consisting of —$C_{1-20}$alkylene-, —$C_{2-20}$alkenylene-, and —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and $R^3$ is selected from the group consisting of H, —(CO)—O—$C_{1-10}$alkyl, and $C_{1-10}$alkyl.

21. The pharmaceutical composition of embodiment 15, wherein said adenosine derivative is a compound of formula (Ii), (Ij), or a pharmaceutically acceptable salt, tautomer, or solvate

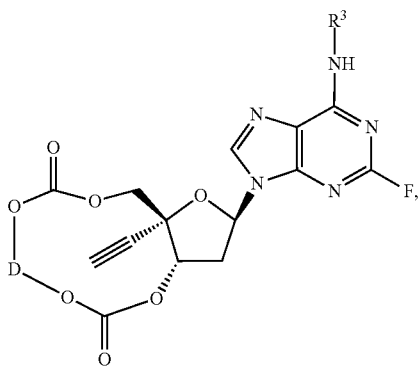

(Ii)

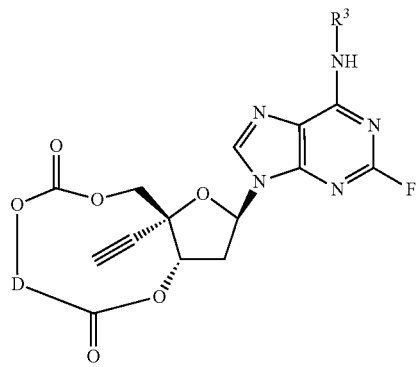

(Ij)

wherein:

D is selected from the group consisting of —$C_{1-20}$alkylene-, —$C_{2-20}$alkenylene-, and —$C_{2-20}$alkynylene-, —$C_{1-20}$haloalkylene-, —$C_{1-20}$alkoxyalkylene-, $C_{3-20}$cycloalkyl, 3- to 20-membered heterocycloalkyl, aryl, and heteroaryl; and $R^3$ is selected from the group consisting of H, —(CO)—O—$C_{1-10}$alkyl, and $C_{1-10}$alkyl.

22. The pharmaceutical composition of embodiment 15, wherein said adenosine derivative is a compound of formula (Ik), (Il), or a pharmaceutically acceptable salt, tautomer, or solvate thereof:

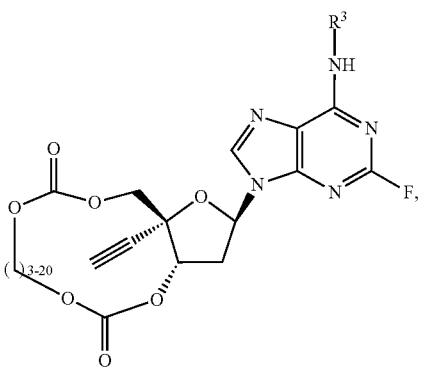

(Ik)

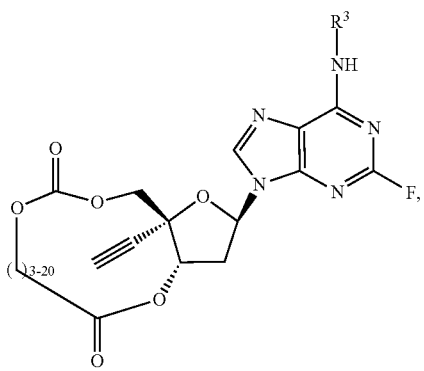

(Il)

wherein:

$R^3$ is selected from the group consisting of H, —(CO)—O—$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

23. The pharmaceutical composition of embodiment 15, wherein said adenosine derivative is a compound of formula (Im) or a pharmaceutically acceptable salt, tautomer, or solvate thereof:

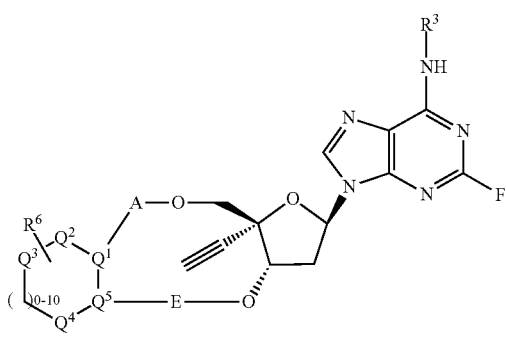

(Im)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

24. The pharmaceutical composition of embodiment 15, wherein said adenosine derivative is a compound of formula (In), (Io), or a pharmaceutically acceptable salt, tautomer, or solvate thereof:

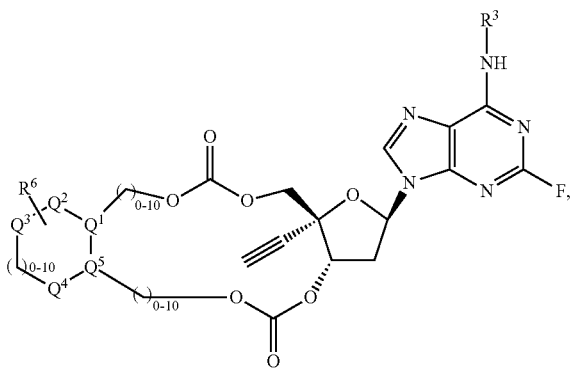

(In)

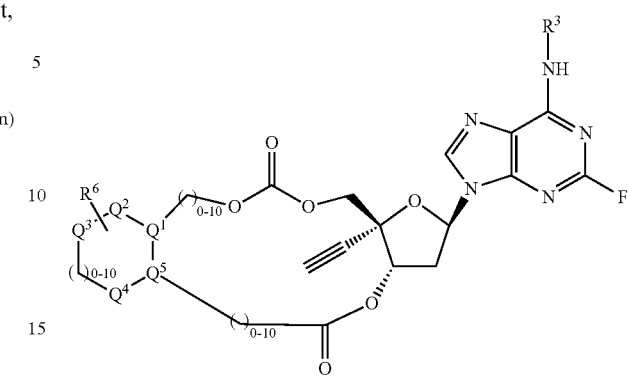

(Io)

wherein:

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl;

$Q^1$, $Q^2$, $Q^3$, $Q^4$, and $Q^5$ form a cyclic ring, wherein said ring is selected from the group consisting of cycloalkyl, heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl 25. The pharmaceutical composition of embodiment 15, wherein said adenosine derivative is a compound of formula (Ip) or a pharmaceutically acceptable salt, tautomer, or solvate thereof:

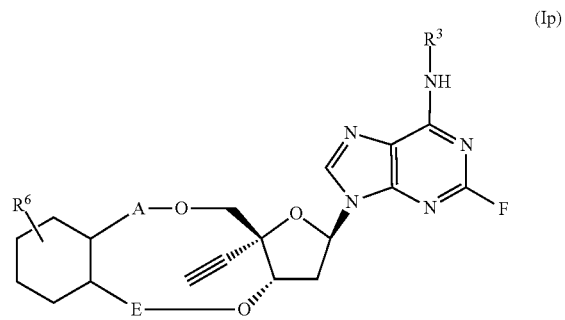

(Ip)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

26. The pharmaceutical composition of embodiment 15, wherein said adenosine derivative is a compound of formula (Iq), (Ir), or a pharmaceutically acceptable salt, tautomer, or solvate thereof:

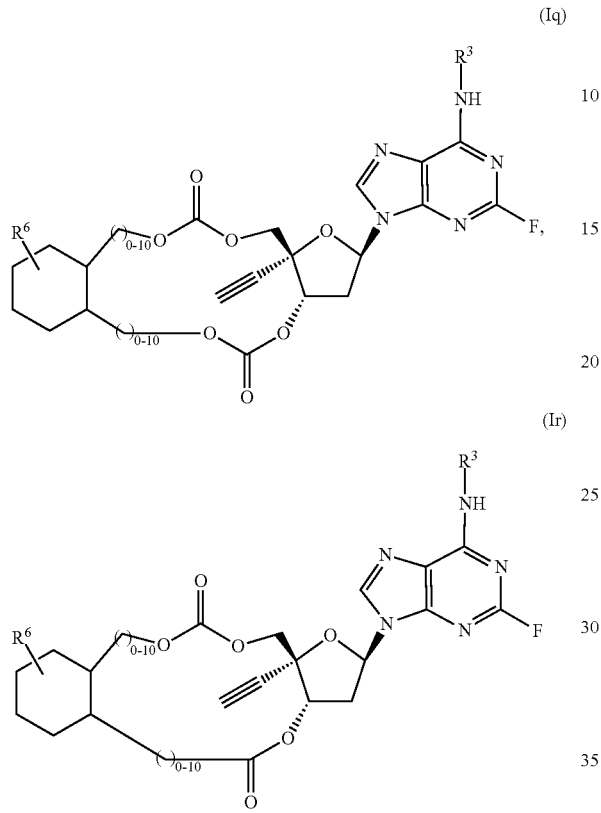

wherein:
$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and
$R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

27. The pharmaceutical composition of embodiment 15, wherein said adenosine derivative is selected from the group consisting of compound as disclosed in Table 1 of embodiment 13 and a pharmaceutically acceptable salt, tautomer, or solvate thereof.

28. The pharmaceutical composition of any one of embodiments 15-27, further comprising a pharmaceutically acceptable carrier.

29. The pharmaceutical composition of any one of embodiments 14-27, further comprising an effective dosage of one or more additional antiviral agent selected from lenacapavir, bictegravir, cabotegravir, atazanavir, atazanavir sulfate, darunavir, dolutegravir, doravirine, efavirenz, emtricitabine, tenofovir disoproxil fumarate, tenofovir alafenamide, etravirine, a combination of darunavir and cobicistat, maraviroc, rilpivirine, MK-8507 or a combination thereof.

30. A method for the treatment of a disease, said method comprising administering a subject in need thereof an effective dosage of a pharmaceutical composition comprising an adenosine derivative having a structure of formula (I) or a pharmaceutically acceptable salt, tautomer, or solvate thereof:

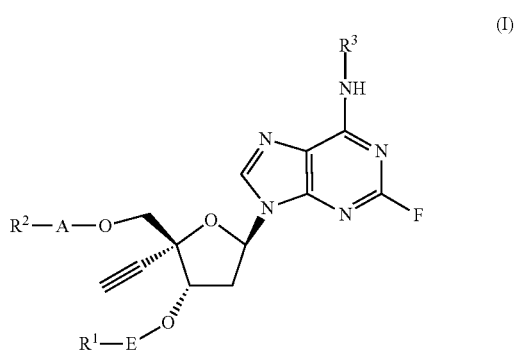

wherein:
A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:
G is selected form the group consisting of a bond, O, NH, and S;
J is selected form the group consisting of a bond, O, NH, S, —(CO)-G-;
$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;
$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H;
$R^1$ and $R^2$ can join together with the atoms to which they are attached to form a 3- to 25-membered heterocyclic ring; and
$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

30a. The adenosine derivative of embodiment 30, wherein A is selected from the group consisting of a bond, —(CO)—, —(CO)-G-, and —(CO)-G-($C_{1-5}$alkylene)-J-.

30b. The adenosine derivative of embodiment 30 or 30a, wherein A is —(CO)-G- or —(CO)-G-($C_{1-5}$alkylene)-J-.

30c. The adenosine derivative of any one of embodiments 30-30b, wherein E is a bond, —(CO)-G-, and —(CO)-G-($C_{1-5}$alkylene)-J-.

30d. The adenosine derivative of any one of embodiments 30-30c, wherein E is a bond.

30e. The adenosine derivative of any one of embodiments 30-30d, wherein G is a bond or O.

30f. The adenosine derivative of any one of embodiments 30-30e, wherein J is a bond or O.

30g. The adenosine derivative of any one of embodiments 30-30f, wherein G is O and J is a bond.

30h. The adenosine derivative of any one of embodiments 30-30g, wherein $R^1$ is H, $C_{1-5}$alkyl, or adamantyl

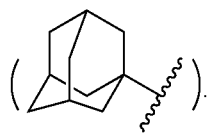

30i. The adenosine derivative of any one of embodiments 30-30h, wherein $R^1$ is H.

30j. The adenosine derivative of any one of embodiments 30-30i, wherein $R^2$ is H, $C_{1-5}$alkyl, or adamantyl.

30k. The adenosine derivative of any one of embodiments 30-30j, wherein $R^2$ is adamantyl

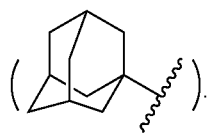

30l. The adenosine derivative of any one of embodiments 30-30g, wherein $R^1$ and $R^2$ taken together with the atoms to which they are attached form a 6- to 15-membered heterocyclic ring.

30m. The adenosine derivative of any one of embodiments 30-30l, wherein $R^3$ is —(CO)—$C_{1-5}$alkyl, —(CO)—O—$C_{1-5}$alkyl, or $C_{1-5}$alkyl.

30n. The adenosine derivative of any one of embodiments 30-30l, wherein $R^3$ is H.

31. The method of embodiment 30, wherein said adenosine derivative is a compound of formula (Ia), (Ib), or a pharmaceutically acceptable salt, tautomer, or solvate thereof:

(Ia)

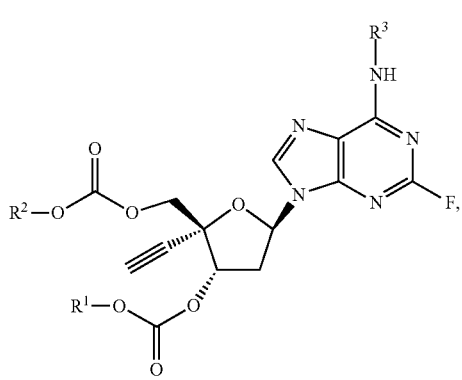

(Ib)

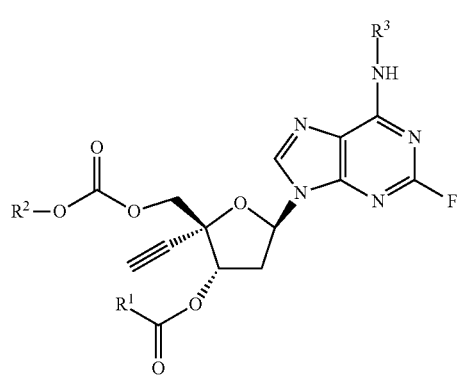

wherein:

$R^1$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl;

$R^2$ is selected from the group consisting of H, $C_{1-20}$alkyl, $C_{1-20}$haloalkyl, $C_{1-20}$alkoxy, $C_{2-20}$alkenyl, $C_{2-20}$alkynyl, $C_{3-20}$cycloalkyl, 3- to 20-membered heterocycloalkyl, aryl, and heteroaryl, wherein at least one of $R^1$ and $R^2$ is not H; and $R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl.

32. The method of embodiment 30, wherein said adenosine derivative is a compound of formula (Ic), (Id), or a pharmaceutically acceptable salt, tautomer, or solvate thereof:

(Ic)

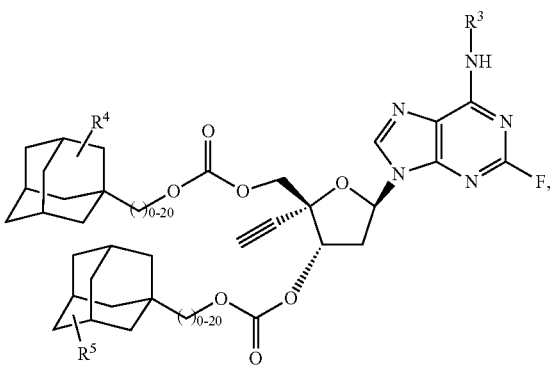

(Id)

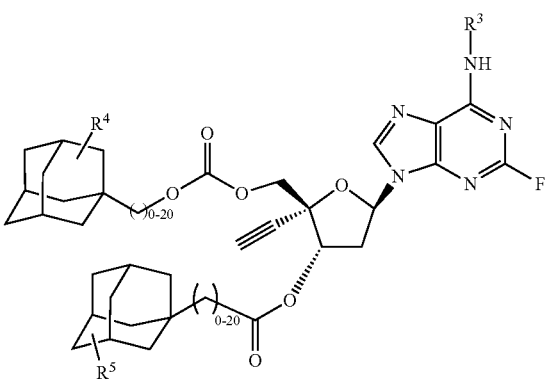

wherein:

$R^3$ is selected from the group consisting of H, —(CO)-G-$C_{1-10}$alkyl, and $C_{1-10}$alkyl;

$R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

33. The method of embodiment 30, wherein said adenosine derivative is a compound of formula (Ie), (If), or a pharmaceutically acceptable salt, tautomer, or solvate thereof:

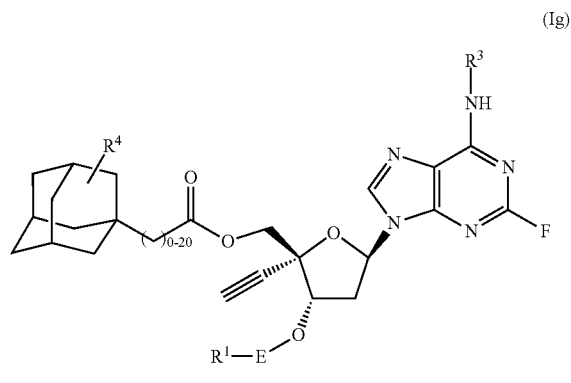

(Ie)

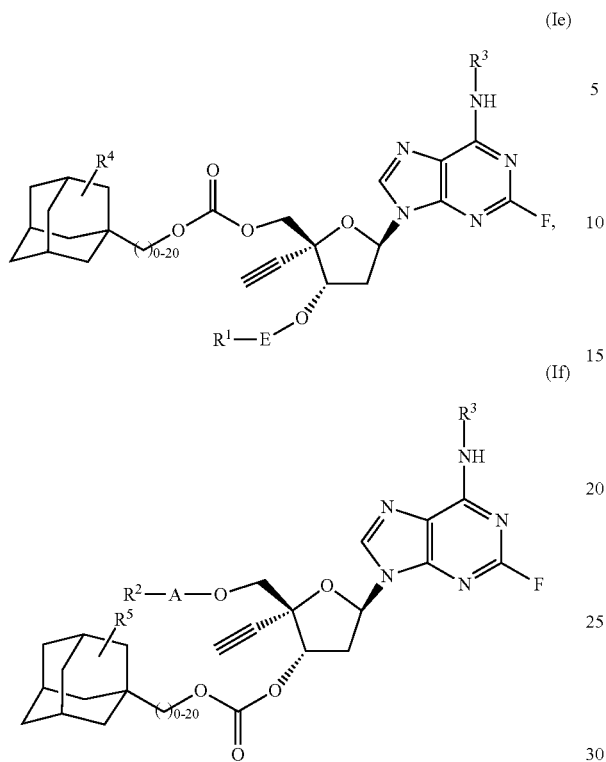

(If)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;

$R^2$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;

$R^3$ is selected from the group consisting of H, —(CO)—O—$C_{1-10}$alkyl, and $C_{1-10}$alkyl; and $R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl; and $R^5$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

34. The method of embodiment 30, wherein said adenosine derivative is a compound of formula (Ig) or a pharmaceutically acceptable salt, tautomer, or solvate thereof:

(Ig)

wherein:

E is selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

$R^1$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-20}$cycloalkyl, 3- to 20-membered heterocycloalkyl, aryl, and heteroaryl;

$R^3$ is selected from the group consisting of H, —(CO)—O—$C_{1-10}$alkyl, and $C_{1-10}$alkyl; and $R^4$ is selected from the group consisting of H, $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl;

35. The method of embodiment 30, wherein said adenosine derivative is a compound of formula (Ih) or a pharmaceutically acceptable salt, tautomer, or solvate thereof:

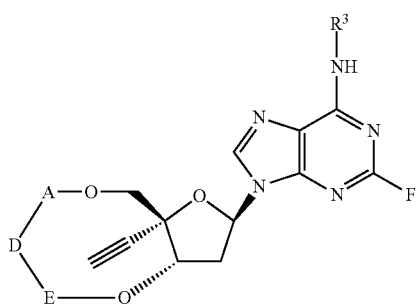

(Ih)

wherein:

A and E are each independently selected from the group consisting of a bond, —(CO)—, —(CO)-G-, —(CO)-G-($C_{1-10}$alkylene)-J-, —(CO)-G-($C_{2-10}$alkenylene)-J-, and —(CO)-G-($C_{2-10}$alkynylene)-J-; wherein:

G is selected form the group consisting of a bond, O, NH, and S;

J is selected form the group consisting of a bond, O, NH, S, —(CO)-G-;

D is selected from the group consisting of —$C_{1-20}$alkylene-, —$C_{2-20}$alkenylene-, and —$C_{2-20}$alkynylene-, —C$_{1-20}$haloalkylene-, —C$_{1-20}$alkoxyalkylene-, C$_{3-20}$cycloalkyl, 3- to 20-membered heterocycloalkyl, aryl, and heteroaryl; and R$^3$ is selected from the group consisting of H, —(CO)—O—C$_{1-10}$alkyl, and C$_{1-10}$alkyl.

36. The method of embodiment 30, wherein said adenosine derivative is a compound of formula (Ii), (Ij), or a pharmaceutically acceptable salt, tautomer, or solvate thereof:

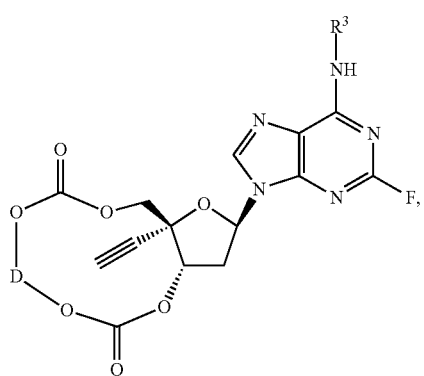

(Ii)

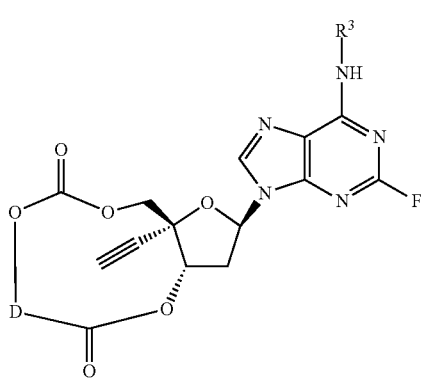

(Ij)

wherein:
D is selected from the group consisting of —C$_{1-20}$alkylene-, —C$_{2-20}$alkenylene-, and —C$_{2-20}$alkynylene-, —C$_{1-20}$haloalkylene-, —C$_{1-20}$alkoxyalkylene-, C$_{3-20}$cycloalkyl, 3- to 20-membered heterocycloalkyl, aryl, and heteroaryl; and R$^3$ is selected from the group consisting of H, —(CO)—O—C$_{1-10}$alkyl, and C$_{1-10}$alkyl.

37. The method of embodiment 30, wherein said adenosine derivative is a compound of formula (Ik), (Il), or a pharmaceutically acceptable salt, tautomer, or solvate thereof:

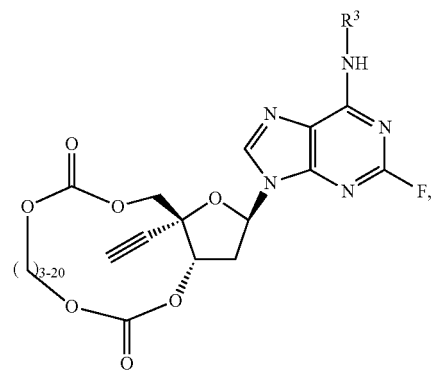

(Ik)

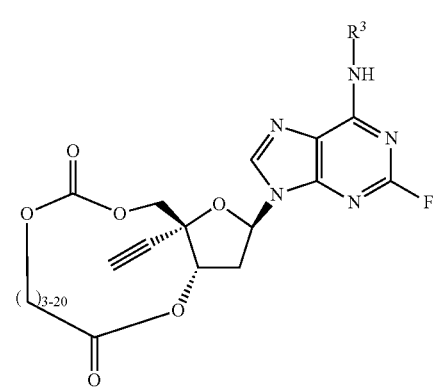

(Il)

wherein:
R$^3$ is selected from the group consisting of H, —(CO)—O—C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

38. The method of embodiment 30, wherein said adenosine derivative is a compound of formula (Im) or a pharmaceutically acceptable salt, tautomer, or solvate thereof:

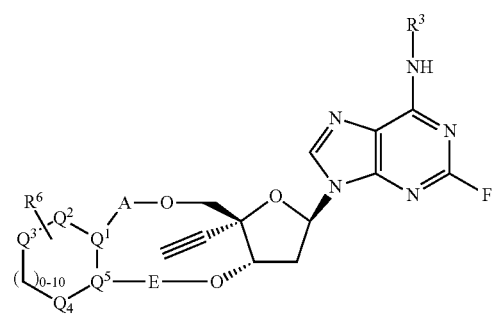

(Im)

wherein:
A and E are each independently selected from the group consisting of a bond, —(CO)—, —(CO)-G-, —(CO)-G-(C$_{1-10}$alkylene)-J-, —(CO)-G-(C$_{2-10}$alkenylene)-J-, and —(CO)-G-(C$_{2-10}$alkynylene)-J-; wherein:
G is selected form the group consisting of a bond, O, NH, and S;
J is selected form the group consisting of a bond, O, NH, S, —(CO)-G-;

R³ is selected from the group consisting of H, —(CO)-G-C₁₋₁₀alkyl, C₁₋₁₀alkyl, C₁₋₁₀haloalkyl, C₂₋₁₀alkenyl, C₂₋₁₀alkynyl, C₃₋₁₂cycloalkyl, 3- to 12-membered heterocycloalkyl, aryl, and heteroaryl;

Q¹, Q², Q³, Q⁴, and Q⁵ form a cyclic ring, wherein said ring is selected from the group consisting of cycloalkyl, heterocycloalkyl, aryl, and heteroaryl; and R⁶ is selected from the group consisting of C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl.

39. The method of embodiment 30, wherein said adenosine derivative is a compound of formula (In), (Io), or a pharmaceutically acceptable salt, tautomer, or solvate thereof:

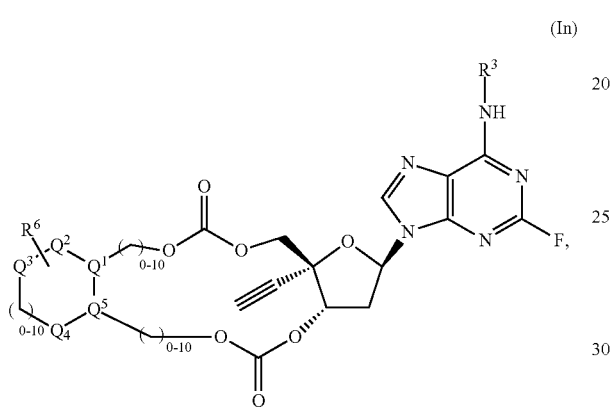

(In)

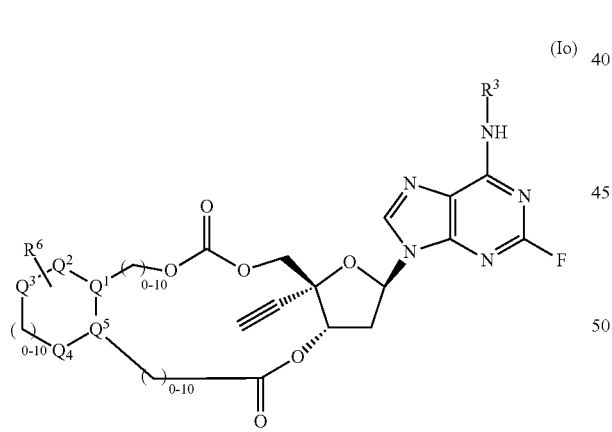

(Io)

wherein:

R³ is selected from the group consisting of H, —(CO)-G-C₁₋₁₀alkyl, C₁₋₁₀alkyl, C₁₋₁₀haloalkyl, C₂₋₁₀alkenyl, C₂₋₁₀alkynyl, C₃₋₁₂cycloalkyl, 3- to 12-membered heterocycloalkyl, aryl, and heteroaryl;

Q¹, Q², Q³, Q⁴, and Q⁵ form a cyclic ring, wherein said ring is selected from the group consisting of cycloalkyl, heterocycloalkyl, aryl, and heteroaryl; and R⁶ is selected from the group consisting of C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl 40. The method of embodiment 30, wherein said adenosine derivative is a compound of formula (Ip) or a pharmaceutically acceptable salt, tautomer, or solvate thereof:

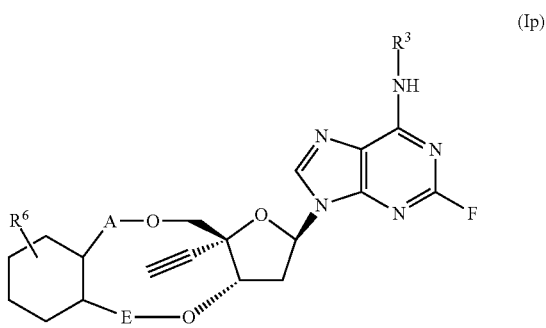

(Ip)

wherein:

A and E are each independently selected from the group consisting of a bond, —(CO)—, —(CO)-G-, —(CO)-G-(C₁₋₁₀alkylene)-J-, —(CO)-G-(C₂₋₁₀alkenylene)-J-, and —(CO)-G-(C₂₋₁₀alkynylene)-J-; wherein:

G is selected form the group consisting of a bond, O, NH, and S;

J is selected form the group consisting of a bond, O, NH, S, —(CO)-G-;

R³ is selected from the group consisting of H, —(CO)-G-C₁₋₁₀alkyl, C₁₋₁₀alkyl, C₁₋₁₀haloalkyl, C₂₋₁₀alkenyl, C₂₋₁₀alkynyl, C₃₋₁₂cycloalkyl, 3- to 12-membered heterocycloalkyl, aryl, and heteroaryl; and R⁶ is selected from the group consisting of C₁₋₁₀alkyl, C₁₋₁₀haloalkyl, C₁₋₁₀alkoxy, C₂₋₁₀alkenyl, C₂₋₁₀alkynyl, C₃₋₁₂cycloalkyl, 3- to 12-membered heterocycloalkyl, aryl, and heteroaryl.

41. The method of embodiment 30, wherein said adenosine derivative is a compound of formula (Iq), (Ir), or a pharmaceutically acceptable salt, tautomer, or solvate thereof:

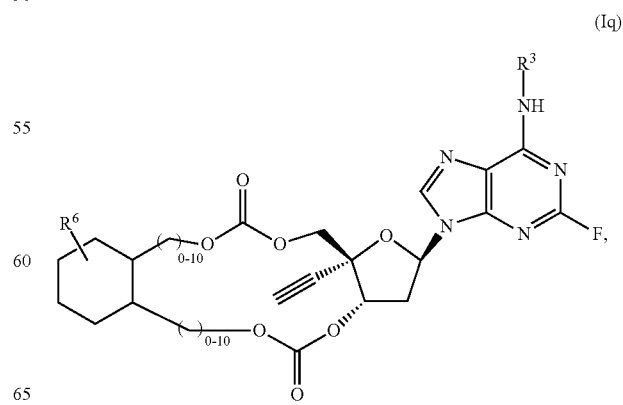

(Iq)

-continued (Ir)

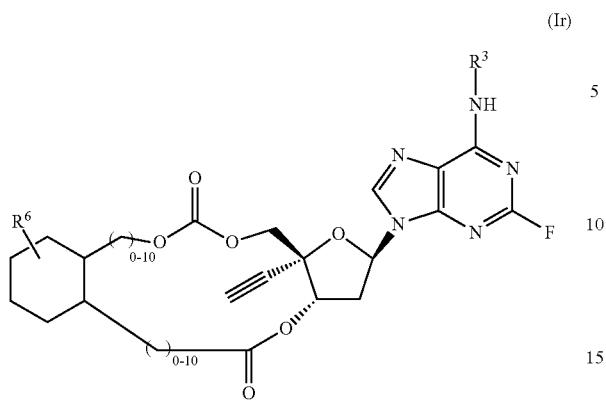

wherein:

$R^3$ is selected from the group consisting of H, —(CO)-G-$C_{1-10}$alkyl, $C_{1-10}$alkyl, $C_{1-10}$haloalkyl, $C_{2-10}$alkenyl, $C_{2-10}$alkynyl, $C_{3-12}$cycloalkyl, 3- to 12-membered heterocycloalkyl, aryl, and heteroaryl; and $R^6$ is selected from the group consisting of $C_{1-10}$alkyl, $C_{1-10}$haloalkyl, $C_{1-10}$alkoxy, $C_{2-10}$alkenyl, $C_{2-10}$alkynyl, $C_{3-12}$cycloalkyl, 3- to 12-membered heterocycloalkyl, aryl, and heteroaryl.

42. The method of embodiment 30, wherein said adenosine derivative is selected from the group consisting of compound as disclosed in Table 1 of embodiment 13 and a pharmaceutically acceptable salt, tautomer, or solvate thereof.

43. The method of any one of embodiments 30-42, said pharmaceutical composition is administered to said subject via intramuscular (IM) injection, subcutaneous (SC) injection, intravenous (IV) injection, oral administration, topical application, implant application or a combination thereof.

44. The method of any one of embodiments 30-43, further comprising measuring a specimen of said subject to determine a measured level of a target drug in said specimen, wherein said target drug has a formula (T-1), wherein X is a halogen selected from the group consisting of F, Cl, Br and I:

(T-1)

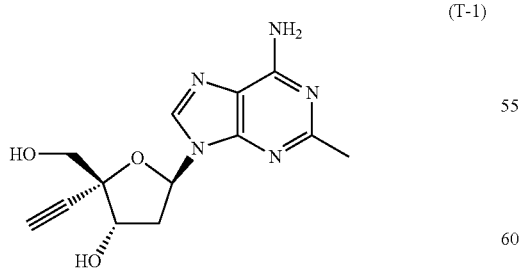

or a pharmaceutically acceptable salt, stereoisomer, tautomer thereof.

45. The method of embodiment 44, wherein said target drug has a formula (T-1A):

(T-1A)

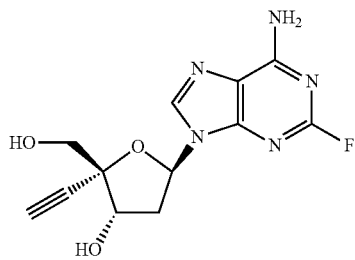

or a pharmaceutically acceptable salt, stereoisomer, tautomer thereof.

46. The method of embodiment 44, wherein said target drug is (2R,3S,5R)-5-(6-amino-2-fluoro-9H-purin-9-yl)-2-ethynyl-2-(hydroxymethyl)tetrahydrofuran-3-ol, or a pharmaceutically acceptable salt thereof.

47. The method of any one of embodiments 44-46, further comprising adjusting said effective dosage to produce a modified effective dosage if said measured level of said target drug is different from a predetermined target level of said target drug and administering said modified effective dosage to said subject.

48. The method of any one of embodiments 30-47, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

49. The method of any one of embodiments 30-48, further comprising administering said subject an effective dosage of one or more additional anti-HIV agents selected from lenacapavir, bictegravir, cabotegravir, atazanavir, atazanavir sulfate, darunavir, dolutegravir, doravirine, efavirenz, emtricitabine, tenofovir disoproxil fumarate, tenofovir alafenamide, etravirine, a combination of darunavir and cobicistat, maraviroc, rilpivirine, MK-8507 or a combination thereof.

50. The method of embodiment 49, wherein said adenosine derivative and said one or more additional anti-HIV agents are administered to said subject together or separately via oral administration, parenteral administration or a combination thereof.

51. The method of embodiment 50, wherein said adenosine derivative and said one or more additional anti-HIV agents are administered to said subject with a daily, weekly, biweekly, monthly, bimonthly, or semiannually administration schedule.

52. Use of the adenosine derivative of any one of embodiments 1-14 for manufacturing a medicament for treating a disease, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

53. A use of the pharmaceutical composition of any one of embodiments 15-29 for the treatment of a disease in a subject in need thereof, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.

54. A use of the method of any one of embodiments 30-51 for the treatment of a disease in a subject in need thereof, wherein said disease is Acquired Immune Deficiency Syndrome (AIDS), wild-type HIV-1, NRTI-resistant HIV-1, HIV-2, HIV having M184V mutations, HIV having K65R, or multidrug resistant HIV.
55. A method for the prevention of infection in a subject in need thereof, said method comprising administering said subject an effective dosage of a pharmaceutical composition of any one of embodiments 15-29, wherein said subject is free from detectable symptoms of said infection.
56. The method of embodiment 55, wherein said infection comprises a disease selected from Acquired Immune Deficiency Syndrome (AIDS), an infection of wild-type HIV-1, NRTI-resistant HIV-1, HIV-2, HIV having M184V mutations, HIV having K65R, or multidrug resistant HIV, or a combination thereof.
57. The method of embodiment 55, wherein said detectable symptoms comprise symptoms of Acquired Immune Deficiency Syndrome (AIDS), symptoms of infection of HIV viruses comprising wild-type HIV-1, NRTI-resistant HIV-1, HIV-2, HIV having M184V mutations, HIV having K65R, multidrug resistant HIV, or a combination thereof.
58. The method of embodiment 55, wherein said pharmaceutical composition administered to said subject with a daily, weekly, biweekly, monthly, bimonthly, or semiannually administration schedule.
59. The method of embodiment 58, further comprising administering said subject an effective dosage of one or more additional anti-HIV agents selected from lenacapavir, atazanavir, atazanavir sulfate, bictegravir, cabotegravir, darunavir, dolutegravir, doravirine, efavirenz, tenofovir disoproxil fumarate, tenofovir alafenamide, etravirine, a combination of darunavir and cobicistat, maraviroc, rilpivirine, or a combination thereof.
60. The method of embodiment 59, wherein said one or more additional anti-HIV agents are administered to said subject together with said pharmaceutical composition or separately.
61. A method for treating HIV infection, comprising: administering a subject in need thereof an effective dosage of the pharmaceutical composition of any one of embodiment 1-29.
62. A method for preventing HIV infection, comprising: administering a subject in need thereof an effective dosage of the pharmaceutical composition of any one of embodiment 1-29.
63. The method of embodiment 61 or 62, wherein the HIV infection is caused by wild-type HIV-1, NRTI-resistant HIV-1, HIV-2, HIV having M184V mutations, HIV having K65R, or multidrug resistant HIV.
64. The method of any one of embodiment 61-63, wherein the administration is by oral administration.
65. The method of any one of embodiment 61-63, wherein the administration is by parenteral administration.
66. The method of embodiment 65, wherein the parenteral administration is by intramuscular or subcutaneous injection.
67. The method of any one of embodiments 61-66, wherein the administration of the pharmaceutical composition results in a higher plasma concentration of EFdA when compared to administration of a dose-equivalent EFdA under the same condition.
68. The method of embodiment 67, wherein the administration of the pharmaceutical composition results in at least 10%, 20%, 30%, 40%, 50%, 60%, 70%, 80%, 90%, 100%, or 200% higher plasma concentration of EFdA when compared to administration of a dose-equivalent EFdA under the same condition.
69. The method of embodiment 67, wherein the administration of the pharmaceutical composition results in 50%-80%, 50%-100%, or 50%-200% higher plasma concentration of EFdA when compared to administration of a dose-equivalent EFdA under the same condition.
70. The method of any one of embodiments 61-69, wherein the administration of the pharmaceutical composition results in a prolonged release of EFdA when compared to administration of a dose-equivalent EFdA under the same condition.
71. The method of any one of embodiments 61-70, wherein the administration of the pharmaceutical composition results in a higher AUC of EFdA when compared to administration of a dose-equivalent EFdA under the same condition.
72. The method of embodiment 71, wherein the administration of the pharmaceutical composition results in at least 10%, 20%, 30%, 40%, 50%, 60%, 70%, 80%, 90%, or 100% higher AUC of EFdA when compared to administration of a dose-equivalent EFdA under the same condition.
73. The method of embodiment 71, wherein the administration of the pharmaceutical composition results in 50%-200%, 50%-150%, or 80%-120% higher AUC of EFdA when compared to administration of a dose-equivalent EFdA under the same condition.

The instant disclosure now will be exemplified in the following non-limiting examples.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1: ((2R,3S,5R)-5-(6-amino-2-fluoro-9H-purin-9-yl)-2-ethynyl-3-hydroxy-tetrahydrofuran-2-yl)methyl 2-(1-adamantyl) acetate (compound 1)

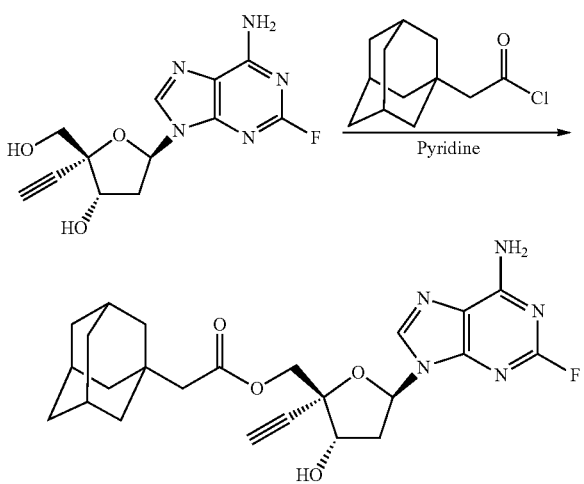

Preparation of ((2R,3S,5R)-5-(6-amino-2-fluoro-9H-purin-9-yl)-2-ethynyl-3-hydroxy-tetrahydrofuran-2-yl)methyl 2-(1-adamantyl) acetate To a solution of (2R,3S,5R)-5-(6-amino-2-fluoro-9H-purin-9-yl)-2-ethynyl-2-(hydroxymethyl)tetrahydrofuran-3-ol (50 mg, 0.17 mmol, 1 eq) in pyridine (2 mL) was added 2-(1-adamantyl)acetyl chloride (39.9 mg, 0.19 mmol, 1.1 eq) slowly at 0° C. The resulting mixture was stirred at 20° C. for 5 h. The reaction mixture was purified by flash silica gel chromatography (ISCO®; 4 g SepaFlash® Silica Flash Column, eluted with 0-5% MeOH/DCM @ 30 mL/min) to give ((2R,3S,5R)-5-(6-amino-2-fluoro-9H-purin-9-yl)-2-ethynyl-3-hydroxy-tetrahydrofuran-2-yl)methyl 2-(1-adamantyl) acetate (17.9 mg, 22.4% yield) as a white solid. LCMS (ESI) m/z, $C_{24}H_{28}FN_5O_4$: calculated 469.21, found (M+H)+: 470.1. $^1$H NMR (400 MHz, CD$_3$CN) δ (ppm) 7.97 (s, 1H), 6.36 (br s, 2H), 6.26-6.23 (m, 1H), 4.76 (q, J=7.2 Hz, 1H), 4.27 (q, J=12 Hz, 2H), 3.72 (d, J=6.4 Hz, 1H), 2.98 (s, 1H), 2.91-2.89 (m, 1H), 2.59-2.55 (m, 1H), 2.22 (s, 1H), 1.84 (br s, 3H), 1.69-1.52 (m, 7H), 1.52-1.42 (m, 6H). $^{19}$F NMR (376 MHz, CD$_3$CN) δ (ppm) −52.74 (s, 1F).

Example 2: ((2R,3S,5R)-5-(6-amino-2-fluoro-9H-purin-9-yl)-2-ethynyl-3-hydroxy-tetrahydrofuran-2-yl)methyl 1-adamantylmethyl carbonate (Compound 2)

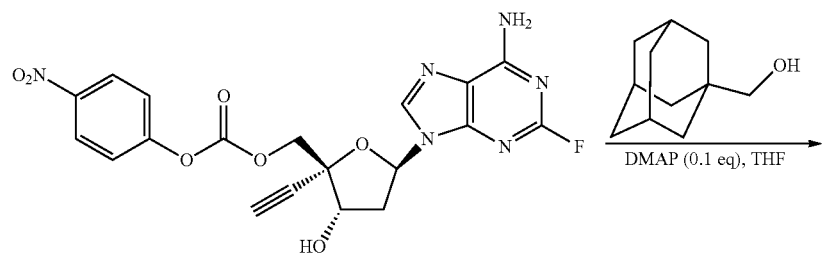

Preparation of ((2R,3S,5R)-5-(6-amino-2-fluoro-9H-purin-9-yl)-2-ethynyl-3-hydroxy-tetrahydrofuran-2-yl)methyl 1-adamantylmethyl carbonate To a solution of [(2R,3S,5R)-5-(6-amino-2-fluoro-9H-purin-9-yl)-2-ethynyl-3-hydroxy-tetrahydrofuran-2-yl]methyl (4-nitrophenyl) carbonate (330 mg, 0.72 mmol, 1 eq) in THF (15 mL) was added DMAP (8.80 mg, 0.072 mol, 0.1 eq) and 1-adamantylmethanol (299 mg, 1.80 mmol, 2.5 eq). The resulting mixture was stirred at 20° C. for 2 h. The reaction mixture was concentrated. The resulting residue was purified by prep-HPLC (column: Phenomenex Gemini-NX 80×30 mm×3 um; mobile phase: [water (10 mM NH$_4$HCO$_3$)-ACN]; B %: 40%-70%, 9 min) to give ((2R,3S,5R)-5-(6-amino-2-fluoro-9H-purin-9-yl)-2-ethynyl-3-hydroxy-tetrahydrofuran-2-yl)methyl 1-adamantylmethyl carbonate (11.1 mg, 3.2% yield) as a white solid. LCMS (ESI) m/z, $C_{24}H_{28}FN_5O_5$: calculated 485.21, found (M+H)+: 486.2. $^1$H NMR (400 MHz, CD$_3$OD) δ (ppm) 8.15 (s, 1H), 6.35-6.32 (m, 1H), 4.86-4.83 (m, 1H), 4.61 (br s, 1H), 4.42 (q, J=12 Hz, 2H), 3.73-3.66 (m, 1H), 3.64-3.56 (m, 1H), 3.20 (s, 1H), 2.87-2.85 (m, 1H), 2.70-2.65 (m, 1H), 1.95 (s, 3H), 1.79-1.72 (m, 3H), 1.71-1.64 (m, 3H), 1.52 (s, 6H). $^{19}$F NMR (376 MHz, CD$_3$OD) δ (ppm) −52.90 (s, 1F).

Example 3: ((2R,3S,5R)-5-(6-amino-2-fluoro-9H-purin-9-yl)-2-ethynyl-3-hydroxy-tetrahydrofuran-2-yl)methyl adamantane-1-carboxylate (Compound 3)

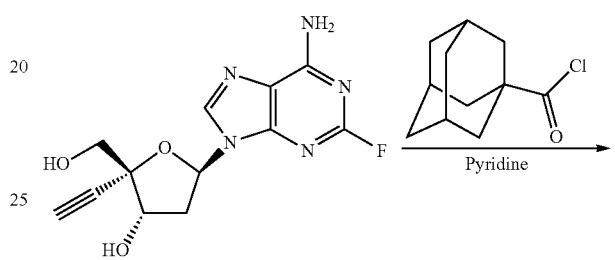

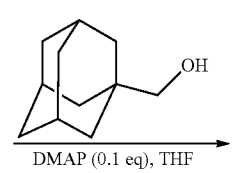

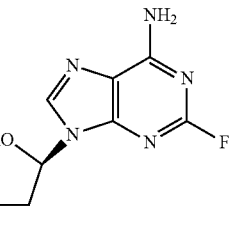

-continued

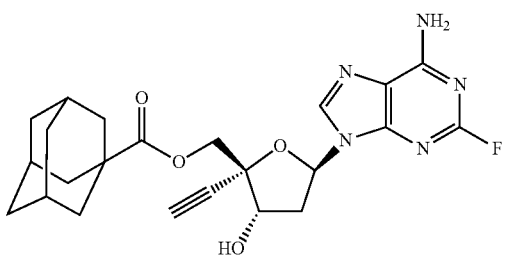

Preparation of ((2R,3S,5R)-5-(6-amino-2-fluoro-9H-purin-9-yl)-2-ethynyl-3-hydroxy-tetrahydrofuran-2-yl)methyl adamantane-1-carboxylate To a solution of (2R,3S,5R)-5-(6-amino-2-fluoro-purin-9-yl)-2-ethynyl-2-(hydroxymethyl)tetrahydrofuran-3-ol (500 mg, 1.71 mmol, 1 eq) in pyridine (5 mL) was added adamantane-1-carbonyl chloride (4.51 g, 22.7 mmol, 13.3 eq) in THE (10 mL) at 0° C. The resulting mixture was stirred at 0° C. for 2 h. The reaction mixture was quenched with H₂O (60 mL) and extracted with DCM (70 mL). The organic layer was washed with H₂O (60 mL), brine (60 mL), dried over Na₂SO₄, and concentrated. The resulting residue was purified by flash silica gel chromatography (ISCO®; 12 g SepaFlash® Silica Flash Column, eluted with 0-8% methanol/dichloromethane gradient @ 40 mL/min) to give ((2R,3S,5R)-5-(6-amino-2-fluoro-9H-purin-9-yl)-2-ethynyl-3-hydroxy-tetrahydrofuran-2-yl)methyl adamantane-1-carboxylate (172 mg, 21.7% yield) as a white solid. LCMS (ESI) m/z, $C_{23}H_{26}FN_5O_4$: calculated 455.20, found (M+H)⁺: 456.2. ¹H NMR (400 MHz, CD₃CN) δ (ppm) 7.98 (s, 1H), 6.32 (br s, 2H), 6.25-6.22 (m, 1H), 4.75-4.69 (m, 1H), 4.27 (q, J=12 Hz, 2H), 3.71-3.70 (m, 1H), 2.97 (s, 1H), 2.97-2.90 (m, 1H), 2.62-2.56 (m, 1H), 1.75-1.54 (m, 15H). ¹⁹F NMR (376 MHz, CD₃CN) δ (ppm) −52.72 (s, 1F).

Example 4, Example 5 and Example 6: ((2R,3S,5R)-5-(6-amino-2-fluoro-9H-purin-9-yl)-2-ethynyl-3-hydroxy-tetrahydrofuran-2-yl)methyl 1-adamantyl carbonate (Compound 4), ((2R,3S,5R)-5-(6-amino-2-fluoro-9H-purin-9-yl)-2-ethynyl-2-(hydroxymethyl)tetrahydrofuran-3-yl) 1-adamantyl carbonate (Compound 5) and (((2R,3S,5R)-3-((((1-adamantyl)oxy)carbonyl)oxy)-5-(6-amino-2-fluoro-9H-purin-9-yl)-2-ethynyltetrahydrofuran-2-yl)methyl) 1-adamantyl carbonate (Compound 6)

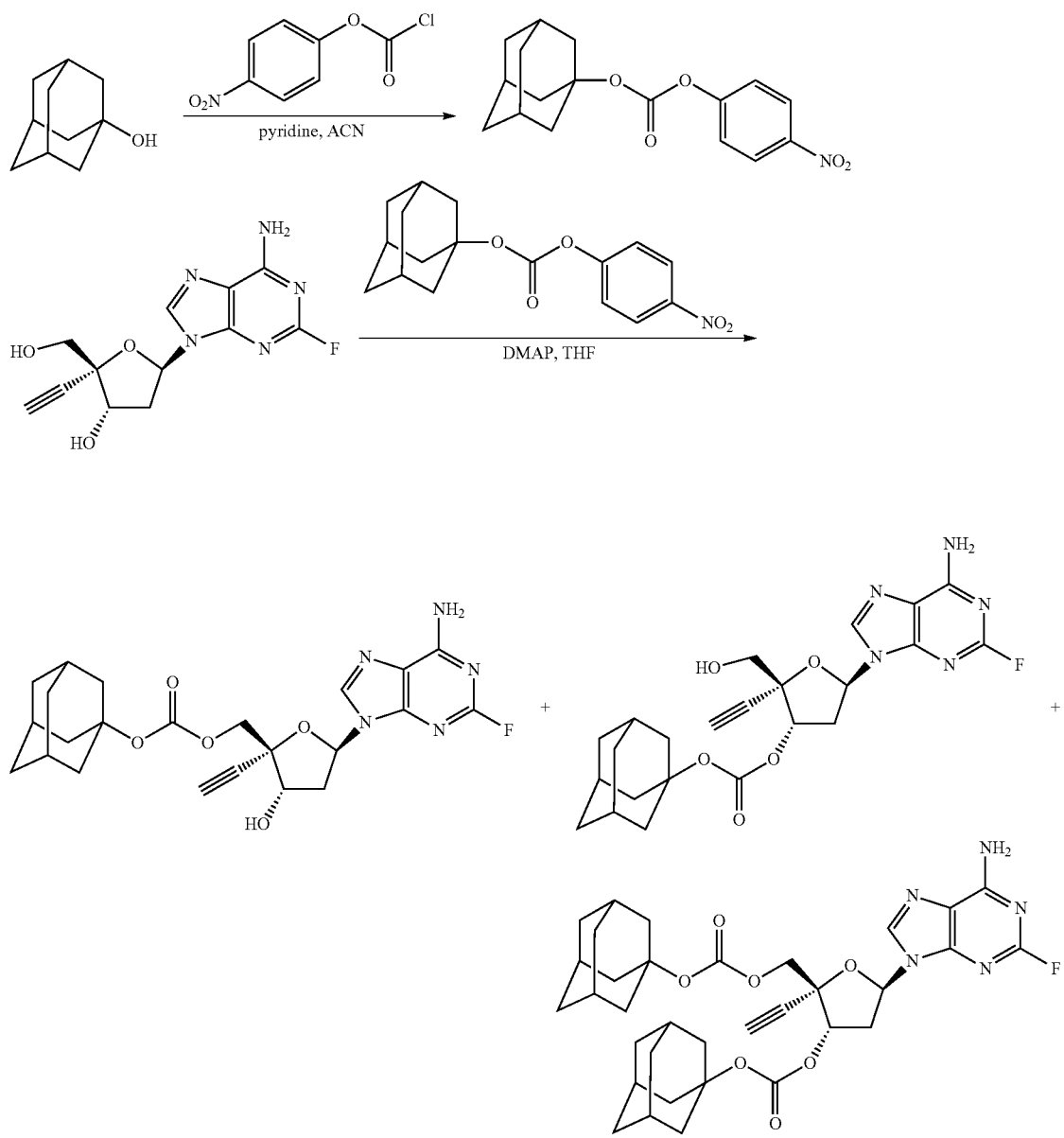

127

Preparation of 1-adamantyl (4-nitrophenyl) carbonate

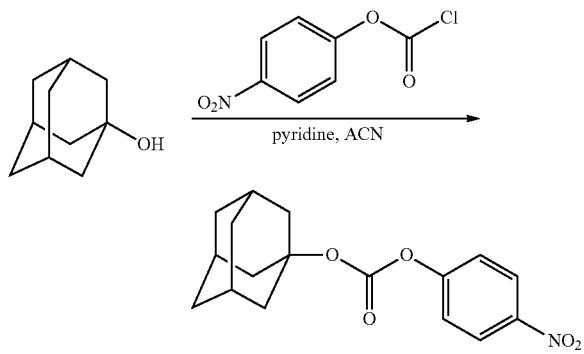

128

To a solution of (4-nitrophenyl) carbonochloridate (992 mg, 4.92 mmol, 1.5 eq) in MeCN (15 mL) was added pyridine (10.6 mL, 131 mmol, 40 eq) and adamantan-1-ol (500 mg, 3.28 mmol, 1 eq). The resulting mixture was stirred at 20° C. for 4 h and then concentrated. The resulting residue was purified by flash silica gel chromatography (ISCO®; 20 g SepaFlash® Silica Flash Column, eluted with 0-10% ethyl acetate/petroleum ether gradient @ 30 mL/min) to give 1-adamantyl (4-nitrophenyl) carbonate (868 mg, 83.4% yield) as a white solid.

Preparation of (((2R,3S,5R)-5-(6-amino-2-fluoro-9H-purin-9-yl)-2-ethynyl-3-hydroxy-tetrahydrofuran-2-yl)methyl 1-adamantyl carbonate, ((2R,3S,5R)-5-(6-amino-2-fluoro-9H-purin-9-yl)-2-ethynyl-2-(hydroxymethyl)tetrahydrofuran-3-yl) 1-adamantyl carbonate and (((2R,3S,5R)-3-((((1-adamantyl)oxy)carbonyl)oxy)-5-(6-amino-2-fluoro-9H-purin-9-yl)-2-ethynyltetrahydrofuran-2-yl)methyl) 1-adamantyl carbonate

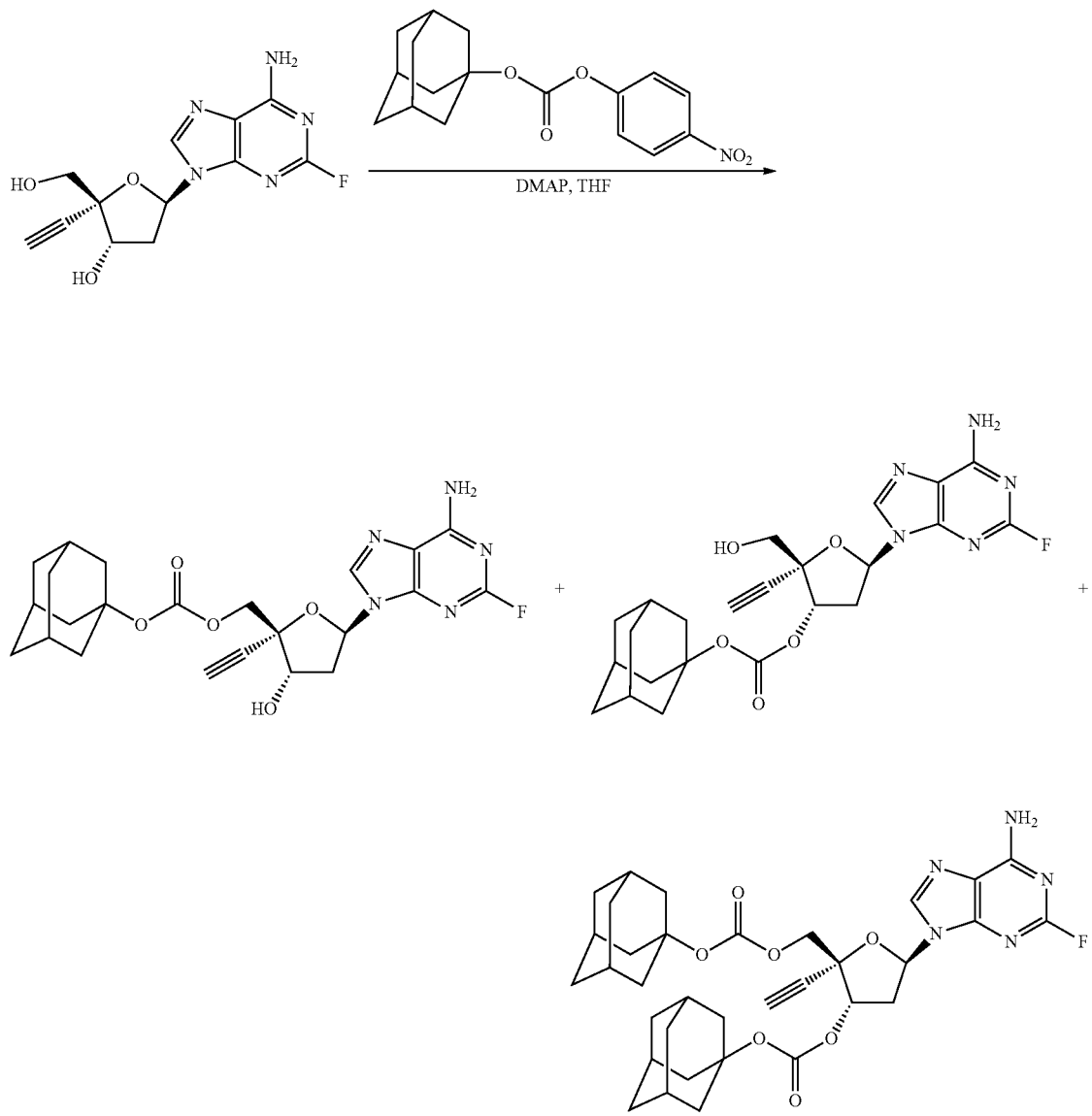

To a solution of (2R,3S,5R)-5-(6-amino-2-fluoro-9H-purin-9-yl)-2-ethynyl-2-(hydroxymethyl)tetrahydrofuran-3-ol (100 mg, 0.34 mol, 1 eq) in THF (20 mL) was added DMAP (8.32 mg, 0.068 mol, 0.2 eq) and 1-adamantyl (4-nitrophenyl) carbonate (162 mg, 0.51 mol, 1.5 eq). The resulting mixture was stirred at 20° C. for 32 h and then concentrated. The resulting residue was purified by prep-HPLC (column: Phenomenex Gemini-NX 80×30 mm×3 um; mobile phase: [water (10 mM NH$_4$HCO$_3$)-ACN]; B %: 49%-79%, 9 min) to give three products.

((2R,3S,5R)-5-(6-amino-2-fluoro-9H-purin-9-yl)-2-ethynyl-3-hydroxy-tetrahydrofuran-2-yl)methyl 1-adamantyl carbonate (16.5 mg, 10.3% yield, white solid): LCMS (ESI) m/z, C$_{23}$H$_{26}$FN$_5$O$_5$: calculated 471.19, found (M+H)$^+$: 472.2. $^1$H NMR (400 MHz, CD$_3$CN) δ (ppm) 7.95 (s, 1H), 6.32 (br s, 2H), 6.24-6.23 (m, 1H), 4.75 (q, J=7.2 Hz, 1H), 4.44 (d, J=12 Hz, 1H), 4.14 (d, J=12 Hz, 1H), 3.70 (d, J=6.4 Hz, 1H), 2.98 (s, 1H), 2.85-2.84 (m, 1H), 2.60-2.50 (m, 1H), 2.14-2.07 (m, 5H), 1.92-1.85 (m, 4H), 1.63 (s, 6H). $^{19}$F NMR (376 MHz, CD$_3$CN) δ (ppm) −52.78 (s, 1F).

((2R,3S,5R)-5-(6-amino-2-fluoro-9H-purin-9-yl)-2-ethynyl-2-(hydroxymethyl)tetrahydrofuran-3-yl) 1-adamantyl carbonate (7.8 mg, 4.87% yield, white solid). LCMS (ESI) m/z, C$_{23}$H$_{26}$FN$_5$O$_5$: calculated 471.19, found (M+H)$^+$: 472.1. $^1$H NMR (400 MHz, CD$_3$CN) δ (ppm) 7.98 (s, 1H), 6.44 (br s, 2H), 6.37-6.33 (m, 1H), 5.49-5.47 (m, 1H), 5.09-5.05 (m, 1H), 3.90-3.75 (m, 2H), 3.05-3.01 (m, 1H), 2.99 (s, 1H), 2.59-2.57 (m, 1H), 2.15 (s, 8H), 1.71 (s, 6H). $^{19}$F NMR (376 MHz, CD$_3$CN) δ (ppm) −53.38 (s, 1F).

((((2R,3S,5R)-3-((((1-adamantyl)oxy)carbonyl)oxy)-5-(6-amino-2-fluoro-9H-purin-9-yl)-2-ethynyltetrahydrofuran-2-yl)methyl) 1-adamantyl carbonate (4.2 mg, 1.90% yield, white solid). LCMS (ESI) m/z, C$_{34}$H$_{40}$FN$_5$O$_7$: calculated 649.29, found (M+H)$^+$: 650.2. $^1$H NMR (400 MHz, CD$_3$CN) δ (ppm) 7.96 (s, 1H), 6.35 (br s, 2H), 6.31-6.28 (m, 1H), 5.58 (t, J=6.4 Hz, 1H), 4.35 (q, J=11.6 Hz, 2H), 3.14-3.12 (m, 1H), 3.04 (s, 1H), 2.77-2.68 (m, 1H), 2.19 (s, 3H), 2.13 (s, 9H), 2.02-1.95 (m, 5H), 1.91 (s, 1H), 1.72-1.59 (m, 12H). $^{19}$F NMR (376 MHz, CD$_3$CN) δ (ppm) −52.46 (s, 1F).

Example 7, Example 8 and Example 9: ((2R,3S,5R)-5-(6-amino-2-fluoro-9H-purin-9-yl)-2-ethynyl-3-hydroxy-tetrahydrofuran-2-yl)methyl 2-(1-adamantyl)ethyl carbonate (Compound 7), ((2R,3S,5R)-5-(6-amino-2-fluoro-9H-purin-9-yl)-2-ethynyl-2-(hydroxymethyl)tetrahydrofuran-3-yl) 2-(1-adamantyl)ethyl carbonate (Compound 8) and ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) 2-(1-adamantyl)ethyl carbonate (Compound 9)

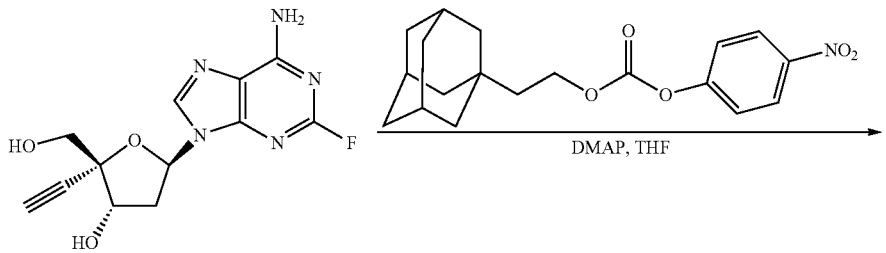

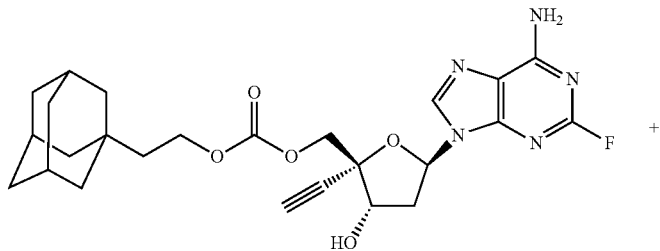

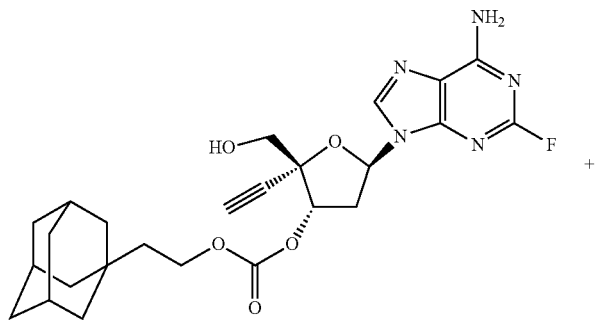

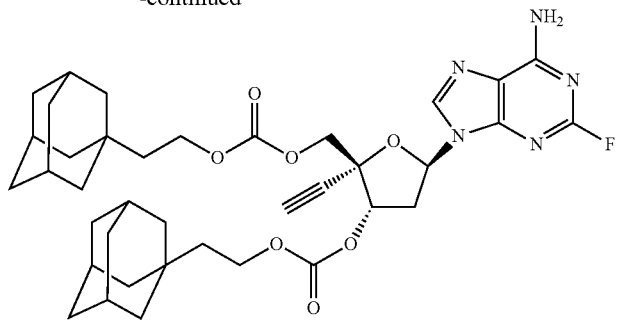

The title compounds were prepared following the procedures of preparation of Example 4, Example 5 and Example 6, substituting 1-adamantyl (4-nitrophenyl) carbonate with 2-(1-adamantyl)ethyl (4-nitrophenyl) carbonate. 2-(1-Adamantyl)ethyl (4-nitrophenyl) carbonate was prepared similarly as 1-adamantyl (4-nitrophenyl) carbonate, except replacing adamantan-1-ol with 2-(1-adamantyl)ethan-1-ol.

((2R,3S,5R)-5-(6-amino-2-fluoro-9H-purin-9-yl)-2-ethynyl-3-hydroxy-tetrahydrofuran-2-yl)methyl 2-(1-adamantyl)ethyl carbonate (12.7 mg, 14.9% yield, white solid). LCMS (ESI) m/z, $C_{25}H_{30}FN_5O_5$: calculated 499.22, found (M+H)$^+$: 500.2. $^1$H NMR (400 MHz, CD$_3$CN) δ (ppm) 7.95 (s, 1H), 6.29 (br s, 2H), 6.27-6.24 (m, 1H), 4.76-4.71 (m, 1H), 4.36 (q, J=12 Hz, 2H), 4.13-4.02 (m, 2H), 3.69 (d, J=6.4 Hz, 1H), 2.99 (s, 1H), 2.87-2.81 (m, 1H), 2.63-2.50 (m, 1H), 1.91 (s, 3H), 1.75-1.58 (m, 6H), 1.49 (s, 6H), 1.35-1.31 (m, 2H). $^{19}$F NMR (376 MHz, CD$_3$CN) δ (ppm) −52.84 (s, 1F).

((2R,3S,5R)-5-(6-amino-2-fluoro-9H-purin-9-yl)-2-ethynyl-2-(hydroxymethyl)tetrahydrofuran-3-yl) 2-(1-adamantyl)ethyl carbonate (5.9 mg, 6.93% yield, white solid). LCMS (ESI) m/z, $C_{25}H_{30}FN_5O_5$: calculated 499.22, found (M+H)$^+$: 500.2. $^1$H NMR (400 MHz, CD$_3$CN) δ (ppm) 7.95 (s, 1H), 6.42 (br s, 2H), 6.38-6.31 (m, 1H), 5.51-5.49 (m, 1H), 5.01-4.97 (m, 1H), 4.27-4.21 (m, 2H), 3.86-3.74 (m, 2H), 3.04-3.02 (m, 1H), 2.95 (s, 1H), 2.59-2.54 (m, 1H), 1.77-1.61 (m, 8H), 1.56 (m, 6H), 1.49-1.46 (m, 2H). $^{19}$F NMR (376 MHz, CD$_3$CN) δ (ppm) −53.33 (s, 1F).

((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) 2-(1-adamantyl)ethyl carbonate (4.2 mg, 3.49% yield, white solid). LCMS (ESI) m/z, $C_{38}H_{48}FN_5O_7$: calculated 705.35, found (M+H)$^+$: 706.3. $^1$H NMR (400 MHz, CD$_3$CN) δ (ppm) 7.95 (s, 1H), 6.32-6.29 (m, 3H), 5.66-5.63 (m, 1H), 4.42 (q, J=11.6 Hz, 2H), 4.28-4.22 (m, 2H), 4.16-4.03 (m, 2H), 3.19-3.08 (m, 1H), 3.03 (s, 1H), 2.76-2.65 (m, 1H), 1.91 (s, 4H), 1.76-1.60 (m, 13H), 1.59-1.44 (m, 15H), 1.35 (t, J=7.2 Hz, 2H). $^{19}$F NMR (376 MHz, CD$_3$CN) δ (ppm) −52.54 (s, 1F).

Example 10 and Example 11: ((2R,3S,5R)-5-(6-amino-2-fluoro-9H-purin-9-yl)-2-ethynyl-3-hydroxy-tetrahydrofuran-2-yl)methyl 3-(1-adamantyl) propyl carbonate (Compound 10) and ((2R,3S,5R)-5-(6-amino-2-fluoro-9H-purin-9-yl)-2-ethynyl-2-(hydroxymethyl)tetrahydrofuran-3-yl) 3-(1-adamantyl)propyl carbonate (Compound 11)

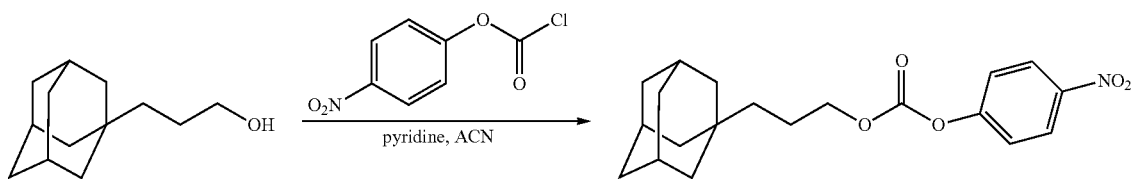

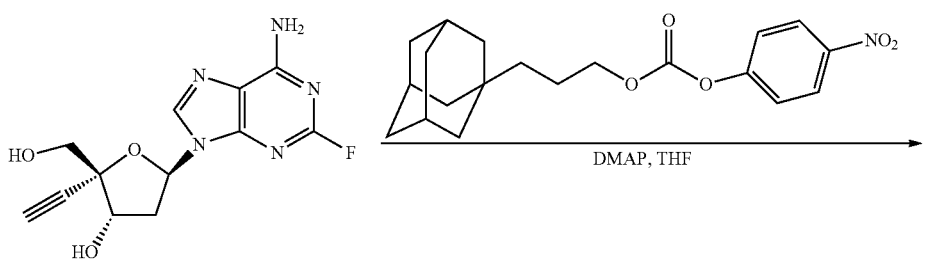

-continued

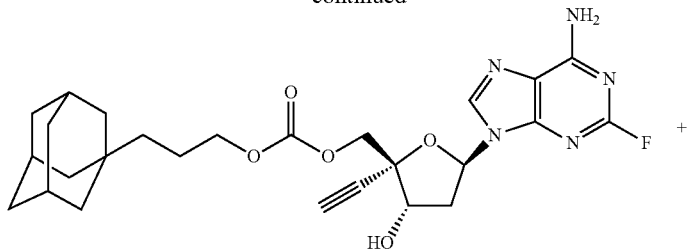

+

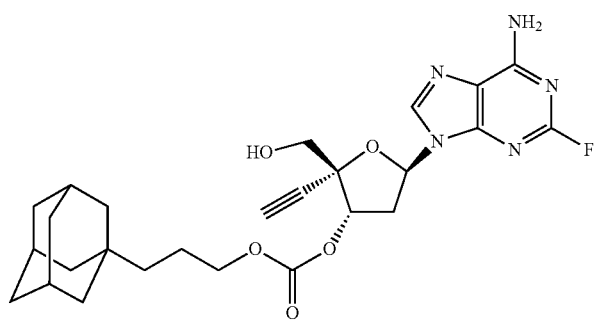

Preparation of 3-(1-adamantyl)propyl (4-nitrophenyl) carbonate

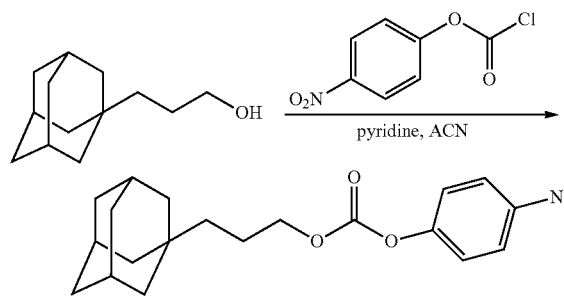

3-(1-adamantyl)propan-1-ol was prepared from 1-adamantylmethanol according to literature procedures (WO 2011/058582 A1).

To a solution of 3-(1-adamantyl)propan-1-ol (100 mg, 0.51 mmol, 1 eq) in MeCN (2 mL) was added pyridine (1.63 g, 20.6 mmol, 40 eq) and (4-nitrophenyl) carbonochloridate (207 mg, 1.03 mmol, 2 eq). The resulting mixture was stirred at room temperature for 4 h and then was concentrated. The resulting residue was purified by flash silica gel chromatography (ISCO®; 4 g SepaFlash® Silica Flash Column, eluted with 0-30% ethyl acetate/petroleum ether gradient @ 15 mL/min) to give 3-(1-adamantyl)propyl (4-nitrophenyl) carbonate (130 mg, 70.9% yield) as a white solid. $^1$H NMR (400 MHz, CDCl$_3$) δ (ppm) 8.31-8.27 (m, 2H), 7.41-7.37 (m, 2H), 4.28-4.25 (m, 2H), 2.00-1.94 (m, 3H), 1.77-1.69 (m, 5H), 1.65-1.61 (m, 3H), 1.52-1.47 (m, 6H), 1.18-1.14 (m, 2H).

Preparation of ((2R,3S,5R)-5-(6-amino-2-fluoro-9H-purin-9-yl)-2-ethynyl-3-hydroxy-tetrahydrofuran-2-yl)methyl 3-(1-adamantyl)propyl carbonate and ((2R,3S,5R)-5-(6-amino-2-fluoro-9H-purin-9-yl)-2-ethynyl-2-(hydroxymethyl)tetrahydrofuran-3-yl) 3-(1-adamantyl)propyl carbonate

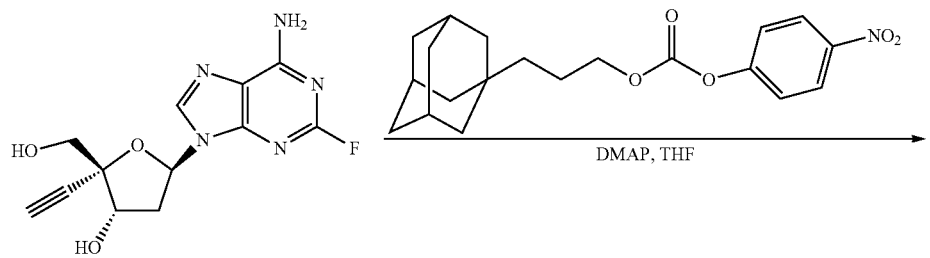

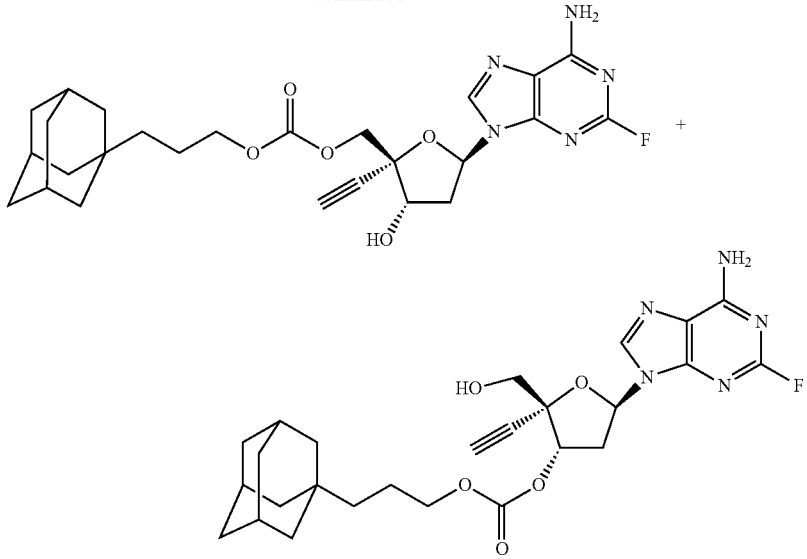

To a solution of 3-(1-adamantyl)propyl (4-nitrophenyl) carbonate (91.6 mg, 0.255 mmol, 1.5 eq) and (2R,3S,5R)-5-(6-amino-2-fluoro-9H-purin-9-yl)-2-ethynyl-2-(hydroxymethyl)tetrahydrofuran-3-ol (50 mg, 0.17 mmol, 1 eq) in THF (2 mL) was added DMAP (4.15 mg, 0.034 mmol, 0.2 eq). The resulting mixture was stirred at room temperature for 32 h, and then was concentrated. The resulting residue was purified by prep-HPLC (column: Phenomenex Gemini-NX 80×30 mm×3 um; mobile phase: [water (10 mM NH$_4$HCO$_3$)-ACN]; B %: 60%-90%, 9 min) to give two products.

((2R,3S,5R)-5-(6-amino-2-fluoro-9H-purin-9-yl)-2-ethynyl-3-hydroxy-tetrahydrofuran-2-yl)methyl 3-(1-adamantyl)propyl carbonate (4.5 mg, 5.2% yield) was obtained as a white solid. LCMS (ESI) m/z, C$_{26}$H$_{32}$FN$_5$O$_5$: calculated 513.24, found (M+H)$^+$: 514.3. $^1$H NMR (400 MHz, CDCl$_3$) δ (ppm) 7.95 (s, 1H), 6.43-6.40 (m, 1H), 6.08-6.01 (m, 2H), 4.77-4.74 (m, 1H), 4.54-4.46 (m, 2H), 4.15-4.11 (m, 2H), 2.95-2.89 (m, 1H), 2.83-2.75 (m, 1H), 2.72-2.66 (m, 1H), 2.50-2.45 (m, 1H), 1.99-1.90 (m, 3H), 1.72-1.69 (m, 3H), 1.65-1.60 (m, 3H), 1.46-1.43 (m, 6H), 1.30-1.26 (m, 1H), 1.12-1.06 (m, 2H). $^{19}$F NMR (376 MHz, CDCl$_3$) δ (ppm) −49.39 (s, 1F).

((2R,3S,5R)-5-(6-amino-2-fluoro-9H-purin-9-yl)-2-ethynyl-2-(hydroxymethyl)tetrahydrofuran-3-yl) 3-(1-adamantyl)propyl carbonate (3.6 mg, 4.1% yield) was obtained as a white solid. LCMS (ESI) m/z, C$_{26}$H$_{32}$FN$_5$O$_5$: calculated 513.24, found (M+H)$^+$: 514.2. $^1$H NMR (400 MHz, CDCl$_3$) δ (ppm) 7.95 (s, 1H), 6.40-6.37 (m, 1H), 6.13-6.08 (m, 2H), 5.65-5.64 (m, 1H), 4.23-4.15 (m, 2H), 4.10-4.07 (m, 1H), 3.99-3.96 (m, 1H), 3.28-3.20 (m, 1H), 2.70-2.65 (m, 1H), 2.62-2.57 (m, 1H), 2.01-1.95 (m, 3H), 1.75-1.72 (m, 3H), 1.70-1.68 (m, 1H), 1.65-1.62 (m, 3H), 1.50-1.45 (m, 7H), 1.17-1.13 (m, 2H). $^{19}$F NMR (376 MHz, CDCl$_3$) δ (ppm) −49.66 (s, 1F).

Example 12 and Example 13: ((2R,3S,5R)-5-(6-amino-2-fluoro-9H-purin-9-yl)-2-ethynyl-3-hydroxy-tetrahydrofuran-2-yl)methyl 4-(1-adamantyl)butyl carbonate (Compound 12) and ((2R,3S,5R)-5-(6-amino-2-fluoro-9H-purin-9-yl)-2-ethynyl-2-(hydroxymethyl)tetrahydrofuran-3-yl) 4-(1-adamantyl)butyl carbonate (Compound 13)

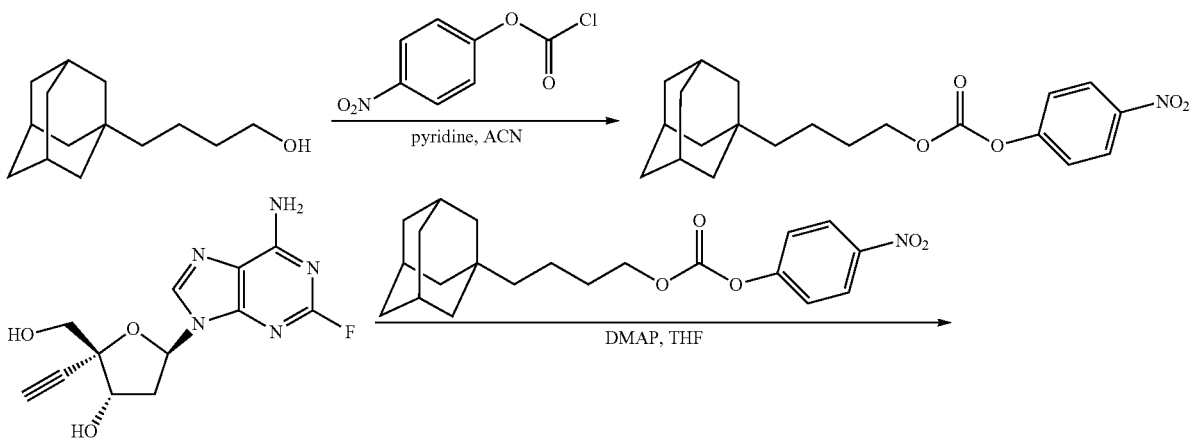

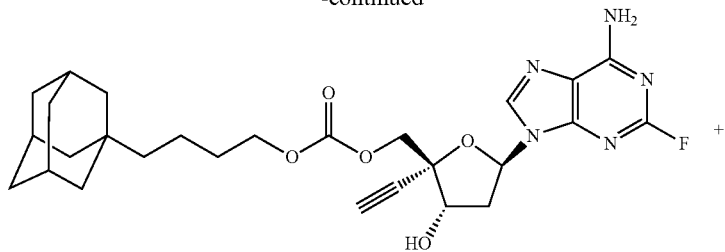

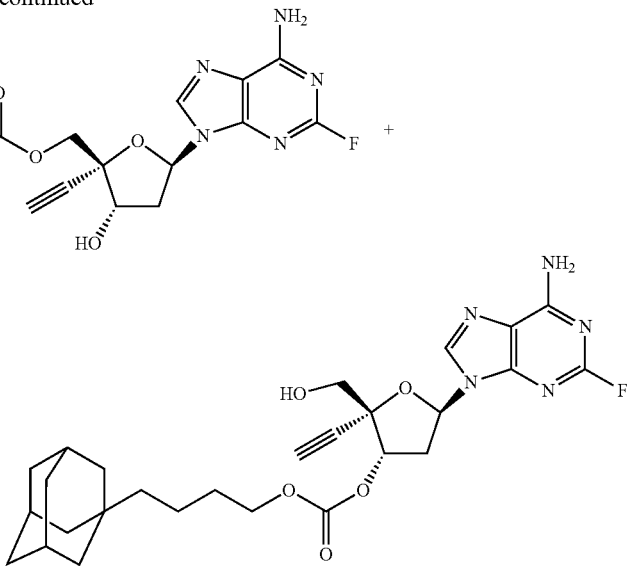

((2R,3S,5R)-5-(6-amino-2-fluoro-9H-purin-9-yl)-2-ethynyl-3-hydroxy-tetrahydrofuran-2-yl)methyl 4-(1-adamantyl)butyl carbonate and ((2R,3S,5R)-5-(6-amino-2-fluoro-9H-purin-9-yl)-2-ethynyl-2-(hydroxymethyl)tetrahydrofuran-3-yl) 4-(1-adamantyl)butyl carbonate were prepared using the same procedure as in the preparation of ((2R,3S,5R)-5-(6-amino-2-fluoro-9H-purin-9-yl)-2-ethynyl-3-hydroxy-tetrahydrofuran-2-yl)methyl 3-(1-adamantyl)propyl carbonate and ((2R,3S,5R)-5-(6-amino-2-fluoro-9H-purin-9-yl)-2-ethynyl-2-(hydroxymethyl)tetrahydrofuran-3-yl) 3-(1-adamantyl)propyl carbonate, substituting 3-(1-adamantyl)propan-1-ol with 4-(1-adamantyl) butan-1-ol. 4-(1-Adamantyl)butan-1-ol was prepared from 2-(1-adamantyl)ethan-1-ol according to literature procedures (WO 2011/058582 A1).

((2R,3S,5R)-5-(6-amino-2-fluoro-9H-purin-9-yl)-2-ethynyl-3-hydroxy-tetrahydrofuran-2-yl)methyl 4-(1-adamantyl)butyl carbonate (4.6 mg, 5.1% yield, white solid). LCMS (ESI) m/z, $C_{27}H_{34}FN_5O_5$: calculated 527.25, found (M+H)$^+$: 528.2. $^1$H NMR (400 MHz, CD$_3$CN) δ (ppm) 7.95 (s, 1H), 6.28-6.25 (m, 3H), 4.75-4.70 (m, 1H), 4.47-4.44 (m, 1H), 4.29-4.26 (m, 1H), 4.07-4.00 (m, 2H), 3.70-3.68 (m, 1H), 3.01-2.96 (m, 1H), 2.86-2.80 (m, 1H), 2.60-2.53 (m, 1H), 1.95-1.90 (m, 3H), 1.72-1.69 (m, 3H), 1.64-1.61 (m, 3H), 1.53-1.48 (m, 2H), 1.45-1.44 (m, 6H), 1.28-1.20 (m, 2H), 1.05-1.00 (m, 2H). $^{19}$F NMR (376 MHz, CD$_3$CN) δ (ppm) -52.85 (s, 1F).

((2R,3S,5R)-5-(6-amino-2-fluoro-9H-purin-9-yl)-2-ethynyl-2-(hydroxymethyl)tetrahydrofuran-3-yl) 4-(1-adamantyl)butyl carbonate (6.4 mg, 7.1% yield, white solid). LCMS (ESI) m/z, $C_{27}H_{34}FN_5O_5$: calculated 527.25, found (M+H)$^+$: 528.2. $^1$H NMR (400 MHz, CD$_3$CN) δ (ppm) 7.95 (m, 1H), 6.40-6.32 (m, 3H), 5.52-5.49 (m, 1H), 4.99-4.96 (m, 1H), 4.20-4.13 (m, 2H), 3.88-3.84 (m, 1H), 3.80-3.74 (m, 1H), 3.08-3.00 (m, 1H), 2.97-2.92 (m, 1H), 2.60-2.55 (m, 1H), 1.95-1.90 (m, 3H), 1.77-1.71 (m, 3H), 1.66-1.59 (m, 5H), 1.50-1.43 (m, 6H), 1.37-1.29 (m, 2H), 1.11-1.06 (m, 2H). $^{19}$F NMR (376 MHz, CD$_3$CN) δ (ppm) -53.34 (s, 1F).

Example 14: ((2R,3S,5R)-5-(6-amino-2-fluoro-9H-purin-9-yl)-2-ethynyl-3-hydroxy-tetrahydrofuran-2-yl)methyl 3-(1-adamantyl)propanoate (Compound 14)

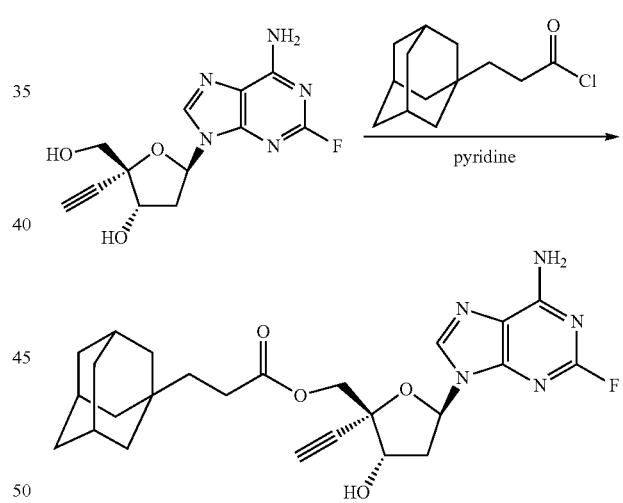

((2R,3S,5R)-5-(6-amino-2-fluoro-9H-purin-9-yl)-2-ethynyl-3-hydroxy-tetrahydrofuran-2-yl)methyl 3-(1-adamantyl)propanoate was prepared (65.1 mg, 53.9% yield, white solid) using the same procedure as in the preparation of ((2R,3S,5R)-5-(6-amino-2-fluoro-9H-purin-9-yl)-2-ethynyl-3-hydroxy-tetrahydrofuran-2-yl)methyl 2-(1-adamantyl) acetate, substituting 2-(1-adamantyl)acetyl chloride with 3-(1-adamantyl) propanoyl chloride. 3-(1-Adamantyl) propanoyl chloride was synthesized from methyl 3-(1-adamantyl) propanoate according to literature procedures (WO 2011/058582 A1).

LCMS (ESI) m/z, $C_{25}H_{30}FN_5O_4$: calculated 483.23, found (M+H)$^+$: 484.2. $^1$H NMR (400 MHz, CDCl$_3$) δ (ppm) 8.10 (s, 1H), 6.36-6.25 (m, 3H), 4.79-4.75 (m, 1H), 4.50-4.42 (m, 2H), 3.00-2.94 (m, 1H), 2.84-2.79 (m, 1H), 2.76-

2.68 (m, 1H), 2.33-2.28 (m, 2H), 1.97-1.93 (m, 3H), 1.71-1.68 (m, 3H), 1.62-1.59 (m, 3H), 1.44-1.43 (m, 6H), 1.40-1.38 (m, 3H). $^{19}$F NMR (376 MHz, CDCl$_3$) δ (ppm)-48.80 (s, 1F).

Example 15: ((2R,3S,5R)-5-(6-amino-2-fluoro-9H-purin-9-yl)-2-ethynyl-3-hydroxy-tetrahydrofuran-2-yl)methyl 4-(1-adamantyl)butanoate (Compound 15)

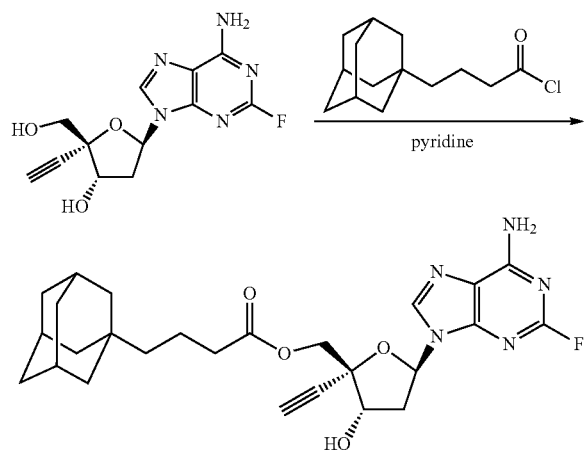

((2R,3S,5R)-5-(6-amino-2-fluoro-9H-purin-9-yl)-2-ethynyl-3-hydroxy-tetrahydrofuran-2-yl)methyl 4-(1-adamantyl)butanoate was prepared (61.4 mg, 51.7% yield, a white solid) using the same procedure as in the preparation of ((2R,3S,5R)-5-(6-amino-2-fluoro-9H-purin-9-yl)-2-ethynyl-3-hydroxy-tetrahydrofuran-2-yl)methyl 3-(1-adamantyl)propanoate, substituting 3-(1-adamantyl) propanoyl chloride with 4-(1-adamantyl) butanoyl chloride. 4-(1-Adamantyl) butanoyl chloride was synthesized from methyl 4-(1-adamantyl)butanoate according to literature procedures (WO 2011/058582 A1).

LCMS (ESI) m/z, C$_{26}$H$_{32}$FN$_5$O$_4$: calculated 497.24, found (M+H)+: 498.3. $^1$H NMR (400 MHz, CD$_3$CN) δ (ppm) 7.96 (s, 1H), 6.30 (br s, 2H), 6.26-6.23 (m, 1H), 4.78-4.73 (m, 1H), 4.41 (d, J=12.0 Hz, 1H), 4.20 (d, J=11.6 Hz, 1H), 3.64 (d, J=6.4 Hz, 1H), 2.98 (s, 1H), 2.83-2.81 (m, 1H), 2.61-2.57 (m, 1H), 2.23-2.19 (m, 1H), 1.93-1.85 (m, 3H), 1.71-1.68 (m, 3H), 1.63-1.60 (m, 3H), 1.46-1.38 (m, 8H), 0.95-0.90 (m, 2H). $^{19}$F NMR (376 MHz, CD$_3$CN) δ(ppm) −52.81 (s, 1F).

Example 16: (10aR,12R,13aS)-12-(6-amino-2-fluoro-9H-purin-9-yl)-10a-ethynylhexahydro-4H,10H-furo[3,2-d][1,3,7,9]tetraoxacyclododecine-2,8-dione (Compound 16)

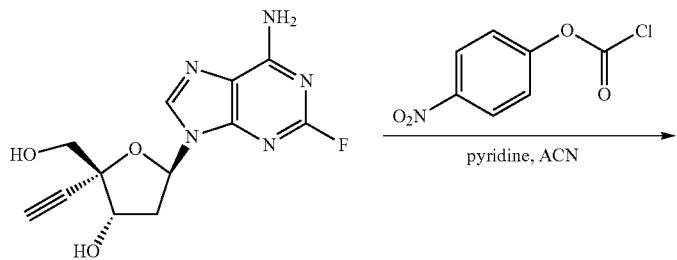

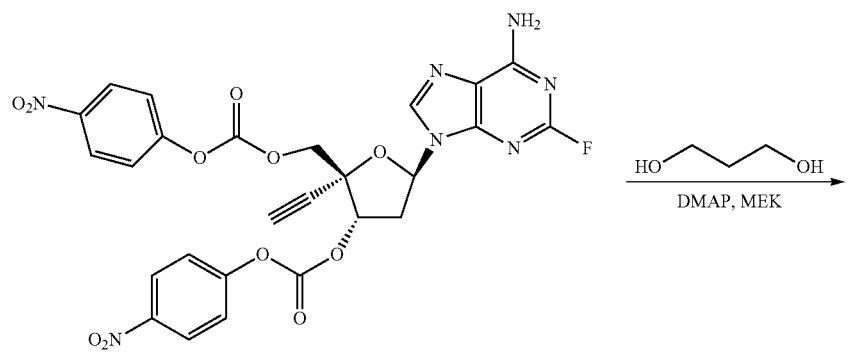

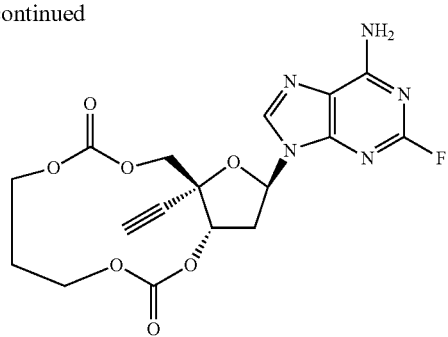

Preparation of (2R,3S,5R)-5-(6-amino-2-fluoro-9H-purin-9-yl)-2-ethynyl-2-((((4-nitrophenoxy)carbonyl)oxy)methyl)tetrahydrofuran-3-yl (4-nitrophenyl) carbonate

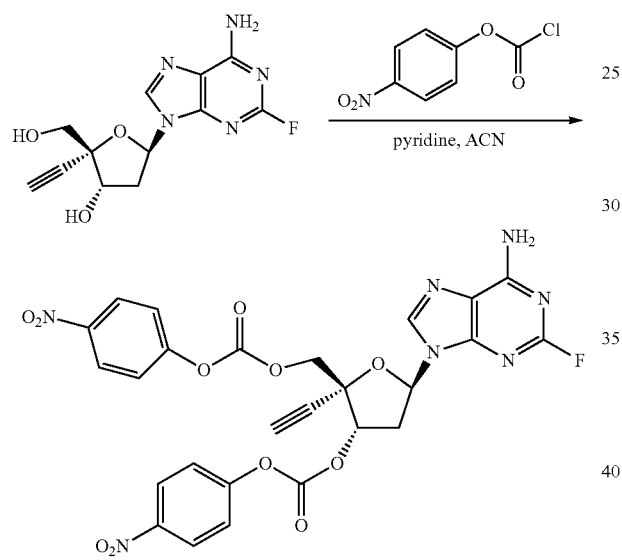

To a solution of (2R,3S,5R)-5-(6-amino-2-fluoro-9H-purin-9-yl)-2-ethynyl-2-(hydroxymethyl)tetrahydrofuran-3-ol (150 mg, 0.512 mmol, 1 eq) in MeCN (15 mL) was added pyridine (1.62 g, 20.4 mmol, 1.65 mL, 40 eq) and (4-nitrophenyl) carbonochloridate (619 mg, 3.07 mmol, 6 eq). The resulting mixture was stirred at 15° C. for 41 h. The reaction mixture was concentrated and purified by flash silica gel chromatography (ISCO®; 12 g SepaFlash® Silica Flash Column, eluted with 0-5% Methanol/DCM gradient @ 50 mL/min) to give (2R,3S,5R)-5-(6-amino-2-fluoro-9H-purin-9-yl)-2-ethynyl-2-((((4-nitrophenoxy)carbonyl)oxy)methyl)tetrahydrofuran-3-yl (4-nitrophenyl) carbonate (250 mg, 78.3% yield) as a white solid.

Preparation of (10aR,12R,13aS)-12-(6-amino-2-fluoro-9H-purin-9-yl)-10a-ethynylhexahydro-4H,10H-furo[3,2-d][1,3,7,9]tetraoxacyclododecine-2,8-dione

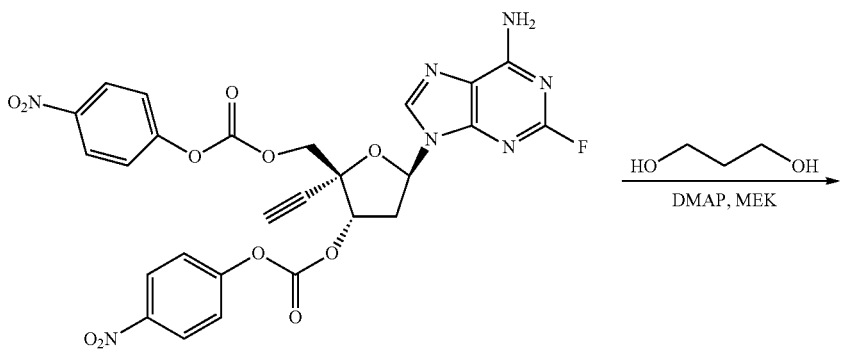

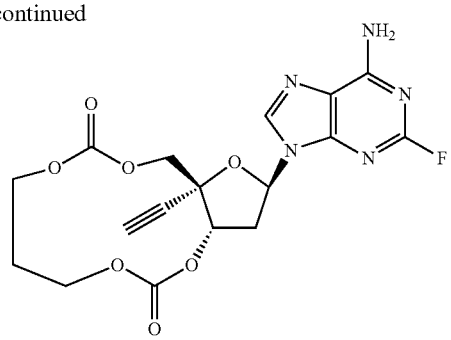

To a solution of (2R,3S,5R)-5-(6-amino-2-fluoro-9H-purin-9-yl)-2-ethynyl-2-((((4-nitrophenoxy)carbonyl)oxy)methyl)tetrahydrofuran-3-yl (4-nitrophenyl) carbonate (300 mg, 0.481 mmol, 1 eq) in MEK (30 mL) was added DMAP (58.8 mg, 0.481 mmol, 1 eq) and propane-1,3-diol (32.9 mg, 0.433 mmol, 0.9 eq). The resulting mixture was stirred at 20° C. for 18 h. The reaction mixture was concentrated and purified by prep-HPLC (column: Welch Xtimate C18 150× 25 mm×5 um; mobile phase: [water (10 mM $NH_4HCO_3$)-ACN]; B %: 17%-47%, 9 min) to give (10aR,12R,13aS)-12-(6-amino-2-fluoro-9H-purin-9-yl)-10a-ethynylhexahydro-4H,10H-furo[3,2-d][1,3,7,9]tetraoxacyclododecine-2,8-dione (5.2 mg, 2.56% yield, white solid). LCMS (ESI) m/z, $C_{17}H_{16}FN_5O_7$: calculated 421.10, found $(M+H)^+$: 422.2. $^1H$ NMR (400 MHz, $CD_3CN$) δ (ppm) 7.96 (s, 1H), 6.34 (br s, 2H), 6.32-6.29 (m, 1H), 6.05-6.01 (m, 1H), 4.57-4.53 (m, 2H), 4.41-4.37 (m, 4H), 3.11 (s, 1H), 2.97-2.94 (m, 1H), 2.85-2.80 (m, 1H), 2.21-2.19 (m, 1H), 2.13-1.94 (m, 2H). $^{19}F$ NMR (376 MHz, $CD_3CN$) δ (ppm) −52.39 (s, 1F).

Example 17: (11aR,13R,14aS)-13-(6-amino-2-fluoro-9H-purin-9-yl)-11a-ethynyloctahydro-11H-furo[3,2-d][1,3,7]trioxacyclotridecine-2,9(4H)-dione (Compound 17)

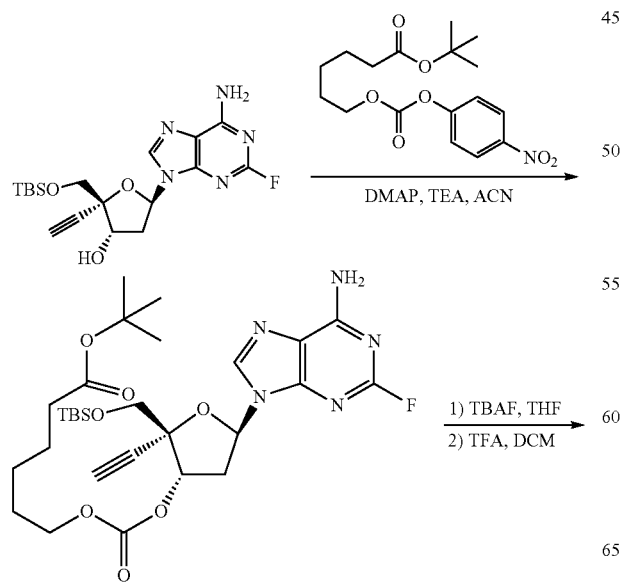

Preparation of tert-butyl 6-[(2R,3S,5R)-5-(6-amino-2-fluoro-purin-9-yl)-2-[[tert-butyl(dimethyl)silyl]oxymethyl]-2-ethynyl-tetrahydrofuran-3-yl]oxycarbonyloxyhexanoate

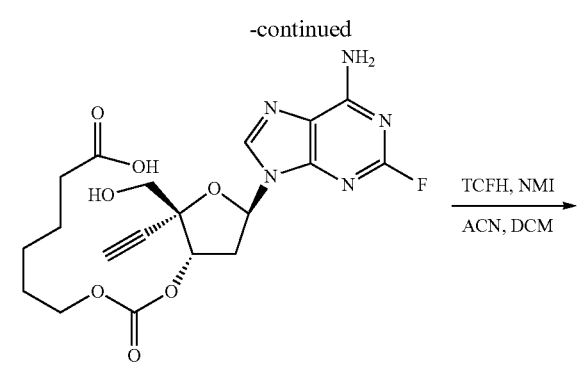

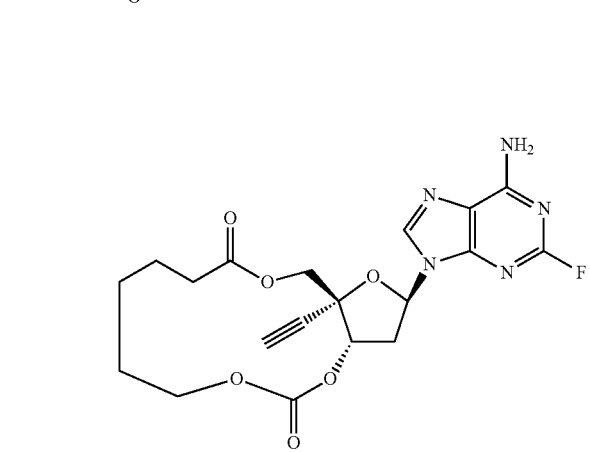

145

-continued

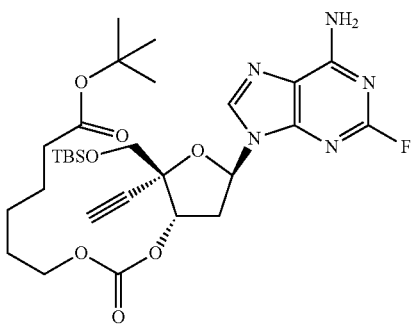

tert-Butyl 6-(4-nitrophenoxy)carbonyloxyhexanoate was prepared using the same procedure as in the preparation of 3-(1-adamantyl)propyl (4-nitrophenyl) carbonate, substituting 3-(1-adamantyl)propan-1-ol with tert-butyl 6-hydroxyhexanoate. tert-Butyl 6-hydroxyhexanoate was synthesized from oxepan-2-one according to literature procedure (WO2015187596 A2).

To a solution of (2R,3S,5R)-5-(6-amino-2-fluoro-purin-9-yl)-2-[[tert-butyl(dimethyl)silyl]oxymethyl]-2-ethynyl-tetrahydrofuran-3-ol (200 mg, 0.49 mmol, 1 eq) in MeCN (20 mL) was added DMAP (60.0 mg, 0.49 mmol, 1 eq), Et$_3$N (149 mg, 1.47 mmol, 3 eq) and tert-butyl 6-(4-nitrophenoxy)carbonyloxyhexanoate (346 mg, 0.98 mmol, 2 eq). The resulting mixture was stirred at 15° C. for 16 h. The reaction mixture was concentrated and purified by flash silica gel chromatography (ISCO®; 12 g SepaFlash® Silica Flash Column, eluted with 0-3% MeOH/DCM @ 30 mL/min) to give tert-butyl 6-[(2R,3S,5R)-5-(6-amino-2-fluoro-purin-9-yl)-2-[[tert-butyl(dimethyl)silyl]oxymethyl]-2-ethynyl-tetrahydrofuran-3-yl]oxycarbonyloxyhexanoate (250 mg, 81.9% yield) as a yellow solid. $^1$H NMR (400 MHz, CD$_3$CN) δ (ppm) 8.22 (s, 1H), 6.52-6.48 (m, 1H), 6.08 (br s, 2H), 5.50-5.48 (m, 1H), 4.25-4.17 (m, 2H), 4.00 (q, J=12 Hz, 2H), 2.82-2.79 (m, 2H), 2.70 (s, 1H), 2.26-2.22 (m, 2H), 1.75-1.71 (m, 2H), 1.65-1.61 (m, 2H), 1.47-1.43 (m, 11H), 0.93 (s, 9H), 0.14 (s, 6H). $^{19}$F NMR (376 MHz, CD$_3$CN) δ (ppm)-49.79 (s, 1F).

Preparation of 6-[(2R,3S,5R)-5-(6-amino-2-fluoro-purin-9-yl)-2-ethynyl-2-(hydroxymethyl)tetrahydrofuran-3-yl]oxycarbonyloxyhexanoic acid

146

-continued

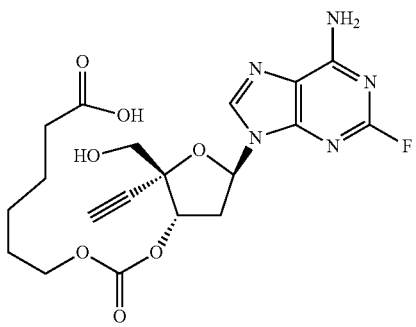

To a solution of tert-butyl 6-[(2R,3S,5R)-5-(6-amino-2-fluoro-purin-9-yl)-2-[[tert-butyl(dimethyl)silyl]oxymethyl]-2-ethynyl-tetrahydrofuran-3-yl]oxycarbonyloxyhexanoate (100 m g, 0.16 mmol, 1 eq) in THE (5 mL) was added TBAF (1 M in THF, 0.25 mL, 1.5 eq). The resulting mixture was stirred at 15° C. for 1 h. The reaction mixture was concentrated and purified by flash silica gel chromatography (ISCO®; 4 g SepaFlash® Silica Flash Column, eluted with 0-4% ethyl acetate/petroleum ether gradient @ 25 mL/min) to give tert-butyl 6-[(2R,3S,5R)-5-(6-amino-2-fluoro-purin-9-yl)-2-ethynyl-2-(hydroxymethyl)tetrahydrofuran-3-yl]oxycarbonyloxyhexanoate (80 mg, 98.0% yield) as a light yellow gum. To a solution of tert-butyl 6-[(2R,3S,5R)-5-(6-amino-2-fluoro-purin-9-yl)-2-ethynyl-2-(hydroxymethyl)tetrahydrofuran-3-yl]oxycarbonyloxyhexanoate (80 mg, 0.16 mmol, 1 eq) in DCM (20 mL) was added TFA (1 mL). The resulting mixture was stirred at 15° C. for 16 h. The reaction mixture was concentrated and purified by prep-TLC (silica gel, DCM/MeOH=10/1) to give 6-[(2R,3S,5R)-5-(6-amino-2-fluoro-purin-9-yl)-2-ethynyl-2-(hydroxymethyl)tetrahydrofuran-3-yl]oxycarbonyloxyhexanoic acid (60 mg, 84.3% yield) as a yellow gum.

Preparation of (11aR,13R,14aS)-13-(6-amino-2-fluoro-9H-purin-9-yl)-11a-ethynyloctahydro-11H-furo[3,2-d][1,3,7]trioxacyclotridecine-2,9(4H)-dione

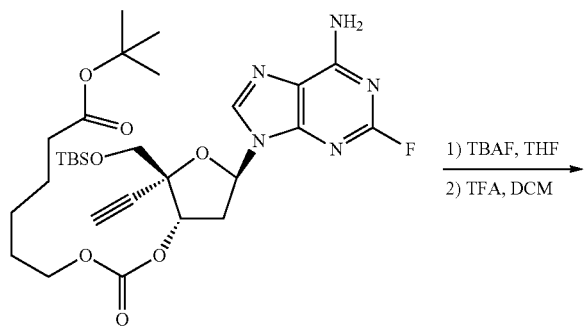

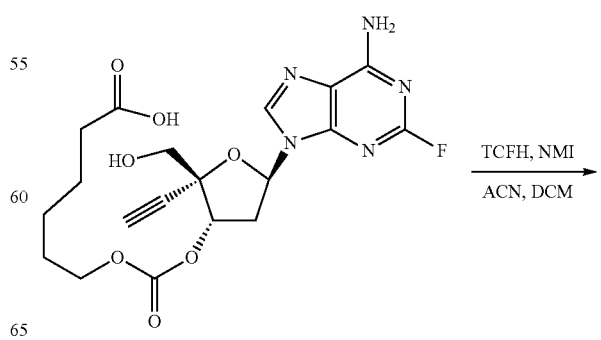

-continued

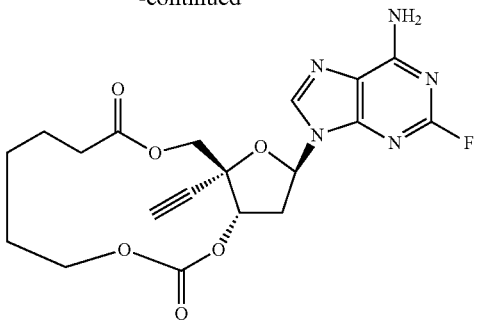

To a solution of 6-[(2R,3S,5R)-5-(6-amino-2-fluoro-purin-9-yl)-2-ethynyl-2-(hydroxymethyl)tetrahydrofuran-3-yl]oxycarbonyloxyhexanoic acid (60 mg, 0.13 mmol, 1 eq) in DCM (6 mL) and ACN (6 mL) was added TCFH (104 mg, 0.37 mmol, 2.8 eq) and NMI (36.0 mg, 0.44 mmol, 3.3 eq). The resulting mixture was stirred at 25° C. for 16 h. The reaction mixture was concentrated and purified by prep-HPLC (NH$_4$HCO$_3$ condition; column: Welch Xtimate C18 150×25 mm×5 um; mobile phase: [water (10 mM NH$_4$HCO$_3$)-ACN]; B %: 32%-62%, 9 min) to give (11aR, 13R,14aS)-13-(6-amino-2-fluoro-9H-purin-9-yl)-11a-ethynyloctahydro-11H-furo[3,2-d][1,3,7]trioxacyclotridecine-2,9(4H)-dione (3.4 mg, 6.03% yield, a white solid). LCMS (ESI) m/z, C$_{19}$H$_{20}$FN$_5$O$_6$: calculated 433.14, found (M+H)$^+$: 434.1. $^1$H NMR (400 MHz, CD$_3$CN) δ (ppm) 7.95 (s, 1H), 6.37-6.34 (m, 3H), 5.86-5.83 (m, 1H), 4.47-4.41 (m, 2H), 4.33 (d, J=10.8 Hz, 1H), 4.17-4.11 (m, 1H), 3.25-3.19 (m, 1H), 3.01 (s, 1H), 2.75-2.68 (m, 1H), 2.43-2.40 (m, 2H), 1.75-1.71 (m, 2H), 1.63-1.55 (m, 2H), 1.37-1.34 (m, 1H), 0.98-0.95 (m, 1H). $^{19}$F NMR (376 MHz, CD$_3$CN) δ (ppm) −52.52 (s, 1F).

Example 18: ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) ethyl carbonate (Compound 18)

((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) ethyl carbonate was prepared (11.2 mg, 19.6% yield, a white solid) using the same procedure as in the preparation of ((2R,3S,5R)-5-(6-amino-2-fluoro-9H-purin-9-yl)-2-ethynyl-3-hydroxy-tetrahydrofuran-2-yl)methyl 2-(1-adamantyl) acetate, substituting 2-(1-adamantyl)acetyl chloride with ethyl carbonochloridate. LCMS (ESI) m/z, C$_{28}$H$_{34}$FN$_5$O$_7$: calculated 571.24, found (M+H)+: 572.3. $^1$H NMR (400 MHz, CD$_3$CN) δ (ppm) 7.95 (s, 1H), 6.34-6.30 (m, 3H), 5.65-5.62 (m, 1H), 4.43 (q, J=11.6 Hz, 2H), 4.24-4.20 (m, 2H), 4.12-4.06 (m, 2H), 3.18-3.11 (m, 1H), 3.04 (s, 1H), 2.74-2.70 (m, 1H), 1.93-1.84 (m, 3H), 1.74-1.61 (m, 6H), 1.54-1.65 (m, 6H), 1.36-1.28 (m, 5H). $^{19}$F NMR (376 MHz, CD$_3$CN) δ (ppm) −52.54 (s, 1F).

Example 19: ((2R,3S,5R)-2-((((2-(1-adamantyl)ethoxy)carbonyl)oxy)methyl)-5-(6-amino-2-fluoro-9H-purin-9-yl)-2-ethynyltetrahydrofuran-3-yl) isobutyrate (Compound 19)

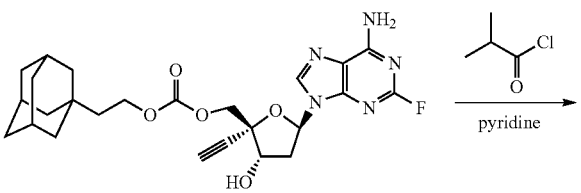

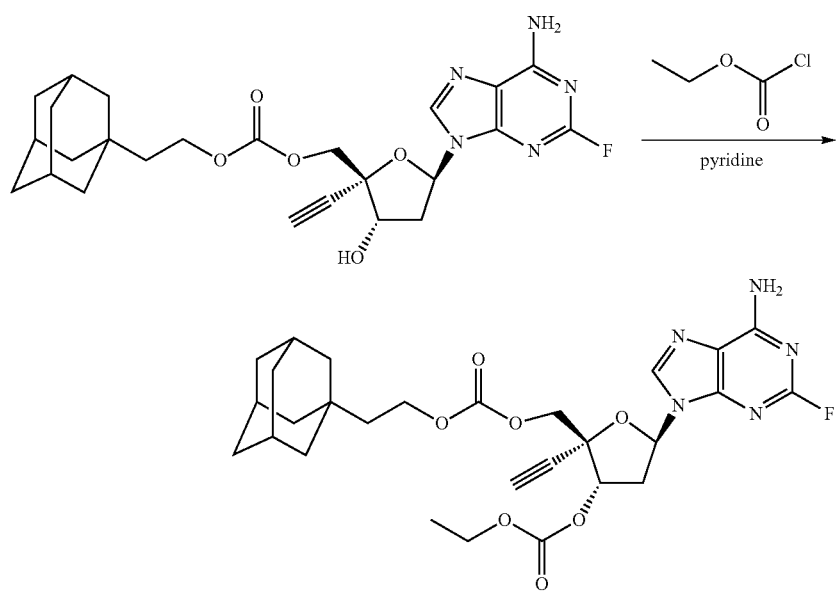

149

-continued

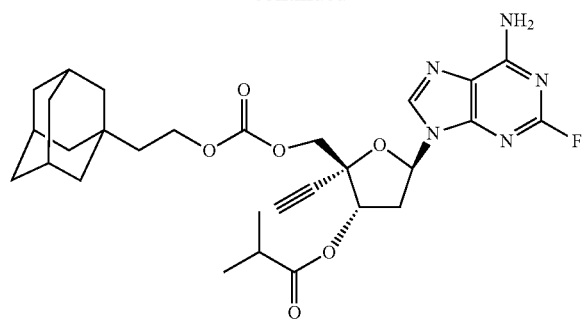

((2R,3S,5R)-2-(((((2-(1-adamantyl)ethoxy)carbonyl)oxy)methyl)-5-(6-amino-2-fluoro-9H-purin-9-yl)-2-ethynyltetrahydrofuran-3-yl) isobutyrate was prepared (12.8 mg, 22.5% yield, a white solid) using the same procedure as in the preparation of ((2R,3S,5R)-5-(6-amino-2-fluoro-9H-purin-9-yl)-2-ethynyl-3-hydroxy-tetrahydrofuran-2-yl)methyl 2-(1-adamantyl) acetate, substituting 2-(1-adamantyl)acetyl chloride with isobutyryl chloride. LCMS (ESI) m/z, $C_{29}H_{36}FN_5O_6$: calculated 569.26, found (M+H)+: 570.3. $^1$H NMR (400 MHz, $CD_3CN$) δ (ppm) 7.98 (s, 1H), 6.38 (br s, 2H), 6.35-6.32 (m, 1H), 5.73-5.70 (m, 1H), 4.41 (q, J=12 Hz, 2H), 4.13-4.06 (m, 2H), 3.12-3.08 (m, 1H), 3.06 (s, 1H), 2.69-2.64 (m, 2H), 1.95-1.90 (m, 3H), 1.74-1.58 (m, 6H), 1.50 (s, 6H), 1.40-1.32 (m, 2H), 1.24-1.16 (m, 6H). $^{19}$F NMR (376 MHz, $CD_3CN$) δ (ppm) −52.63 (s, 1F).

Example 20: ((2R,3S,5R)-2-(((((1-adamantyl)methoxy)carbonyl)oxy)methyl)-5-(6-amino-2-fluoro-9H-purin-9-yl)-2-ethynyltetrahydrofuran-3-yl) isobutyrate (Compound 20)

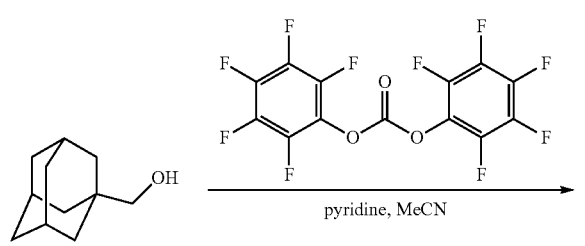

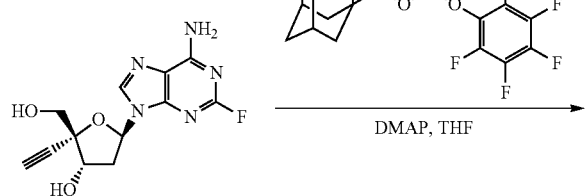

150

-continued

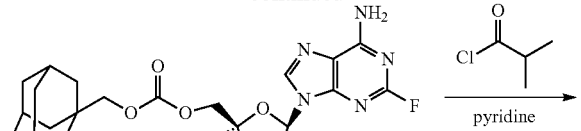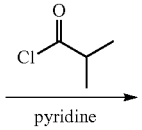

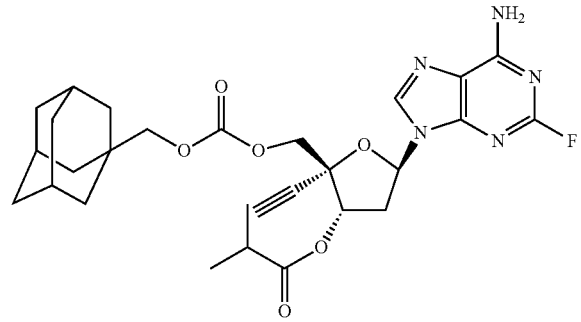

Preparation of 1-adamantylmethyl (2,3,4,5,6-pentafluorophenyl) carbonate

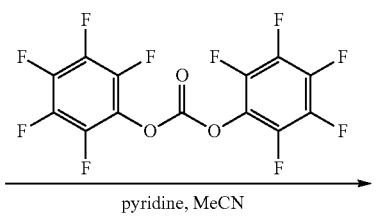

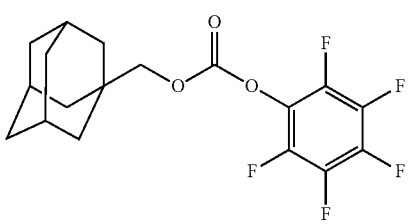

To a solution of 1-adamantylmethanol (1.00 g, 6.01 mmol, 1 eq) in pyridine (5 mL) and MeCN (5 mL) was added bis(2,3,4,5,6-pentafluorophenyl) carbonate (3.08 g, 7.82 mmol, 1.3 eq). The reaction mixture was stirred at 15° C. for 16 h and then was concentrated. The resulting residue was purified by flash silica gel chromatography (ISCO®; 40 g SepaFlash® Silica Flash Column, eluent of 0-1% ethyl acetate/petroleum ether gradient @25 mL/min) to give 1-adamantylmethyl (2,3,4,5,6-pentafluorophenyl) carbonate (2.20 g, 98% yield) as a white solid.

Preparation of 1-adamantylmethyl [(2R,3S,5R)-5-(6-amino-2-fluoro-purin-9-yl)-2-ethynyl-3-hydroxy-tetrahydrofuran-2-yl]methyl carbonate

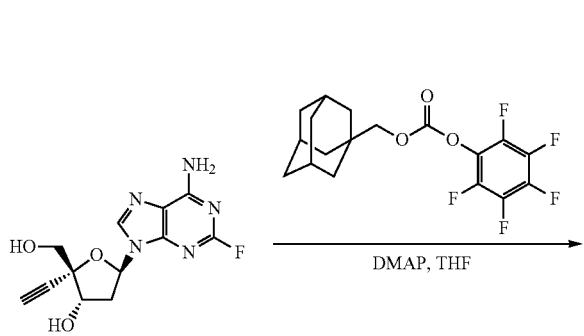

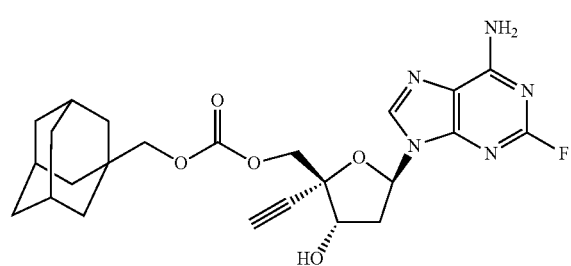

To a solution of (2R,3S,5R)-5-(6-amino-2-fluoro-purin-9-yl)-2-ethynyl-2-(hydroxymethyl)tetrahydrofuran-3-ol (200 mg, 0.68 mmol, 1 eq) in pyridine (2 mL) and DCM (0.5 mL) was added DMAP (8.33 mg, 0.068 mmol, 0.1 eq) and 1-adamantylmethyl (2,3,4,5,6-pentafluorophenyl) carbonate (898 mg, 2.39 mmol, 3.5 eq) at 0° C. The reaction mixture was stirred at 15° C. for 20 h. The resulting mixture was purified by flash silica gel chromatography (ISCO®; 20 g SepaFlash® Silica Flash Column, eluent of 0-1.5% MeOH/DCM @ 35 mL/min) to give 1-adamantylmethyl [(2R,3S,5R)-5-(6-amino-2-fluoro-purin-9-yl)-2-ethynyl-3-hydroxy-tetrahydrofuran-2-yl]methyl carbonate (150 mg, 45% yield) as a white solid.

Preparation of ((2R,3S,5R)-2-(((((1-adamantyl)methoxy)carbonyl)oxy)methyl)-5-(6-amino-2-fluoro-9H-purin-9-yl)-2-ethynyltetrahydrofuran-3-yl) isobutyrate

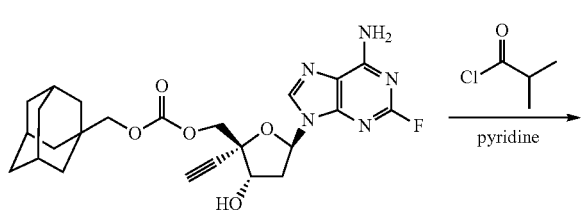

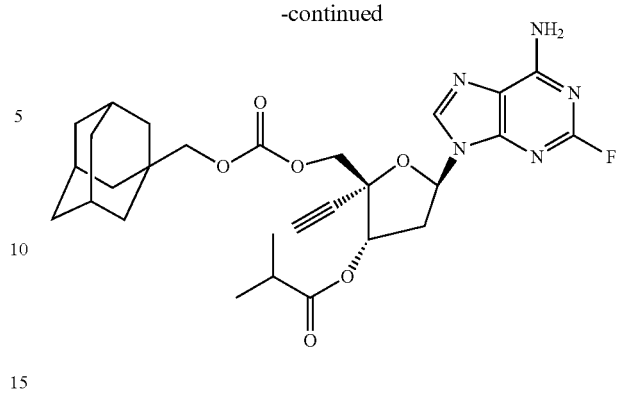

To a solution of 1-adamantylmethyl [(2R,3S,5R)-5-(6-amino-2-fluoro-purin-9-yl)-2-ethynyl-3-hydroxy-tetrahydrofuran-2-yl]methyl carbonate (150 mg, 0.309 mmol, 1 eq) in pyridine (5 mL) was added 2-methylpropanoyl chloride (98.8 mg, 0.927 mmol, 3 eq) at 0° C. The resulting mixture was stirred at 0° C. for 0.5 h. The reaction mixture was quenched with ice water (20 mL) and exacted with ethyl acetate (30 mL). The organic layer was washed with $H_2O$ (30 mL), brine (30 mL), dried over $Na_2SO_4$, and concentrated. The resulting residue was purified by flash silica gel chromatography (ISCO®; 12 g SepaFlash® Silica Flash Column, eluent of 0-1% MeOH/DCM @ 25 mL/min) to give the crude product. The crude product was further purified by prep-TLC ($SiO_2$, DCM:MeOH=10:1) to give the title compound (100 mg, 58% yield) as a white solid. LCMS (ESI) m/z, $C_{28}H_{34}FN_5O_6$: calculated 555.25, found (M+H)$^+$: 556.2. $^1$H NMR (400 MHz, $CD_3CN$) δ (ppm) 7.99 (s, 1H), 6.36-6.33 (m, 3H), 5.73-5.69 (m, 1H), 4.42 (AB q, J=11.2 Hz, 2H), 3.72-3.64 (m, 2H), 3.08-3.06 (m, 1H), 3.01 (s, 1H), 2.66-2.62 (m, 2H), 1.95-1.93 (m, 3H), 1.79-1.71 (m, 3H), 1.71-1.59 (m, 3H), 1.50-1.49 (m, 6H), 1.22-1.18 (m, 6H). $^{19}$F NMR (376 MHz, $CD_3CN$) δ (ppm) −52.62 (s, 1F).

Example 21: ((2R,3S,5R)-2-(((((3-(1-adamantyl)propoxy)carbonyl)oxy)methyl)-5-(6-amino-2-fluoro-9H-purin-9-yl)-2-ethynyltetrahydrofuran-3-yl) isobutyrate (Compound 21)

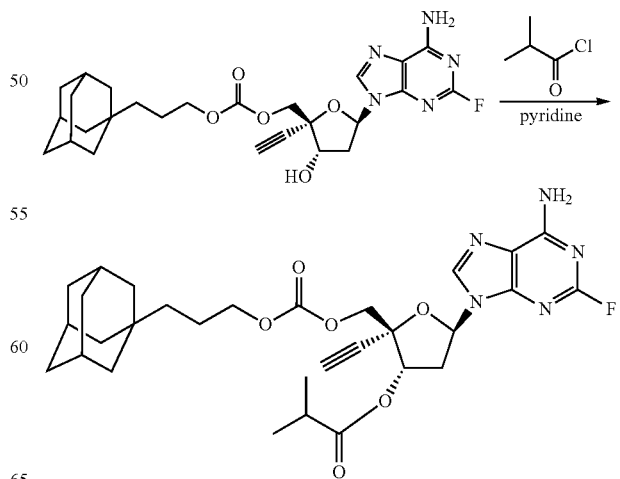

To a solution of 3-(1-adamantyl)propyl [(2R,3S,5R)-5-(6-amino-2-fluoro-purin-9-yl)-2-ethynyl-3-hydroxy-tetrahydrofuran-2-yl]methyl carbonate (24 mg, 0.047 mmol, 1 eq) in pyridine (1 mL) was added 2-methylpropanoyl chloride (0.1 mL, 0.94 mmol, 20 eq) at 0° C. The resulting mixture was stirred at 0° C. for 1 h. The reaction mixture was quenched with water (10 mL) and diluted with EtOAc (40 mL). The organic layer was washed with $H_2O$ (40 mL×3) and brine (40 mL), dried over $Na_2SO_4$ and concentrated. The residue was purified by prep-HPLC (column: Phenomenex Gemini-NX 80×30 mm×3 um; mobile phase: [water (10 mM $NH_4HCO_3$)-ACN]; B %: 73%-100%, 9 min) to give the title compound (5.6 mg, 20.4% yield) as a white solid. LCMS (ESI) m/z, $C_{30}H_{38}FN_5O_6$: calculated 583.28, found $(M+H)^+$: 584.3. $^1H$ NMR (400 MHz, $CD_3CN$) δ (ppm) 7.98 (s, 1H), 6.37-6.32 (m, 3H), 5.72-5.69 (m, 1H), 4.49 (d, J=11.6 Hz, 1H), 4.33 (d, J=11.6 Hz, 1H), 4.04-3.96 (m, 2H), 3.11-3.05 (m, 1H), 3.01 (s, 1H), 2.68-2.60 (m, 2H), 1.91 (br s, 3H), 1.72-1.61 (m, 6H), 1.57-1.51 (m, 2H), 1.45 (d, J=2.4 Hz, 6H), 1.22-1.18 (m, 6H), 1.06-1.02 (m, 2H). $^{19}F$ NMR (376 MHz, $CD_3CN$) δ (ppm) −52.62 (s, 1F).

To a solution of 3-(1-adamantyl)propan-1-ol (28.0 mg, 0.144 mmol, 3 eq) and [(2R,3S,5R)-5-(6-amino-2-fluoro-purin-9-yl)-2-ethynyl-2-[(4-nitrophenoxy)carbonyloxymethyl]tetrahydrofuran-3-yl] (4-nitrophenyl) carbonate (30 mg, 0.048 mmol, 1 eq) in THF (2 mL) was added DMAP (5.88 mg, 0.048 mmol, 1 eq). The reaction mixture was stirred at 15° C. for 32 h was concentrated in vacuum. The residue was purified by prep-HPLC (column: Phenomenex Gemini-NX 80×30 mm×3 um; mobile phase: [water (10 mM $NH_4HCO_3$)-ACN]; B %: 82%-100%, 9 min) to give the title compound (10.1 mg, 28.7% yield) as a white solid. LCMS (ESI) m/z, $C_{40}H_{52}FN_5O_7$: calculated 733.39, found $(M+H)^+$: 734.4. $^1H$ NMR (400 MHz, $CD_3CN$) δ (ppm) 7.71 (s, 1H), 6.28-6.05 (m, 3H), 5.37 (t, J=7.2 Hz, 1H), 4.27 (d, J=11.6 Hz, 1H), 4.07 (d, J=11.6 Hz, 1H), 3.91-3.86 (m, 2H), 3.75-3.73 (m, 2H), 2.88-2.86 (m, 1H), 2.78 (s, 1H), 2.48-2.46 (m, 1H), 1.69-1.67 (m, 6H), 1.44-1.38 (m, 12H), 1.24-1.19 (m, 16H), 0.87-0.80 (m, 4H). $^{19}F$ NMR (376 MHz, $CD_3CN$) δ (ppm) −52.49 (s, 1F).

Example 23: ((2R,3S,5R)-3-(1-adamantylmethoxycarbonyloxy)-5-(6-amino-2-fluoro-9H-purin-9-yl)-2-ethynyl-tetrahydrofuran-2-yl)methyl 1-adamantylmethyl carbonate (Compound 23)

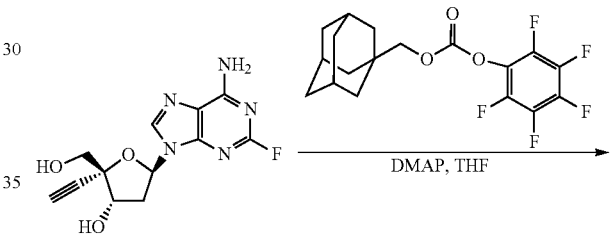

Example 22: ((2R,3S,5R)-3-[3-(1-adamantyl)propoxycarbonyloxy]-5-(6-amino-2-fluoro-9H-purin-9-yl)-2-ethynyl-tetrahydrofuran-2-yl)methyl 3-(1-adamantyl)propyl carbonate

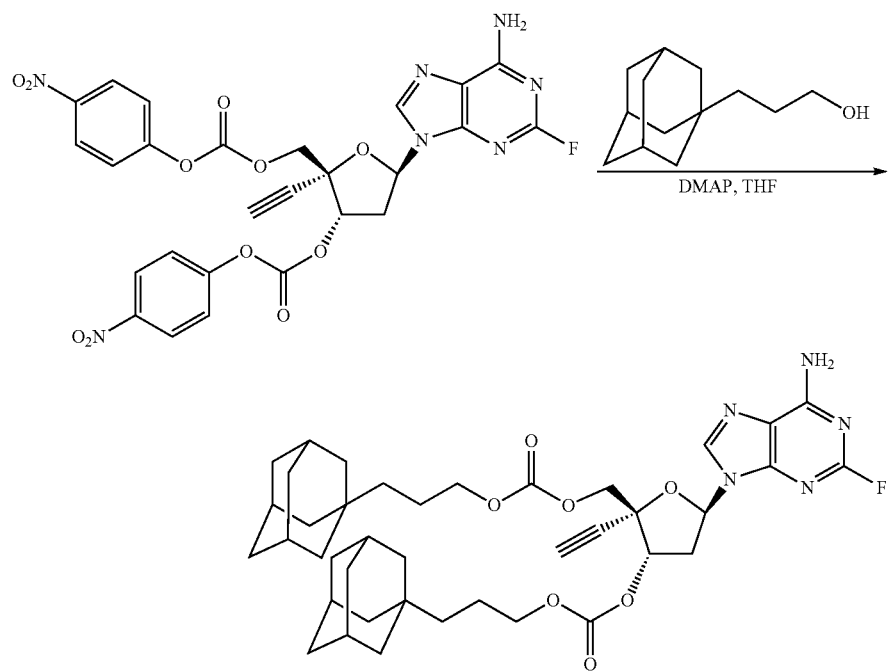

155

-continued

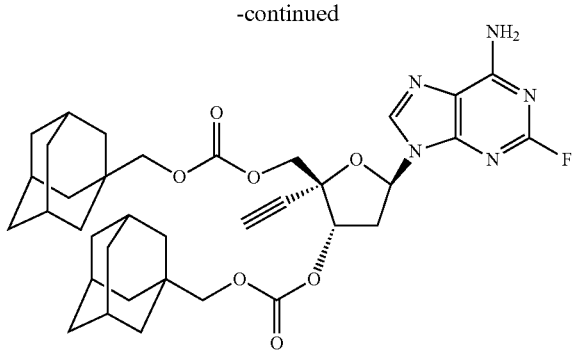

To a solution of (2R,3S,5R)-5-(6-amino-2-fluoro-purin-9-yl)-2-ethynyl-2-(hydroxymethyl)tetrahydrofuran-3-ol (35 mg, 0.119 mmol, 1 eq) in THF (5 mL) was added DMAP (29.2 mg, 0.239 mmol, 2 eq) and 1-adamantylmethyl (2,3,4,5,6-pentafluorophenyl) carbonate (404 mg, 1.07 mmol, 9 eq). The mixture was stirred at 15° C. for 40 h and was concentrated. The resulting residue was purified by flash silica gel chromatography (ISCO®; 12 g SepaFlash® Silica Flash Column, eluent of 0-4% i-PrOH/DCM @25 mL/min) to the title compound (72.8 mg, 90% yield) as a white solid. LCMS (ESI) m/z, $C_{36}H_{44}FN_5O_7$: calculated 677.32, found (M+H)$^+$: 678.3. $^1$H NMR (400 MHz, $CD_3CN$) δ (ppm) 7.98 (s, 1H), 6.38-6.32 (m, 3H), 5.63 (t, J=5.6 Hz, 1H), 4.44 (d, J=11.6 Hz, 2H), 3.81 (d, J=11.6 Hz, 2H), 3.71-3.63 (m, 2H), 3.18-3.11 (m, 1H), 3.05 (s, 1H), 2.77-2.70 (m, 1H), 2.15-2.10 (m, 2H), 2.11-1.96 (m, 4H), 1.77-1.63 (m, 12H), 1.58-1.57 (m, 6H), 1.50-1.49 (m, 6H). $^{19}$F NMR (376 MHz, $CD_3CN$) δ(ppm) −52.49 (s, 1F).

Example 24: ((2R,3S,5R)-2-(1-adamantylmethoxycarbonyloxymethyl)-5-(6-amino-2-fluoro-9H-purin-9-yl)-2-ethynyl-tetrahydrofuran-3-yl) ethyl carbonate (Compound 24)

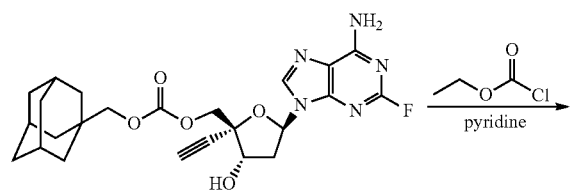

156

-continued

To a solution of 1-adamantylmethyl [(2R,3S,5R)-5-(6-amino-2-fluoro-purin-9-yl)-2-ethynyl-3-hydroxy-tetrahydrofuran-2-yl]methyl carbonate (15 mg, 0.031 mmol, 1 eq) in pyridine (2 mL) was added ethyl carbonochloridate (0.07 mL, 0.74 mmol, 24 eq). The mixture was stirred at 0° C. for 2 h. The reaction mixture was diluted with water (20 mL) and extracted with ethyl acetate (30 mL). The organic layer was washed with brine (15 mL×3), dried over $Na_2SO_4$, and concentrated. The residue was purified by prep-HPLC (column: Welch Xtimate C18 150×25 mm×5 um; mobile phase: [water (10 mM $NH_4HCO_3$)-ACN]; B %: 67%-97%, 9 min) to give the title compound (2.5 mg, 11% yield) as a white solid. LCMS (ESI) m/z, $C_{27}H_{32}FN_5O_7$: calculated 557.23, found (M+H)$^+$: 558.2. $^1$H NMR (400 MHz, $CD_3CN$) δ (ppm) 7.72 (s, 1H), 6.13-6.07 (m, 3H), 5.40-5.37 (m, 1H), 4.28 (d, J=11.6 Hz, 1H), 4.10 (d, J=11.6 Hz, 1H), 4.00-3.96 (m, 2H), 3.46-3.38 (m, 2H), 2.90-2.88 (m, 1H), 2.80 (s, 1H), 2.50-2.48 (m, 1H), 1.69-1.68 (m, 3H), 1.46-1.41 (m, 3H), 1.38-1.24 (m, 3H), 1.26-1.21 (m, 6H), 1.05 (t, J=7.2 Hz, 3H). $^{19}$F NMR (376 MHz, $CD_3CN$) δ (ppm) −52.51 (s, 1F).

Example 25: ((2R,3S,5R)-2-(1-adamantylmethoxycarbonyloxymethyl)-5-(6-amino-2-fluoro-9H-purin-9-yl)-2-ethynyl-tetrahydrofuran-3-yl) ethyl carbonate (Compound 25)

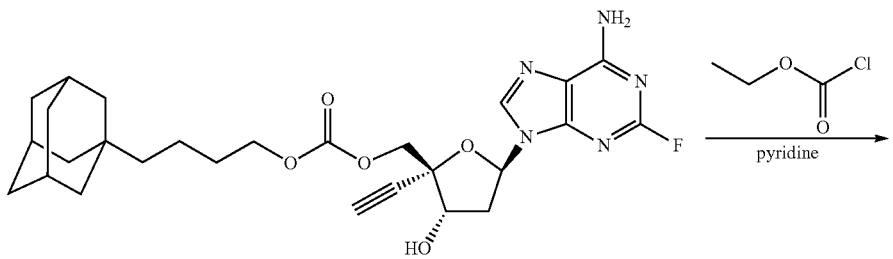

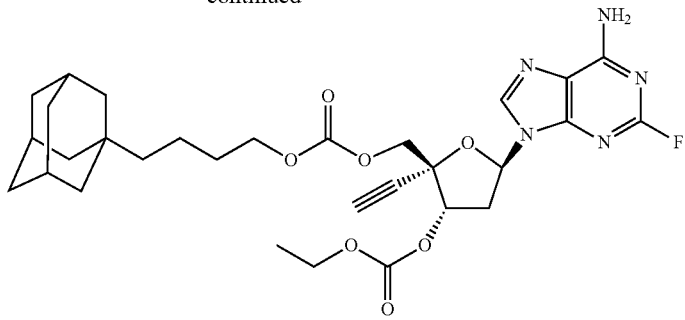

To a solution of 4-(1-adamantyl)butyl [(2R,3S,5R)-5-(6-amino-2-fluoro-purin-9-yl)-2-ethynyl-3-hydroxy-tetrahydrofuran-2-yl]methyl carbonate (20 mg, 0.038 mmol, 1 eq) in pyridine (2 mL) was added ethyl carbonochloridate (0.20 mL, 2.09 mmol, 55 eq). The mixture was stirred at 0° C. for 16 h. The reaction mixture was diluted with water (50 mL) and extracted with ethyl acetate (100 mL). The organic layer was washed with brine (30 mL), dried over $Na_2SO_4$, and concentrated. The residue was purified by prep-HPLC (column: Welch Xtimate C18 150×25 mm×5 um; mobile phase: [water (10 mM $NH_4HCO_3$)-ACN]; B %: 70%-100%, 9 min) to give the title compound (4.8 mg, 21% yield) as a white solid. LCMS (ESI) m/z, $C_{30}H_{38}FN_5O_7$: calculated 599.28, found (M+H)+: 600.3. $^1H$ NMR (400 MHz, $CD_3CN$) δ (ppm) 7.73 (s, 1H), 6.12 (br s, 1H), 6.11-6.07 (m, 2H), 5.41-5.38 (m, 1H), 4.30 (d, J=11.6 Hz, 1H), 4.10 (d, J=11.6 Hz, 1H), 4.09-3.98 (m, 2H), 3.82-3.78 (m, 2H), 2.92-2.89 (m, 1H), 2.81 (s, 1H), 2.50-2.46 (m, 1H), 1.72 (s, 3H), 1.48-1.45 (m, 3H), 1.40-1.37 (m, 3H), 1.32-1.25 (m, 2H), 1.22-1.21 (d, J=2.4 Hz, 6H), 1.8-1.04 (m, 3H), 1.03-0.97 (m, 2H), 0.81-0.77 (m, 2H). $^{19}F$ NMR (376 MHz, $CD_3CN$) δ (ppm) −52.55 (s, 1F).

Example 26: ((2R,3S,5R)-2-[3-(1-adamantyl)propoxycarbonyloxymethyl]-5-(6-amino-2-fluoro-9H-purin-9-yl)-2-ethynyl-tetrahydrofuran-3-yl) ethyl carbonate (Compound 26)

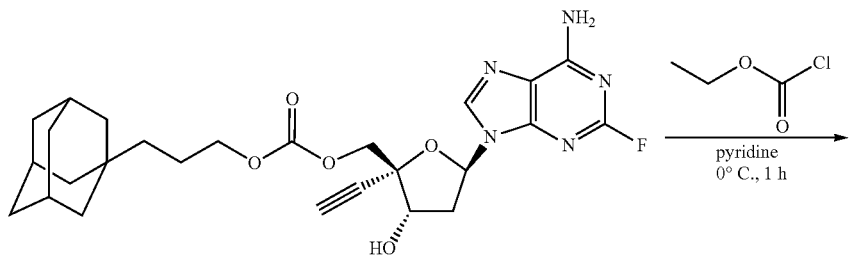

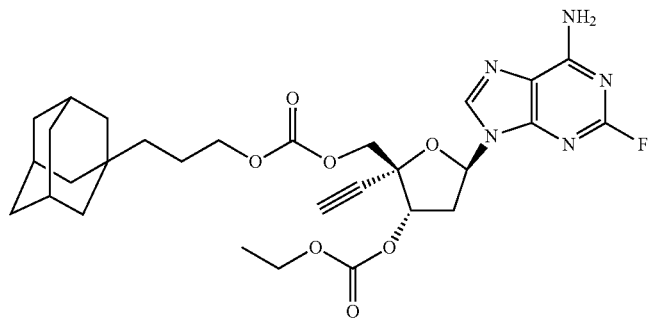

To a solution of 3-(1-adamantyl)propyl [(2R,3S,5R)-5-(6-amino-2-fluoro-purin-9-yl)-2-ethynyl-3-hydroxy-tetrahydrofuran-2-yl]methyl carbonate (20 mg, 0.039 mmol, 1 eq) in pyridine (2 mL) was added ethyl carbonochloridate (0.07 mL, 0.74 mmol, 19 eq). The mixture was stirred at 0° C. for 1 h. The reaction mixture was diluted with water (20 mL) and extracted with ethyl acetate (30 mL). The organic layer was washed with brine (15 mL), dried over $Na_2SO_4$ and concentrated. The residue was purified by prep-HPLC (column: Welch Xtimate C18 150×25 mm×5 um; mobile phase: [water (10 mM $NH_4HCO_3$)-ACN]; B %: 67%-97%, 9 min) to give the title compound (1.3 mg, 5.7% yield) as a white solid. LCMS (ESI) m/z, $C_{29}H_{36}FN_5O_7$: calculated 585.26, found (M+H)$^+$: 586.3. $^1$H NMR (400 MHz, $CD_3CN$) δ (ppm) 7.74 (s, 1H), 6.10 (t, J=6.4 Hz, 3H), 5.40 (t, J=7.2 Hz, 1H), 4.31 (d, J=11.2 Hz, 1H), 4.15-4.07 (d, J=11.2 Hz, 1H), 4.05-3.95 (m, 2H), 3.85-3.70 (m, 2H), 2.94-2.90 (m, 1H), 2.82 (s, 1H), 2.53-2.45 (m, 1H), 1.70-1.68 (m, 3H), 1.53-1.45 (m, 3H), 1.44-1.37 (m, 3H), 1.36-1.26 (m, 2H), 1.27-1.20 (m, 6H), 1.07 (t, J=7.2 Hz, 3H), 0.84-0.79 (m, 2H). $^{19}$F NMR (376 MHz, $CD_3CN$) δ (ppm) −52.54 (s, 1F).

Example 27: 1-adamantyl ((2R,3S,5R)-5-(6-amino-2-fluoro-purin-9-yl)-3-ethoxycarbonyloxy-2-ethynyl-tetrahydrofuran-2-yl)methyl carbonate (Compound 27)

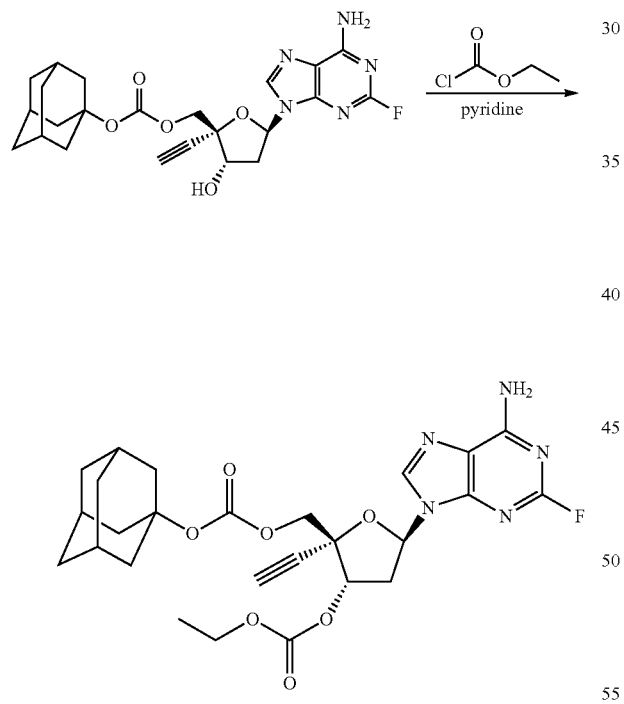

To a solution of 1-adamantyl [(2R,3S,5R)-5-(6-amino-2-fluoro-purin-9-yl)-2-ethynyl-3-hydroxy-tetrahydrofuran-2-yl]methyl carbonate (15 mg, 0.032 mmol, 1 eq) in pyridine (1 mL) was added ethyl carbonochloridate (0.175 mL, 1.86 mmol, 58 eq). The mixture was stirred at 0° C. for 2 h. The reaction mixture was quenched by water (5 mL) at 0° C., and then diluted with DCM (10 mL) and extracted with DCM (10 mL×3). The combined organic layers were washed with brine (10 mL), dried over $Na_2SO_4$, filtered and concentrated. The residue was purified by prep-HPLC (column: Welch Xtimate C18 150×25 mm×5 um; mobile phase: [water (10 mM $NH_4HCO_3$)-ACN]; B %: 57%-87%, 9 min) to give the title compound (5.0 mg, 28.67% yield) as a white solid. LCMS (ESI) m/z, $C_{26}H_{30}FN_5O_7$: calculated 543.21, found (M+H)$^+$: 544.0. $^1$H NMR (400 MHz, $CD_3CN$) δ (ppm) 7.96 (s, 1H), 6.36-6.29 (m, 3H), 5.67-5.63 (m, 1H), 4.51 (d, J=11.6 Hz, 1H), 4.26-4.20 (m, 3H), 3.19-3.12 (m, 1H), 3.03 (s, 1H), 2.75-2.68 (m, 1H), 2.14-2.11 (m, 5H), 1.95-1.93 (m, 2H), 1.90-1.88 (m, 2H), 1.64 (s, 6H), 1.32-1.27 (m, 3H). $^{19}$F NMR (376 MHz, $CD_3CN$) δ (ppm) −52.48 (s, 1F).

Example 28: ((2R,3S,5R)-2-(1-adamantyloxycarbonyloxymethyl)-5-(6-amino-2-fluoro-9H-purin-9-yl)-2-ethynyl-tetrahydrofuran-3-yl) 2-methylpropanoate (Compound 28)

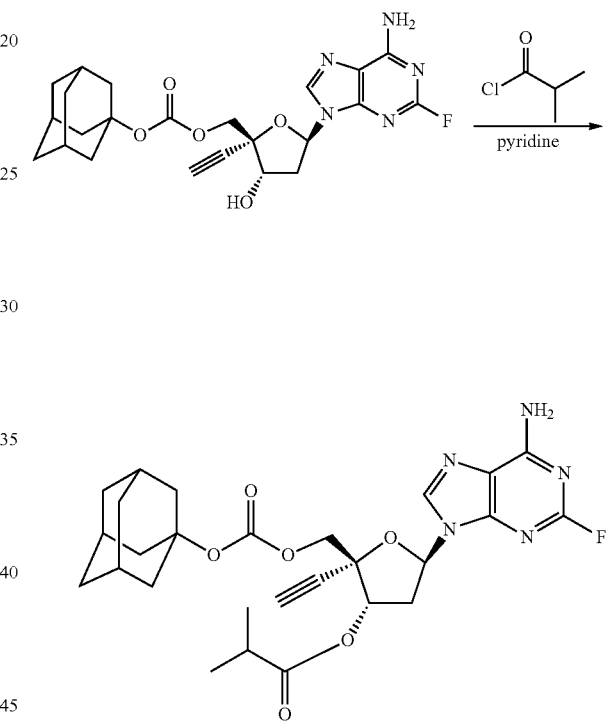

To a solution of 1-adamantyl [(2R,3S,5R)-5-(6-amino-2-fluoro-purin-9-yl)-2-ethynyl-3-hydroxy-tetrahydrofuran-2-yl]methyl carbonate (15 mg, 0.032 mmol, 1 eq) in pyridine (1 mL) was added 2-methylpropanoyl chloride (0.2 mL, 1.92 mmol, 60 eq). The mixture was stirred at 0° C. for 1 h. The resulting mixture was diluted with EtOAc (30 mL), then washed with $H_2O$ (20 mL×2), brine (20 mL), dried over $Na_2SO_4$, and concentrated. The residue was purified by prep-HPLC (column: Welch Xtimate C18 150×25 mm×5 um; mobile phase: [water (10 mM $NH_4HCO_3$)-ACN]; B %: 66%-99%, 9 min) to give the title compound (2.6 mg, 15.0% yield) as a white solid. LCMS (ESI) m/z, $C_{27}H_{32}FN_5O_6$: calculated 541.23, found (M+H)$^+$: 542.0. $^1$H NMR (400 MHz, $CD_3CN$) δ (ppm) 7.98 (s, 1H), 6.37-6.29 (m, 3H), 5.74-5.71 (m, 1H), 4.47 (d, J=12.0 Hz, 1H), 4.21 (d, J=11.6 Hz, 1H), 3.13-3.06 (m, 1H), 3.01 (s, 1H), 2.68-2.60 (m, 2H), 2.13-2.09 (m, 6H), 2.01-1.96 (m, 3H), 1.64 (br s, 6H), 1.22-1.18 (m, 6H). $^{19}$F NMR (376 MHz, $CD_3CN$) δ (ppm) −52.58 (s, 1F).

Example 29: (1R,13R,15R)-15-(6-amino-2-fluoro-9H-purin-9-yl)-13-ethynyl-2,9,11,14-tetraoxabicyclo[11.3.0]hexadecane-3,10-dione (Compound 29)
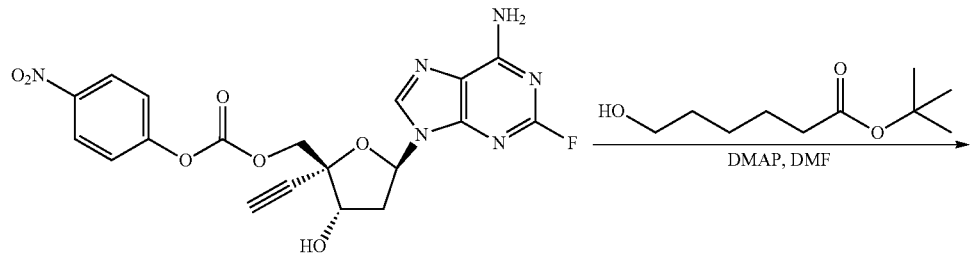
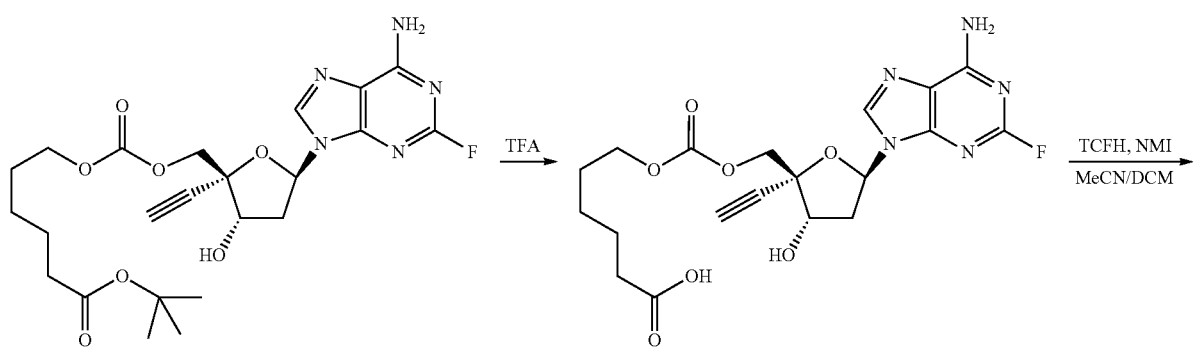
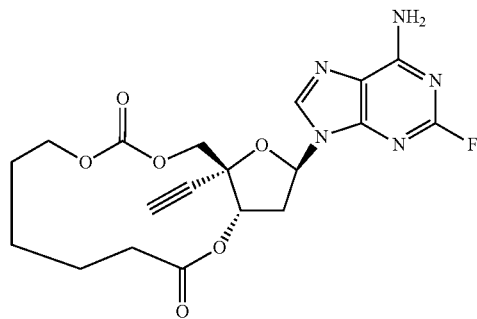
Preparation of tert-butyl 6-[[(2R,3S,5R)-5-(6-amino-2-fluoro-purin-9-yl)-2-ethynyl-3-hydroxy-tetrahydrofuran-2-yl]methoxycarbonyloxy]hexanoate
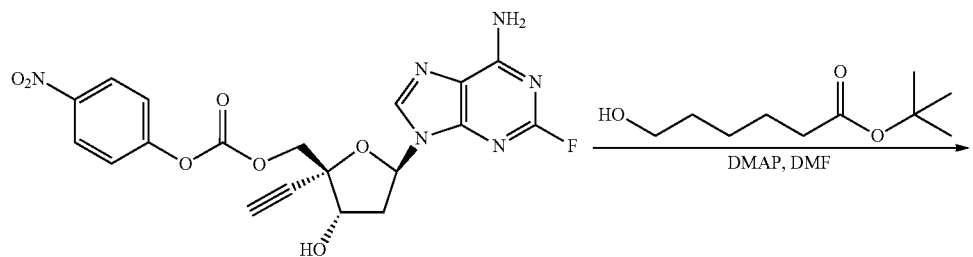

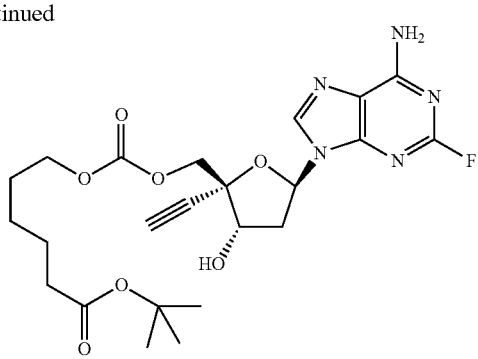

To a solution of [(2R,3S,5R)-5-(6-amino-2-fluoro-purin-9-yl)-2-ethynyl-3-hydroxy-tetrahydrofuran-2-yl]methyl (4-nitrophenyl) carbonate (150 mg, 0.327 mmol, 1 eq) in THF (10 mL) was added DMAP (4.03 mg, 0.033 mmol, 0.1 eq) and tert-butyl 6-hydroxyhexanoate (185 mg, 0.982 mmol, 3 eq). The mixture was stirred at 15° C. for 16 h and then was concentrated. The resulting residue was purified by flash silica gel chromatography (ISCO®; 4 g SepaFlash® Silica Flash Column, eluent of 0-3% MeOH/DCM @22 mL/min) to give tert-butyl 6-[[(2R,3S,5R)-5-(6-amino-2-fluoro-purin-9-yl)-2-ethynyl-3-hydroxy-tetrahydrofuran-2-yl]methoxycarbonyloxy]hexanoate (60 mg, 36% yield) as a light yellow gum.

Preparation of 6-[[(2R,3S,5R)-5-(6-amino-2-fluoro-purin-9-yl)-2-ethynyl-3-hydroxy-tetrahydrofuran-2-yl]methoxycarbonyloxy]hexanoic acid

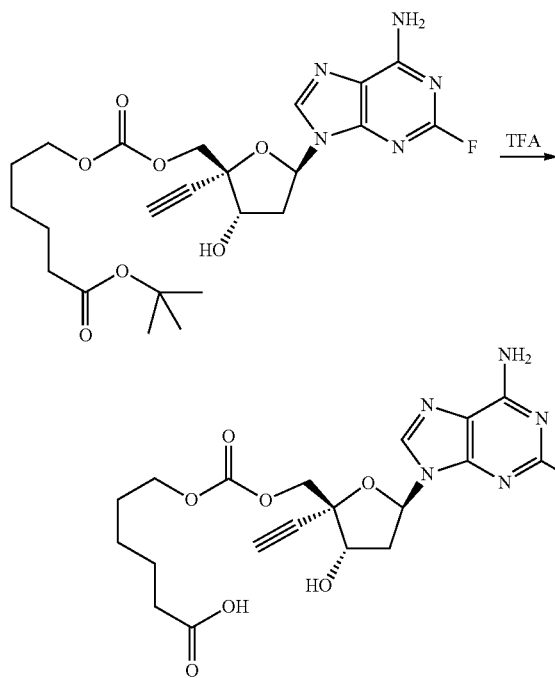

To a solution of tert-butyl 6-[[(2R,3S,5R)-5-(6-amino-2-fluoro-purin-9-yl)-2-ethynyl-3-hydroxy-tetrahydrofuran-2-yl]methoxycarbonyloxy]hexanoate (90 mg, 0.177 mmol, 1 eq) in DCM (5 mL) was added TFA (1 mL). The mixture was stirred at 15° C. for 16 h and then was concentrated. The resulting residue was purified by prep-TLC (SiO₂, DCM:MeOH=10:1) to give 6-[[(2R,3S,5R)-5-(6-amino-2-fluoro-purin-9-yl)-2-ethynyl-3-hydroxy-tetrahydrofuran-2-yl]methoxycarbonyloxy]hexanoic acid (40 mg, 50% yield) as a yellow gum.

Preparation of (1R,13R,15R)-15-(6-amino-2-fluoro-purin-9-yl)-13-ethynyl-2,9,11,14-tetraoxabicyclo[11.3.0]hexadecane-3,10-dione

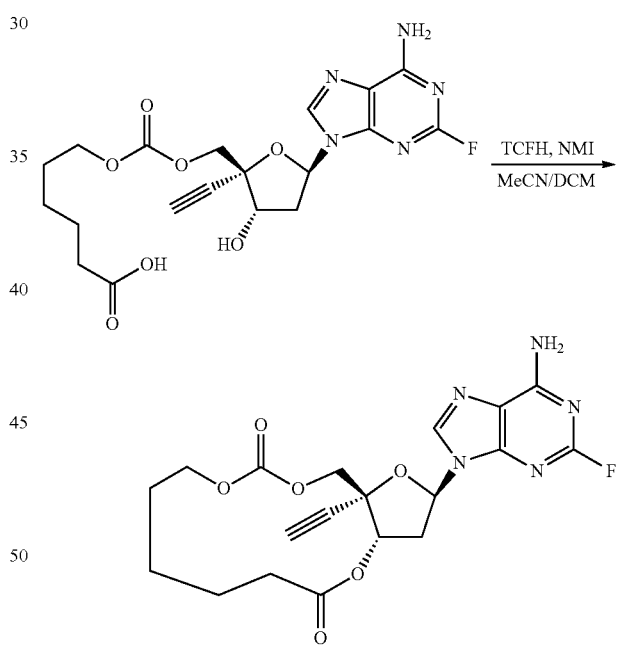

To a solution of 6-[[(2R,3S,5R)-5-(6-amino-2-fluoro-purin-9-yl)-2-ethynyl-3-hydroxy-tetrahydrofuran-2-yl]methoxycarbonyloxy]hexanoic acid (40 mg, 0.089 mmol, 1 eq) in MeCN (3 mL) and DCM (3 mL) was added TCFH (69.9 mg, 0.248 mmol, 2.8 eq) and 1-methylimidazole (24.1 mg, 0.292 mmol, 3.3 eq). The mixture was stirred at 15° C. for 40 h and then was concentrated. The resulting residue was purified by prep-HPLC (NH₄HCO₃ condition; column: Phenomenex Gemini-NX 80×30 mm×3 um; mobile phase: [water (10 mM NH₄HCO₃)-ACN]; B %: 31%-61%, 9 min) to give the title compound (2.3 mg, 6.0% yield) as a white solid. LCMS (ESI) m/z, $C_{19}H_{20}FN_5O_6$: calculated 433.14, found (M+H)⁺: 434.1. ¹H NMR (400 MHz, CD₃CN) δ (ppm) 7.95 (s, 1H), 6.33-6.31 (m, 3H), 5.83-5.79 (m, 1H), 4.76 (d, J=10.8 Hz, 1H), 4.58-4.57 (m, 1H), 4.16 (d, J=11.2 Hz, 1H), 4.07-4.05 (m, 1H), 3.08-3.04 (m, 2H), 2.61-2.51 (m, 1H), 2.50-2.35 (m, 1H), 2.24-2.19 (m, 1H), 1.75-1.65 (m, 4H), 1.68-1.52 (m, 1H), 1.47-1.29 (m, 1H). ¹⁹F NMR (376 MHz, CD₃CN) δ (ppm) -52.44 (s, 1F).

Example 30: (6R,8R,10R)-8-(6-amino-2-fluoro-9H-purin-9-yl)-10-ethynyl-3,5,9,12,14-pentaoxatricyclo[14.4.0.06,10]icosane-4,13-dione (Compound 30)

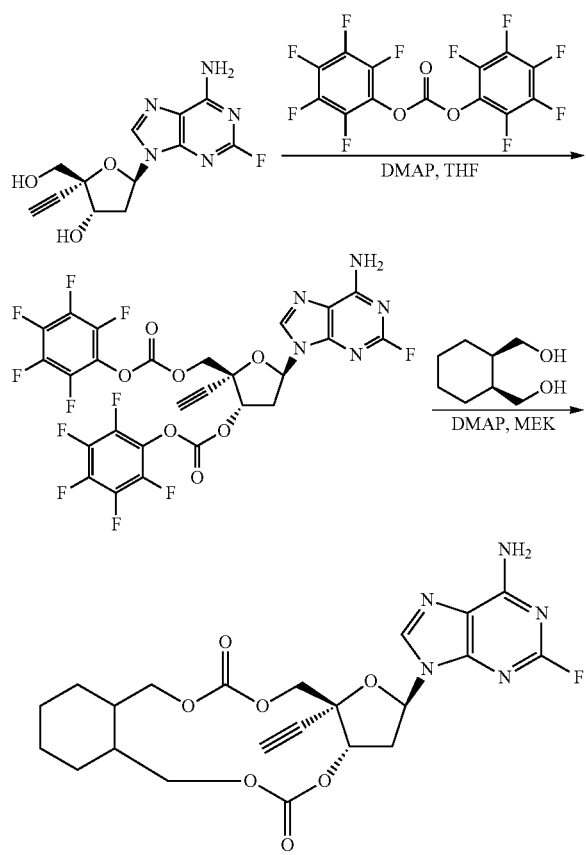

Preparation of [(2R,3S,5R)-5-(6-amino-2-fluoro-purin-9-yl)-2-ethynyl-2-[(2,3,4,5,6-pentafluorophenoxy)carbonyloxymethyl]tetrahydrofuran-3-yl] (2,3,4,5,6-pentafluorophenyl) carbonate

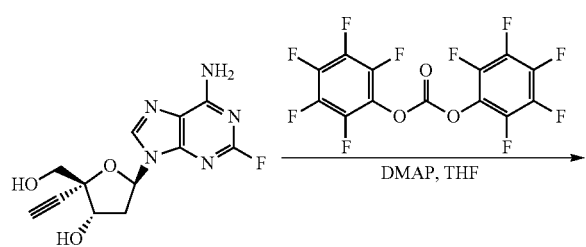

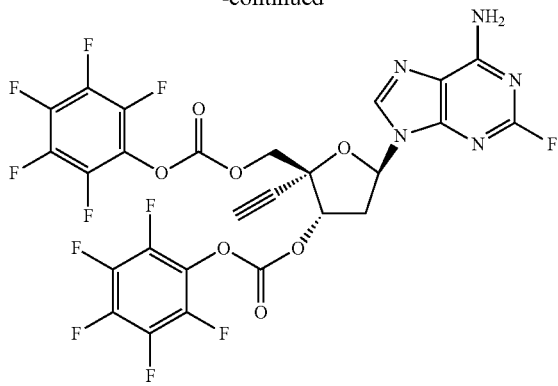

To a solution of (2R,3S,5R)-5-(6-amino-2-fluoro-purin-9-yl)-2-ethynyl-2-(hydroxymethyl)tetrahydrofuran-3-ol (100 mg, 0.341 mmol, 1 eq) in THF (10 mL) was added DMAP (8.3 mg, 0.068 mmol, 0.2 eq) and bis(2,3,4,5,6-pentafluorophenyl) carbonate (282 mg, 0.716 mmol, 2.1 eq). The mixture was stirred at 10° C. for 6 h and then was concentrated. The residue was purified by flash silica gel chromatography (ISCO®; 4 g SepaFlash® Silica Flash Column, Eluent of 0~5% MeOH/DCM gradient @ 50 mL/min) to give [(2R,3S,5R)-5-(6-amino-2-fluoro-purin-9-yl)-2-ethynyl-2-[(2,3,4,5,6-pentafluorophenoxy)carbonyloxymethyl]tetrahydrofuran-3-yl] (2,3,4,5,6-pentafluorophenyl) carbonate (80 mg, 32.9% yield) as a white solid.

Preparation of (6R,8R,10R)-8-(6-amino-2-fluoro-purin-9-yl)-10-ethynyl-3,5,9,12,14-pentaoxatricyclo[14.4.0.06,10]icosane-4,13-dione

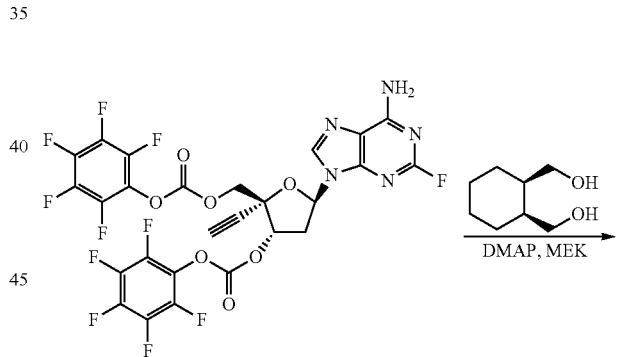

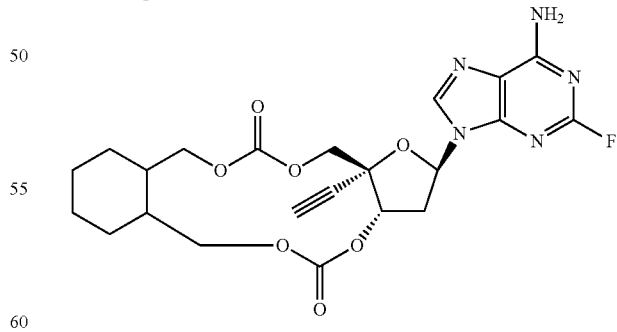

To a solution of [(2R,3S,5R)-5-(6-amino-2-fluoro-purin-9-yl)-2-ethynyl-2-[(2,3,4,5,6-pentafluorophenoxy)carbonyloxymethyl]tetrahydrofuran-3-yl] (2,3,4,5,6-pentafluorophenyl) carbonate (80 mg, 0.112 mmol, 1 eq) in THF (12 mL) was added DMAP (13.7 mg, 0.112 mmol, 1 eq) and [(1R,2S)-2-(hydroxymethyl)cyclohexyl]methanol (16.2 mg, 0.112 mmol, 1 eq). The mixture was stirred at 10° C. for 44 h and then was concentrated. The residue was purified by prep-TLC (SiO$_2$, DCM:MeOH=10:1) to give (6R,8R,10R)-8-(6-amino-2-fluoro-purin-9-yl)-10-ethynyl-3,5,9,12,14-pentaoxatricyclo[14.4.0.06,10]icosane-4,13-dione (2.8 mg, 5.1% yield) as a white solid. LCMS (ESI) m/z, $C_{22}H_{24}FN_5O_7$: calculated 489.17, found (M+H)$^+$: 490.2. $^1$H NMR (400 MHz, CD$_3$CN) δ (ppm) 7.95 (d, J=9.6 Hz, 1H), 6.36-6.31 (m, 2H), 6.14-6.10 (m, 0.5H), 5.63-5.61 (m, 0.5H), 4.78 (d, J=11.2 Hz, 0.5H), 4.57-4.37 (m, 2.5H), 4.22-4.15 (m, 2H), 4.01-3.91 (m, 1H), 3.25-3.17 (m, 0.5H), 3.03 (d, J=3.2 Hz, 1H), 2.98-2.91 (m, 0.5H), 2.82-2.74 (m, 0.5H), 2.67-2.61 (m, 0.5H), 2.47 (br s, 0.5H), 2.21 (br s, 0.5H), 1.78-1.57 (m, 2.5H), 1.54-1.23 (m, 7.5H). $^{19}$F NMR (376 MHz, CD$_3$CN) δ (ppm) −52.45 (s, 1F).

Example 31: Conversion and Stability of the Adenosine Derivative Prodrugs

Stability of prodrugs and conversion of the prodrugs to the parent EFdA (formula T-1A) were measured in both plasma and liver S9 assays and the data are shown in Table 2.

Plasma Stability

The pooled frozen plasma was thawed in a water bath at 37° C. prior to experiment. Plasma was centrifuged at 4000 rpm for 5 min and the clots were removed if any. The pH will be adjusted to 7.4±0.1 if required.

Preparation of test compounds and positive control (propantheline bromide): 1 mM intermediate solution was prepared by diluting 10 μL of the stock solution with 90 μL MeOH; 1 mM intermediate of positive control Propantheline was prepared by diluting 10 μL of the stock solution with 90 μL ultrapure water. 100 μM dosing solution was prepared by diluting 20 μL of the intermediate solution (1 mM) with 180 μL MeOH. 98 μL of blank plasma was spiked with 2 μL of dosing solution (100 μM) to achieve 2 μM of the final concentration in duplicate and samples were incubated at 37° C. in a water bath. At each time point (0, 10, 30, 60 and 120 min), 400 μL of stop solution (0.1% FA in MeOH containing 200 ng/mL tolbutamide and 200 ng/mL Labetalol) was added to precipitate protein and mixed thoroughly. Centrifuged sample plates at 4,000 rpm for 10 min. An aliquot of supernatant (100 μL) was transferred from each well to another plates. Data analysis: The % remaining of test compound after incubation in plasma was calculated using following equation:

% Remaining=100×(PAR at appointed incubation time/PAR at T0 time)

where PAR is the peak area ratio of analyte versus internal standard (IS) (LC/MS/MS mobile phase condition: 0.1% Formic Acid in Water/0.1% Formic Acid in Acetonitrile. The appointed incubation time points are T0 (0 min), Tn (n=0, 10, 30, 60, 120 min).

Liver S9 Stability

Intermediate solution: Dilute 5 μL of compounds or controls (7-ethoxycoumarin) from stock solution (10 mM) with 495 μL MeOH (Conc.: 100 μM, 1% DMSO, 99% MeOH). Stop solution: Cold ACN (including 100 ng/mL Tolbutamide and Labetalol as internal standard). Add 2 μL test compound or control working solution/well to all plates (T0, T5, T10, T20, T30, T60, NCF60) except matrix blank. Add 600 μL/well stop solution (cold in 4° C., including 100 ng/mL Tolbutamide/100 ng/mL Labetalol) to terminate the T0 plate, then put it on ice. Dispense 840 μL/well S9 solution to 96-well plate as reservoir according to plate map. Then add 100 μL/well to every plate by Apricot. Incubate S9 solution and compound at 37° C. for about 10 min except NCF60 and T0. After adding S9 solution and 98μ LPB buffer to NCF60, incubate at 37° C. without pre-warming, start timer 1. After 60 min, add 600 μL/well stop solution to terminate the reaction. After pre-warming, dispense 760 μL/well cofactor solution to 96-well plate as reservoir according to plate map. Then add 98 μL/well to every plate by Apricot to start reaction. Incubate at 37° C., start timer 2, Add 600 μL/well stop solution (cold in 4° C., including 100 ng/mL Tolbutamide and Labetalol) to terminate the reaction. Samples are centrifuged at 4000 rpm for 20 min. While centrifuging, load 8×new 96-well plate with 300 μL HPLC water, then transfer 100 μL supernatant, mix with water for LC/MS/MS, transferred to Bioanalytical Services for LC-MS/MS analysis. Use equation of first order kinetics to calculate $t_{1/2}$ and CL: Equation of first order kinetics:

$$C_t = C_0 \cdot e^{-k_e \cdot t}$$

$$C_t = \frac{1}{2}C_0, T_{1/2} = \frac{\text{Ln } 2}{-k_e} = \frac{0.693}{-k_e}$$

$$CL_{int(S9)} = Vd \cdot k_e$$

$$Vd = 1 \text{ mL/mg}$$

The stability results of exemplary compounds in human plasm and human liver S9 were listed in Table 2 below.

TABLE 2

Conversion and Half Life Data.

| Compound | Stability in Human Plasma Half-life | Formation of EFdA at 30 min | Stability in Human Liver S9 Half-life | Formation of EFdA at 30 min |
|---|---|---|---|---|
| 1 | A | No | C | Yes |
| 2 | B | Yes | C | Yes |
| 3 | C | No | C | Yes |
| 4 | A | Yes | C | Yes |
| 6 | A | No | C | Yes |
| 7 | C | Yes | C | Yes |
| 8 | B | Yes | C | Yes |
| 9 | A | No | C | Yes |
| 10 | C | Yes | C | Yes |
| 11 | NA | NA | C | Yes |
| 12 | C | Yes | C | Yes |
| 13 | NA | NA | C | Yes |
| 14 | C | Yes | C | Yes |
| 15 | C | Yes | C | Yes |
| 16 | B | Yes | NA | NA |
| 17 | A | Yes | C | Yes |
| 18 | C | No | C | Yes |
| 19 | C | No | C | Yes |
| 20 | B | No | C | Yes |
| 21 | B | Yes | C | Yes |
| 22 | A | No | B | Yes |
| 23 | A | No | C | Yes |
| 24 | B | Yes | C | Yes |
| 25 | B | Yes | C | Yes |
| 26 | C | Yes | C | Yes |
| 27 | A | No | C | Yes |
| 28 | A | No | C | Yes |
| 29 | C | Yes | C | Yes |
| 30 | B | No | C | Yes |

Half-life ranges: A: >200 minutes; B: 50-200 minutes; C: <50 minutes; NA: not tested.

Example 32: Plasma Exposures Following Intramuscular Administration of Prodrugs to Cynomolgus Monkeys The pharmacokinetics of EFdA and Compound 2, 7, 10 and 12 were studied in cynomolgus monkeys after a single intramuscular (IM) administration of 10 mg/kg.

Formulations: The prodrugs were formulated as homogenous opaque suspensions at 100 mg/ml, in 20% PEG400, 10% solutol, and 88% water within 0.5 hour prior to dose.

Dose Administration and Sample Collection: The in-life phase of this study was conducted at the WuXi Apptec (Suzhou) Co., Ltd, Suzhou, China in accordance with the WuXi Institutional Animal Care and Use Committee (IACUC) standard animal procedures along with the IACUC guidelines that are in compliance with the Animal Welfare Act, the Guide for the Care and Use of Laboratory Animals. and was approved by the IACUA Committee. Non-naïve male cynomolgus monkey (3+/−1 kg) were used for the studies. Each drug was administered as a single dose of 10 mg/kg by intramuscular injection (0.1 ml/kg). Plasma samples were collected at 0 (pre-dose), 15 and 30 min, 1, 2, 4, 7, 12, 24, 48, 72, 96, 120, 144 and 168 h post-dose. Blood (approximately 0.9 mL) was processed immediately for plasma by centrifugation at 3,500 rpm at 5° C. for 10 min immediately after collection using commercially available ice-cold $K_2$EDTA tubes pre-aliquoted with concentrated cocktail blood stabilizer (1:9 ratio). Plasma samples were frozen and maintained at −70° C. until analyzed.

Determination of EFdA and Prodrugs in plasma: Briefly, plasma (20 µL) was mixed with 200 µl acetonitrile containing internal standards to precipitate protein. Consistent with sample collection procedure, the same cocktail protocol was also added to stabilize the prodrug in the standard and QC samples.

Bioanalysis: A Sciex API-6500 plus triplequadrupole mass spectrometer coupled with a Waters ACQUITY UPLC system (Milford, MA) was used for quantitative analysis of plasma samples. The column was a Waters HSS T3 column (2.1×50 mm, 1.8 mm). The mobile phases used were: A, 0.1% formic acid in water; B, 0.1% formic acid in acetonitrile. The flow rate was 0.6 mL/min with a total run time of 2.0 min. The UPLC gradient was initiated at 95% A/5% B, followed by linear gradient increase to 30% B over the next 0.7 min; the gradient was subsequently increased to 98% of mobile B over the next 0.5 min and then held for additional 0.6 min before ramping down to 5% mobile phase B within the following 0.2 min. Detection of the prodrug and EFdA were achieved using positive ion electrospray mass spectroscopic mode using unit resolution mode. Multiple reaction monitoring (MRM) modes were used to quantify both prodrugs and EFdA. Peak areas were integrated by the Sciex program Analyst®, version 1.6.3 where concentrations were determined by a weighted (1/×2) linear regression of peak area ratios (peak area of EFdA/peak area of corresponding IS) versus the nominal concentrations of the plasma calibration standards. Calculations were performed on unrounded numbers. Overall, Analyst® determined the precision and accuracy for the calibration standards and QC samples.

Pharmacokinetic Calculations: The noncompartmental (NCA) analysis of EFdA and prodrug individual plasma concentration-time data were conducted using WinNonlin module in the Phoenix PK/PD Platform (Certara Inc., Princeton, NJ 08540). Calculations were performed prior to rounding and nominal sampling times were used in the pharmacokinetic analysis. Exposures were expressed as areas under concentration curves in plasma from zero to 168 hours ($AUC_{0-168\ h}$). The AUC values were calculated using the linear trapezoidal rule.

Figure 2:
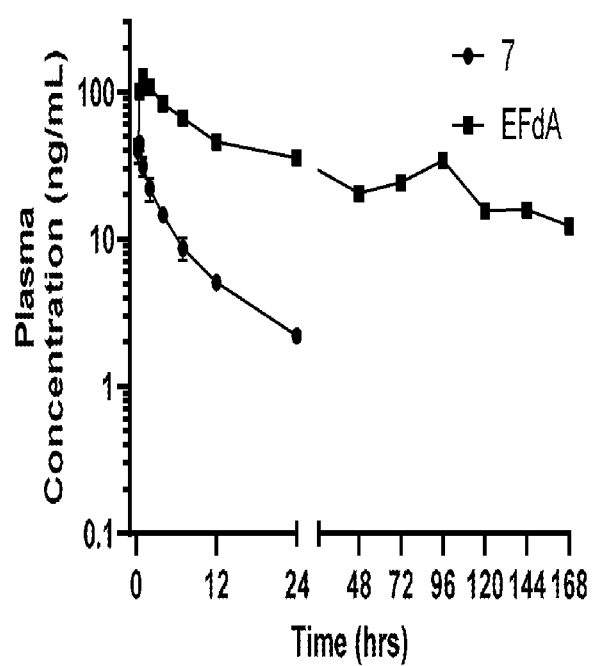
FIG. 2 shows a Plasma Concentration—Time profile of Compound 7 and EFdA after single IM injection of Compound 7 (10 mg/kg) in cynomolgus monkeys.
Figure 3:
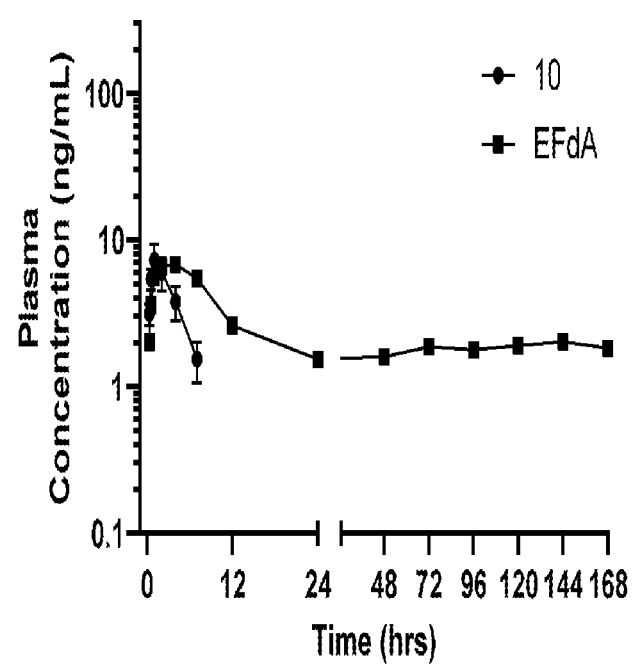
FIG. 3 shows a Plasma Concentration—Time profile of Compound 10 and EFdA after single IM injection of Compound 10 (10 mg/kg) in cynomolgus monkeys.
Figure 4:
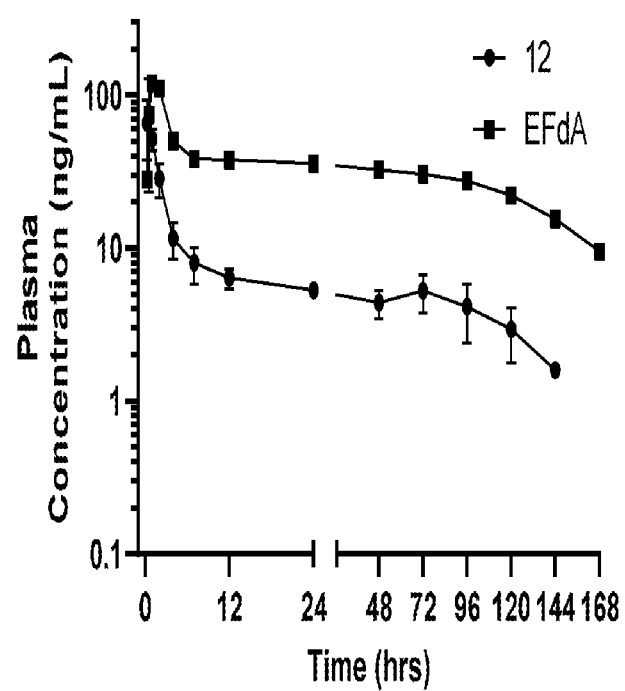
FIG. 4 shows a Plasma Concentration—Time profile of Compound 12 and EFdA after single IM injection of Compound 12 (10 mg/kg) in cynomolgus monkeys.

Plasma Concentrations: The results of the PK studies are shown in Table 3 and FIGS. 1-4. These data establish in vivo that Compound 2, 7, 10 and 12 can be readily delivered intramuscularly, and can efficiently release EFdA in vivo with minimal to low levels of prodrug detected in the systemic circulation.

TABLE 3

EFdA and compound 2, 7, 10 and 12 exposures in plasma after a single intramuscular injection of compound 2, 7, 10 and 12 to Cynomolgus monkeys

| | | PK Parameters | | | |
|---|---|---|---|---|---|
| Compound administered | Dose (mg/kg) | Compound | $AUC_{0-168\ hr}$ (ng*hr/mL) | $T_{max}$ (hr) | $C_{max}$ (ng/mL) |
| 2 | 10 | Compound 2 | 27.3 | 0.917 | 5.23 |
|   |    | EFdA       | 6408 | 12.7  | 142  |
| 7 | 10 | Compound 7 | 232  | 0.417 | 44.6 |
|   |    | EFdA       | 5859 | 1.00  | 127  |
| 10| 10 | Compound 10| 34.1 | 1.00  | 7.25 |
|   |    | EFdA       | 900  | 3.33  | 6.95 |
| 12| 10 | Compound 12| 813  | 0.583 | 79.6 |
|   |    | EFdA       | 5252 | 1.33  | 121  |

The invention claimed is:

1. An adenosine derivative having a structure of formula (I) or a pharmaceutically acceptable salt thereof:

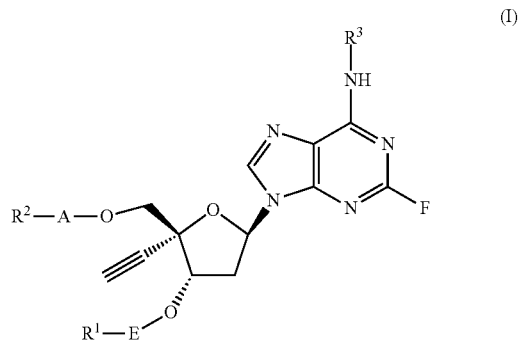

wherein:

A and E are each independently selected from the group consisting of a bond, —(CO)—, —(CO)-G-, —(CO)-

G-(C$_{1-10}$alkylene)-J-, —(CO)-G-(C$_{2-10}$alkenylene)-J-, and —(CO)-G-(C$_{2-10}$alkynylene)-J-; wherein:

G is selected form the group consisting of a bond, O, NH, and S;

J is selected form the group consisting of a bond, O, NH, S, —(CO)-G-;

R$^1$ is

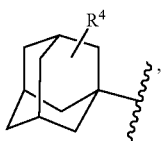

wherein R$^4$ is H, C$_{1-5}$alkyl, C$_{1-5}$haloalkyl, or C$_{1-5}$alkoxy;

R$^2$ is selected from the group consisting of H, C$_{1-20}$alkyl, C$_{1-20}$haloalkyl, C$_{1-20}$alkoxy, C$_{2-20}$alkenyl, C$_{2-20}$alkynyl, C$_{3-20}$cycloalkyl, 3- to 20-membered heterocycloalkyl, aryl, and heteroaryl; and R$^3$ is selected from the group consisting of H, —(CO)-G-C$_{1-10}$alkyl, C$_{1-10}$alkyl, C$_{1-10}$haloalkyl, C$_{2-10}$alkenyl, C$_{2-10}$alkynyl, C$_{3-12}$cycloalkyl, 3- to 12-membered heterocycloalkyl, aryl, and heteroaryl.

2. The adenosine derivative or pharmaceutically acceptable salt of claim 1, wherein A is selected from the group consisting of a bond, —(CO)—, —(CO)-G-, and —(CO)-G-(C$_{1-5}$alkylene)-J-.

3. The adenosine derivative or pharmaceutically acceptable salt of claim 2, wherein A is a bond or —(CO)-G-(C$_{1-5}$alkylene)-J-.

4. The adenosine derivative or pharmaceutically acceptable salt of claim 1, wherein E is a bond, —(CO)-G-, and —(CO)-G-(C$_{1-5}$alkylene)-J-.

5. The adenosine derivative or pharmaceutically acceptable salt of claim 4, wherein E is a bond or —(CO)-G-(C$_{1-5}$alkylene)-J-.

6. The adenosine derivative or pharmaceutically acceptable salt of claim 1, wherein G is a bond or O.

7. The adenosine derivative or pharmaceutically acceptable salt of claim 1, wherein J is a bond or O.

8. The adenosine derivative or pharmaceutically acceptable salt of claim 1, wherein G is O and J is a bond.

9. The adenosine derivative or pharmaceutically acceptable salt of claim 1, wherein R$^2$ is H, C$_{1-5}$alkyl, or

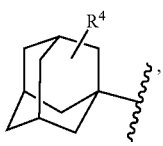

wherein R$^4$ is H, C$_{1-5}$alkyl, C$_{1-5}$haloalkyl, or C$_{1-5}$alkoxy.

10. The adenosine derivative or pharmaceutically acceptable salt of claim 9, wherein R$^4$ is H.

11. The adenosine derivative or pharmaceutically acceptable salt of claim 1, wherein R$^2$ is

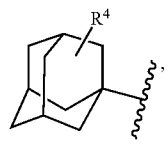

wherein R$^4$ is H.

12. The adenosine derivative or pharmaceutically acceptable salt of claim 1, wherein R$^2$ is H.

13. The adenosine derivative or pharmaceutically acceptable salt of claim 1, wherein R$^3$ is H, —(CO)—C$_{1-5}$alkyl, —(CO)—O—C$_{1-5}$alkyl, or C$_{1-5}$alkyl.

14. The adenosine derivative or pharmaceutically acceptable salt of claim 13, wherein R$^3$ is H.

15. The adenosine derivative or pharmaceutically acceptable salt of claim 1, wherein said adenosine derivative is selected from the group consisting of:

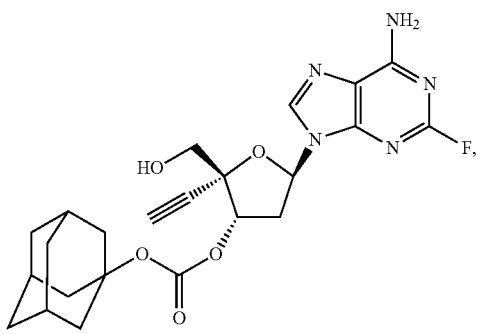

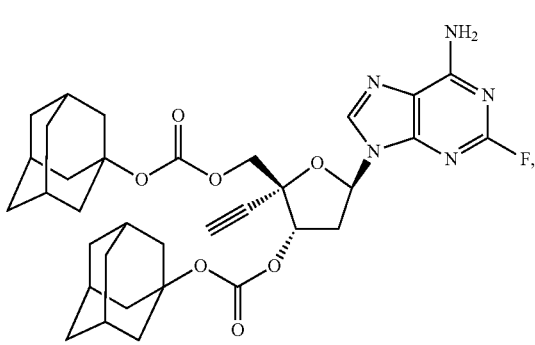

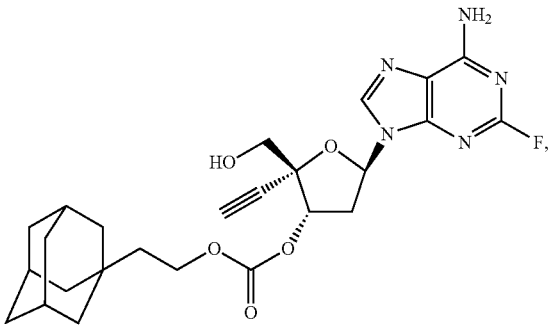

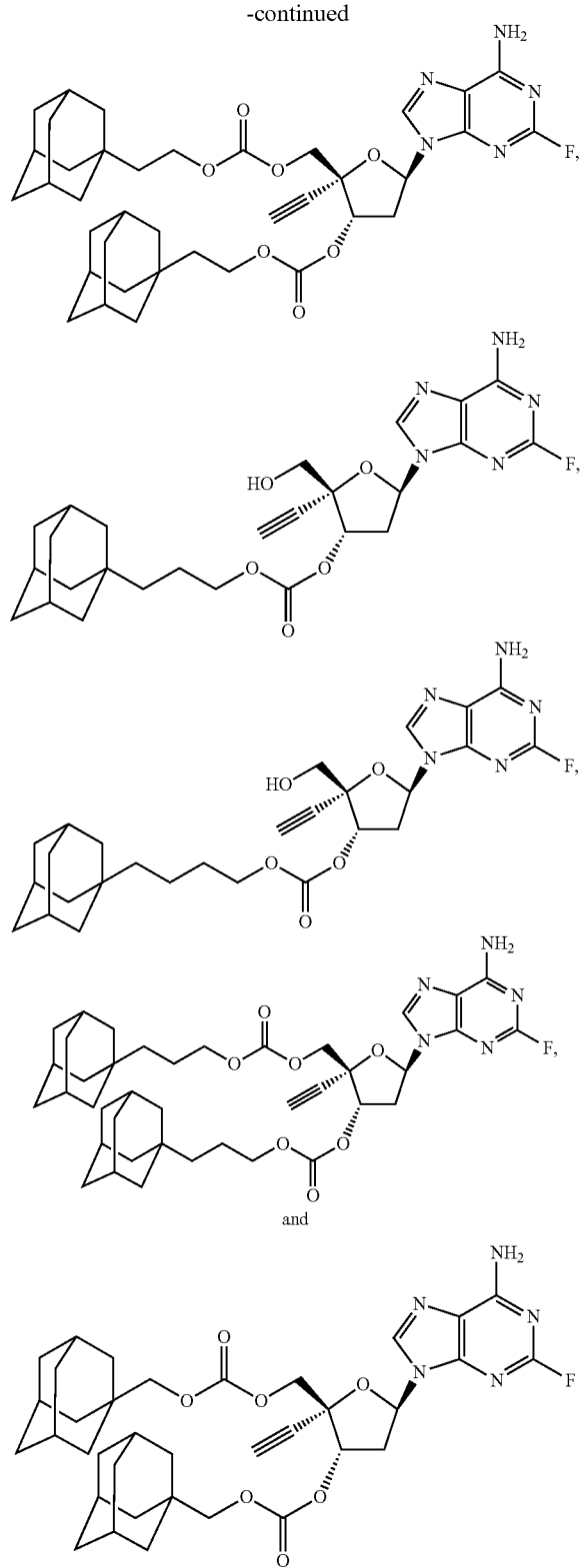

or a pharmaceutically acceptable salt thereof.

16. The adenosine derivative or pharmaceutically acceptable salt of claim 1, wherein said adenosine derivative is selected from the group consisting of:

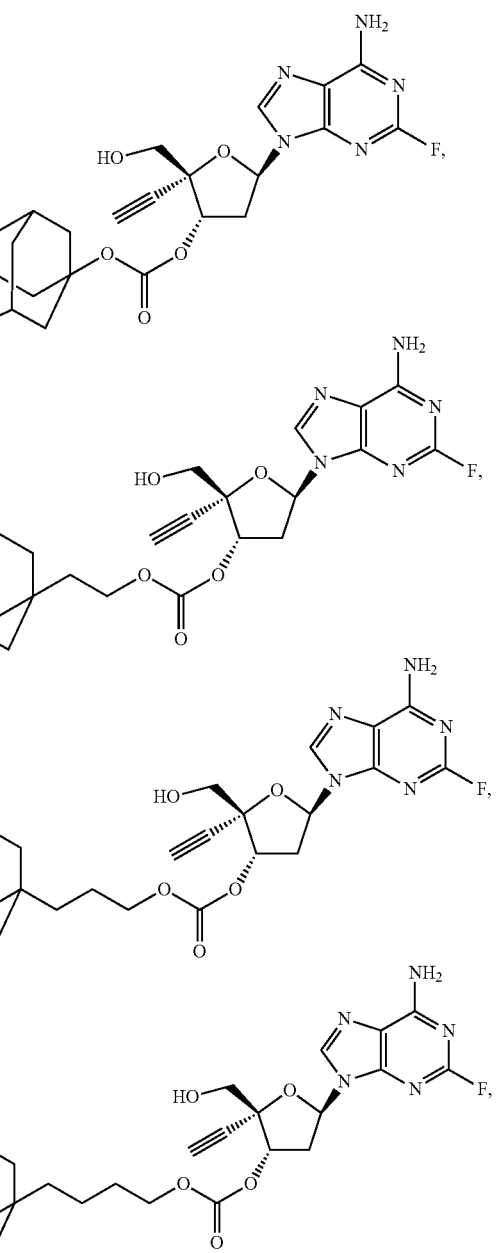

and a pharmaceutically acceptable salt thereof.

17. The adenosine derivative or pharmaceutically acceptable salt of claim 1, wherein said adenosine derivative is a reverse transcriptase inhibitor activity in vivo, a reverse transcriptase chain terminator activity in vivo, DNA translocation inhibitor activity in vivo, or a combination thereof.

18. A pharmaceutical composition comprising the adenosine derivative or pharmaceutically acceptable salt of claim 1 and a pharmaceutically acceptable carrier.

19. A method for treating an HIV infection, comprising administering a subject in need thereof an effective dosage of the pharmaceutical composition of claim 18.

* * * * *